US010815247B2

(12) United States Patent
Flemming et al.

(10) Patent No.: US 10,815,247 B2
(45) Date of Patent: Oct. 27, 2020

(54) FUNCTIONALIZED NANOLUC INHIBITORS

(71) Applicant: PROMEGA CORPORATION, Madison, WI (US)

(72) Inventors: Roderick G. Flemming, McFarland, WI (US); Mary Hall, Waunakee, WI (US); Thomas Machleidt, Madison, WI (US); Poncho Meisenheimer, San Luis Obispo, CA (US); Nidhi Nath, Madison, WI (US); Matthew B. Robers, Madison, WI (US); Joel R. Walker, San Luis Obispo, CA (US); Wenhui Zhou, San Luis Obispo, CA (US)

(73) Assignee: PROMEGA CORPORATION, Madison, WI (US)

(*) Notice: Subject to any disclaimer, the term of this patent is extended or adjusted under 35 U.S.C. 154(b) by 228 days.

(21) Appl. No.: 15/856,302

(22) Filed: Dec. 28, 2017

(65) Prior Publication Data
US 2018/0222916 A1 Aug. 9, 2018

Related U.S. Application Data

(60) Provisional application No. 62/439,600, filed on Dec. 28, 2016.

(51) Int. Cl.
C07D 495/04 (2006.01)
C12Q 1/26 (2006.01)
G01N 21/76 (2006.01)
C07D 403/12 (2006.01)
C07D 417/14 (2006.01)
C07D 519/00 (2006.01)
C07D 209/12 (2006.01)
C07D 209/42 (2006.01)
C07D 413/12 (2006.01)
C07D 493/10 (2006.01)
C07F 5/02 (2006.01)

(52) U.S. Cl.
CPC ........ C07D 495/04 (2013.01); C07D 209/12 (2013.01); C07D 209/42 (2013.01); C07D 403/12 (2013.01); C07D 413/12 (2013.01); C07D 417/14 (2013.01); C07D 493/10 (2013.01); C07D 519/00 (2013.01); C07F 5/022 (2013.01); C12Q 1/26 (2013.01); C12Y 113/12007 (2013.01); G01N 21/763 (2013.01)

(58) Field of Classification Search
None
See application file for complete search history.

(56) References Cited

U.S. PATENT DOCUMENTS 4,981,975 A 1/1991 Spang et al.
5,814,471 A 9/1998 Wood
8,557,970 B2 10/2013 Encell et al.
8,669,103 B2 3/2014 Binkowski et al.
2008/0248511 A1 10/2008 Daily et al.
2012/0107849 A1 5/2012 Klaubert et al.
2012/0117667 A1 5/2012 Klaubert et al.
2013/0130289 A1 5/2013 Benink et al.
2015/0212078 A1 7/2015 Zhou et al.
2015/0307916 A1 10/2015 Zhou et al.
2016/0355523 A1 12/2016 Levin et al.
2016/0376568 A1 12/2016 Duellman et al.

FOREIGN PATENT DOCUMENTS

WO 2003/040100 A1 5/2003
WO 2003/044014 A1 5/2003
WO 2005/110410 A2 11/2005
WO 2007/088277 A1 8/2007
WO 2008/118445 A1 10/2008
WO 2009/046165 A1 4/2009
WO 2010/118208 A1 10/2010
WO 2011/100359 A1 8/2011
WO 2014/052653 A1 4/2014
WO 2015/067302 A1 5/2015
WO 2016/210294 A1 12/2016
WO 2018/125992 A1 7/2018

OTHER PUBLICATIONS

Beija et al., "Synthesis and applications of Rhodamine derivatives as fluorescent probes," Chem. Soc. Rev., 2009, 38, 2410-2433.
Document No. 140:357208, retrieved from STN; entered in STN on May 3, 2004.
Document No. 151:51014, retrieved from STN; entered in STN on Apr. 23, 2009.
Document No. 155:115659, retrieved from STN; entered in STN on May 26, 2011.
Document No. 156:302194, retrieved from STN; entered in STN on Dec. 22, 2011.
Hall et al., "Engineered Luciferase Reporter from a Deep Sea Shrimp Utilizing a Novel Imidazopyrazinone Substrate," ACS Chemical Biology, 2012, 7(11)1848-1857.
Kvach et al., "Practical Synthesis of Isomerically Pure 5- and 6-Carboxytetramethylrhodamines, Useful Dyes for DNA Probes," Bioconjugate Chem. 2009, 20, 1673-1682.
Lai et al., "Induced protein degradation: an emerging drug discovery paradigm," Nature Reviews Drug Discovery, 2017, 16(2)101-114.
Langley et al., "Molecular Basis of beta-Galactosidase alpha-Complementation," PNAS, 1975, 72:1254-1257.
Levit and Berger, "Ribonuclease S-Peptide, A Model for Molecular Recognition," J. Biol. Chem., 1976, 251:1333-1339.
Nazare et al., "Fragment Deconstruction of Small, Potent Factor Xa Inhibitors: Exploring the Superadditivity Energetics of Fragment Linking in Protein-Ligand Complexes", Angewandte Chemie International Edition, vol. 51, No. 1, Jan. 23, 2012, pp. 905-911.

(Continued)

Primary Examiner — Susan M Hanley
(74) Attorney, Agent, or Firm — Casimir Jones, S.C.; Anne M. Reynolds

(57) ABSTRACT

Compounds that may inhibit *Oplophorus*-derived luciferases are disclosed as well as compositions and kits comprising the compounds, and methods of using the compounds.

40 Claims, 15 Drawing Sheets
Specification includes a Sequence Listing.

(56) References Cited

OTHER PUBLICATIONS

Nisha et al., "Profiling 976 ToxCast Chemicals across 331 Enzymatic and Receptor Signaling Assays", XP002760866, retrieved from STN Database accession No. 2013:631295, Chemical Research in Toxicology, 26(6), pp. 878-895.

Schena et al., "Modulating protein activity using tethered ligands with mutually exclusive biding sites," Nature communications 6, 2015, Article No. 7830.

Nalker et al., "Highly Potent Cell-Permeable and Impermeable NanoLuc Luciferase Inhibitors," ACS Chemical Biology, 2017, 12(4):1028-1037.

Yamaguchi et al., "Turn-ON fluorescent affinity labeling using a small bifunctional O-nitrobenzoxadiazole unit," Chemical Science, 2014, 5, 1021-1029.

Yu et al., "From Spirolactam Mixtures to Regioisomerically Pure 5- and 6-Rhodamines: A Chemodosimeter-Inspired Strategy," Org. Lett., 2012, 14 (8), pp. 2014-2017.

International Search Report and Written Opinion for Application No. PCT/US2016/039307 dated Sep. 14, 2016 (16 pages).

International Search Report and Written Opinion for Application No. PCT/US2017/068686 dated Mar. 22, 2018 (14 pages).

United States Patent Office Action for U.S. Appl. No. 15/192,420 dated Jan. 12, 2018 (11 pages).

United States Patent Office Action for U.S. Appl. No. 15/192,420 dated Jul. 25, 2018 (9 pages).

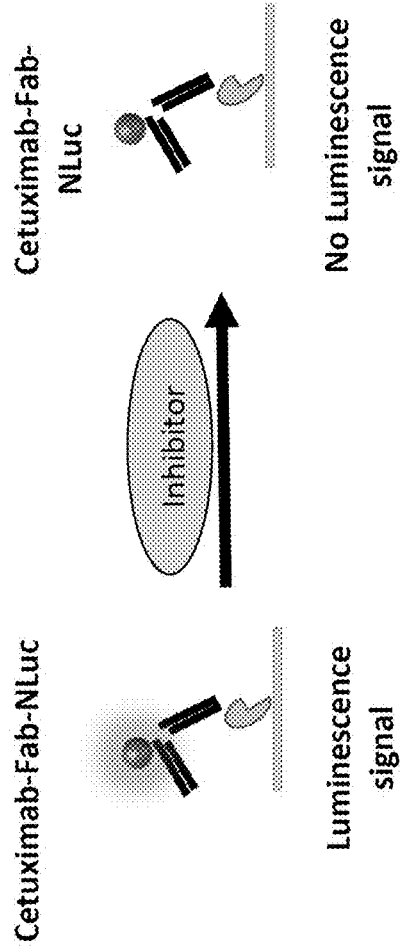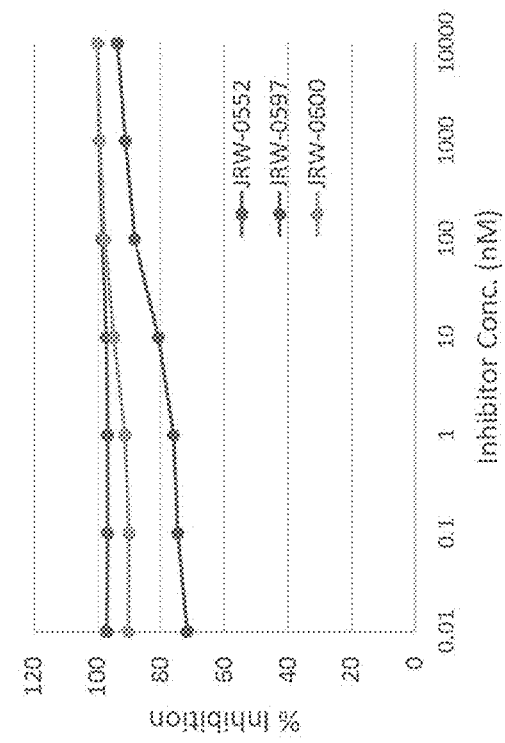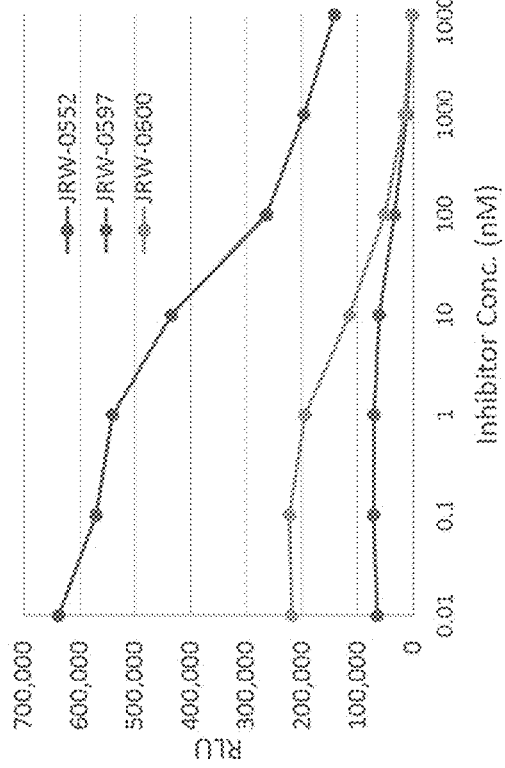
FIG. 8A
FIG. 8B
FIG. 8C

SEQUENCE LISTING

```
<160> NUMBER OF SEQ ID NOS: 2

<210> SEQ ID NO 1
<211> LENGTH: 169
<212> TYPE: PRT
<213> ORGANISM: Artificial Sequence
<220> FEATURE:
<223> OTHER INFORMATION: Synthetic Peptide - Native Mature Oplophorus
      luciferase

<400> SEQUENCE: 1

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Pro Tyr Glu Gly
    50                  55                  60
```

```
Leu Ser Gly Phe Gln Met Gly Leu Ile Glu Met Ile Phe Lys Val Val
 65                  70                  75                  80

Tyr Pro Val Asp Asp His His Phe Lys Ile Ile Leu His Tyr Gly Thr
                 85                  90                  95

Leu Val Ile Asp Gly Val Thr Pro Asn Met Ile Asp Tyr Phe Gly Arg
                100                 105                 110

Pro Tyr Pro Gly Ile Ala Val Phe Asp Gly Lys Gln Ile Thr Val Thr
            115                 120                 125

Gly Thr Leu Trp Asn Gly Asn Lys Ile Tyr Asp Glu Arg Leu Ile Asn
130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165
```

<210> SEQ ID NO 2
<211> LENGTH: 171
<212> TYPE: PRT
<213> ORGANISM: Artificial Sequence
<220> FEATURE:
<223> OTHER INFORMATION: Synthetic Peptide - Nluc

<400> SEQUENCE: 2

```
Met Val Phe Thr Leu Glu Asp Phe Val Gly Asp Trp Arg Gln Thr Ala
  1               5                  10                  15

Gly Tyr Asn Leu Asp Gln Val Leu Glu Gln Gly Gly Val Ser Ser Leu
                 20                  25                  30

Phe Gln Asn Leu Gly Val Ser Val Thr Pro Ile Gln Arg Ile Val Leu
             35                  40                  45

Ser Gly Glu Asn Gly Leu Lys Ile Asp Ile His Val Ile Ile Pro Tyr
 50                  55                  60

Glu Gly Leu Ser Gly Asp Gln Met Gly Gln Ile Glu Lys Ile Phe Lys
 65                  70                  75                  80

Val Val Tyr Pro Val Asp His His Phe Lys Val Ile Leu His Tyr
                 85                  90                  95

Gly Thr Leu Val Ile Asp Gly Val Thr Pro Asn Met Ile Asp Tyr Phe
                100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

FUNCTIONALIZED NANOLUC INHIBITORS

CROSS-REFERENCE TO RELATED APPLICATIONS

This application claims priority to U.S. Provisional Patent Application No. 62/439,600, filed on Dec. 28, 2016, the entire contents of which are incorporated herein by reference.

TECHNICAL FIELD

The present disclosure is directed to compounds that may inhibit *Oplophorus*-derived luciferases.

BACKGROUND

Reporter molecules are routinely used to monitor molecular events in the fields of biology, biochemistry, immunology, cell biology, and molecular biology. Luciferases based on the luciferase secreted from the deep-sea shrimp, *Oplophorus gracilirostris*, may be used as reporter molecules and have been shown to have advantageous characteristics including broad substrate specificity, high activity, and high quantum yield. It may be further advantageous, in certain applications, to control the luminescent signal from *Oplophorus* luciferases. Selective luciferase inhibitors are useful in luminescent assays. Luciferase inhibitors may be further derivatized to provide desirable properties useful for studying enzyme activities and cellular processes.

SUMMARY

In one aspect, the disclosure provides a compound of formula (I), or a salt thereof:

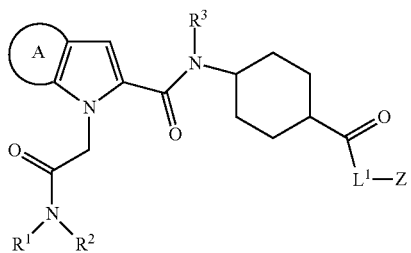

(I)

wherein:

A is absent, an optionally substituted phenyl ring, or an optionally substituted thienyl ring;

$L^1$ is absent or —$(CR^{a1}R^{a2})_{m1}$—, wherein m1 is 1 to 100, optionally wherein one or more $CR^{a1}R^{a2}$ groups are replaced by a heteroatom or heteroatom group selected from the group consisting of O, $N(R^{a3})$, $S(=O)$, and $S(=O)_2$, optionally wherein one or more $CR^{a1}R^{a2}$ groups are replaced by $C(=O)$, optionally wherein two adjacent $CR^{a1}R^{a2}$ groups form $CR^{a1}=CR^{a1}$, and optionally wherein one or more $CR^{a1}R^{a2}$ groups are replaced by a -Cy- group, wherein each Cy is independently selected from the group consisting of aryl, heteroaryl, cycloalkyl, cycloalkenyl, and heterocycle; wherein $R^{a1}$, $R^{a2}$, and $R^{a3}$ are independently selected from the group consisting of hydrogen and $C_1$-$C_4$-alkyl;

Z is $C_1$-$C_{10}$ haloalkyl, a leaving group Y, a bioactive agent, or a dye, wherein the leaving group Y is selected from the group consisting of $OR^4$, halogen, heteroaryl, and heterocyclyl;

$R^1$ is hydrogen or $C_1$-$C_8$ alkyl;

$R^2$ is selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;

$R^3$ is hydrogen or $C_1$-$C_8$ alkyl; and $R^4$ is selected from the group consisting of optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl.

In one aspect, the disclosure provides a method of inhibiting an *Oplophorus*-derived luciferase, the method comprising contacting the *Oplophorus*-derived luciferase with a compound described herein.

In one aspect, the disclosure provides a method for modulating luminescence of an *Oplophorus*-derived luciferase in a sample, the method comprising,
(a) contacting the sample with a coelenterazine substrate and a compound described herein, and
(b) detecting luminescence in the sample,
wherein the compound causes a decrease in the luminescence from the *Oplophorus*-derived luciferase.

In one aspect, the disclosure provides a method to detect an interaction between a first protein and a second protein in a sample, the method comprising:
(a) contacting a sample with a coelenterazine substrate a compound described herein, wherein the sample comprises:
 (i) a first polynucleotide encoding a first fusion protein, wherein the first fusion protein comprises a first fragment of an *Oplophorus*-derived luciferase and a first protein; and
 (ii) a second polynucleotide encoding a second fusion protein, wherein the second fusion protein comprises a second fragment of the *Oplophorus*-derived luciferase and a second protein; and
(b) detecting luminescence in the sample,
wherein the detection of luminescence indicates an interaction between the first protein and the second protein.

In one aspect, the disclosure provides a method to detect an interaction between a first protein and a second protein in a sample, the method comprising:
(a) contacting a sample with a coelenterazine substrate and a compound described herein, wherein the sample comprises:
 (i) a first polynucleotide encoding a first fusion protein, wherein the first fusion protein comprises an *Oplophorus*-derived luciferase and a first protein, wherein the *Oplophorus*-derived luciferase is a bioluminescent donor; and
 (ii) a second polynucleotide encoding a second fusion protein, wherein the second fusion protein comprises a fluorescent acceptor molecule and a second protein;
(b) detecting bioluminescence resonance energy transfer (BRET) in the sample, indicating an interaction or close proximity of the bioluminescent donor and the fluorescence acceptor.

In one aspect, the disclosure provides a bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a fluorescent acceptor molecule; a coelenterazine substrate, and a compound described herein.

In one aspect, the disclosure provides a kit comprising:
(a) a compound described herein; and
(b) an *Oplophorus*-derived luciferase.

In one aspect, the disclosure provides a method of inducing protein degradation, the method comprising contacting a cell with a compound disclosed herein, wherein the cell comprising a luciferase fusion protein and at least one protease, whereby the fusion protein is degraded by the protease.

In one aspect, the disclosure provides a method of labeling a target protein, the method comprising contacting a target protein with a compound disclosed herein, whereby the target protein forms a covalent bond with a protein labeling moiety of the compound.

In one aspect, the disclosure provides a method to detect an interaction between a molecule of interest and a target protein in a sample, the method comprising:
(a) detecting a first bioluminescence resonance energy transfer (BRET) signal in a sample, the sample comprising:
 (i) a polynucleotide encoding a fusion protein, the fusion protein comprising an *Oplophorus*-derived luciferase and a target protein, wherein the *Oplophorus*-derived luciferase is a bioluminescent donor;
 (ii) a coelenterazine substrate;
 (iii) a compound described herein; and
 (iv) a fluorescent tracer comprising a fluorescent acceptor molecule and a ligand that binds to the target protein;
(b) contacting the sample with a molecule of interest; and
(c) detecting a second BRET signal in the sample, wherein a decrease in the second BRET signal compared to the first BRET signal indicates an interaction between the molecule of interest and the target protein.

In one aspect, the disclosure provides a bioluminescence resonance energy transfer (BRET) system comprising: a fusion protein including a target protein and a bioluminescence donor molecule, wherein the bioluminescence donor molecule is an *Oplophorus*-derived luciferase; a fluorescent tracer comprising a fluorescent acceptor molecule and a ligand that binds to the target protein; a coelenterazine substrate, and a compound described herein.

In one aspect, the disclosure provides a method to detect an interaction between a first target protein and a second target protein in a sample, the method comprising:
(a) contacting a sample with a coelenterazine substrate, a compound described herein, and a HALOTAG® ligand, wherein the HALOTAG® ligand comprises a fluorescent acceptor molecule, wherein the sample comprises:
 (i) a first polynucleotide encoding a first fusion protein, wherein the first fusion protein comprises an *Oplophorus*-derived luciferase and a first target protein, wherein the *Oplophorus*-derived luciferase is a bioluminescent donor; and
 (ii) a second polynucleotide encoding a second fusion protein, wherein the second fusion protein comprises a HALOTAG® protein and a second target protein;
(b) detecting bioluminescence resonance energy transfer (BRET) in the sample thereby detecting an interaction or indicating a close proximity of the first target protein and the second target protein.

In one aspect, the disclosure provides a bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a HALOTAG® protein; a HALOTAG® ligand comprising a fluorescent acceptor molecule; a coelenterazine substrate, and a compound described herein.

BRIEF DESCRIPTION OF THE DRAWINGS

FIG. 2A shows inhibition of Nluc and Nluc-HT. FIG. 2B shows inhibition of Nluc-HT and Nluc-HT-618.

FIG. 5A shows a BRET reaction under conditions without inhibitor present. FKBP binds to FRB in the presence of rapamycin, bringing Nluc into contact with the HT-NanoBRET™ 618 ligand complex and enabling BRET. Under these conditions, the BRET ratio increases with increasing concentrations of rapamycin, increasing the ratio of 610 nm:460 nm light emitted. FIG. 5B shows the same association/dissociation model in the presence of JRW-0308. In conditions with low concentrations of rapamycin present, FKB does not bind to FRB and Nluc remains unbound from the HT-JRW-0308 complex. The addition of rapamycin induces FKB/FRB binding, which brings the HT-inhibitor complex into contact with the Nluc causing decreased signal. FIG. 5C shows that rapamycin displays a similar EC50 for both of the above described models.

FIG. 8A, FIG. 8B and FIG. 8C show a comparison of succinate ester functionalized inhibitors and a potent reversible inhibitor using an EGFR/Cetuximab binding assay. FIG. 8A shows a schematic illustrating the concept of the binding assay. Cetuximab is appended to a HT-NLuc fusion protein (Cetux-Fab-Nluc) and added to an EGFR plate. Under control conditions, Cetuximab binds EGFR and the Nluc signal is high. The addition of inhibitor diminishes the Nluc signal. FIG. 8B shows the Nluc inhibitory activities of succinate ester functionalized inhibitors (JRW-0552 and JRW-0600) and a potent reversible inhibitor (JRW-0597). An EGFR coated plate was treated with 3 µg/ml Cetux-Fab-Nluc. The plate was treated with the indicated concentration of inhibitors. Plates were read following addition of furimazine (10 µM final concentration) using a BMG Clariostar. FIG. 8C shows the % inhibition of the tested compounds relative to control.

DETAILED DESCRIPTION

Figure 1:
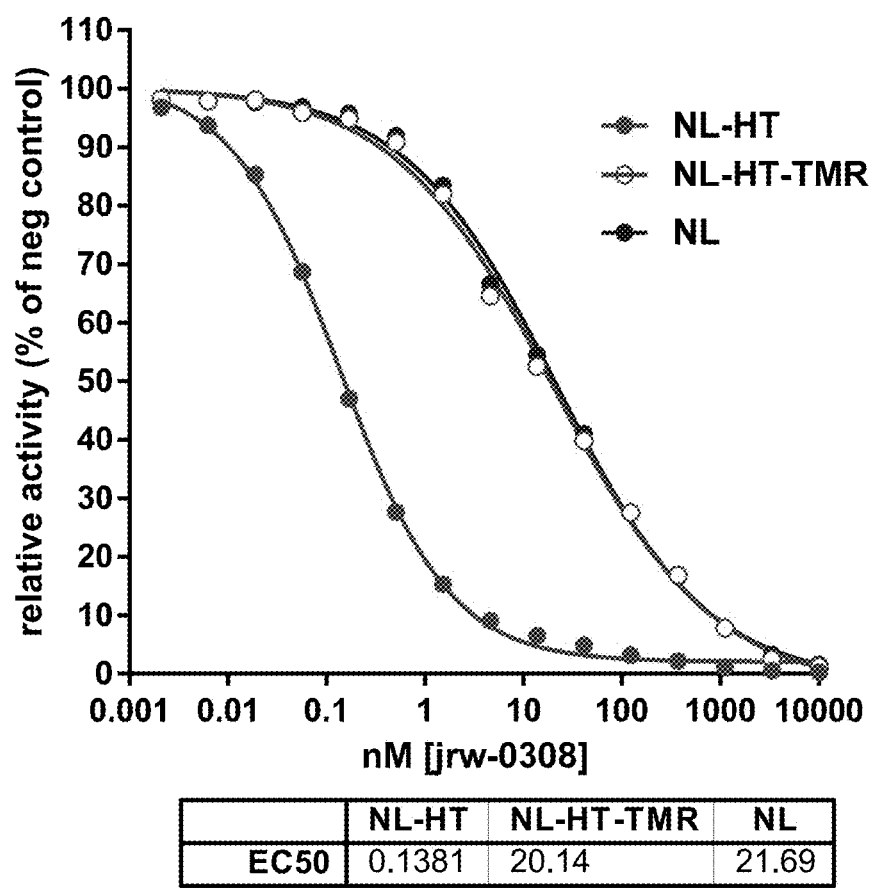
FIG. 1 shows the inhibition of NANOLUC® (Nluc) enzyme by JRW-0308. Nluc, Nluc-HaloTag (HT), and Nluc-HT-TMR were diluted to a final concentration of 0.05 nM in PBS/0.05% BSA and incubated with the indicated concentration of JRW-0308 for 2 hours at room temperature. Samples were analyzed after addition of furimazine (10 μM final concentration) using a BMG Clariostar plate reader.

The disclosed compounds may selectively inhibit *Oplophorus*-derived luciferases, such as a luciferase of SEQ ID NO:2 (also interchangeably referred to herein as "NanoLuc", "Nluc," "Nluc luciferase," and "Nluc enzyme"). Due to their stabilities and their potential to be excreted from cells, it may be advantageous to use selective inhibitors to suppress the luminescence from *Oplophorus*-derived luciferases in certain applications. For example, in applications involving temporal multiplexing of multiple luminescent systems, it can be beneficial to have selective inhibitors for each system to allow for the measurement and/or detection of only one luminescent signal at a time. Additionally, in some plate-based assays, a certain amount of luciferase may be excreted from cells. An extracellular inhibitor compound would allow for luminescence from excreted luciferase to be selectively suppressed and may, therefore, help to improve the signal-to-noise ratio in certain assays.

The compounds may compete for binding of the coelenterazine substrates of the luciferases and can be modified to produce both cell-permeable and cell-impermeable inhibitors. The disclosed compounds may contain tethered functional groups that extend out of the enzyme pocket and into solvent without impacting the compounds' inhibition potency. The disclosed compounds can be applied in relief-of-inhibition assays (such as target engagement binding assay or target enzyme activity assay), used as a biosensor molecule, yield a NanoLuc® suicide inhibitor, and/or used as a fluorescent tag for NanoLuc-based cell sorting and labeling.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "substituent" or "suitable substituent" is intended to mean a chemically acceptable functional group e.g., a moiety that does not negate the activity of the inventive compounds. Illustrative examples of suitable substituents include, but are not limited to halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, sulfonic acid groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents. The substituents can also be in salt forms (e.g., a sulfonic acid group can be in the form of a sulfonate group.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

As used herein, the term "alkenyl" refers a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyl groups of the present invention may be unsubstituted or substituted by one or more suitable substituents, preferably 1 to 3 suitable substituents, as defined above.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkoxyalkoxy" refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

As used herein, the term "alkoxyalkyl" refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

As used herein, the term "alkoxycarbonyl" refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, ethoxycarbonylmethyl, 3-methoxycarbonylpropyl, 4-ethoxycarbonylbutyl, and 2-tert-butoxycarbonylethyl.

As used herein, the term "alkyl" refers to a linear or branched hydrocarbon radical, suitably having 1 to 30 carbon atoms, 1 to 12 carbon atoms, 1 to 10 carbon atoms, 1 to 8 carbon atoms, 1 to 6 carbon atoms, or 1 to 4 carbon atoms. The term "$C_1$-$C_8$-alkyl" is defined to include alkyl groups having 1, 2, 3, 4, 5, 6, 7 or 8 carbons in a linear or branched arrangement. For example, "$C_1$-$C_8$-alkyl" specifically includes methyl, ethyl, n-propyl, iso-propyl, n-butyl, sec-butyl, iso-butyl, tert-butyl, pentyl (e.g., n-pentyl), hexyl (e.g., n-hexyl), heptyl (e.g., n-heptyl) and octyl (e.g., n-octyl). The term "$C_1$-$C_6$-alkyl" is defined to include alkyl groups having 1, 2, 3, 4, 5, or 6 carbons in a linear or branched arrangement. For example, "$C_1$-$C_6$-alkyl" specifically includes methyl, ethyl, n-propyl, iso-propyl, n-butyl, sec-butyl, iso-butyl, tert-butyl, pentyl (e.g., n-pentyl), and hexyl (e.g., n-hexyl). The term "$C_1$-$C_4$-alkyl" is defined to include alkyl groups having 1, 2, 3, or 4 carbons in a linear or branched arrangement. For example, "$C_1$-$C_4$-alkyl" specifically includes methyl, ethyl, n-propyl, i-propyl, n-butyl, sec-butyl, iso-butyl and tert-butyl. Alkyl groups of the present invention may be unsubstituted or substituted by one or more suitable substituents, such as 1 to 3 suitable substituents, as defined above. For example, an alkyl group can be substituted with one or more halo substituents to form a haloalkyl group, or with one or more hydroxy substituents to form a hydroxyalkyl group, or with one or more alkoxy groups to form an alkoxyalkyl group.

As used herein, the term "alkylamino" refers to an alkyl group, as defined herein, appended to the parent molecular moiety through an amino group, as defined herein. Representative examples of alkylamino include, but are not limited to, methylamino, ethylamino, iso-propylamino, butylamino and sec-butylamino.

As used herein, the term "alkylaminoalkyl" refers to an alkyl group, as defined herein, appended to the parent molecular moiety through an aminoalkyl group, as defined herein. Representative examples of alkylaminoalkyl groups include, but are not limited to, methylaminoethyl and methylamino-2-propyl.

As used herein, the term "alkylcarbonyl" refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

As used herein, the term "alkylcarbonylalkyl" refers to an alkylcarbonyl group, as defined herein, appended to the parent molecular moiety through an alkyl group, as defined herein.

As used herein, the term "alkylcarbonylalkylamido" refers to an alkylcarbonyl group, as defined herein, appended to the parent molecular moiety through an alkylamido group, as defined herein.

The term "alkylene" means a divalent group derived from a saturated, straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, —$CH_2C(CH_3)_2$—, and —$CH_2CH(CH_3)CH_2$—.

As used herein, the term "alkynyl" refers to a straight or branched hydrocarbon radical having 2, 3, 4, 5, 6, 7, 8, 9 or 10 carbons, and having one or more carbon-carbon triple bonds. Alkynyl groups of the present invention include, but are not limited to, ethynyl, propynyl, and butynyl. Alkynyl groups of the present invention may be unsubstituted or substituted by one or more suitable substituents, preferably 1 to 3 suitable substituents, as defined above.

As used herein, the term "amido" refers to an amino group appended to the parent molecular moiety through a carbonyl group, as defined herein (i.e., —$CONH_2$). The term "alkylamido," as used herein, refers to an alkylamino group or dialkylamino group appended to the parent molecular moiety through a carbonyl group, as defined herein. Representative examples of alkylamido include, but are not limited to, methylaminocarbonyl, dimethylaminocarbonyl, ethylmethylaminocarbonyl, and n-hexylaminocarbonyl.

As used herein, the term "amino" refers to an —$NH_2$ group.

As used herein, the term "aminoalkyl" refers to at least one amino group, as defined herein, appended to the parent molecular moiety through an alkyl group, as defined herein. Representative examples of aminoalkyl include, but are not limited to, aminomethyl, 2-aminoethyl, 3-aminopropyl, 4-aminobutyl, 5-aminopentyl, and 6-aminohexyl.

As used herein, the term "aminoalkylamido" refers to at least one amino group, as defined herein, appended to the parent molecular moiety through an alkylamido group, as defined herein.

As used herein, the term "amino protecting group," refers to a moiety that prevents chemical reactions from occurring on the nitrogen atom to which that protecting group is attached. An amino protecting group must also be removable by a chemical reaction. Such groups are well known in the art and include those described in detail in Protecting Groups in Organic Synthesis, T. W. Greene and P. G. M. Wuts, 3rd edition, John Wiley & Sons, 1999, the entirety of which is incorporated herein by reference. Suitable amino protecting groups include, but are not limited to, carbobenzyloxy (—NHCO—$OCH_2C_6H_5$ or —NH-Cbz); t-butyloxycarbonyl (—NHCO—$OC(CH_3)_3$ or —NH-Boc); 9-fluorenylmethyloxycarbonyl (—NH-Fmoc), 2,2,2-trichloroethyloxycarbonyl (—NH-Troc), and allyloxycarbonyl (—NH-Alloc). (In each of the above, the —NH— represents the nitrogen from the amino group that is being protected.)

As used herein, the term "aminoluciferin" refers to (4S)-2-(6-amino-1,3-benzothiazol-2-yl)-4,5-dihydrothiazole-4-carboxylic acid, or a substituted analog of this molecule.

As used herein, the term "aryl" means monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups of the present invention may be optionally substituted by one or more suitable substituents, preferably 1 to 5 suitable substituents, as defined above.

As used herein, the term "arylalkyl" refers to an aryl group, as defined herein, appended to the parent molecular moiety through an alkyl group, as defined herein. Representative examples of arylalkyl include, but are not limited to, phenylmethyl (i.e. benzyl) and phenylethyl.

As used herein, the term "arylcarbonyl" refers to an aryl group, as defined herein, appended to the parent molecular moiety through a carbonyl group, as defined herein.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "carboxy" refers to a —C(O)OH group.

As used herein, the term "carboxyalkyl" refers to a carboxy group as defined herein, appended to the parent molecular moiety through an alkyl group as defined herein.

As used herein, the term "carboxyalkylamido" refers to a carboxyalkyl group as defined herein, appended to the parent molecular moiety through an amido group as defined herein.

As used herein, the term "cycloalkyl" refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups of the present invention may be unsubstituted or substituted by one or more suitable substituents, preferably 1 to 5 suitable substituents, as defined above.

As used herein, the term "cycloalkylalkyl" refers to a cycloalkyl group, as defined herein, appended to the parent molecular moiety through an alkyl group, as defined herein. Representative examples of cycloalkylalkyl include, but are not limited to, cyclohexylmethyl.

As used herein, the term "cycloalkylamido" refers to a cycloalkyl group, as defined herein, appended to the parent molecular moiety through an amido group, as defined herein.

As used herein, the term "dialkylamino" refers to two independently selected alkyl groups, as defined herein, appended to the parent molecular moiety through an amino group, as defined herein. Representative examples of dialkylamino include, but are not limited to, N,N-dimethylamino, N-ethyl-N-methylamino, and N-isopropyl-N-methylamino.

As used herein, the term "dialkylaminoalkyl" refers to a dialkylamino group, as defined herein, appended to the parent molecular moiety through an alkyl group, as defined herein. Representative examples of dialkylaminoalkyl include, but are not limited to, N,N-dimethylaminoethyl and N,N-methyl(2-propyl)aminoethyl.

As used herein, the term "dialkylaminoalkylamido" refers to a dialkylamino group, as defined herein, appended to the parent molecular moiety through an alkylamido group, as defined herein.

As used herein, the term "halogen" or "halo" refers to a fluoro, chloro, bromo or iodo radical.

As used herein, the term "haloalkoxy" refers to an alkoxy group, as defined herein, substituted by one, two, three, or four halogen atoms. Representative examples of haloalkoxy include, but are not limited to, chloromethoxy, 2-fluoroethoxy, trifluoromethoxy, and pentafluoroethoxy.

As used herein, the term "haloalkyl" refers to an alkyl group, as defined herein, substituted by one, two, three, or four halogen atoms. Representative examples of haloalkyl include, but are not limited to, chloromethyl, 2-fluoroethyl, trifluoromethyl, pentafluoroethyl, 2-chloro-3-fluoropentyl, and 4,4,4-trifluorobutyl.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. Heteroaryl groups of the present invention may be unsubstituted or substituted by one or more suitable substituents, preferably 1 to 5 suitable substituents, as defined above.

As used herein, the term "heteroarylalkyl" refers to a heteroaryl group, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

As used herein, the term "heterocycle" or "heterocyclyl" refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2,5-dioxo-pyrrolidinyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.1$^{3,7}$]decane. Heterocyclic groups of the present invention may be unsubstituted or substituted by one or more suitable substituents, preferably 1 to 3 suitable substituents, as defined above. Heterocyclic groups of the present invention may contain one or more oxo groups (=O) or thioxo (=S) groups attached to the ring.

As used herein, the term "heterocyclylalkyl" refers to a heterocyclyl group, as defined herein, appended to the parent molecular moiety through an alkyl group, as defined herein. Representative examples of heterocyclylalkyl include, but are not limited to, piperidin-4-ylmethyl, piperazin-1-ylmethyl, 3-methyl-1-pyrrolidin-1-ylbutyl, (1R)-3-methyl-1-pyrrolidin-1-ylbutyl, (1S)-3-methyl-1-pyrrolidin-1-ylbutyl, and 3-morpholinopropyl.

As used herein, the term "heterocyclylamido" refers to a heterocyclyl group, as defined herein, appended to the parent molecular moiety through an amido group, as defined herein.

As used herein, the term "hydroxy" refers to an —OH group.

As used herein, the term "hydroxyalkoxy" refers to an alkoxy group, as defined herein, substituted by at least one hydroxy group. Representative examples of hydroxyalkoxy include, but are not limited to, hydroxyethoxy, and 2-hydroxypropoxy.

As used herein, the term "hydroxyalkyl" refers to an alkyl group, as defined herein, substituted by at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

The term "hydroxyalkylamido" as used herein refers to a hydroxyalkyl group attached to an amido group, e.g., -amido-alkyl-OH.

As used herein, the term "hydroxycarbonyl" refers to a hydroxy group, as defined herein, appended to the parent molecular moiety through a carbonyl group, as defined herein.

As used herein, the term "methylenedioxy" refers to a —OCH$_2$O— group wherein the oxygen atoms of the methylenedioxy are attached to the parent molecular moiety through two adjacent carbon atoms.

As used herein, the term "oxo" refers to a double bonded oxygen (=O) radical wherein the bond partner is a carbon atom. Such a radical can also be thought as a carbonyl group.

The term "peptide" or "polypeptide" refers to a sequence of at least two amino acids. In some embodiments, a peptide may contain no more than 80 amino acids, or no more than 35 amino acids, no more than 10 amino acids, or no more than 5 amino acids.

A prefix attached to a multi-component substituent only applies to the first component it precedes. To illustrate, the term "cycloalkylalkyl" contains two components: alkyl and cycloalkyl. Thus, the $C_1$-$C_6$-prefix on $C_1$-$C_6$-cycloalkylalkyl means that the alkyl component of the cycloalkylalkyl contains from 1 to 6 carbon atoms; the $C_1$-$C_6$-prefix does not describe the cycloalkyl component. To illustrate further, the term "halo-$C_1$-$C_6$-alkyl" refers to halomethyl, haloethyl, halopropyl, halobutyl, halopentyl, and halohexyl. To illustrate further, the prefix "halo" on haloalkoxyalkyl indicates that only the alkoxy component of the alkoxyalkyl substituent is substituted with one or more halogen radicals. If the halogen substitution may only occur on the alkyl component, the substituent would instead be described as "alkoxyhaloalkyl."

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted," a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

When a substituent is referred to as "unsubstituted" or not referred to as "substituted" or "optionally substituted," it means that the substituent does not have any substituents. If a substituent is described as being "optionally substituted," the substituent may be either (1) unsubstituted or (2) substituted. If a substituent is described as being optionally substituted with up to a particular number of non-hydrogen radicals, which substituent may be either (1) unsubstituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

If substituents are described as being "independently selected" from a group, each substituent is selected independent of the other. Each substituent, therefore, may be identical to or different from the other substituent(s).

As used herein, the term "bioluminescence" or "luminescence" may refer to light produced as a result of a reaction between an enzyme and a substrate that generates light. Examples of such enzymes (bioluminescent enzymes) include *Oplophorus* luciferase, e.g., *Oplophorus gracilirostris*, firefly luciferase, e.g. *Photinus pyralis* or *Photuris pennsylvanica*, click beetle luciferase, *Renilla luciferase*, cypridina luciferase, *Aequorin photoprotein*, obelin photoprotein and the like.

As used herein, the term "coelenterazine substrate" refers to a class of reporter molecules that luminesce when acted upon by a wide variety of bioluminescent proteins such as luciferases (e.g., marine luciferases). Coelenterazine substrates include coelenterazine as well as analogs and derivatives thereof.

The term "energy acceptor" or "acceptor molecule" refers to any small molecule (e.g., chromophore), macromolecule (e.g., autofluorescent protein, phycobiliproteins, nanoparticle, surface, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes)(Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog). In certain embodiments, energy acceptors include, but are not limited to, small molecule fluorescent dyes such as NCT, quenchers, fluorescent particles such as Quantum dots, luminescent metal complexes, and any other known energy acceptors.

The term "luminescent enzyme," "bioluminescent enzyme," or "luciferase" as used interchangeably herein refers to a class of oxidative enzymes used in bioluminescence wherein the enzyme produces and emits light when given a substrate. The luciferase may be a naturally occurring, recombinant, or mutant luciferase that uses a luciferase substrate. The luciferase substrate may be luciferin, a luciferin derivative or analog, a pre-luciferin derivative or analog, a coelenterazine, or a coelenterazine derivative or analog. The luminescent enzyme, if naturally occurring, may be obtained easily by the skilled person from an organism. If the luminescent enzyme is one that occurs naturally or is a recombinant or mutant luminescent enzyme, e.g. one which retains activity in a luciferase-coelenterazine or luciferase-luciferin reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods, such as from the Oplophoroidea (e.g. *Oplophorus*-derived luciferases), beetle luciferases (e.g., *Photinus pyralis, Photuris pennsylvanica*, etc.), marine organisms such as cnidarians (e.g., *Renilla* luciferase), Aristeidae, Solenoceridae, Luciferidae, Sergestidae, Pasipheidae and Thalassocarididae decapoda families, copepod luciferases, such as *Gaussia* luciferase, such as *Gaussia princeps* luciferase, *Metridia* luciferases, such as *Metridia longa* and *Metridia pacifica* luciferases, *Vargula* luciferases, such as *Vargula hilgendorfii* luciferase, *Pleuromamma xiphias* luciferase, and photoproteins, such as *Aequorin*, and variants, recombinants, and mutants thereof.

A "luminescent reaction mixture" contains materials that will allow the luminescent enzyme to generate a light signal, i.e., luminescence. The mixture may also contain the enzyme, e.g., the luciferase enzyme or luciferase. The materials, and the particular concentrations and/or amounts, needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

As used herein, the terms "*Oplophorus* luciferase" and "*Oplophorus*-derived luciferase" are used interchangeably and refer to a luciferase secreted from the deep-sea shrimp *Oplophorus gracilirostris* (e.g., SEQ ID NO: 1), including wild-type, variants, and mutants thereof. For example, suitable *Oplophorus* luciferase variants are described in U.S. Pat. Nos. 8,557,970 and 8,669,103, each of which is incorporated herein by reference in its entirety. Exemplary *Oplophorus*-derived luciferases include, for example, that of SEQ ID NO: 2 (also interchangeably referred to herein as "NanoLuc", "Nluc," "Nluc luciferase," and "Nluc enzyme").

As used herein, the term "reporter moiety" may refer to a moiety that, under appropriate conditions, directly or indirectly generates a detectable signal. Exemplary reporter moieties include, but are not limited to, fluorophores, luminescent molecules, dyes, radiolabels and substrates for enzymes such as luciferase. In some embodiments, a reporter moiety may indirectly generate a detectable signal, for example, when the reporter moiety is a substrate for an enzyme. The reaction of the enzyme with the substrate then produces a detectable signal such as fluorescence or luminescence. As used herein, the term "bioluminescent reporter moiety" may refer to a moiety that is a substrate for a luciferase. For example, the bioluminescent reporter moiety can be a luciferin, a luciferin derivative, e.g., pre-luciferin, aminoluciferin, quionolyl-luciferin, napthyl luciferin, fluorolucifeirn, chloroluciferin, precursors of luciferin derivatives, a coelenterazine or a coelenterazine derivative or analog, e.g., furimazine. The luminescent signal generated may be detected using a luminometer. As used herein, the term "fluorescent reporter moiety" may refer to a moiety that fluoresces. For example, the fluorescent reporter moiety may be a fluorophore, such as coumarin, R110, fluorescein, DDAO, resorufin, cresyl violet, sily xanthene, or carbopyronine. Fluorescence may be detected using a fluorometer.

As used herein, the term "bioactive agent" may refer to a molecule or a functional component of a molecule that is capable of interacting with a biological molecule (such as proteins and nucleic acids) and cause a change in the biological activity of the biological molecule. For example, the biological molecule may function as an enzyme, a transporter, or a receptor that regulates the signal transduction, metabolism, and other biological processes in a cell. The bioactive agent may enhance or inhibit the activity of such biological molecule. The bioactive agent may include, for example, a pharmaceutical agent for a disease or disorder, an enzyme inhibitor, or an inhibitor of a cellular receptor. Suitable bioactive agent may include a kinase inhibitor, such as dasatinib. The bioactive agent may also include proteins and surfaces that interact with a biological molecule. For example, the bioactive agent may include a protein, such as HaloTag® proteins.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

Provided herein are compounds that may inhibit *Oplophorus*-derived luciferases and/or *Oplophorus*-derived luciferase activity. The present compounds include compounds of formula (I) and salts thereof:

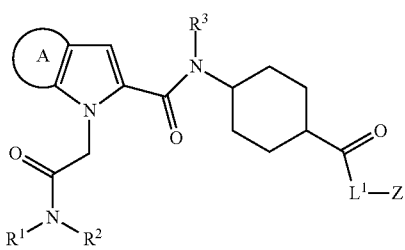

(I)

wherein:

A is absent, an optionally substituted phenyl ring, or an optionally substituted thienyl ring;

$L^1$ is absent or $—(CR^{a1}R^{a2})_{m1}—$, wherein m1 is 1 to 100, optionally wherein one or more $CR^{a1}R^{a2}$ groups are replaced by a heteroatom or heteroatom group selected from the group consisting of O, $N(R^{a3})$, $S(=O)$, and $S(=O)_2$, optionally wherein one or more $CR^{a1}R^{a2}$ groups are replaced by $C(=O)$, optionally wherein two adjacent $CR^{a1}R^{a2}$ groups form $CR^{a1}=CR^{a1}$, and optionally wherein one or more $CR^{a1}R^{a2}$ groups are replaced by a -Cy- group, wherein each Cy is independently selected from the group consisting of aryl, heteroaryl, cycloalkyl, cycloalkenyl, and heterocycle; wherein $R^{a1}$, $R^{a2}$, and $R^{a3}$ are independently selected from the group consisting of hydrogen and $C_1$-$C_4$-alkyl;

Z is $C_1$-$C_{10}$ haloalkyl, a leaving group Y, a bioactive agent, or a dye, wherein the leaving group Y is selected from the group consisting of $OR^4$, halogen, heteroaryl, and heterocyclyl;

$R^1$ is hydrogen or $C_1$-$C_8$ alkyl;

$R^2$ is selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;

$R^3$ is hydrogen or $C_1$-$C_8$ alkyl; and $R^4$ is selected from the group consisting of optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl.

In some embodiments, A is a phenyl ring. In some embodiments, A is a thienyl ring.

In some embodiments, $R^1$ is selected from the group consisting of hydrogen, methyl, ethyl, n-hexyl, 2-(2-methoxyethoxy)ethyl and benzyl. In some embodiments, $R^1$ is ethyl.

In some embodiments, $R^2$ is an optionally substituted aryl. For example, in some embodiments, $R^2$ is an optionally substituted phenyl. In some embodiments, $R^2$ is a phenyl having 0, 1, 2, 3, 4, or substituents, each independently selected from the group consisting of $C_1$-$C_4$ alkyl, cyano, amido, $C_1$-$C_4$ alkoxy, $C_1$-$C_4$ haloalkyl, and hydroxyalkyl. In some embodiments, $R^2$ is a phenyl substituted with at least one substituent selected from the group consisting of $C_1$-$C_4$ alkyl, cyano, amido, $C_1$-$C_4$ alkoxy, $C_1$-$C_4$ haloalkyl, and hydroxyalkyl. In some embodiments, $R^2$ is a phenyl substituted with at least one $C_1$-$C_4$ alkyl (such as methyl or ethyl) or $C_1$-$C_4$ haloalkyl (such as $—CH_2Br$ or $—CH_2CH_2CH_2Br$). In some embodiments, $R^2$ is a phenyl substituted with one $C_1$-$C_4$ alkyl or $C_1$-$C_4$ haloalkyl. In some embodiments, $R^2$ is a phenyl substituted with one methyl group, one ethyl group, one $—CH_2Br$ group, or one $—CH_2CH_2CH_2Br$.

In some embodiments, $R^1$ is $C_1$-$C_4$ alkyl and $R^2$ is optionally substituted phenyl. In some embodiments, $R^1$ is ethyl and $R^2$ is phenyl substituted with one substituent selected from the group consisting of methyl, ethyl, $—CH_2Br$, and $—CH_2CH_2CH_2Br$.

In some embodiments, $R^3$ is hydrogen or $C_1$-$C_4$ alkyl. In some embodiments, $R^3$ is hydrogen. In some embodiments, $R^4$ is optionally substituted $C_1$-$C_8$ alkyl, optionally substituted aryl, optionally substituted heteroaryl, or optionally substituted heterocycle. In some embodiments, $R^4$ is $C_1$-$C_4$ alkyl or phenyl optionally substituted with 1, 2, 3, 4, or 5 substituents independently selected from the group consisting of alkyl, alkoxy, amino, halo, hydroxyl and cyano.

In some embodiments, the compound has formula (Ia):

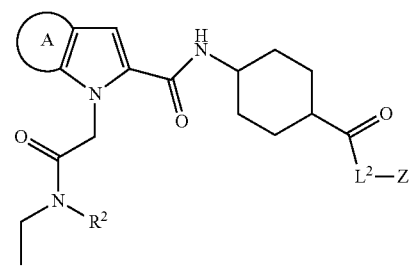

(Ia)

wherein:

A is absent, a phenyl ring, or a thienyl ring;

$R^2$ is phenyl substituted with at least one $C_1$-$C_4$ alkyl or $C_1$-$C_4$ haloalkyl; and $L^2$ is absent or $—(CR^{a1}R^{a2})_{m2}—$, wherein m2 is 1 to 90, and wherein each $CR^{a1}R^{a2}$ is as defined as above.

In some embodiments, the compound has formula (Ib):

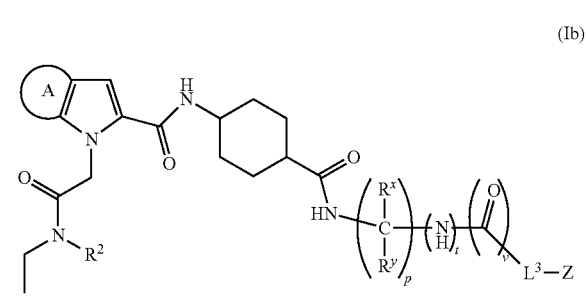

(Ib)

wherein:

A is absent, a phenyl ring, or a thienyl ring;

$R^2$ is phenyl substituted with at least one $C_1$-$C_4$ alkyl or $C_1$-$C_4$ haloalkyl;

$R^x$ and $R^y$ at each occurrence is independently hydrogen or $C_1$-$C_4$ alkyl;

p is 4, 5, 6, 7, 8, 9, or 10;

t is 0 or 1;

v is 0 or 1; and $L^3$ is absent or $—(CR^{a1}R^{a2})_{m3}—$, wherein m3 is 1 to 80, and wherein each $CR^{a1}R^{a2}$ is as above.

In some embodiments, $L^3$ is $—(CR^{a1}R^{a2})_{m3}—$, wherein m3 is 1-20, and $R^{a1}$ and $R^{a2}$, at each occurrence are independently hydrogen or $C_1$-$C_4$ alkyl. In some embodiments, $L^3$ comprises one or more $—CH_2—CH_2—O—$ units.

For example, in some embodiments, $L^3$ is $-Q^1-(CH_2-CH_2-O)_{k1}-Q^2-(CH_2-CH_2-O)_{k2}-Q^3-(CH_2-CH_2-O)_{k3}-$, wherein:

$Q^1$ is absent, O, or NH;
$Q^2$ is absent,

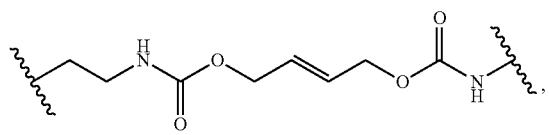 [SMILES: *CCNC(=O)OC/C=C/COC(=O)N*]

—CO—NH—, —CH$_2$—CH$_2$—CO—, —CH$_2$—CH$_2$—NH—CO, or —CH$_2$—CH$_2$—CO—NH—

Q3 is absent, —CO—NH—, or —CH$_2$—CH$_2$—;
k1 is 1-10;
k2 is 0-10; and
k3 is 0-10.

In some embodiments, k1 is 1, 2, 3, 4, 5, or 6. In some embodiments, k2 is 0, 1, 2, 3, or 4. In some embodiment, k3 is 0, 1, 2, 3, or 4. In some embodiments, $L^3$ is selected from the group consisting of:

In some embodiments, $L^3$ is absent. In some embodiments, $L^3$ is selected from the group consisting of:

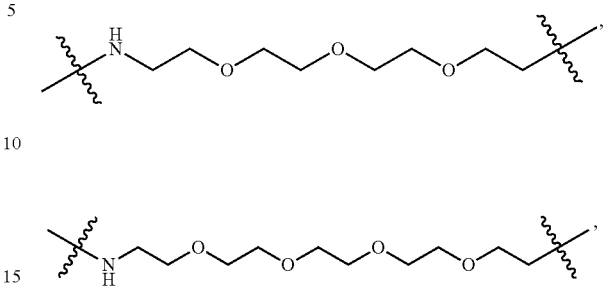

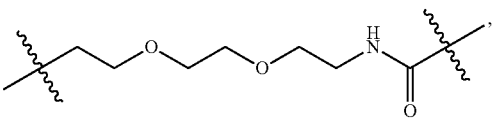

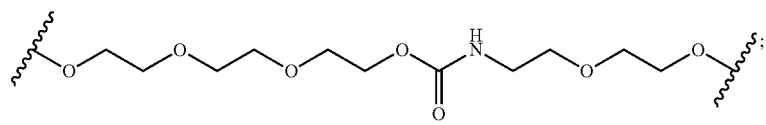

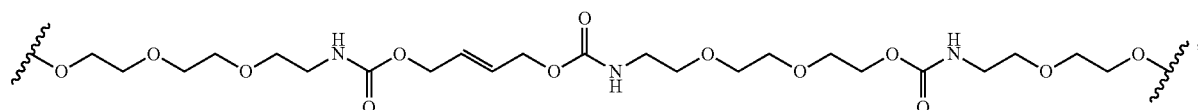

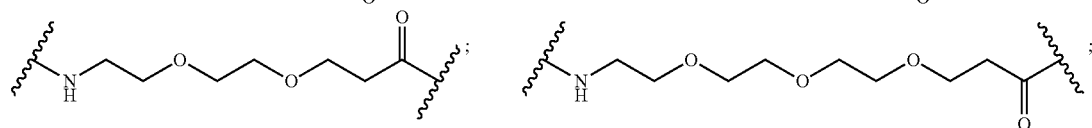

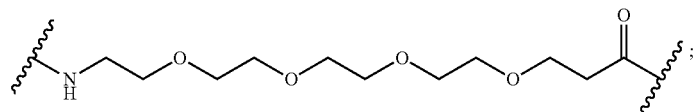

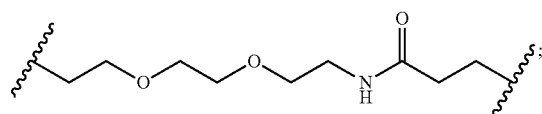

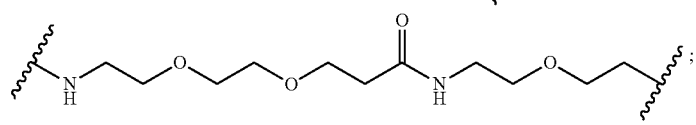

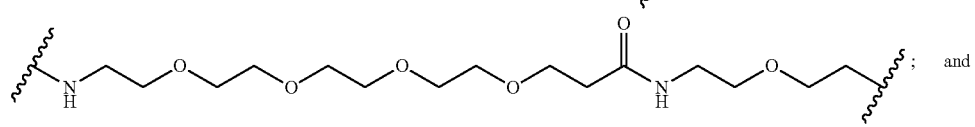 ; and

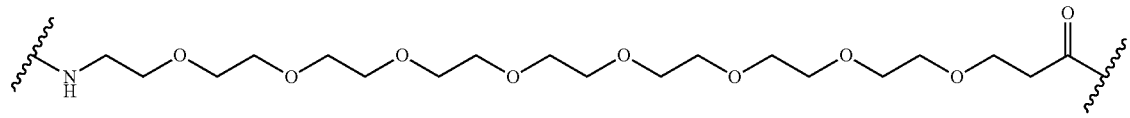

-continued

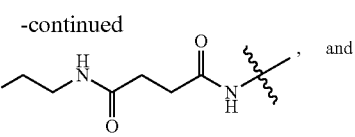, and

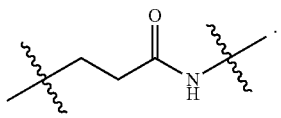.

In some embodiments, $L^3$ may be selected from the linker groups disclosed in U.S. patent application Ser. No. 15/172,860 to Levin et al., "CELL-PERMEABLE, CELL-COMPATIBLE, AND CLEAVABLE LINKERS FOR COVALENT TETHERING OF FUNCTIONAL ELEMENTS," filed Jun. 3, 2016, which is incorporated by reference herein in its entirety.

In some embodiments, Z is $C_1$-$C_{10}$ haloalkyl, such as $C_1$-$C_{10}$ chloroalkyl, $C_1$-$C_{10}$ bromoalkyl, or $C_1$-$C_{10}$ iodoalkyl. For example, such compounds may have formula (Ic):

(Ic)

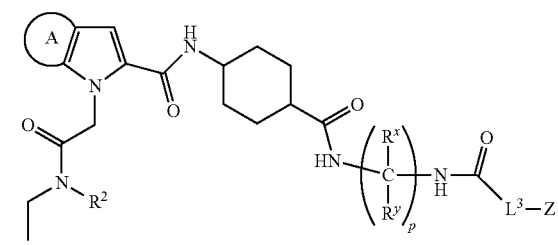

wherein:
A is a phenyl ring or thienyl ring;
$R^2$ is phenyl substituted with one methyl or ethyl group;
$R^x$ and $R^y$ at each occurrence is independently hydrogen or $C_1$-$C_4$ alkyl;
p is 4, 5, 6, 7, 8, 9, or 10; and
$L^3$ is as described above.

In some embodiments of compounds of formula (Ic), $L^3$ is

In some embodiments of compounds of formula (Ic), Z is —$(CH_2)_6$—Cl.

In some embodiments, Z is a leaving group Y, where in Y is selected from the group consisting of $OR^4$, halogen, heteroaryl, and heterocyclyl. For example, such compounds may have formula (Id):

(Id)

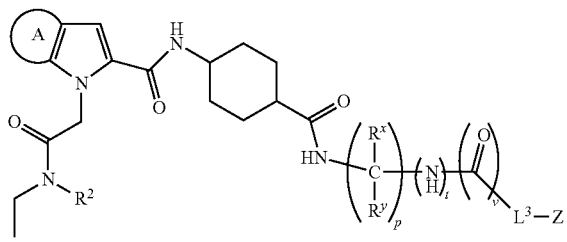

wherein:
A is a phenyl ring or a thienyl ring;
$R^2$ is phenyl substituted with one substituent selected from the group consisting of methyl, ethyl, —$CH_2Br$, and —$CH_2CH_2CH_2Br$;
$R^x$ and $R^y$ at each occurrence is independently hydrogen or $C_1$-$C_4$ alkyl;
p is 4, 5, 6, 7, 8, 9, or 10;
t is 0 or 1;
v is 0 or 1; and
$L^3$ is as described above.

In some embodiments of compounds of formula (Id), $L^3$ is absent, $C_1$-$C_4$ alkylene (such as —$CH_2$— or —$CH_2$—$CH_2$—),

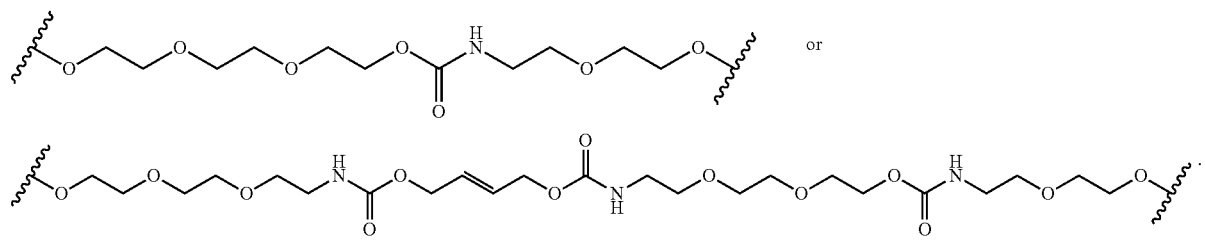

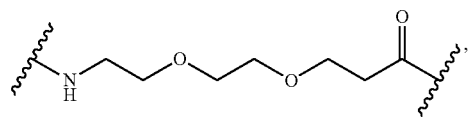 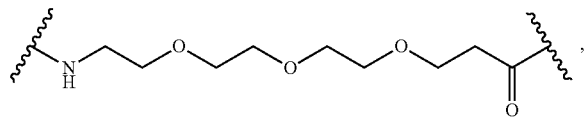

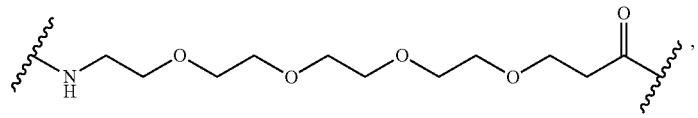

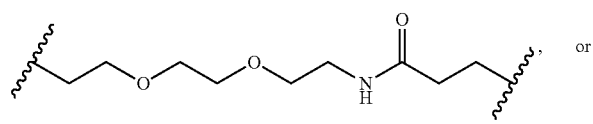 or

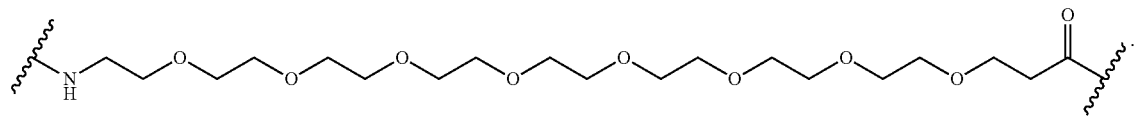

In some embodiments of compounds of formula (Id), Z is a halogen, such as chloro, bromo, or iodo. For example, in some embodiments of compounds of formula (Id), t is 0; v is 0; $L^3$ is absent; and Z is bromo or iodo. In some embodiments of compounds of formula (Id), t is 1; v is 1; $L^3$ is $C_1$-$C_4$ alkylene (such as —$CH_2$— or —$CH_2$—$CH_2$—); and Z is chloro, bromo, or iodo.

In some embodiments of compounds of formula (Id), Z is $OR^4$, wherein $R^4$ is optionally substituted $C_1$-$C_8$ alkyl, optionally substituted phenyl, or optionally substituted heterocycle. In some embodiments, $R^4$ is $C_1$-$C_4$ alkyl or phenyl optionally substituted with 1, 2, 3, 4, or 5 substituents independently selected from the group consisting of alkyl, alkoxy, amino, halo, hydroxyl and cyano. For example, in some embodiments of compounds of formula (Id), $L^3$ is absent, and Z is $C_1$-$C_4$ alkoxy, phenoxy,

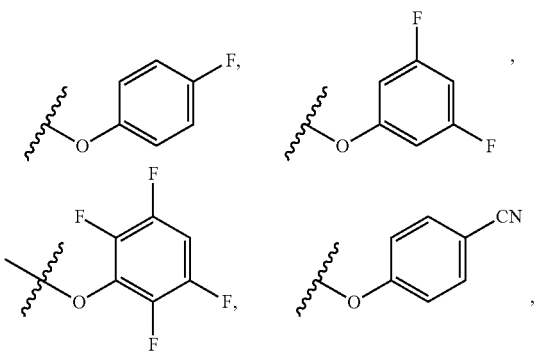

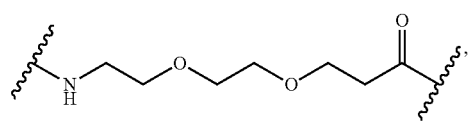 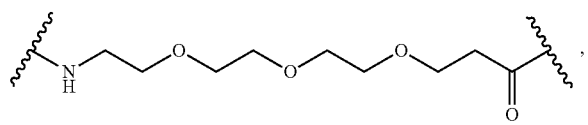

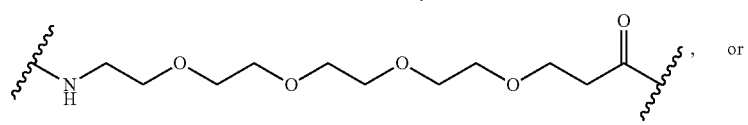 or

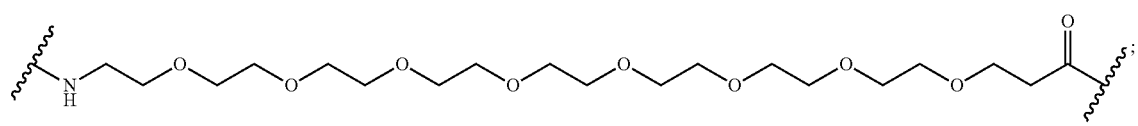

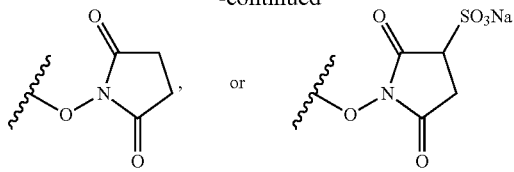

In some embodiments of compounds of formula (Id), $L^3$ is —CH$_2$—CH$_2$— or

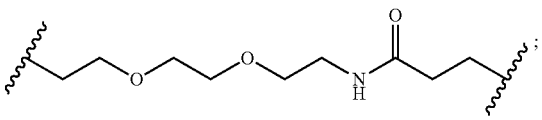 [SMILES: *CCOCCOCCNC(=O)CC*]

and
Z is

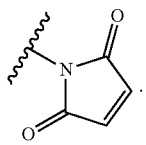 [SMILES: *N1C(=O)C=CC1=O]

In some embodiments of compounds of formula (Id), Z is —OR$^4$, wherein R$^4$ is optionally substituted aryl, optionally substituted heteroaryl, or optionally substituted heterocycle, and wherein the R$^4$ group is capable of forming a covalent bond with a protein in a reaction between the compound and the protein. In some embodiments, R$^4$ forms a label on the protein after forming the covalent bond with the protein, such as a fluorescent label. For example, R$^4$ may be a nitrobenzoxadiazole (NBD) dye moiety, represented by

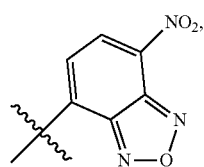 [SMILES: *c1ccc([N+](=O)[O-])c2nonc12]

which may form a covalent bond with a lysine residue in a protein and provide a fluorescent label after attachment to the protein. Suitable fluorescent label moieties include those disclosed in Yamaguchi et al., Chemical Science, 2014, 5, 1021-1029, which is incorporated herein by reference in its entirety.

In some embodiments of compounds of formula (Id), t is 0; v is 0; $L^3$ is absent; Z is

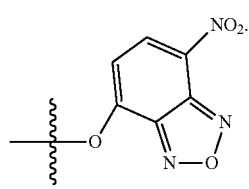 [SMILES: *Oc1ccc([N+](=O)[O-])c2nonc12]

In some embodiments, Z is bioactive agent. For example, Z may be an enzyme inhibitor or receptor inhibitor. In some embodiments, Z is pharmaceutical agent. In some embodiments, Z is a kinase inhibitor, such as dasatinib. In some embodiments, Z is a moiety which induces protein degradation. For example, the compound may have formula (Ie):

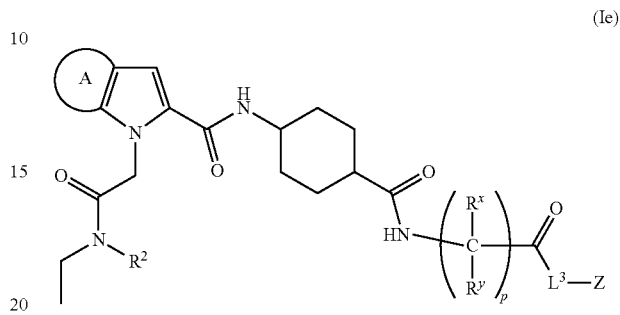

(Ie)

wherein:
A is absent, a phenyl ring or a thienyl ring;
R$^2$ is phenyl substituted with one methyl or ethyl group;
R$^x$ and R$^y$ at each occurrence is independently hydrogen or C$_1$-C$_4$ alkyl;
p is 4, 5, 6, 7, 8, 9, or 10; and
L$^3$ is as described above.

In some embodiments of compounds of formula (Ie), Z is

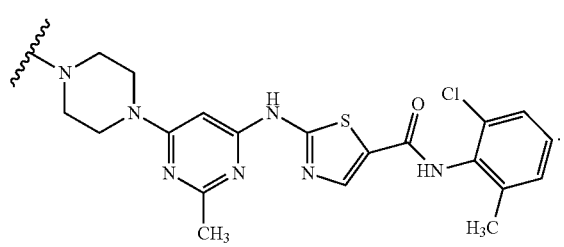 [SMILES: *N1CCN(c2cc(Nc3ncc(C(=O)Nc4c(C)cccc4Cl)s3)nc(C)n2)CC1]

In some embodiments of compounds of formula (Ie), Z is a moiety that induces protein degradation. For example, Z may be a moiety which recruits protein degradation pathways within live cells. Suitable Z moieties to induce protein degradation include those disclosed in Lai et al., Nature Reviews Drug Discovery, 2017, 16, 101-114, which is incorporated herein by references in its entirety. In some embodiments, Z is a hydrophobic group, such as adamantane or Arg-Boc$_3$, which induces protein degradation through hydrophobic tagging (HyT). In some embodiments, Z is a moiety from nutlin-3a, bestatin, VHL ligand, pomalidomide, and other small molecules as disclosed in Lai et al. (shown below), which induces protein degradation through proteolysis-targeting chimaera (PROTAC) tagging.

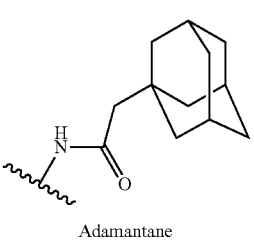

Adamantane

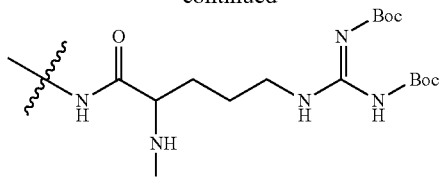
Arg-Boc₃
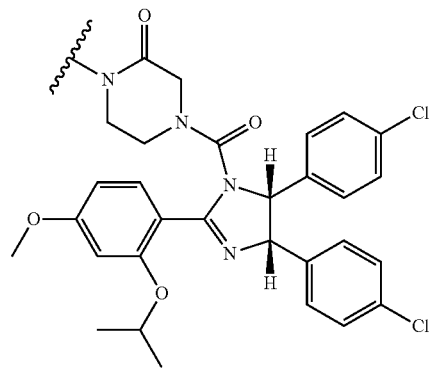
Nutlin-3a
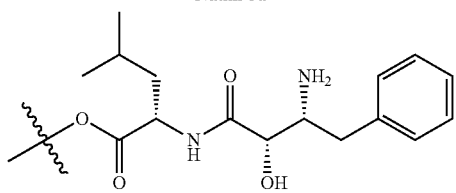
Bestatin
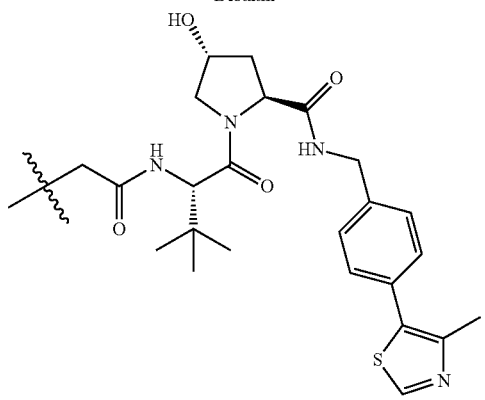
VHL ligand
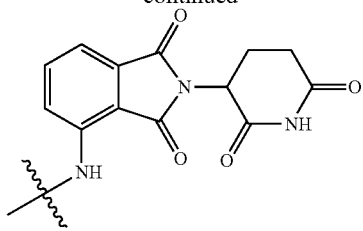
Pomalidomide
In some embodiments, Z is
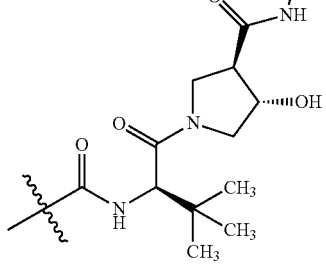
In some embodiments of compounds of formula (Ie), L³ is
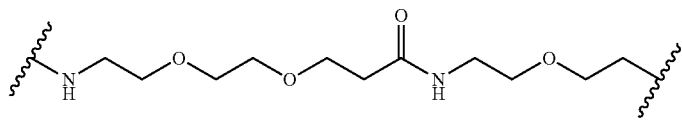
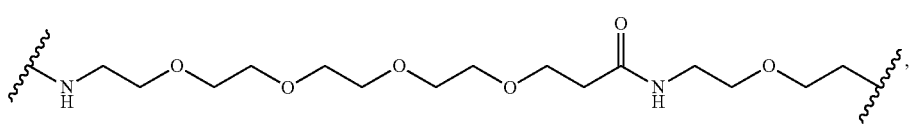,
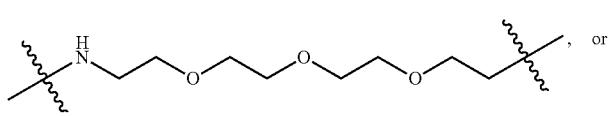, or

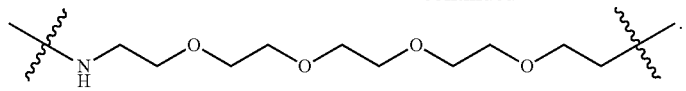

In some embodiments of compounds of formula (Ie), $L^3$ is

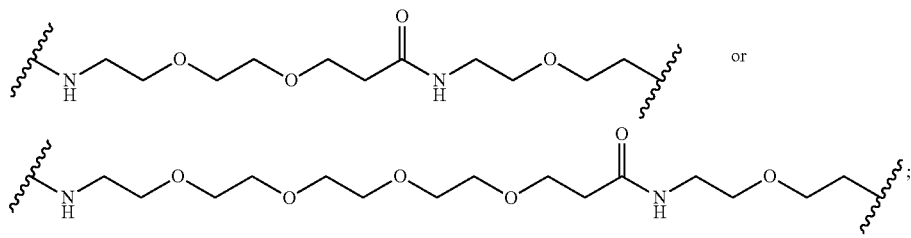

and Z is

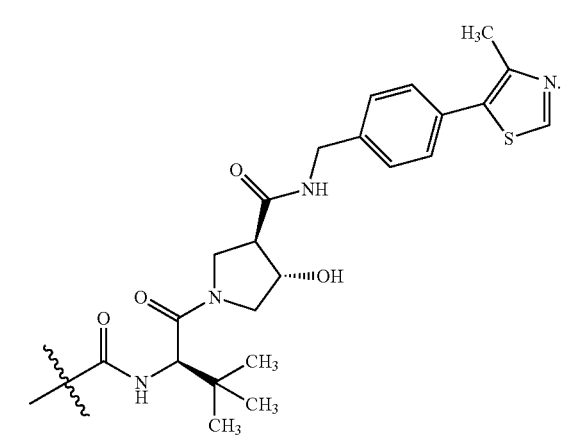 [SMILES: *C(=O)N[C@@H](C(=O)N1C[C@@H](O)[C@H](C(=O)NCc2ccc(-c3scnc3C)cc2)C1)C(C)(C)C]

In some embodiments of compounds of formula (Ie), $L^3$ is

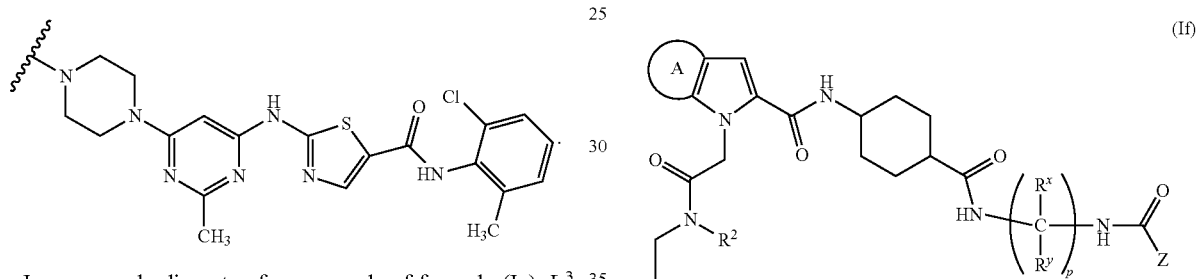

In some embodiments, Z is a dye, such as a fluorescent dye or a fluorogenic dye. In some embodiments, Z is a fluorescent dye or a fluorophore. For example, the compound may have formula (If):

(If)

wherein:

A is a phenyl ring or thienyl ring;
$R^2$ is phenyl substituted with one methyl or ethyl group;
$R^x$ and $R^y$ at each occurrence is independently hydrogen or $C_1$-$C_4$ alkyl; and
p is 4, 5, 6, 7, 8, 9, or 10.

In some embodiments of formula (If), Z is

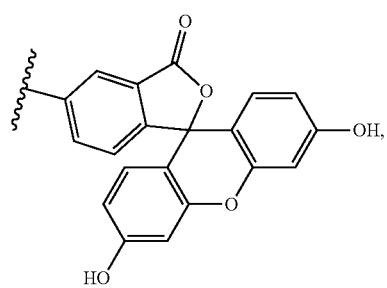

31
-continued

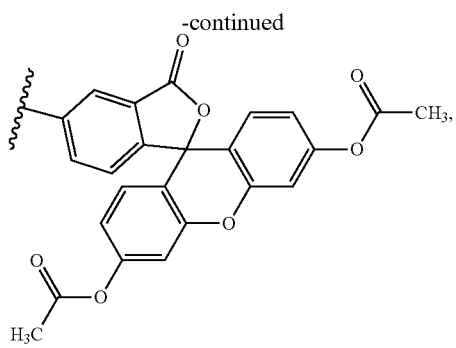

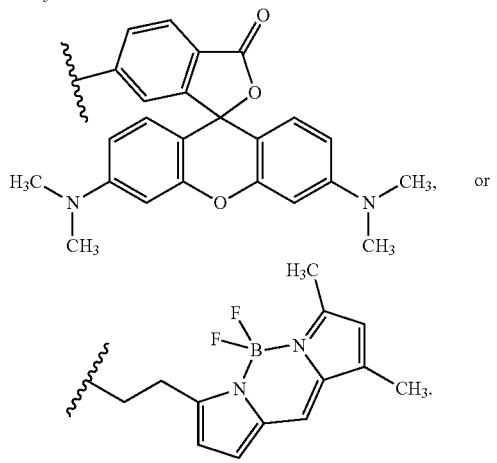

In some embodiments, Z is a dye, such as a fluorescent dye or a fluorogenic dye. In some embodiments, Z is a fluorescent dye or a fluorophore. For example, the compound may have formula (If'):

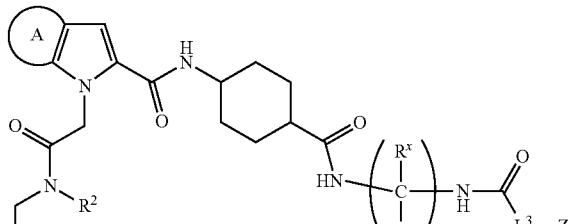
(If')

wherein:
A is a phenyl ring or thienyl ring;
$R^2$ is phenyl substituted with one methyl or ethyl group;
$R^x$ and $R^y$ at each occurrence is independently hydrogen or $C_1$-$C_4$ alkyl;
p is 4, 5, 6, 7, 8, 9, or 10; and
$L^3$ is as described above.
In some embodiments of compounds of formula (If'), $L^3$ is absent,

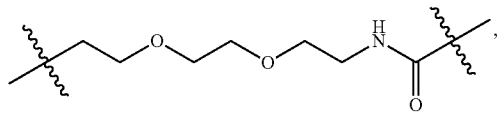

32
-continued

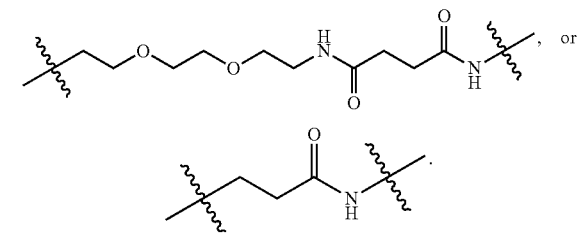

In some embodiments of compounds of formula (If'), Z is

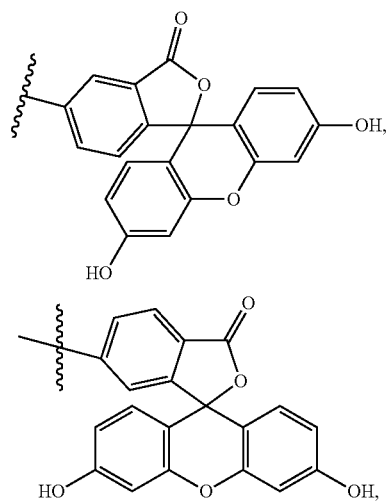

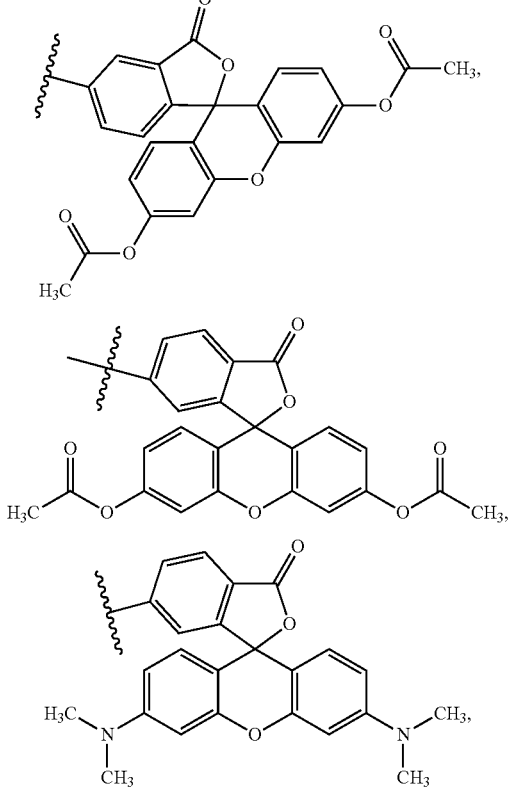

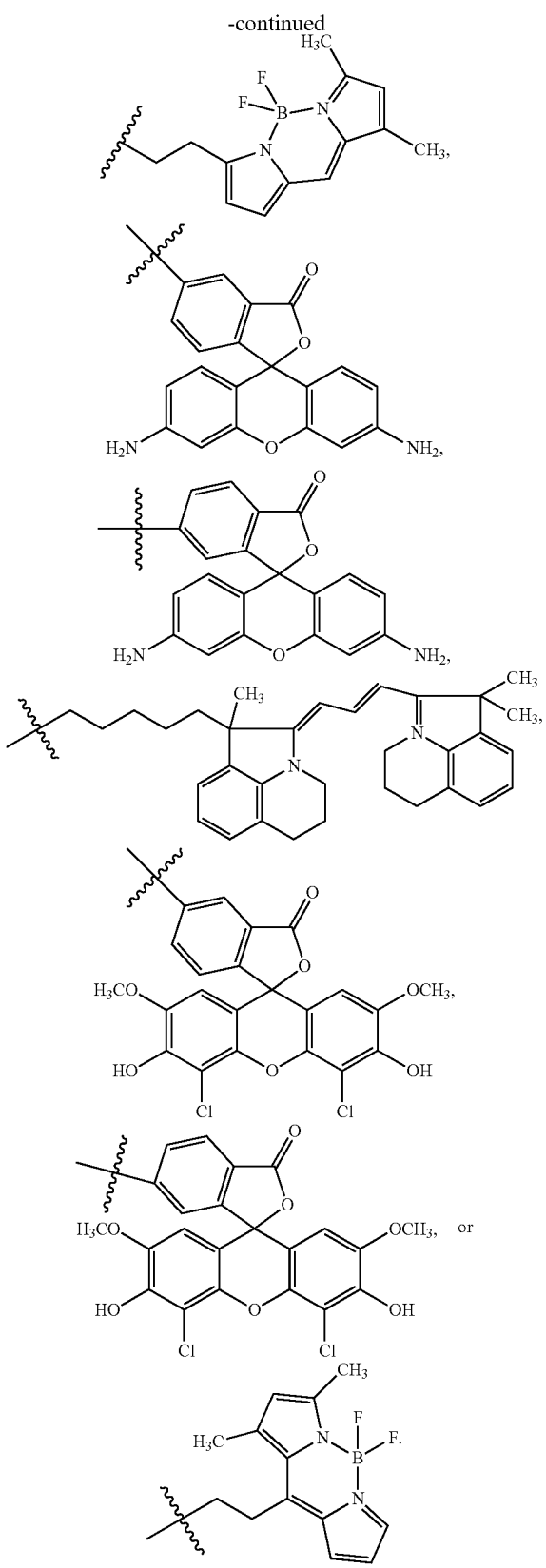

Suitable compounds include the following:

1-(trans-4-(4-(2-(ethyl(m-tolyl)amino)-2-oxoethyl)-4H-thieno[3,2-b]pyrrole-5-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

[(E)-30-chloro-6,17-dioxo-5,10,13,16,21,24-hexaoxa-7,18-diazatriacont-2-en-1-yl (1-(trans-4-(4-(2-(ethyl(3-ethylphenyl)amino)-2-oxoethyl)-4H-thieno[3,2-b]pyrrole-5-carboxamido)cyclohexyl)-1,10-dioxo-11,14,17-trioxa-2,9-diazanonadecan-19-yl)carbamate;

[(E)-30-chloro-6,17-dioxo-5,10,13,16,21,24-hexaoxa-7,18-diazatriacont-2-en-1-yl (1-(trans-4-(1-(2-(ethyl(3-ethylphenyl)amino)-2-oxoethyl)-1H-indole-2-carboxamido)cyclohexyl)-1,10-dioxo-11,14,17-trioxa-2,9-diazanonadecan-19-yl)carbamate;

1-(trans-4-(4-(2-(ethyl(3-ethylphenyl)amino)-2-oxoethyl)-4H-thieno[3,2-b]pyrrole-5-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

1-(trans-4-(1-(2-(ethyl(3-ethylphenyl)amino)-2-oxoethyl)-1H-indole-2-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oate;

2,5-dioxopyrrolidin-1-yl 1-((1r,4r)-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oate;

N-(trans-4-((6-(3-(2,5-dioxo-2,5-dihydro-1H-pyrrol-1-yl)propanamido)hexyl)carbamoyl)cyclohexyl)-4-(2-(ethyl(m-tolyl)amino)-2-oxoethyl)-4H-thieno[3,2-b]pyrrole-5-carboxamide;

N-(trans-4-((1-(2,5-dioxo-2,5-dihydro-1H-pyrrol-1-yl)-3,13-dioxo-7,10-dioxa-4,14-diazaicosan-20-yl)carbamoyl)cyclohexyl)-4-(2-(ethyl(m-tolyl)amino)-2-oxoethyl)-4H-thieno[3,2-b]pyrrole-5-carboxamide;

methyl trans-4-(4-(2-((3-(bromomethyl)phenyl)(ethyl)amino)-2-oxoethyl)-4H-thieno[3,2-b]pyrrole-5-carboxamido)cyclohexane-1-carboxylate;

methyl trans-4-(4-(2-((3-(3-bromopropyl)phenyl)(ethyl)amino)-2-oxoethyl)-4H-thieno[3,2-b]pyrrole-5-carboxamido)cyclohexane-1-carboxylate;

2,5-dioxopyrrolidin-1-yl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

methyl 8-(trans-4-(1-(2-(ethyl(3-ethylphenyl)amino)-2-oxo-ethyl)-1H-indole-2-carboxamido)cyclohexane-1-carboxamido)octanoate;
methyl 6-(trans-4-(1-(2-(ethyl(3-ethylphenyl)amino)-2-oxo-ethyl)-1H-indole-2-carboxamido)cyclohexane-1-carboxamido)hexanoate;
2,5-dioxopyrrolidin-1-yl 8-(trans-4-(1-(2-(ethyl(3-ethylphenyl)amino)-2-oxoethyl)-1H-indole-2-carboxamido)cyclohexane-1-carboxamido)octanoate;
2,5-dioxopyrrolidin-1-yl 6-(trans-4-(1-(2-(ethyl(3-ethylphenyl)amino)-2-oxoethyl)-1H-indole-2-carboxamido)cyclohexane-1-carboxamido)hexanoate;
phenyl 8-(trans-4-(1-(2-(ethyl(3-ethylphenyl)amino)-2-oxo-ethyl)-1H-indole-2-carboxamido)cyclohexane-1-carboxamido)octanoate;
phenyl 6-(trans-4-(1-(2-(ethyl(3-ethylphenyl)amino)-2-oxo-ethyl)-1H-indole-2-carboxamido)cyclohexane-1-carboxamido)hexanoate;
1-(2-(ethyl(3-ethylphenyl)amino)-2-oxoethyl)-N-(trans-4-((6-iodohexyl)carbamoyl)cyclohexyl)-1H-indole-2-carboxamide;
N-(trans-4-((6-bromohexyl)carbamoyl)cyclohexyl)-1-(2-(ethyl(3-ethylphenyl)amino)-2-oxoethyl)-1H-indole-2-carboxamide;
1-(2-(ethyl(3-ethylphenyl)amino)-2-oxoethyl)-N-(trans-4-((8-iodooctyl)carbamoyl)cyclohexyl)-1H-indole-2-carboxamide;
4-fluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;
3,5-difluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;
4-cyanophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;
sodium 1-((8-(trans-4-(4-(2-(ethyl(m-tolyl)amino)-2-oxoethyl)-4H-thieno[3,2-b]pyrrole-5-carboxamido)cyclohexane-1-carboxamido)octanoyl)oxy)-2,5-dioxopyrrolidine-3-sulfonate;
N-(trans-4-((5-(2-chloroacetamido)pentyl)carbamoyl)cyclohexyl)-4-(2-(ethyl(m-tolyl)amino)-2-oxoethyl)-4H-thieno[3,2-b]pyrrole-5-carboxamide;
N-(trans-4-((6-(2-chloroacetamido)hexyl)carbamoyl)cyclohexyl)-4-(2-(ethyl(m-tolyl)amino)-2-oxoethyl)-4H-thieno[3,2-b]pyrrole-5-carboxamide;
2,3,5,6-tetrafluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;
N-(trans-4-((5-(2-bromoacetamido)pentyl)carbamoyl)cyclohexyl)-4-(2-(ethyl(m-tolyl)amino)-2-oxoethyl)-4H-thieno[3,2-b]pyrrole-5-carboxamide;
N-(trans-4-((1-(4-(6-((5-((2-chloro-6-methylphenyl)carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl(m-tolyl)amino)-2-oxoethyl)-4H-thieno[3,2-b]pyrrole-5-carboxamide;
N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,18-trioxo-12,15,22-trioxa-2,9,19-triazatetracosan-24-yl)piperazin-1-yl)-2-methylpyrimidin-4-yl)amino)thiazole-5-carboxamide;
N-(trans-4-((1-(4-(6-((5-((2-chloro-6-methylphenyl)carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl(3-ethylphenyl)amino)-2-oxoethyl)-4H-thieno[3,2-b]pyrrole-5-carboxamide;
N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,24-trioxo-12,15,18,21,28-pentaoxa-2,9,25-triazatriacontan-30-yl)piperazin-1-yl)-2-methylpyrimidin-4-yl)amino)thiazole-5-carboxamide;
N-(trans-4-((1-(4-(6-((5-((2-chloro-6-methylphenyl)carbamoyl)thiazol-2-yl)amino)-2-methylpyrimidin-4-yl)piperazin-1-yl)-7,23-dioxo-3,10,13,16,19-pentaoxa-6,22-diazaoctacosan-28-yl)carbamoyl)cyclohexyl)-4-(2-(ethyl(3-ethylphenyl)amino)-2-oxoethyl)-4H-thieno[3,2-b]pyrrole-5-carboxamide;
N-(trans-4-((6-(3',6'-dihydroxy-3-oxo-3H-spiro[isobenzofuran-1,9'-xanthene]-5-carboxamido)hexyl)carbamoyl)cyclohexyl)-4-(2-(ethyl(m-tolyl)amino)-2-oxoethyl)-4H-thieno[3,2-b]pyrrole-5-carboxamide;
5-((6-(trans-4-(1-(2-(ethyl(3-ethylphenyl)amino)-2-oxo-ethyl)-1H-indole-2-carboxamido)cyclohexane-1-carboxamido)hexyl)carbamoyl)-3-oxo-3H-spiro[isobenzofuran-1,9'-xanthene]-3',6'-diyl diacetate;
N-(trans-4-((6-(3',6'-dihydroxy-3-oxo-3H-spiro[isobenzofuran-1,9'-xanthene]-5-carboxamido)hexyl)carbamoyl)cyclohexyl)-1-(2-(ethyl(3-ethylphenyl)amino)-2-oxo-ethyl)-1H-indole-2-carboxamide;
N-(trans-4-((6-(3',6'-bis(dimethylamino)-3-oxo-3H-spiro[isobenzofuran-1,9'-xanthene]-6-carboxamido)hexyl)carbamoyl)cyclohexyl)-1-(2-(ethyl(3-ethylphenyl)amino)-2-oxoethyl)-1H-indole-2-carboxamide;
N-(trans-4-((6-(3',6'-bis(dimethylamino)-3-oxo-3H-spiro[isobenzofuran-1,9'-xanthene]-6-carboxamido)hexyl)carbamoyl)cyclohexyl)-4-(2-(ethyl(m-tolyl)amino)-2-oxoethyl)-4H-thieno[3,2-b]pyrrole-5-carboxamide;
N-(trans-4-((6-(3-(5,5-difluoro-7,9-dimethyl-5H-514,614-dipyrrolo[1,2-c:2',1'-f][1,3,2]diazaborinin-3-yl)propanamido)hexyl)carbamoyl)cyclohexyl)-1-(2-(ethyl(3-ethylphenyl)amino)-2-oxoethyl)-1H-indole-2-carboxamide;
N-(trans-4-((6-(3-(5,5-difluoro-7,9-dimethyl-5H-514,614-dipyrrolo[1,2-c:2',1'-f][1,3,2]diazaborinin-3-yl)propanamido)hexyl)carbamoyl)cyclohexyl)-4-(2-(ethyl(m-tolyl)amino)-2-oxoethyl)-4H-thieno[3,2-b]pyrrole-5-carboxamide;
N-(trans-4-((6-(3',6'-diamino-3-oxo-3H-spiro[isobenzofuran-1,9'-xanthene]-5,6-carboxamido)hexyl)carbamoyl)cyclohexyl)-1-(2-(ethyl(3-ethylphenyl)amino)-2-oxo-ethyl)-1H-indole-2-carboxamide;
N-(trans-4-((6-(3',6'-diamino-3-oxo-3H-spiro[isobenzofuran-1,9'-xanthene]-6-carboxamido)hexyl)carbamoyl)cyclohexyl)-4-(2-(ethyl(m-tolyl)amino)-2-oxoethyl)-4H-thieno[3,2-b]pyrrole-5,6-carboxamide;
N-(trans-4-((8-(3',6'-dihydroxy-3-oxo-3H-spiro[isobenzofuran-1,9'-xanthene]-5-carboxamido)octyl)carbamoyl)cyclohexyl)-1-(2-(ethyl(3-ethylphenyl)amino)-2-oxo-ethyl)-1H-indole-2-carboxamide;
N-(trans-4-((8-(3',6'-dihydroxy-3-oxo-3H-spiro[isobenzofuran-1,9'-xanthene]-5-carboxamido)octyl)carbamoyl)cyclohexyl)-4-(2-(ethyl(m-tolyl)amino)-2-oxoethyl)-4H-thieno[3,2-b]pyrrole-5-carboxamide;
N-(trans-4-((8-(3',6'-diamino-3-oxo-3H-spiro[isobenzofuran-1,9'-xanthene]-5,6-carboxamido)octyl)carbamoyl)cyclohexyl)-1-(2-(ethyl(3-ethylphenyl)amino)-2-oxo-ethyl)-1H-indole-2-carboxamide;
N-(trans-4-((8-(3',6'-diamino-3-oxo-3H-spiro[isobenzofuran-1,9'-xanthene]-5-carboxamido)octyl)carbamoyl)cyclohexyl)-4-(2-(ethyl(m-tolyl)amino)-2-oxoethyl)-4H-thieno[3,2-b]pyrrole-5,6-carboxamide;

N-(trans-4-((8-(3-(5,5-difluoro-7,9-dimethyl-5H-5λ4,6λ4-dipyrrolo[1,2-c:2',1'-f][1,3,2]diazaborinin-3-yl)propanamido)octyl)carbamoyl)cyclohexyl)-1-(2-(ethyl(3-ethylphenyl)amino)-2-oxoethyl)-1H-indole-2-carboxamide;

N-(trans-4-((8-(3-(5,5-difluoro-7,9-dimethyl-5H-5λ4,6λ4-dipyrrolo[1,2-c:2',1'-f][1,3,2]diazaborinin-3-yl)propanamido)octyl)carbamoyl)cyclohexyl)-4-(2-(ethyl(m-tolyl)amino)-2-oxoethyl)-4H-thieno[3,2-b]pyrrole-5-carboxamide;

N-(trans-4-((1-(3',6'-bis(dimethylamino)-3-oxo-3H-spiro[isobenzofuran-1,9'-xanthen]-6-yl)-1,11-dioxo-5,8-dioxa-2,12-diazaoctadecan-18-yl)carbamoyl)cyclohexyl)-1-(2-(ethyl(3-ethylphenyl)amino)-2-oxoethyl)-1H-indole-2-carboxamide;

N-(trans-4-((1-(3',6'-dihydroxy-3-oxo-3H-spiro[isobenzofuran-1,9'-xanthen]-5,6-yl)-1,11-dioxo-5,8-dioxa-2,12-diazaicosan-20-yl)carbamoyl)cyclohexyl)-1-(2-(ethyl(3-ethylphenyl)amino)-2-oxoethyl)-1H-indole-2-carboxamide;

N-(trans-4-((1-(3',6'-bis(dimethylamino)-3-oxo-3H-spiro[isobenzofuran-1,9'-xanthen]-6-yl)-1,11-dioxo-5,8-dioxa-2,12-diazaicosan-20-yl)carbamoyl)cyclohexyl)-1-(2-(ethyl(3-ethylphenyl)amino)-2-oxoethyl)-1H-indole-2-carboxamide;

N-(trans-4-((8-(6-((Z)-2-((E)-3-(1,1-dimethyl-1,4,5,6-tetrahydro-3λ4-pyrrolo[3,2,1-ij]quinolin-2-yl)allylidene)-1-methyl-1,2,5,6-tetrahydro-4H-pyrrolo[3,2,1-ij]quinolin-1-yl)hexanamido)octyl)carbamoyl)cyclohexyl)-1-(2-(ethyl(3-ethylphenyl)amino)-2-oxoethyl)-1H-indole-2-carboxamide;

N-(trans-4-((8-(4',5'-dichloro-3',6'-dihydroxy-2',7'-dimethoxy-3-oxo-3H-spiro[isobenzofuran-1,9'-xanthene]-5,6-carboxamido)octyl)carbamoyl)cyclohexyl)-1-(2-(ethyl(3-ethylphenyl)amino)-2-oxoethyl)-1H-indole-2-carboxamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(1-(trans-4-(1-(2-(ethyl(3-ethylphenyl)amino)-2-oxoethyl)-1H-indole-2-carboxamido)cyclohexyl)-1,10-dioxo-13,16-dioxa-2,9-diazaoctadecan-18-yl)succinamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(8-(trans-4-(1-(2-(ethyl(3-ethylphenyl)amino)-2-oxoethyl)-1H-indole-2-carboxamido)cyclohexane-1-carboxamido)octyl)succinamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(1-(trans-4-(1-(2-(ethyl(3-ethylphenyl)amino)-2-oxoethyl)-1H-indole-2-carboxamido)cyclohexyl)-1,12-dioxo-15,18-dioxa-2,11-diazaicosan-20-yl)succinamide;

4-(2-(ethyl(m-tolyl)amino)-2-oxoethyl)-N-(trans-4-((8-((7-nitrobenzo[c][1,2,5]oxadiazol-4-yl)oxy)octyl)carbamoyl)cyclohexyl)-4H-thieno[3,2-b]pyrrole-5-carboxamide;

4-(2-(ethyl(m-tolyl)amino)-2-oxoethyl)-N-(trans-4-((6-((7-nitrobenzo[c][1,2,5]oxadiazol-4-yl)oxy)hexyl)carbamoyl)cyclohexyl)-4H-thieno[3,2-b]pyrrole-5-carboxamide;

1-(2-(ethyl(3-ethylphenyl)amino)-2-oxoethyl)-N-(trans-4-((8-((7-nitrobenzo[c][1,2,5]oxadiazol-4-yl)oxy)octyl)carbamoyl)cyclohexyl)-1H-indole-2-carboxamide;

1-(2-(ethyl(3-ethylphenyl)amino)-2-oxoethyl)-N-(trans-4-((6-((7-nitrobenzo[c][1,2,5]oxadiazol-4-yl)oxy)hexyl)carbamoyl)cyclohexyl)-1H-indole-2-carboxamide;

4-(2-(ethyl(m-tolyl)amino)-2-oxoethyl)-N-(trans-4-(((R)-3-((3 S,4R)-3-hydroxy-4-((4-(4-methylthiazol-5-yl)benzyl)carbamoyl)pyrrolidine-1-carbonyl)-2,2-dimethyl-5,18-dioxo-8,11,14-trioxa-4,17-diazatricosan-23-yl)carbamoyl)cyclohexyl)-4H-thieno[3,2-b]pyrrole-5-carboxamide;

4-(2-(ethyl(m-tolyl)amino)-2-oxoethyl)-N-(trans-4-(((R)-3-((3 S,4R)-3-hydroxy-4-((4-(4-methylthiazol-5-yl)benzyl)carbamoyl)pyrrolidine-1-carbonyl)-2,2-dimethyl-5,21-dioxo-8,11,14,17-tetraoxa-4,20-diazahexacosan-26-yl)carbamoyl)cyclohexyl)-4H-thieno[3,2-b]pyrrole-5-carboxamide;

4-(2-(ethyl(m-tolyl)amino)-2-oxoethyl)-N-(trans-4-(((R)-3-((3 S,4R)-3-hydroxy-4-((4-(4-methylthiazol-5-yl)benzyl)carbamoyl)pyrrolidine-1-carbonyl)-2,2-dimethyl-5,18-dioxo-8,11,14-trioxa-4,17-diazapentacosan-25-yl)carbamoyl)cyclohexyl)-4H-thieno[3,2-b]pyrrole-5-carboxamide; and 4-(2-(ethyl(m-tolyl)amino)-2-oxoethyl)-N-(trans-4-(((R)-3-((3 S,4R)-3-hydroxy-4-((4-(4-methylthiazol-5-yl)benzyl)carbamoyl)pyrrolidine-1-carbonyl)-2,2-dimethyl-5,21-dioxo-8,11,14,17-tetraoxa-4,20-diazaoctacosan-28-yl)carbamoyl)cyclohexyl)-4H-thieno[3,2-b]pyrrole-5-carboxamide, or a salt thereof.

(1) Salt Forms

A thienopyrrole compound described herein can be in the form of a salt. A neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular thienopyrrole compound herein also includes salt forms thereof.

(2) Isomers

Certain thienopyrrole compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

In some embodiments, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In some embodiments, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In some embodiments, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

The present compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_3$-alkyl or propyl includes n-propyl and iso-propyl; C$_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

3. *OPLOPHORUS* LUCIFERASES

The disclosed compounds may be used to inhibit *Oplophorus*-derived luciferases. The disclosed compounds may inhibit the luciferase activity of the *Oplophorus*-derived luciferases. The *Oplophorus*-derived luciferase may be a wild-type *Oplophorus* luciferase or a variant of an *Oplophorus* luciferase, such as a luciferase of SEQ ID NO:2. *Oplophorus* luciferase variants are described in U.S. Pat. Nos. 8,557,970 and 8,669,103, each of which is incorporated herein by reference in its entirety.

The polypeptide sequence of the mature 19 kDa subunit of the naturally-occurring form of the *Oplophorus gracilirostris* luciferase is provided in SEQ ID NO: 1. An exemplary polypeptide sequence for a synthetic *Oplophorus*-derived luciferase, which can be used in the methods described herein, is provided in SEQ ID NO: 2 (also interchangeably referred to herein as "NanoLuc", "Nluc," "Nluc luciferase," and "Nluc enzyme").

4. COELENTERAZINE SUBSTRATES

The disclosed compounds of the present invention may be used to inhibit luciferase activity by competing or interfering with a coelenterazine or coelenterazine-derivative substrate from binding to a luciferase. Coelenterazine substrates are a class of reporter molecules that luminesce when acted upon by luciferases and other bioluminescent proteins. Examples of coelenterazine substrates include but are not limited to: coelenterazine; coelenterazine derivatives and/or analogs such as 2-furanylmethyl-deoxy-coelenterazine (furimazine), coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl-coelenterazine, in addition to those disclosed in WO 2003/040100, U.S. Patent Publication No. 2008/0248511, and U.S. Patent Publication No. US 2012/0117667; pro-coelenterazines (i.e. compounds that are not substrates for a non-luminescent enzyme, which converts the compound to a substrate for a luciferase), quinone-masked coelenterazines, and the like. Further examples of coelenterazine substrates are described in, for example, U.S. Publication No. 2012/0107849, U.S. Publication No. 2013/0130289, U.S. patent application Ser. No. 14/608,910, and U.S. patent application Ser. No. 14/609,372, each of which is incorporated herein by reference.

5. METHODS OF INHIBITING *OPLOPHORUS* LUCIFERASE ACTIVITY

The disclosed compounds may be used in methods to inhibit *Oplophorus* luciferase activity. The method may include contacting a compound disclosed herein with a cell expressing or containing an *Oplophorus*-derived luciferase, wherein the disclosed compounds may selectively inhibit the *Oplophorus*-derived luciferase. The method may include contacting a compound disclosed herein with a binding partner in an *Oplophorus*-derived luciferase fusion protein, wherein the disclosed compound inhibits the *Oplophorus*-derived luciferase when the fusion protein is intact. The disclosed compounds may be used in assays that are used detect the presence or activity of enzymes using *Oplophorus* luciferases, to selectively inhibit the signal from the *Oplophorus* luciferase. For example, they may be used in a bioluminogenic method which employs an *Oplophorus* luciferase and a coelenterazine or coelenterazine-derivative substrate to detect one or more molecules in a sample, e.g., a protein of interest (e.g., an enzyme, a binding partner, a ligand, etc.), a cofactor for an enzymatic reaction, an enzyme substrate, an enzyme inhibitor, an enzyme activator, or OH radicals, or one or more conditions, e.g., redox conditions. While the coelenterazine substrate serves as a substrate for the *Oplophorus* luciferase, the disclosed compounds may serve to inhibit the luciferase to selectively suppress the luminescent signal in embodiments in which such suppression may be desired, such as in applications involving temporal multiplexing of multiple bioluminescent systems, or in some plate-based luminescent assays. For example, the disclosed compounds may be used to inhibit intracellular and/or extracellular *Oplophorus* luciferase activities.

(1) Functionalized Inhibitors

Formula (I) compounds disclosed herein may be used as inhibitors of *Oplophorus*-derived luciferase. In addition, the disclosed compounds may contain functional groups extending out of the enzyme pocket and into solvent without impacting inhibition potency. The functional group may be appended to the luciferase inhibitor molecule by a linker, such as the $L^1$, $L^2$, or $L^3$ groups described above. As non-limiting examples, the compounds of formula (I) may have a $C_1$-$C_{10}$ haloalkyl group (such as the compounds of formula (Ic)), which may inhibit a HaloTag-NanoLuc® fusion enzymes, such that the compounds may be used as a bio-sensor in a variety of NanoLuc® assays (such as caspase detection). The compounds of formula (I) may have a leaving group (such as the compounds of formula (Id)) and function as a NanoLuc suicide inhibitor in an immunoassay (such as ELISA). The compounds of formula (I) may contain a kinase inhibitor moiety (such as the compounds of formula (Ie)), which may be used in kinase inhibition assays. The compounds of formula (I) may contain a fluorescent or fluorogenic dye moiety (such as the compounds of formula (If)), which may be used as a fluorescent tag for NanoLuc-based cell sorting and labeling applications.

In some embodiments, the disclosed compounds may be used to label proteins or surfaces. For example, a compound of Formula (I) may interact with a target protein (such as an enzyme or a receptor) through a reactive or functional group (such as halogen or an inhibitor), which is attached to the compound by an appropriate linker. In some embodiments, the disclosed compounds may be used to capture NLuc fusion proteins, or create a surface, resin, or biomolecule that may quench NLuc bioluminescence.

(2) Use of Cell-Impermeable Compounds

In certain embodiments, the methods disclosed herein include contacting a sample (e.g., a cell) with a mixture of a cell-permeable coelenterazine substrate and a compound described herein that is modified such that it is cell-impermeable. In such embodiments, the disclosed compounds and methods may be used to build up the initial brightness of a high-throughput screening operation assay format, and then selectively inhibit any luciferases that may be excreted from cells, to selectively inhibit luminescence that may occur outside of the cells. Such methods may provide for a more selective signal within cells.

(3) Use of Cell-Permeable Compounds

In certain embodiments, the methods disclosed herein include contacting a sample (e.g., a cell) with a mixture of a cell-permeable coelenterazine substrate and a compound described herein that is cell-permeable. In such embodiments, the disclosed compounds can enter in to cells and selectively inhibit an *Oplophorus* luciferase therein. Such methods may be advantageous in multiplexing assays that involve use of two or more luciferases, and may allow for inhibition of luminescence from an *Oplophorus* luciferase so as to selectively view luminescence from another luciferase inside the cell.

(4) Use of Tethered Compounds

In certain embodiments, the disclosed compounds may be tethered to a binding partner in an *Oplophorus* luciferase fusion protein. In these embodiments, the tethered compounds may inhibit bioluminescence of the *Oplophorus* luciferase when the fusion protein is intact. Upon cleavage of the fusion protein, the disclosed compounds remain tethered to the binding partner such that bioluminescence of the luciferase may be disinhibited. In some embodiments, the disclosed tethered compounds may be used in HALOTAG®- and NanoLuc®-based technologies. In these embodiments, the disclosed compounds may be appended to a chloroalkane to bind to the HALOTAG® protein. In such embodiments, the disclosed compounds are thus tethered to the HALOTAG® protein, which is considered the binding partner in the *Oplophorus* luciferase fusion protein. In such embodiments, the disclosed compounds inhibit bioluminescence of the *Oplophorus* luciferase when the Nluc-HT fusion protein is intact. Upon cleavage of the Nluc-HT fusion protein, the disclosed compound remains tethered to the HT protein and Nluc bioluminescence is disinhibited.

In other embodiments, the disclosed compounds may be tethered to a binding partner in an association/dissociation model of Nluc activity. In some embodiments, the disclosed compounds may be tethered to a binding partner in a first fusion protein comprising the binding partner and a first protein of interest. The *Oplophorus* luciferase may be bound to a second protein of interest. When the first protein of interest and the second protein of interest do not interact, bioluminescence from the *Oplophorus* luciferase is emitted in the presence of a luciferase substrate. When binding between the first protein of interest and the second protein of interest occurs, the disclosed compound is brought into close proximity to the *Oplophorus* luciferase and inhibits bioluminescence.

(5) Use with Transcriptional Reporters

The disclosed compounds may be used with genetic transcriptional reporter systems. In certain embodiments, provided is a method for measuring the activity of a promoter in a sample, wherein the promoter is operably linked to a gene encoding an *Oplophorus*-derived luciferase or a variant thereof. The method includes (a) contacting the sample with a coelenterazine substrate; (b) determining the activity of the promoter by measuring luminescence of the sample, wherein the sample comprises the promoter. The method can further include a step of contacting the sample with a compound described herein, to selectively inhibit the luminescence. The promoter may be operably linked to the gene via a translational or transcriptional fusion. A biological pathway of interest, for example, may be examined by treating a cell that comprises the promoter, which is operably linked to a gene encoding the luciferase, with an inducer agent of the pathway. This promoter activity may then be measured and monitored to study any correlation between the activity of the promoter and the pathway of interest, as well as obtain kinetic measurements relating to gene expression (e.g. inducibility, repression and activation). The compound described herein can be used to selectively inhibit the luminescence.

(6) Multiplexing

The disclosed compounds may be used to inhibit *Oplophorus* luciferases as applied to temporal multiplexing with other luciferases and assays. In some embodiments, the *Oplophorus*-derived luciferase or variant thereof may be multiplexed with another enzyme (e.g. a luciferase) that emits light at a different wavelength, e.g., green firefly luciferase, e.g., *Photinus pyralis* (e.g., Luc2; Promega Corp) or red click beetle luciferase (CHROMA-LUC™ luciferase; Promega Corp.). For example, if an *Oplophorus* luciferase is used as a functional reporter, then the green firefly luciferase or red CHROMA-LUC™ luciferase could be used to control for non-specific effects on genetic regulation or to normalize for transfection efficiency. In some embodiments, luminescence generated from the *Oplophorus* luciferase (approximately 460 nm) and red CHROMA-LUC (approximately 610 nm) can be easily resolved using a luminometer with wavelength-discriminating filters, enabling the measurement of both signals from the same sample. In such embodiments, a compound described herein can be used to selectively inhibit the *Oplophorus* luciferase, such that the signal from the other luciferase can be selectively viewed.

In another example, an *Oplophorus* luciferase could be used as a transcriptional reporter and paired with a luciferase that emits light at a different wavelength contained in an assay reagent. In another example, an *Oplophorus* luciferase may be used with one or more additional luciferases, where the luminescence of each luciferase may be separately measured through the use of selective enzyme inhibitors. For example, the luminescence of the *Oplophorus* luciferase may be measured upon addition of appropriate substrates and buffers, followed by measurement of a second luciferase upon a subsequent addition of appropriate substrates and buffers and one or more compounds described herein, which are selective for the an *Oplophorus* luciferase. In another example, the *Oplophorus* luciferase contained in an assay reagent may be used for measuring a specific aspect of cellular physiology, for example ATP to estimate cell viability or caspase activity to estimate cellular apoptosis.

In some embodiments, the *Oplophorus*-derived luciferase or variant thereof may be multiplexed with another enzyme (e.g. a luciferase) that emits light at the same wavelength. In some embodiments, NANOBIT® technology (Promega Corporation) may be used. For example, purified large BiT (LgBiT; 18 kDa) can be added to a detection reagent containing furimazine as a means to detect and quantitate proteins of interest that are fused to high affinity BiT (HiBiT, 1.3 kDa). HiBiT and LgBiT have low nM affinity and spontaneously interact in the presence of furimazine to produce luminescence.

(7) Bioluminescence Resonance Energy Transfer (BRET)

The disclosed compounds may be used in any method in which an *Oplophorus* luciferase is used for detecting ligand-protein and/or protein-protein interactions. In various embodiments, the *Oplophorus* luciferase may be used to transfer energy to an energy acceptor. One such method is Bioluminescence Resonance Energy Transfer (BRET). With respect to BRET, energy transfer from a bioluminescent donor to a fluorescent acceptor results in a shift in the spectral distribution of the emission of light. This energy transfer may enable real-time monitoring of protein-protein or ligand-protein interaction in vitro or in vivo. In some embodiments, the BRET method may be an Nluc-Mediated Bioluminescence Resonance Energy Transfer (such as NanoBRET) Assay for ligand-protein and protein-protein interactions. NANOBRET™ comprises two different methods: 1) using HALOTAG®- and NanoLuc®-based technologies, Bioluminescence Resonance Energy Transfer (BRET) to detect protein-protein and/or ligand-protein interactions may be achieved with increased signal and decreased spectral overlap; and 2) using Nluc luciferase fused to a protein of interest and a fluorescent tracer to detect ligand-receptor interaction in living cells.

In some embodiments, the disclosed compounds may be used in a method to detect an interaction between a molecule of interest and a target protein in a sample. The sample includes (i) a polynucleotide encoding a fusion protein, the fusion protein comprising an *Oplophorus*-derived luciferase and a target protein, wherein the *Oplophorus*-derived luciferase is a bioluminescent donor; (ii) a coelenterazine substrate; (iii) the disclosed compound described above; and (iv) a fluorescent tracer comprising a fluorescent acceptor molecule and a ligand that binds to the target protein. The method includes (a) detecting a first bioluminescence resonance energy transfer (BRET) signal in the sample, (b) contacting the sample with a molecule of interest; and (c) detecting a second BRET signal in the sample, wherein a decrease in the second BRET signal compared to the first BRET signal indicates an interaction between the molecule of interest and the target protein. In some embodiments, the target protein can include a kinase, a histone deacetylase, or a bromodomain-containing protein, such as a member of the bromodomain and extra terminal domain (BET) family.

In some embodiments, the disclosed compounds may be part of a bioluminescence resonance energy transfer (BRET) system. The BRET system can include a fusion protein including a target protein and a bioluminescence donor molecule, wherein the bioluminescence donor molecule is an *Oplophorus*-derived luciferase; a fluorescent tracer comprising a fluorescent acceptor molecule and a ligand that binds to the target protein; a coelenterazine substrate, and the disclosed compound described above. In some embodiments, the target protein can include a kinase, a histone deacetylase, or a bromodomain-containing protein, such as a member of the bromodomain and extra terminal domain (BET) family.

In some embodiments, the disclosed compounds may be used in a method to detect an interaction between a first target protein and a second target protein in a sample. The sample includes (i) a first polynucleotide encoding a first fusion protein, wherein the first fusion protein comprises an *Oplophorus*-derived luciferase and a first target protein, wherein the *Oplophorus*-derived luciferase is a bioluminescent donor; and (ii) a second polynucleotide encoding a second fusion protein, wherein the second fusion protein comprises a HALOTAG® protein and a second target protein. The method includes (a) contacting a sample with a coelenterazine substrate, the disclosed compound described above, and a HALOTAG® ligand, wherein the HALOTAG® ligand comprises a fluorescent acceptor molecule; (b) detecting bioluminescence resonance energy transfer (BRET) in the sample thereby detecting an interaction or indicating a close proximity of the first target protein and the second target protein. In some embodiments, the HALOTAG® ligand comprises NanoBRET™ 618 ligand. In some embodiments, the method may be used to detect the interaction between FKBP and FRB.

In some embodiments, the disclosed compounds may be part of a bioluminescence resonance energy transfer (BRET) system. The BRET system can include a first fusion protein including a first target protein and a bioluminescence donor molecule, wherein the bioluminescence donor molecule is an *Oplophorus*-derived luciferase; a second fusion protein including a second target protein and a HALOTAG® protein; a HALOTAG® ligand comprising a fluorescent acceptor molecule; a coelenterazine substrate, and the disclosed compound described above. In some embodiments, the HALOTAG® ligand comprises NanoBRET™ 618 ligand.

In some embodiments, the luminescent enzymes (i.e. *Oplophorus* luciferases) used in BRET analysis can be used to determine if two molecules are capable of binding to each other or co-localize in a cell. For example, a luminescent enzyme can be used as a bioluminescence donor molecule, which is combined with a molecule or protein of interest to create a first fusion protein. In various embodiments, the first fusion protein contains a luminescent enzyme and a protein of interest. In various embodiments, the first fusion proteins containing the luminescent enzyme can be used in BRET analysis to detect protein/protein interaction in systems including but not limited to cell lysates, intact cells, and living animals. In various embodiments, the HALOTAG® protein can be used as a fluorescent acceptor molecule. In some embodiments, the HALOTAG® protein can be fused to a second protein of interest or to a luminescent enzyme. For example, a luminescent enzyme can be fused to a HALOTAG® protein, expressed in cells or animals, and labeled with a fluorescent HALOTAG® ligand such as HALOTAG® TMR ligand. The fusion can subsequently be excited to fluoresce in the presence of a cell-permeant luminescent enzyme substrate. In some embodiments, BRET may be performed using luminescent enzymes in combination with fluorescent proteins, including but not limited to Green Fluorescent Protein (GFP) or Red Fluorescent Protein (RFP) or fluorescent labels including fluorescein, rhodamine green, Oregon green, or Alexa 488, to name a few non-limiting examples.

In some embodiments, quenching the signal from excreted Nluc can improve the signal to noise ratio when using the NanoBRET™ plate assay.

In certain embodiments, a cell-permeable compound may be used to inhibit intracellular BRET. In certain embodiments, a cell-impermeable compound may be used to inhibit extracellular BRET. In certain embodiments, a cell-impermeable compound may be used in a target engagement model.

(8) Protein Proximity Assays for Live Cells or Lytic Formats

In some embodiments, *Oplophorus* luciferases may be used in circularly permuted (CP) or straight split (SS) luminescent enzyme fusion proteins to measure protein proximity. The *Oplophorus* luciferase is permuted or split via insertion of a protease substrate amino acid sequence (e.g., TEV) to generate low bioluminescence. The inactive luciferase is tethered (e.g., via genetic fusion) to a monitor protein. A potential interacting protein is tethered (e.g., via genetic fusion) to a protease (e.g., TEV). When the two monitor proteins interact or are in sufficient proximity (e.g., via a constitutive interaction, a drug stimulus or a pathway response), the luminescent enzyme is cleaved to generate increased bioluminescence activity. The example may be applied to measurements of protein proximity in cells or in biochemical assays.

(9) Biosensor Capabilities

In some embodiments, disclosed compounds may be used in *Oplophorus* luciferase fusion proteins as a biosensor. In some embodiments, the disclosed compounds may be used in *Oplophorus* luciferase fusion proteins to measure enzyme activity. In certain embodiments, the disclosed compounds may be used in *Oplophorus* luciferase fusion proteins to measure protease activity. In some embodiments, the protease may be a caspase protein. In some embodiments, the fusion protein of interest may comprise an *Oplophorus* luciferase bound to a protein by a protease-sensitive linker. As a non-limiting example, Nluc may be bound to the HALOTAG® protein by a DEVD linker (Nluc-DEVD-HT). In these embodiments, the intact Nluc-DEVD-HT fusion protein will emit high levels of bioluminescence in the presence of a Nluc substrate. In these embodiments, the DEVD linker is susceptible to caspase-mediated cleavage such that the activation of caspase leads to the separation of Nluc from the HT. In some embodiments, the compounds disclosed herein may be used to inhibit bioluminescence from the Nluc-DEVD-HT fusion protein. Activation of caspase leads to the separation of Nluc from the HT-inhibitor complex, thereby increasing bioluminescence.

(10) Protein Complementation Assays

In some embodiments, the disclosed compounds may be used to inhibit an *Oplophorus* luciferase when such a luciferase is used in other methods for detecting ligand-protein and protein-protein interactions or proximity, such as the protein complementation assay (PCA) or enzyme fragmentation assay. Protein complementation assays (PCA) provide a means to detect the interaction of two biomolecules, e.g., polypeptides. PCA utilizes two fragments of the same protein, e.g., enzyme, that are fused to polypeptides of interest that produce light only when brought into close proximity with each other via the binding interactions of their fusion partners and can reconstitute into a functional, active protein. In some embodiments, the NANOBIT® technology (Promega Corporation) may be used to detect molecular proximity by virtue of the reconstitution of a luminescent enzyme via the binding interaction of enzyme components or subunits. The NanoBiT® system may comprise two subunits that are expressed as fusions to target proteins of interest. The two subunits may comprise Large BiT (LgBiT; 18 kDa) and Small BiT (SmBiT; 1.3 kDa).

For example, a luminescent enzyme can be separated into two fragments at a site(s) tolerant to separation and each fragment of the separated luminescent enzyme can be fused to one of a pair of polypeptides of interest believed to interact, e.g., FKBP and FRB. If the two polypeptides of interest do in fact interact, the luminescent enzyme fragments, for example, then come into close proximity with each other to reconstitute the functional, active luminescent enzyme. In some embodiments, the activity of the reconstituted luminescent enzyme can then be detected and measured. In some embodiments, the split luminescent enzyme can be used in a more general complementation system similar to lac-Z (Langley et al., *PNAS* 72:1254-1257 (1975)) or ribonuclease S (Levit and Berger, *J. Biol. Chem.* 251: 1333-1339 (1976)). In some embodiments, a luminescent enzyme fragment (designated "A") known to complement with another luminescent enzyme fragment ("B") can be fused to a target protein, and the resulting fusion can be monitored via luminescence in a cell or cell lysate containing fragment B. In some embodiments, the source of fragment B could be the same cell (e.g., if the gene for fragment B is integrated into the genome of the cell or is contained on another plasmid within the cell) or it could be a lysate or purified protein derived from another cell. In some embodiments, this same fusion protein (fragment A) could be captured or immobilized using a fusion between fragment B and a polypeptide such as a HALOTAG® protein capable of attachment to a solid support. In some embodiments, luminescence can be used to demonstrate successful capture or to quantify the amount of material captured.

(11) Dimerization Assay

In some embodiments, the disclosed compounds may be used with full-length circularly permuted luminescent enzymes fused to respective binding partners, e.g., FRB and FKBP, and used in a protein complementation-type assay. The key difference between the method disclosed herein and traditional protein complementation is that there was no complementation, but rather there was dimerization of two full length enzymes, e.g., circularly permuted luminescent enzymes.

Briefly, the circularly permuted reporter proteins similarly configured for low activity are fused to both of the fusion protein partners. For example, each fusion partner may be linked to identically structured, permuted reporters. Interaction of the fusion partners brought the permuted reporters into close proximity, thereby allowing reconstitution of a hybrid reporter having higher activity.

(12) Protein Isolation

In some embodiments, the disclosed compounds may be used to isolate *Oplophorus* luciferase fusion proteins. In some embodiments, the disclosed compounds may be used to isolate *Oplophorus* luciferase fusion proteins using Nano-Luc®- and HALOTAG®-based technologies. In some embodiments, the disclosed compounds may be appended to various biomolecules and macromolecules such as drugs, nucleotides, sugars, proteins, polymers, and solid surfaces for use in *Oplophorus* luciferase fusion protein isolation.

(13) Suicide Inhibition

In some embodiments, the disclosed compounds may be used as suicide inhibitors which irreversibly inhibit *Oplophorus* luciferase. In some embodiments, the disclosed compounds may be used as suicide inhibitors applied to a ligand-receptor binding assay. In certain embodiments, the disclosed compounds may be applied as suicide inhibitors in an ELISA.

(14) Cell Uptake and Sorting

In some embodiments, the disclosed compounds may be appended to various biomolecules and macromolecules such as drugs, nucleotides, sugars, proteins, polymers, solid surfaces, etc. for uses in cell uptake or cell sorting and labeling. For example, a monoclonal antibody (e.g., Nluc-Trastuzumab) could be chemically conjugated and bound to the HER2 receptor expressed on the surface of SKBR3 cells. A cell impermeable Nluc inhibitor could be applied to inhibit extracellular Nluc-Trastuzumab. Upon addition of a coelenterazine substrate, a gain of signal assay could be used to kinetically measure active/passively internalized Trastuzumab-Nluc-HER2 receptor, which can be extended to other antibodies, proteins, receptors, drugs, drug carriers, peptides, sugars, fatty acids, nanoparticles, or other biomolecules chemically conjugated to Nluc.

In another example, Nluc-GPCRs (e.g., Nluc-B2AR) could be genetically fused and expressed in mammalian cells. A cell impermeable thienopyrrole compound (inhibitor) as described herein could be applied to inhibit extracellular or membrane bound Nluc-B2AR. Upon addition of coelenterazine substrate, a gain of signal assay could be used to kinetically measure active/passively internalized or recycled Nluc-GPCR, which can be extended to other proteins or receptors genetically fused to Nluc.

In another example, the disclosed compounds may be appended to a dye, such as a fluorescent dye or a fluorogenic dye. For example, the disclosed compounds may be appended to a fluorescent dye for use in fluorescence activated cell sorting (FACS). Cells may be transfected with a Nluc fusion protein, such as a Nluc-HT fusion protein, and exposed to the inhibitor-dye conjugate. A cell permeable inhibitor-dye conjugate will bind to Nluc in cells expressing the Nluc fusion protein, generating fluorescence. After appropriate incubation and wash steps, the fluorescent cells can be sorted by FACS and used for future biochemical experiments.

(15) Kinase Inhibition

In some embodiments, the disclosed compounds may be appended to a kinase inhibitor for use in a kinase inhibition assay. The disclosed compounds may be appended to a kinase inhibitor and used in an assay to monitor cellular processes regulated by kinases, such as cell signaling, cell division and growth, development, differentiation, and cell death.

(16) Induced Protein Degradation

In some embodiments, the disclosed compounds may include a moiety of a small molecule which may recruit protein degradation pathways within live cells, either through hydrophobic tagging (HyT) or proteolysis-targeting chimaera (PROTAC) tagging (Lai et al., Nature Reviews Drug Discovery, 2017, 16, 101-114). For example, the disclosed compounds may include a luciferase inhibitor structure appended to a HyT or PROTAC moiety. Such compound may bind to luciferase fusion proteins (such as NanoLuc® fusion proteins) and target these fusion proteins for degradation. Thus, the compounds disclosed herein may be used in the studies of the pharmacology and function of luciferase fusion proteins in a cellular context.

Disclosed is a method of inducing protein degradation, the method comprising contacting a cell with a compound as disclosed herein, the cell comprising a luciferase fusion protein and at least one protease, whereby the fusion protein is degraded by the protease. In some embodiments, the fusion protein is an *Oplophorus*-derived luciferase fusion protein, such as NanoLuc® fusion proteins.

(17) Protein Labeling

In some embodiments, the disclosed compounds may include to a protein labeling moiety, such as a nitrobenzoxadiazole (NBD) dye moiety. Upon binding to a target protein (such as a luciferase), the protein labeling moiety of disclosed compound may react with a specific amino acid of the luciferase to form a fluorescent label. For example, some disclosed compounds include a NBD group, which may react with a lysine residue in a luciferase, such as lysine 78 on NanoLuc, to form a fluorescent label on NanoLuc. In some embodiments, the disclosed compounds are not fluorescent with the NBD group appended through an ether bond. However, after binding to the target protein, the ether bond is replaced with an amine bond formed between the amino group of a lysine residue of the target protein and the NBD group, and the resultant label may be fluorescent (for example, excitation at approximately 478 nm, emission at approximately 530 nm). Thus, the compound disclosed herein may be used in turn-on fluorescent affinity labeling applications (Yamaguchi et al., Chemical Science, 2014, 5, 1021-1029).

Disclosed is a method of labeling a target protein, the method comprising contacting a target protein with a compound as disclosed herein having a protein labeling moiety, whereby the target protein form a covalent bond with the protein labeling moiety. In some embodiments, the compound having a protein labeling moiety is a compound of formula (I), (Ia), (Ib), or (Id), wherein Z is —OR$^4$, wherein R$^4$ is optionally substituted aryl, optionally substituted heteroaryl, or optionally substituted heterocycle, and wherein the R$^4$ group is capable of forming a covalent bond with a protein in a reaction between the compound and the protein. In some embodiments, the method comprises contacting a compound of formula (I), (Ia), (Ib), or (Id), wherein Z contains a nitrobenzoxadiazole (NBD) dye moiety, represented by

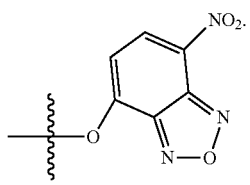 [SMILES: *Oc1ccc([N+](=O)[O-])c2nonc12]

In some embodiments, the target protein is *Oplophorus*-derived luciferase fusion protein, such as NanoLuc® fusion proteins. In some embodiments, the protein labeling moiety is a dye, such as a fluorescent dye. In some embodiments, the covalent bond is formed between the amino group of a lysine residue of the target protein and the protein labeling moiety. In some embodiments, the method further comprises allowing the amino group of a lysine residue of the target protein to react with the disclosed compound. In some embodiments, the method further comprises detecting fluorescence of the target protein after the covalent bond is formed.

6. SAMPLE

The disclosed compounds may be used with samples containing biological components. The sample may comprise cells. The sample may comprise heterogeneous mixtures of components (including intact cells, cell extracts, cell lysates, bacteria, viruses, organelles, exosomes, and mixtures thereof) or a single component or homogeneous group of components (e.g., natural or synthetic amino acid, nucleic acid or carbohydrate polymers, or lipid membrane complexes). The disclosed compounds may be generally nontoxic to living cells and other biological components within the concentrations of use.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). In certain embodiments, the sample may be a cell. In some embodiments, the sample may be a live cell. The cell may be a eukaryotic cell, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cell may or may not express a luciferase. The cells may have been genetically modified via recombinant techniques.

7. KITS

Disclosed are kits for determining the presence or activity of one or more enzymes (e.g., an *Oplophorus* or *Oplophorus* variant luciferase). The kit may include one or more of the following: a compound or composition of the invention that may inhibit the *Oplophorus* or *Oplophorus* variant luciferase, a coelenterazine or coelenterazine-derivative substrate, an *Oplophorus* or *Oplophorus* variant luciferase, instructions for carrying out a luminescence assay, and reaction buffer(s). The reaction buffers may be present in individual formulations for the non-luciferase enzyme reactions and the luminescent enzyme reactions or in a single formulation for a single step assay. The kits may also contain other inhibitors, activators and/or enhancers for the non-luciferase enzyme(s). The kits may also contain a positive and/or negative control for the assay.

8. EXAMPLES

Example 1

Syntheses of Haloalkane Compounds

Compounds of formula (I) having haloalkane group (such as chloroalkane group) can be synthesized according to Scheme 1. Other suitable synthesis methods are disclosed in U.S. patent application Ser. No. 15/192,420 to Duellman et al., "THIENOPYRROLE COMPOUNDS AND USES THEREOF," filed Jun. 24, 2016, which is incorporated by reference herein in its entirety.

Scheme 1. Synthesis of compounds of formula (I) having chloroalkane group.

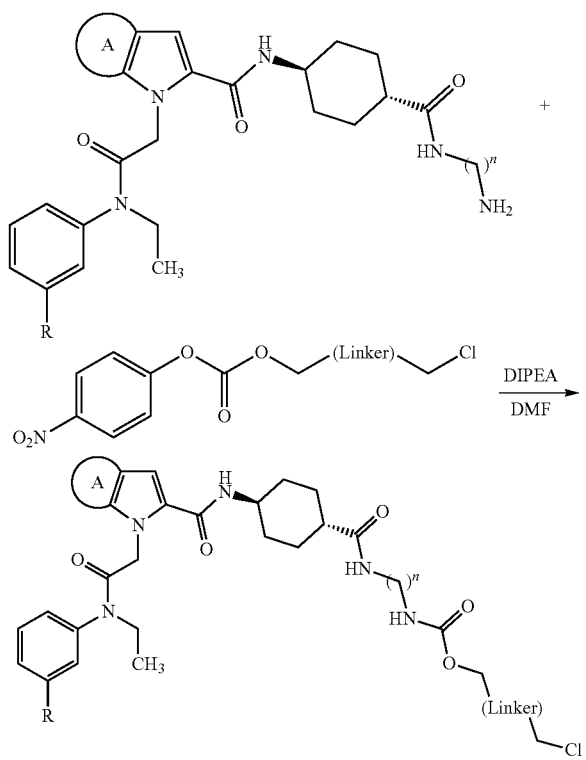

Example 2

1-(trans-4-(4-(2-(ethyl)m-tolyl)amino)-2-oxoethyl)-4H-thieno[3,2-b]pyrrole-5-carboxamido)cyclohexyl)-1,10-dioxo-11,14,17-trioxa-2,9-diazanonadecan-19-yl (2-(2-((6-chlorohexyl)oxy)ethoxy)ethyl) carbamate (JRW-0308)

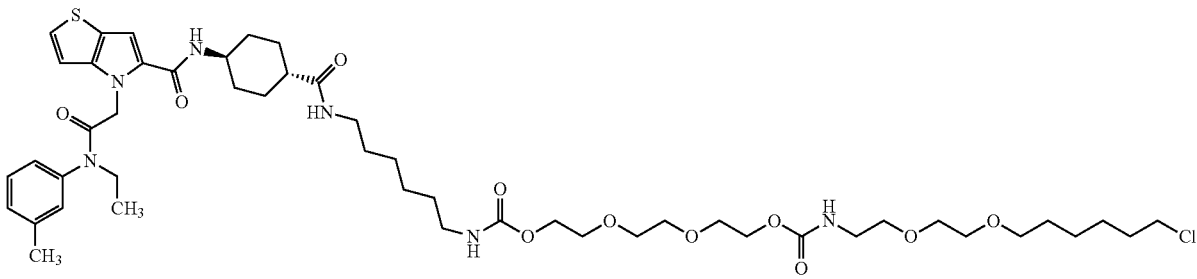 [SMILES: CCN(C(=O)Cn1c(C(=O)N[C@H]2CC[C@H](C(=O)NCCCCCCNC(=O)OCCOCCOCCOC(=O)NCCOCCOCCCCCCCl)CC2)cc2sccc21)c1cccc(C)c1]

To a solution of N-(trans-4-(((6-aminohexyl)carbamoyl)cyclohexyl)-4-(2-(ethyl(m-tolyl)amino)-2-oxoethyl)-4H-thieno[3,2-b]pyrrole-5-carboxamide (101 mg, 0.18 mmol) in DMF (5 mL), 2-(2-(2-(((4-nitrophenoxy)carbonyl)oxy)ethoxy)ethoxy)ethyl (2-(2-((6-chlorohexyl)oxy)ethoxy)ethyl)carbamate (112 mg, 0.20 mmol) and diisopropylethylamine (70 mg, 0.54 mmol) was added. The solution stirred at RT for 18 h. The mixture was diluted with ethyl acetate and washed with water. The organic layers were combined, dried with sodium sulfate, filtered, concentrated, and purified with preparative HPLC to afford the desired product (89 mg, 50%) as a colorless gum. $^1$H NMR (300 MHz, DMSO-$d_6$) δ 7.95-7.79 (m, 1H), 7.70-7.61 (m, 1H), 7.45-7.34 (m, 2H), 7.34-7.05 (s, 7H), 4.97 (s, 2H), 4.06-3.97 (m, 4H), 3.68-3.27 (m, 21H), 3.13-3.05 (m, 2H), 3.03-2.88 (m, 4H), 2.37 (s, 3H), 2.12-1.93 (m, 1H), 1.90-1.61 (m, 6H), 1.56-1.15 (m, 18H), 1.05-0.93 (m, 3H); ESI MS m/z 991 [M+H]+; HPLC>99% (AUC), $T_R$ 7.18 min; UV (MeOH) λ 289 nm, ε 25731.

Example 3

[(E)-30-chloro-6,17-dioxo-5,10,13,16,21,24-hexaoxa-7,18-diazatriacont-2-en-1-yl (1-(trans-4-(4-(2-(ethyl(3-ethylphenyl)amino)-2-oxoethyl)-4H-thieno[3,2-b]pyrrole-5-carboxamido)cyclohexyl)-1,10-dioxo-11,14,17-trioxa-2,9-diazanonadecan-19-yl) carbamate (JRW-0494)

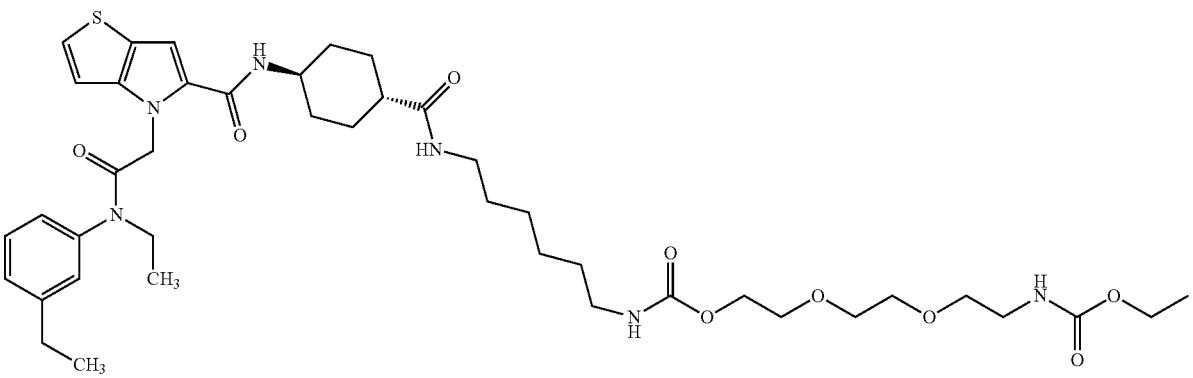

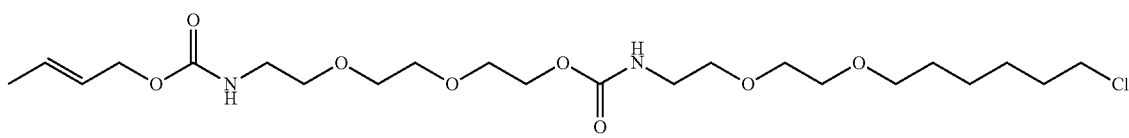

To a solution of N-(trans-4-((6-aminohexyl)carbamoyl)cyclohexyl)-4-(2-(ethyl(3-ethylphenyl)amino)-2-oxoethyl)-4H-thieno[3,2-b]pyrrole-5-carboxamide (25 mg, 0.043 mmol) in DMF (2 mL), (E)-1-(4-nitrophenoxy)-1,12-dioxo-2,5,8,13-tetraoxa-11-azaheptadec-15-en-17-yl (23-chloro-10-oxo-3,6,9,14,17-pentaoxa-11-azatricosyl)carbamate (28 mg, 0.032 mmol) and diisopropylethylamine (17 mg, 0.13 mmol) was added. The solution stirred at RT for 18 h. The mixture was diluted with ethyl acetate and washed with water. The organic layers were combined, dried with sodium sulfate, filtered, concentrated, and purified with silica gel chromatography to afford the desired product (31 mg, 56%) as a colorless oil. $^1$H NMR (300 MHz, DMSO-d$_6$) δ 7.94-7.80 (m, 1H), 7.73-7.59 (m, 1H), 7.46-7.04 (m, 11H), 5.81-5.72 (m, 2H), 5.05-4.83 (m, 2H), 4.50-4.38 (s, 4H), 4.07-3.97 (m, 4H), 3.68-3.41 (m, 22H), 3.40-3.32 (m, 10H), 3.16-3.04 (m, 6H), 3.04-2.87 (m, 4H), 2.74-2.58 (m, 2H), 2.10-1.98 (m, 1H), 1.88-1.61 (m, 6H), 1.52-1.18 (m, 18H), 1.07-0.95 (m, 3H); ESI MS m/z 1293 [M+H]+; HPLC 99.2% (AUC), T$_R$ 6.05 min.

Example 4

[(E)-30-chloro-6,17-dioxo-5,10,13,16,21,24-hexaoxa-7,18-diazatriacont-2-en-1-yl (1-(trans-4-(1-(2-(ethyl(3-ethylphenyl)amino)-2-oxoethyl)-1H-indole-2-carboxamido)cyclohexyl)-1,10-dioxo-11,14,17-trioxa-2,9-diazanonadecan-19-yl)carbamate (JRW-0495)

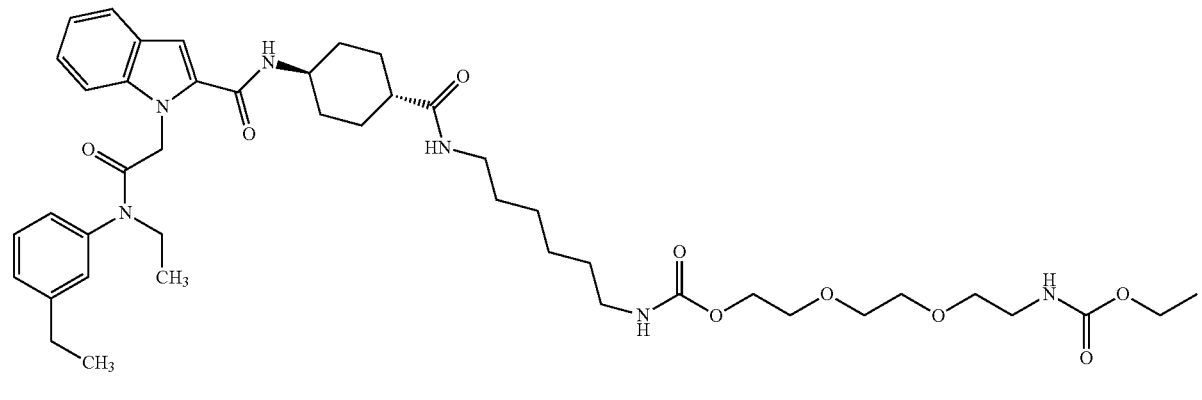

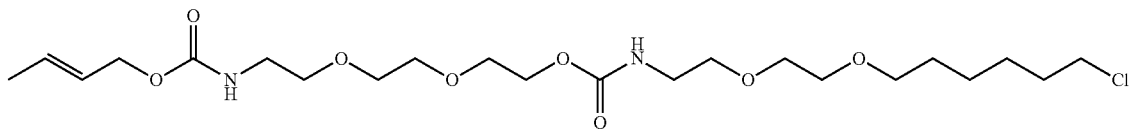

To a solution of N-(trans-4-((6-aminohexyl)carbamoyl)cyclohexyl)-1-(2-(ethyl(3-ethylphenyl)amino)-2-oxoethyl)-1H-indole-2-carboxamide (23 mg, 0.040 mmol) in DMF (2 mL), (E)-1-(4-nitrophenoxy)-1,12-dioxo-2,5,8,13-tetraoxa-11-azaheptadec-15-en-17-yl (23-chloro-10-oxo-3,6,9,14,17-pentaoxa-11-azatricosyl)carbamate (25 mg, 0.030 mmol) and diisopropylethylamine (15 mg, 0.12 mmol) was added. The solution stirred at RT for 18 h. The mixture was diluted with ethyl acetate and washed with water. The organic layers were combined, dried with sodium sulfate, filtered, concentrated, and purified with silica gel chromatography to afford the desired product (30 mg, 58%) as a colorless oil. $^1$H NMR (300 MHz, DMSO-d$_6$) δ 8.25-8.16 (m, 1H), 7.71-7.62 (m, 1H), 7.62-7.52 (m, 1H), 7.49-7.01 (m, 12H), 5.80-5.72 (m, 2H), 5.10-4.92 (m, 2H), 4.50-4.40 (m, 4H), 4.05-3.96 (s, 4H), 3.69-3.41 (m, 22H), 3.41-3.32 (m, 10H), 3.16-3.05 (m, 6H), 3.04-2.86 (m, 4H), 2.77-2.61 (m, 2H), 2.12-1.95 (m, 1H), 1.92-1.61 (m, 6H), 1.51-1.18 (m, 18H), 1.10-0.95 (m, 3H); ESI MS m/z 1287 [M+H]+; HPLC 97.9% (AUC), T$_R$ 6.17 min.

Example 5

1-(trans-4-(4-(2-(ethyl(3-ethylphenyl)amino)-2-oxo-ethyl)-4H-thieno[3,2-b]pyrrole-5-carboxamido)cyclohexyl)-1,10-dioxo-11,14,17-trioxa-2,9-diazanonadecan-19-yl (2-(2-((6-chlorohexyl)oxy)ethoxy)ethyl)carbamate (JRW-0497)

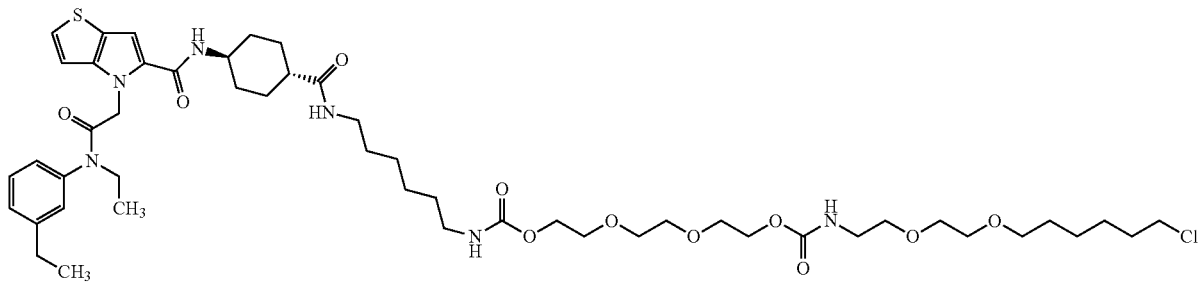 [SMILES: CCc1cccc(N(CC)C(=O)Cn2c(C(=O)N[C@H]3CC[C@H](C(=O)NCCCCCCNC(=O)OCCOCCOCCOC(=O)NCCOCCOCCCCCCCl)CC3)cc3sccc32)c1]

To a solution of N-(trans-4-(((6-aminohexyl)carbamoyl)cyclohexyl)-4-(2-(ethyl(3-ethylphenyl)amino)-2-oxoethyl)-4H-thieno[3,2-b]pyrrole-5-carboxamide (86 mg, 0.15 mmol) in DMF (3 mL), 2-(2-(2-(((4-nitrophenoxy)carbonyl)oxy)ethoxy)ethoxy)ethyl (2-(2-((6-chlorohexyl)oxy)ethoxy)ethyl)carbamate (62 mg, 0.11 mmol) and diisopropylethylamine (57 mg, 0.44 mmol) was added. The solution stirred at RT for 18 h. The mixture was diluted with ethyl acetate and washed with water. The organic layers were combined, dried with sodium sulfate, filtered, concentrated, and purified with preparative HPLC to afford the desired product (70 mg, 47%) as a colorless oil. $^1$H NMR (300 MHz, DMSO-$d_6$) δ 7.91-7.83 (m, 1H), 7.70-7.61 (m, 1H), 7.48-6.98 (m, 9H), 5.08-4.79 (m, 2H), 4.10-3.96 (m, 4H), 3.71-3.28 (s, 21H), 3.15-3.04 (m, 2H), 3.04-2.87 (m, 4H), 2.74-2.61 (m, 2H), 2.10-1.98 (m, 1H), 1.92-1.62 (m, 6H), 1.56-1.10 (m, 18H), 1.10-0.93 (m, 3H); ESI MS m/z 1005 [M+H]+; HPLC>99% (AUC), $T_R$ 6.15 min; UV (MeOH) λ 288 nm, ε 18514.

To a solution of N-(trans-4-(((6-aminohexyl)carbamoyl)cyclohexyl)-1-(2-(ethyl(3-ethylphenyl)amino)-2-oxoethyl)-1H-indole-2-carboxamide (87 mg, 0.15 mmol) in DMF (3 mL), 2-(2-(2-(((4-nitrophenoxy)carbonyl)oxy)ethoxy)ethoxy)ethyl (2-(2-((6-chlorohexyl)oxy)ethoxy)ethyl)carbamate (64 mg, 0.13 mmol) and diisopropylethylamine (58 mg, 0.45 mmol) was added. The solution stirred at RT for 18 h. The mixture was diluted with ethyl acetate and washed with water. The organic layers were combined, dried with sodium sulfate, filtered, concentrated, and purified with preparative HPLC to afford the desired product (71 mg, 47%) as a colorless oil. $^1$H NMR (300 MHz, DMSO-$d_6$) δ 8.28-8.10 (m, 1H), 7.71-7.62 (m, 1H), 7.61-7.55 (m, 1H), 7.50-7.02 (s, 10H), 5.02 (s, 2H), 4.05-3.98 (m, 4H), 3.70-3.28 (m, 21H), 3.14-3.05 (m, 2H), 3.04-2.86 (s, 4H), 2.76-2.62 (m, 2H), 2.12-1.98 (m, 1H), 1.90-1.65 (m, 6H), 1.54-1.15 (m, 18H), 1.06-0.95 (s, 3H); ESI MS m/z 1000 [M+2]+; HPLC>99% (AUC), $T_R$ 6.30 min; UV (MeOH) λ 291 nm, ε 19216.

Example 6

1-(trans-4-(1-(2-(ethyl(3-ethylphenyl)amino)-2-oxo-ethyl)-1H-indole-2-carboxamido)cyclohexyl)-1,10-dioxo-11,14,17-trioxa-2,9-diazanonadecan-19-yl (2-(2-((6-chlorohexyl)oxy)ethoxy)ethyl)carbamate (JRW-0498)

Example 7

Synthesis of Succinate Ester and Maleimide Compounds

Compounds of formula (I) having succinate ester or maleimide group can be synthesized according to Scheme 2.

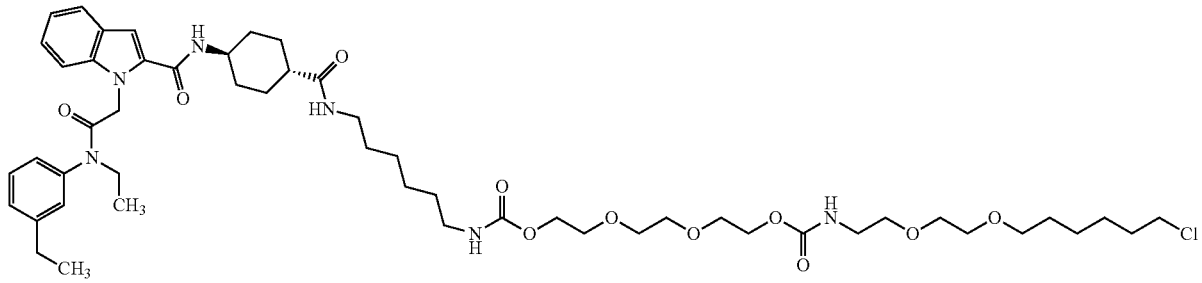 [SMILES: CCc1cccc(N(CC)C(=O)Cn2c(C(=O)N[C@H]3CC[C@H](C(=O)NCCCCCCNC(=O)OCCOCCOCCOC(=O)NCCOCCOCCCCCCCl)CC3)cc3ccccc32)c1]

Scheme 2. Synthesis of succinate esters
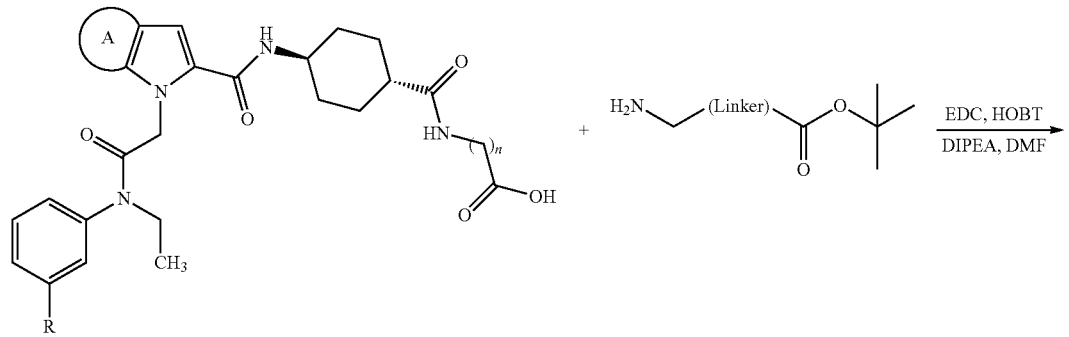
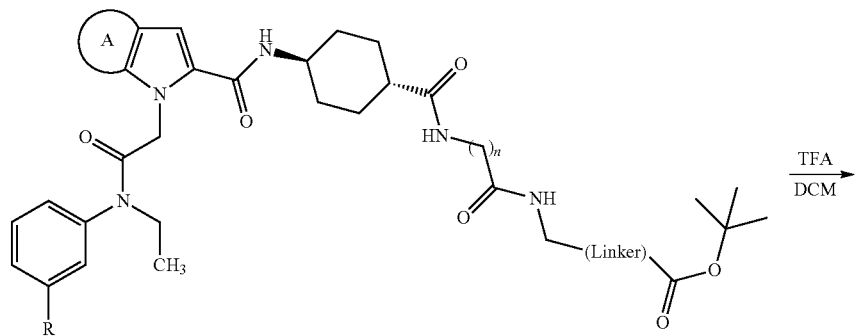
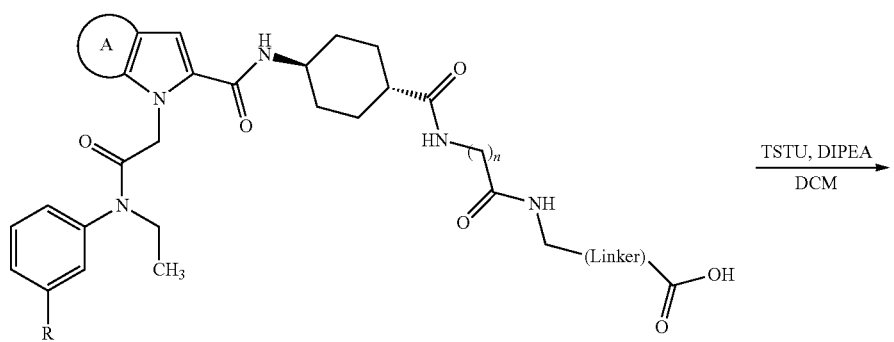
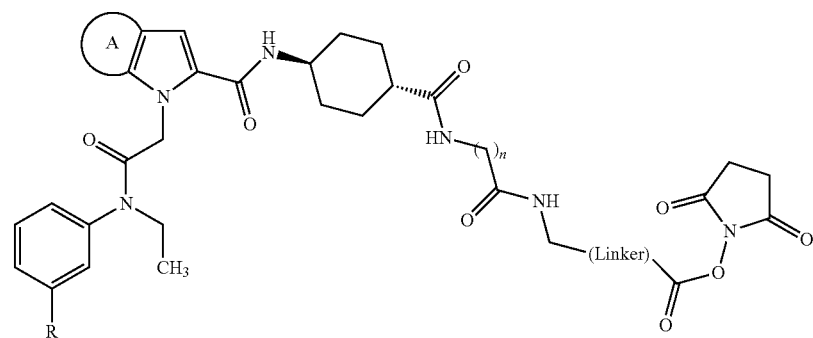

Example 8

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oate (JRW-0520)

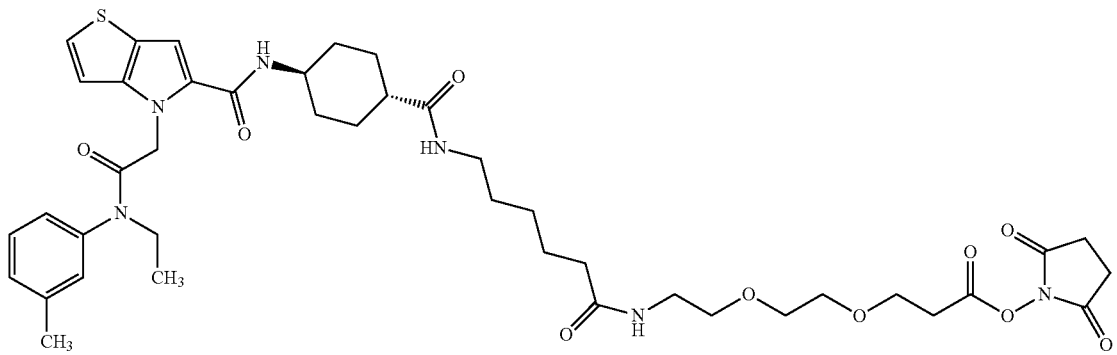 [SMILES: CCN(C(=O)Cn1c(C(=O)N[C@H]2CC[C@H](C(=O)NCCCCCC(=O)NCCOCCOCCC(=O)ON3C(=O)CCC3=O)CC2)cc2sccc21)c1cccc(C)c1]

Step 1. tert-butyl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oate (JRW-0518)

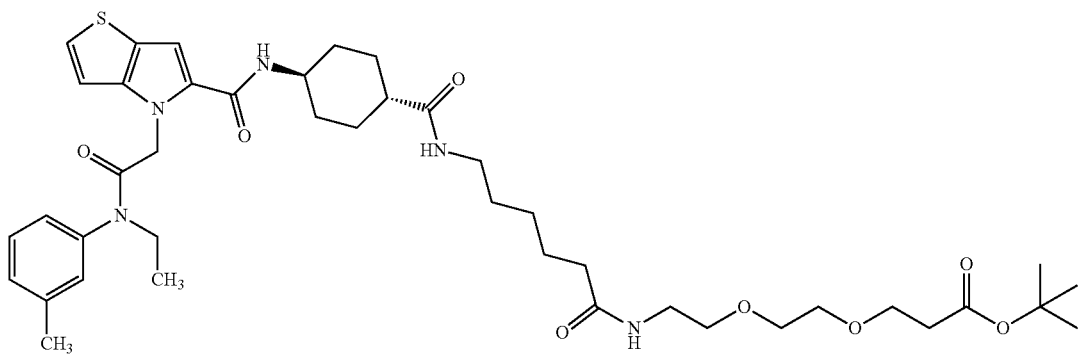 [SMILES: CCN(C(=O)Cn1c(C(=O)N[C@H]2CC[C@H](C(=O)NCCCCCC(=O)NCCOCCOCCC(=O)OC(C)(C)C)CC2)cc2sccc21)c1cccc(C)c1]

To a solution of 6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid (52 mg, 0.089 mmol) in DMF (3 mL), HOBT (27 mg, 0.18 mmol), EDC (34 mg, 0.18 mmol), diisopropyethylamine (34 mg, 0.27 mmol), and tert-butyl 3-(2-(2-aminoethoxy)ethoxy)propanoate (31 mg, 0.13 mmol) was added. The solution was heated to 60° C. for 1 h. The mixture was diluted with ethyl acetate and washed with water. The organic layers were combined, dried with sodium sulfate, filtered, concentrated, and purified with silica gel chromatography to afford the desired product (71 mg, quant) as a colorless oil. ESI MS m/z 796 [M+1]+.

Step 2. 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oic acid (JRW-0519)

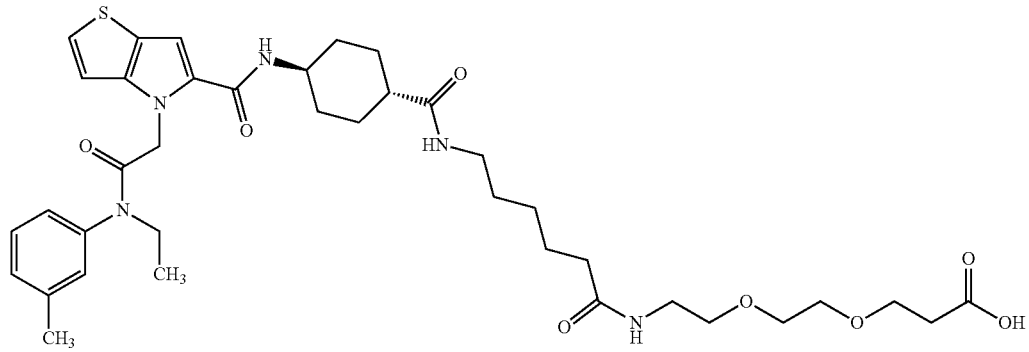 [SMILES: CCN(C(=O)Cn1c(C(=O)N[C@H]2CC[C@H](C(=O)NCCCCCC(=O)NCCOCCOCCC(=O)O)CC2)cc2sccc21)c1cccc(C)c1]

To a solution of tert-butyl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oate (70 mg, 0.088 mmol) in DCM (5 mL), TFA (0.5 mL) was added. The solution stirred at RT for 18 h. The mixture was diluted with toluene, concentrated, resuspended in toluene, and concentrated. This was repeated two times. The crude product was used in the next step. ESI MS m/z 740 [M+1]+.

Step 3. 2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oate (JRW-0520)

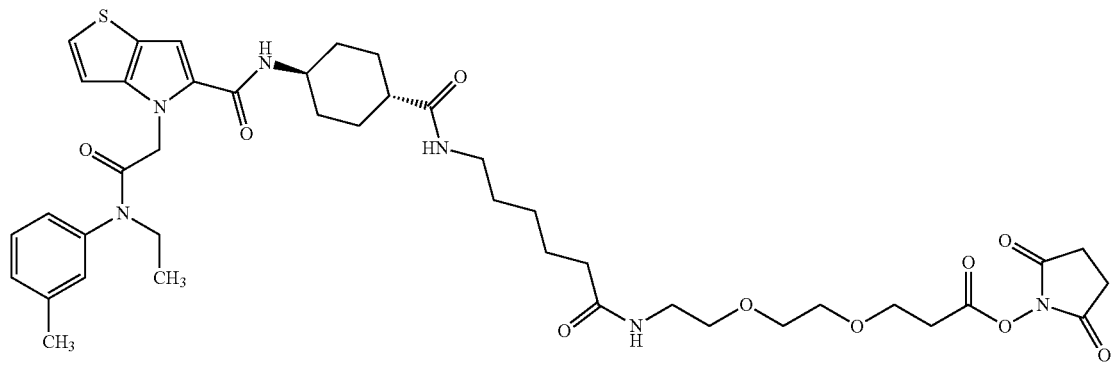 [SMILES: CCN(C(=O)Cn1c(C(=O)N[C@H]2CC[C@H](C(=O)NCCCCCC(=O)NCCOCCOCCC(=O)ON3C(=O)CCC3=O)CC2)cc2sccc21)c1cccc(C)c1]

To a solution of 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oic acid (0.088 mmol) in DCM (5 mL), TSTU (34 mg, 0.11 mmol) and diisopropylethylamine (36 mg, 0.28 mmol) was added. The solution stirred at RT for 2 h. The mixture was diluted with DCM and washed with HCl (1 M). The organic layers were combined, dried with sodium sulfate, filtered, concentrated, and purified with silica gel chromatography to afford the desired product (57 mg, 72%) as a white solid. $^1$H NMR (300 MHz, DMSO-$d_6$) δ 7.92-7.84 (m, 1H), 7.82-7.73 (m, 1H), 7.70-7.62 (m, 1H), 7.45-7.33 (m, 2H), 7.33-7.16 (m, 3H), 7.11-7.05 (s, 2H), 4.96 (s, 2H), 3.74-3.55 (m, 5H), 3.55-3.44 (m, 4H), 3.41-3.33 (m, 2H), 3.20-3.11 (m, 2H), 3.04-2.94 (m, 2H), 2.90 (t, J=6.0, 2H), 2.78 (s, 4H), 2.36 (s, 3H), 2.10-1.98 (m, 3H), 1.88-1.68 (m, 4H), 1.53-1.13 (m, 10H), 1.05-0.95 (m, 3H); ESI MS m/z 837 [M+H]+; HPLC 99.4% (AUC), $T_R$ 5.58 min; UV (MeOH) λ 289 nm, ε 25408.

Example 9

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oate (JRW-0525)

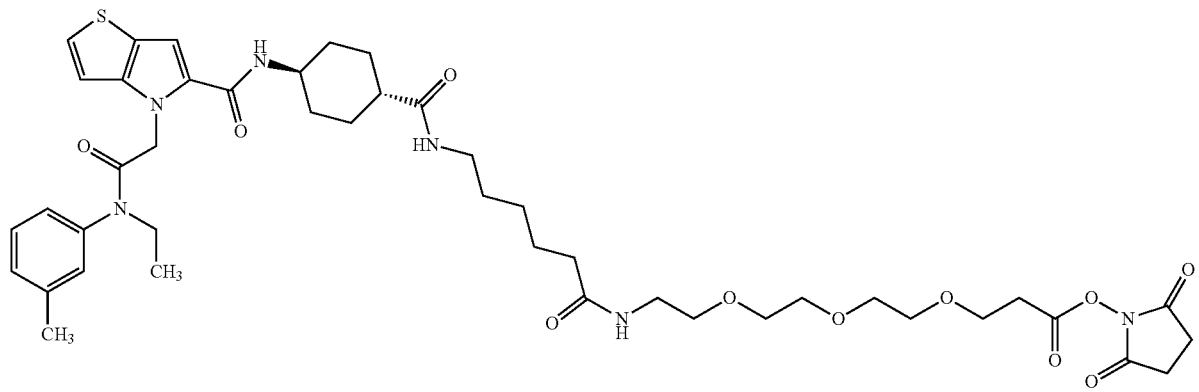 [SMILES: CCN(C(=O)Cn1c(C(=O)N[C@H]2CC[C@H](C(=O)NCCCCCC(=O)NCCOCCOCCOCCC(=O)ON3C(=O)CCC3=O)CC2)cc2sccc21)c1cccc(C)c1]

Step 1. tert-butyl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oate (JRW-0522)

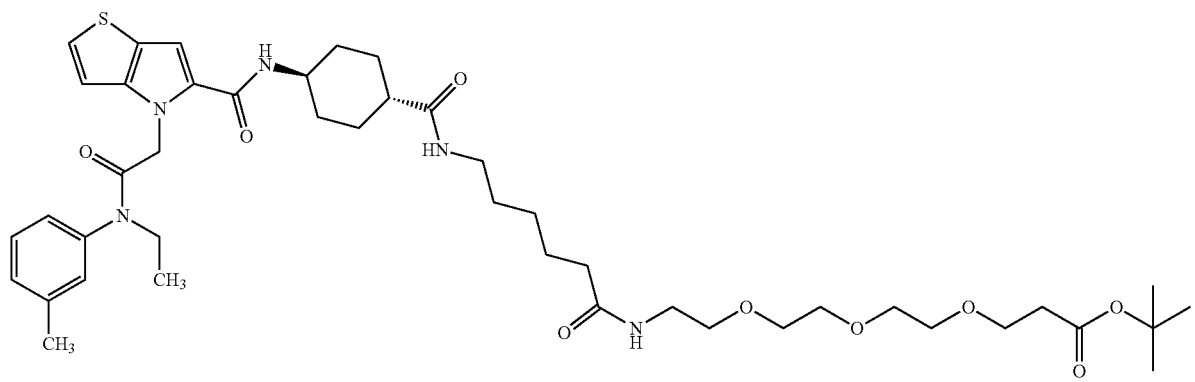 [SMILES: CCN(C(=O)Cn1c(C(=O)N[C@H]2CC[C@H](C(=O)NCCCCCC(=O)NCCOCCOCCOCCC(=O)OC(C)(C)C)CC2)cc2sccc21)c1cccc(C)c1]

To a solution of 6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid (50 mg, 0.086 mmol) in DMF (3 mL), HOBT (26 mg, 0.17 mmol), EDC (33 mg, 0.17 mmol), diisopropyethylamine (33 mg, 0.26 mmol), and tert-butyl 3-(2-(2-(2-aminoethoxy)ethoxy)ethoxy)propanoate (35 mg, 0.13 mmol) was added. The solution was heated to 60° C. for 2 h. The mixture was diluted with ethyl acetate and washed with water. The organic layers were combined, dried with sodium sulfate, filtered, concentrated, and purified with silica gel chromatography to afford the desired product (97 mg, crude) as a colorless oil. ESI MS m/z 840 [M+1]+.

Step 2. 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oic acid (JRW-0524)

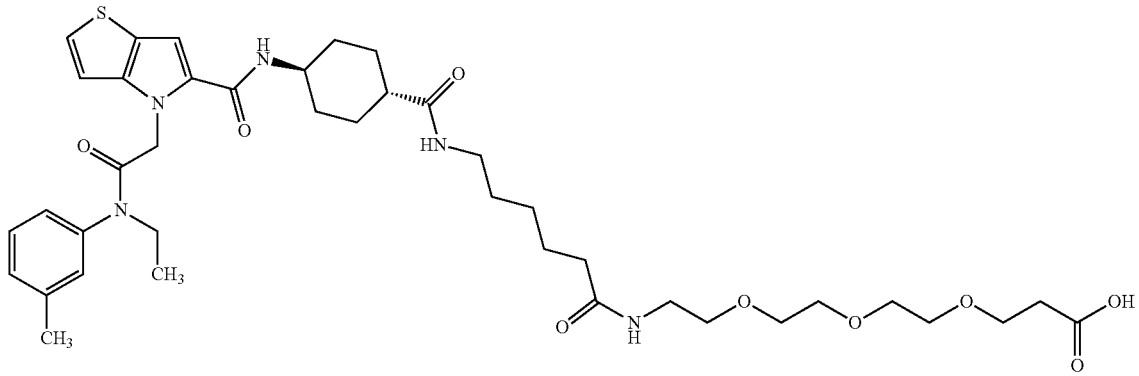 [SMILES: CCN(C(=O)Cn1c(C(=O)N[C@H]2CC[C@H](C(=O)NCCCCCC(=O)NCCOCCOCCOCCC(=O)O)CC2)cc2sccc21)c1cccc(C)c1]

To a solution of tert-butyl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oate (0.086 mmol) in DCM (5 mL), TFA (0.5 mL) was added. The solution stirred at RT for 18 h. The mixture was diluted with toluene, concentrated, resuspended in toluene, and concentrated. This was repeated two times. The crude product was used in the next step. ESI MS m/z 784 [M+H]+.

Step 3. 2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oate (JRW-0525)

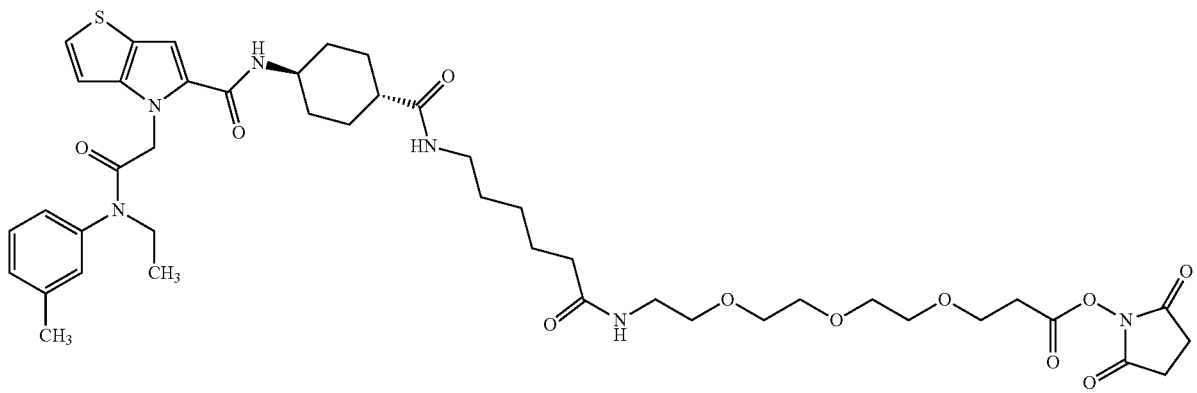 [SMILES: CCN(C(=O)Cn1c(C(=O)N[C@H]2CC[C@H](C(=O)NCCCCCC(=O)NCCOCCOCCOCCC(=O)ON3C(=O)CCC3=O)CC2)cc2sccc21)c1cccc(C)c1]

To a solution of 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oic acid (0.086 mmol) in DCM (10 mL), TSTU (31 mg, 0.10 mmol) and diisopropylethylamine (33 mg, 0.26 mmol) was added. The solution stirred at RT for 1 h. The mixture was diluted with DCM and washed with HCl (1 M). The organic layers were combined, dried with sodium sulfate, filtered, concentrated, and purified with silica gel chromatography to afford the desired product (57 mg, 76%) as a white solid. $^1$H NMR (300 MHz, DMSO-$d_6$) δ 7.87 (d, J=8.2, 1H), 7.83-7.75 (m, 1H), 7.70-7.64 (m, 1H), 7.45-7.34 (m, 2H), 7.32-7.16 (m, 3H), 7.11-7.04 (m, 2H), 4.96 (s, 2H), 3.73-3.55 (m, 5H), 3.55-3.45 (m, 8H), 3.40-3.33 (t, J=5.9, 2H), 3.20-3.11 (m, 2H), 3.03-2.94 (m, 2H), 2.90 (t, J=6.0, 2H), 2.78 (s, 4H), 2.36 (s, 3H), 2.09-1.96 (m, 3H), 1.89-1.68 (m, 4H), 1.52-1.12 (m, 10H), 1.08-0.93 (s, 3H); ESI MS m/z 881 [M+H]+; HPLC 94.9% (AUC), $T_R$ 5.56 min; UV (MeOH) λ 288 nm, ε 26337.

Example 10

2,5-dioxopyrrolidin-1-yl 1-(trans-4-(4-(2-(ethyl)m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate (JRW-0533)

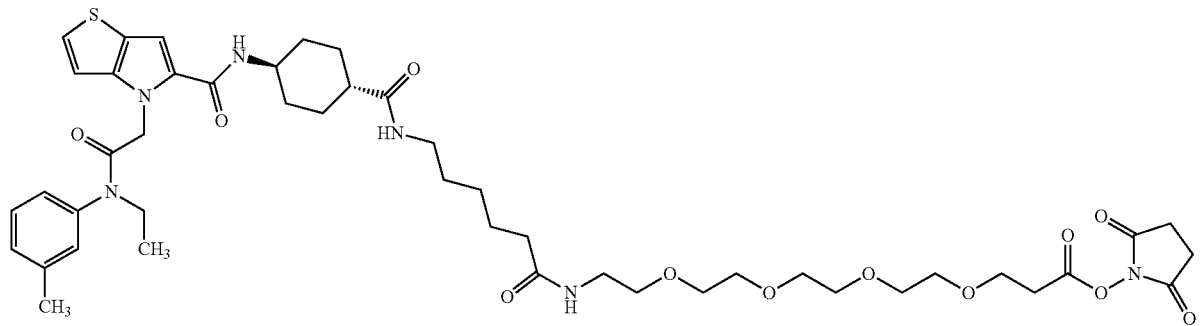 [SMILES: CCN(C(=O)Cn1c(C(=O)N[C@H]2CC[C@H](C(=O)NCCCCCC(=O)NCCOCCOCCOCCOCCC(=O)ON3C(=O)CCC3=O)CC2)cc2sccc21)c1cccc(C)c1]

Step 1. tert-butyl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate (JRW-0529)

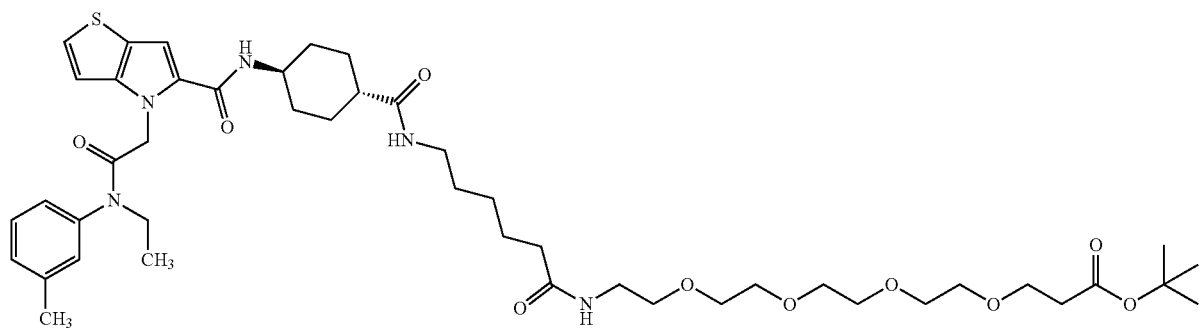 [SMILES: CCN(C(=O)Cn1c(C(=O)N[C@H]2CC[C@H](C(=O)NCCCCCC(=O)NCCOCCOCCOCCOCCC(=O)OC(C)(C)C)CC2)cc2sccc21)c1cccc(C)c1]

To a solution of 6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid (75 mg, 0.13 mmol) in DMF (4 mL), HOBT (40 mg, 0.26 mmol), EDC (49 mg, 0.26 mmol), diisopropyethylamine (50 mg, 0.39 mmol), and tert-butyl 1-amino-3,6,9,12-tetraoxapentadecan-15-oate (62 mg, 0.19 mmol) was added. The solution was heated to 65° C. for 3 h. The mixture was diluted with ethyl acetate and washed with water. The organic layers were combined, dried with sodium sulfate, filtered, concentrated, and purified with silica gel chromatography to afford the desired product (130 mg, crude) as a colorless oil. ESI MS m/z 884 [M+1]+.

Step 2. 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oic acid (JRW-0532)

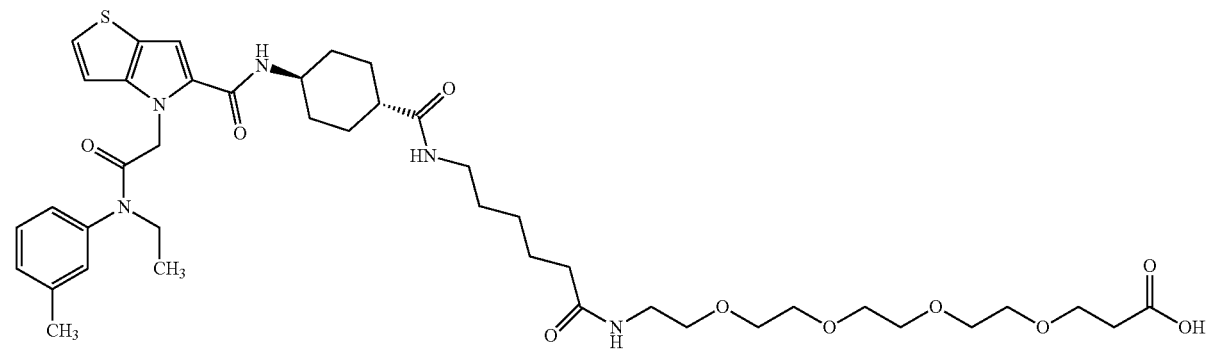 [SMILES: CCN(C(=O)Cn1c(C(=O)N[C@H]2CC[C@H](C(=O)NCCCCCC(=O)NCCOCCOCCOCCOCCC(=O)O)CC2)cc2sccc21)c1cccc(C)c1]

To a solution of tert-butyl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate (0.13 mmol) in DCM (5 mL), TFA (0.5 mL) was added. The solution stirred at RT for 3 h. The mixture was diluted with toluene, concentrated, resuspended in toluene, and concentrated. This was repeated two times. The crude product was used in the next step. ESI MS m/z 828 [M+H]+.

Step 3. 2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate (JRW-0533)

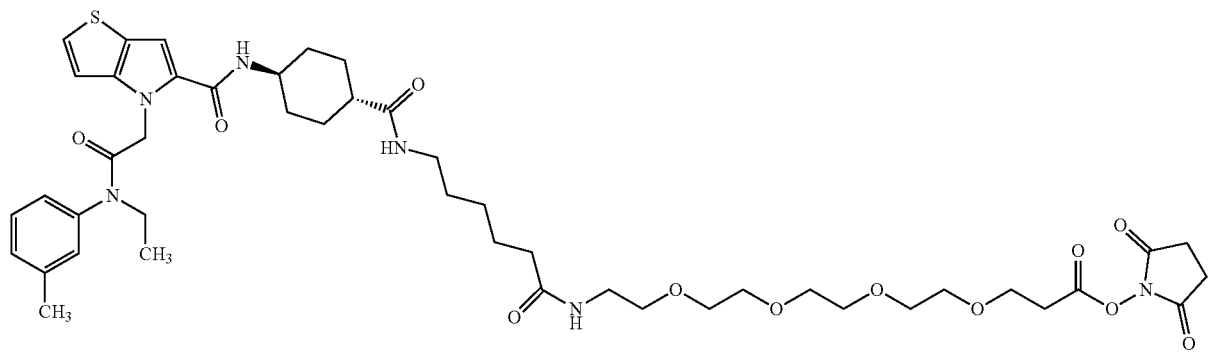 [SMILES: CCN(C(=O)Cn1c(C(=O)N[C@H]2CC[C@H](C(=O)NCCCCCC(=O)NCCOCCOCCOCCOCCC(=O)ON3C(=O)CCC3=O)CC2)cc2sccc21)c1cccc(C)c1]

To a solution of 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oic acid (0.13 mmol) in DCM (5 mL), TSTU (46 mg, 0.15 mmol) and diisopropylethylamine (50 mg, 0.39 mmol) was added. The solution stirred at RT for 30 min. The mixture was diluted with DCM and washed with HCl (1 M). The organic layers were combined, dried with sodium sulfate, filtered, concentrated, and purified with silica gel chromatography to afford the desired product (89 mg, 75%) as a white foam. $^1$H NMR (300 MHz, DMSO-$d_6$) δ 7.87 (d, J=8.1, 1H), 7.83-7.75 (m, 1H), 7.68-7.62 (m, 1H), 7.43-7.34 (m, 2H), 7.33-7.16 (m, 3H), 7.11-7.05 (m, 2H), 4.96 (s, 2H), 3.73-3.55 (m, 5H), 3.55-3.43 (m, 12H), 3.37 (t, J=6.0, 2H), 3.16 (q, J=5.8, 2H), 2.98 (q, J=5.9, 2H), 2.90 (t, J=6.0, 2H), 2.78 (s, 4H), 2.36 (s, 3H), 2.10-1.97 (m, 3H), 1.88-1.68 (s, 4H), 1.53-1.10 (m, 10H), 1.08-0.94 (s, 3H); ESI MS m/z 925 [M+H]+; HPLC 98.5% (AUC), $T_R$ 5.54 min; UV (MeOH) λ 288 nm, ε 26726.

Example 11

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oate (JRW-0544)

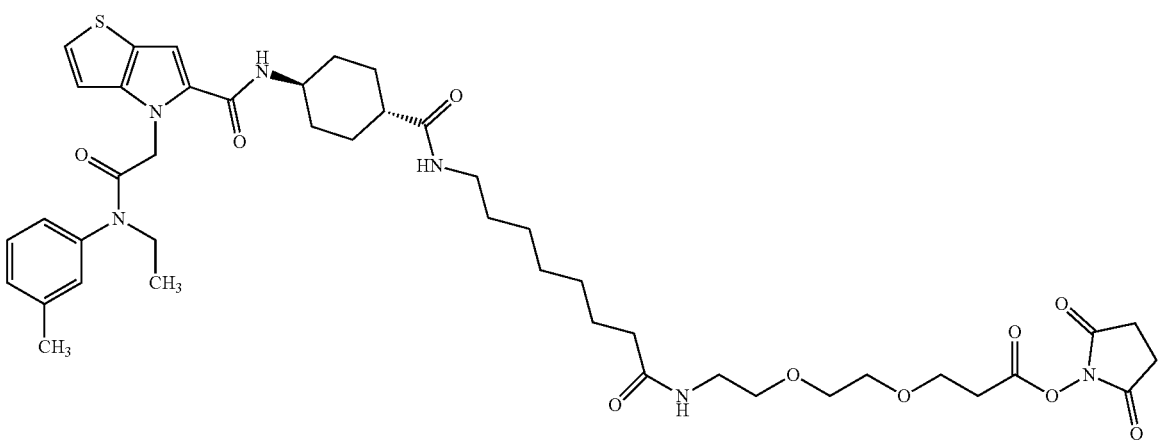 [SMILES: CCN(C(=O)Cn1c(C(=O)N[C@H]2CC[C@H](C(=O)NCCCCCCCC(=O)NCCOCCOCCC(=O)ON3C(=O)CCC3=O)CC2)cc2sccc21)c1cccc(C)c1]

Step 1. tert-butyl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oate (JRW-0536)

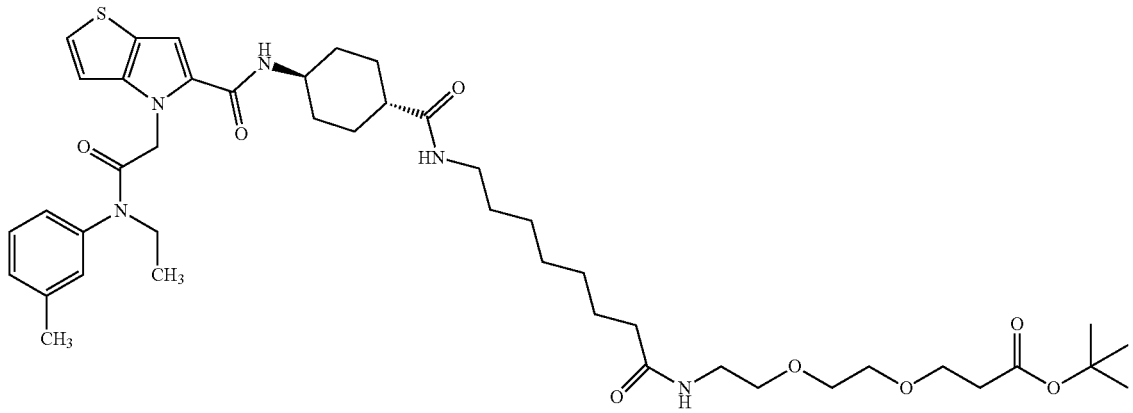 [SMILES: CCN(C(=O)Cn1c(C(=O)N[C@H]2CC[C@H](C(=O)NCCCCCCCC(=O)NCCOCCOCCC(=O)OC(C)(C)C)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (50 mg, 0.082 mmol) in DMF (3 mL), HOBT (25 mg, 0.16 mmol), EDC (31 mg, 0.16 mmol), diisopropyethylamine (31 mg, 0.12 mmol), and tert-butyl 3-(2-(2-aminoethoxy)ethoxy)propanoate (29 mg, 0.12 mmol) was added. The solution was heated to 65° C. for 3 h. The mixture was diluted with ethyl acetate and washed with water. The organic layers were combined, dried with sodium sulfate, filtered, concentrated, and purified with silica gel chromatography to afford the desired product (40 mg, 60%) as a colorless oil. ESI MS m/z 824 [M+1]+.

Step 2. 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oic acid (JRW-0540)

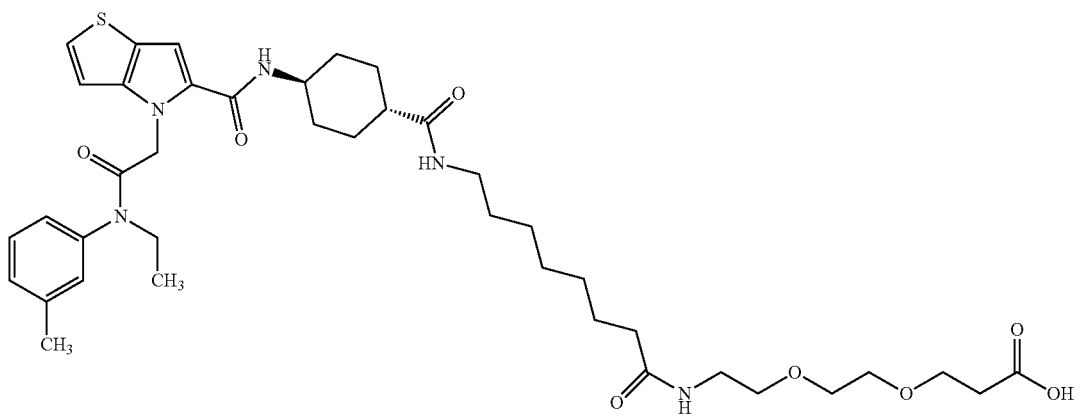 [SMILES: CCN(C(=O)Cn1c(C(=O)N[C@H]2CC[C@H](C(=O)NCCCCCCCC(=O)NCCOCCOCCC(=O)O)CC2)cc2sccc21)c1cccc(C)c1]

To a solution of tert-butyl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oate (40 mg, 0.048 mmol) in DCM (5 mL), TFA (1 mL) was added. The solution stirred at RT for 2 h. The mixture was diluted with toluene, concentrated, resuspended in toluene, and concentrated. This was repeated two times. The crude product was used in the next step. ESI MS m/z 768 [M+H]+.

Step 3. 2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oate (JRW-0544)

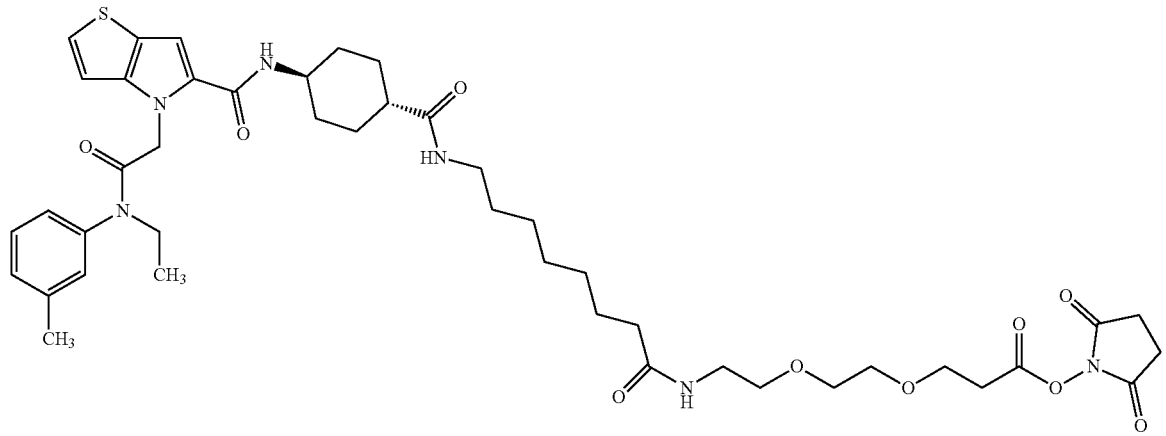 [SMILES: CCN(C(=O)Cn1c(C(=O)N[C@H]2CC[C@H](C(=O)NCCCCCCCC(=O)NCCOCCOCCC(=O)ON3C(=O)CCC3=O)CC2)cc2sccc21)c1cccc(C)c1]

To a solution of 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oic acid (39 mg, 0.051 mmol) in DCM (5 mL), TSTU (23 mg, 0.076 mmol) and diisopropylethylamine (20 mg, 0.15 mmol) was added. The solution stirred at RT for 1 h. The mixture was diluted with DCM and washed with HCl (1 M). The organic layers were combined, dried with sodium sulfate, filtered, concentrated, and purified with silica gel chromatography to afford the desired product (34 mg, 79%) as a white foam. $^1$H NMR (300 MHz, DMSO-$d_6$) δ 7.95-7.86 (m, 1H), 7.85-7.76 (m, 1H), 7.74-7.65 (m, 1H), 7.46-7.37 (m, 2H), 7.34-7.20 (m, 3H), 7.14-7.06 (m, 2H), 4.99 (s, 2H), 3.76-3.57 (m, 5H), 3.58-3.45 (m, 4H), 3.42-3.35 (m, 2H), 3.18 (q, J=5.8, 2H), 3.06-2.97 (m, 2H), 2.92 (t, J=5.9, 2H), 2.81 (s, 4H), 2.39 (s, 3H), 2.11-1.99 (m, 3H), 1.91-1.70 (m, 4H), 1.54-1.15 (m, 14H), 1.10-0.95 (m, 3H); ESI MS m/z 865 [M+H]+; HPLC 96.7% (AUC), $T_R$ 5.81 min; UV (MeOH) λ 288 nm, ε 23742.

Example 12

2,5-dioxopyrrolidin-1-yl 1-((1r,4r)-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oate (JRW-0545)

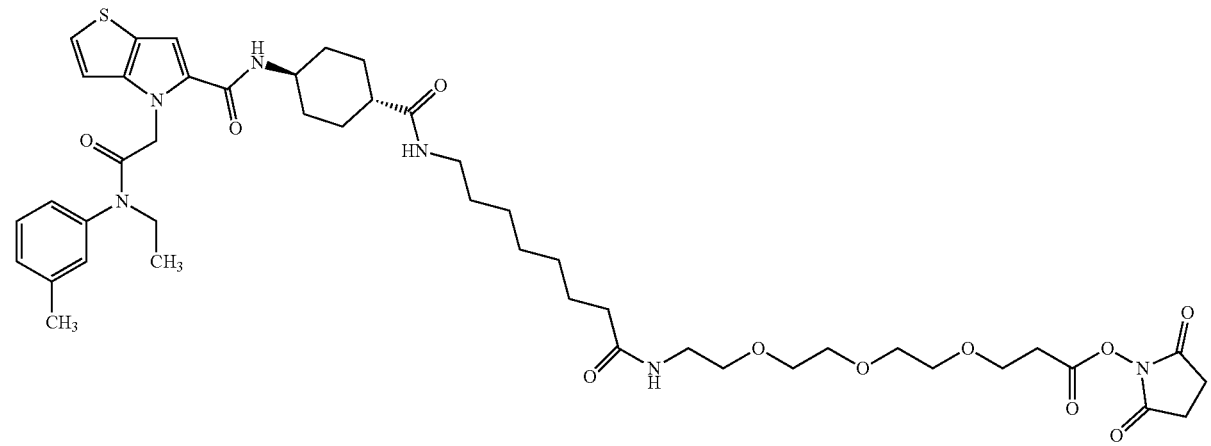 [SMILES: CCN(C(=O)Cn1c(C(=O)N[C@H]2CC[C@H](C(=O)NCCCCCCCC(=O)NCCOCCOCCOCCC(=O)ON3C(=O)CCC3=O)CC2)cc2sccc21)c1cccc(C)c1]

Step 1. tert-butyl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oate (JRW-0537)

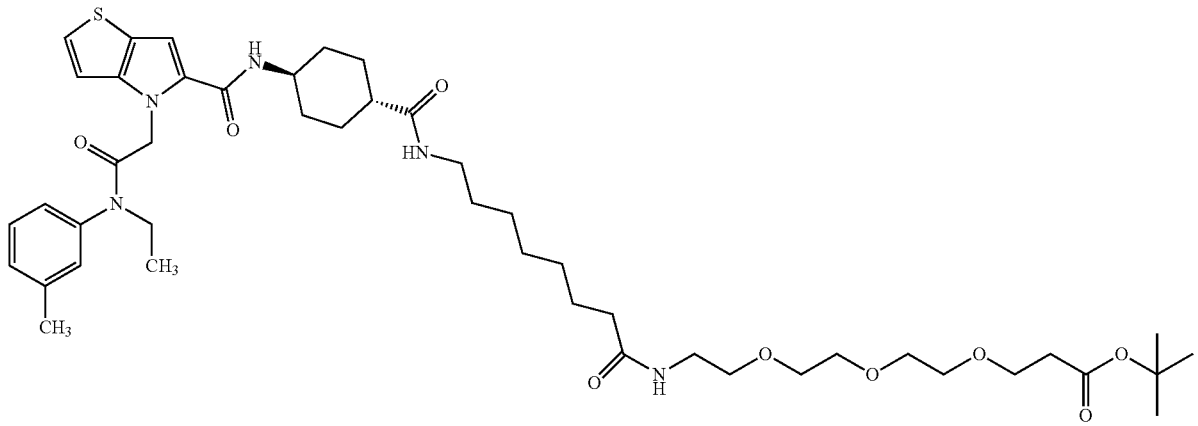 [SMILES: CCN(C(=O)Cn1c(C(=O)N[C@H]2CC[C@H](C(=O)NCCCCCCCC(=O)NCCOCCOCCOCCC(=O)OC(C)(C)C)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (54 mg, 0.088 mmol) in DMF (4 mL), HOBT (27 mg, 0.17 mmol), EDC (34 mg, 0.17 mmol), diisopropyethylamine (23 mg, 0.26 mmol), and tert-butyl 3-(2-(2-(2-aminoethoxy)ethoxy)ethoxy)propanoate (37 mg, 0.13 mmol) was added. The solution was heated to 60° C. for 3 h. The mixture was diluted with ethyl acetate and washed with water. The organic layers were combined, dried with sodium sulfate, filtered, concentrated, and purified with silica gel chromatography to afford the desired product (51 mg, 66%) as a white foam. ESI MS m/z 868 [M+1]+.

Step 2. 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oic acid (JRW-0541)

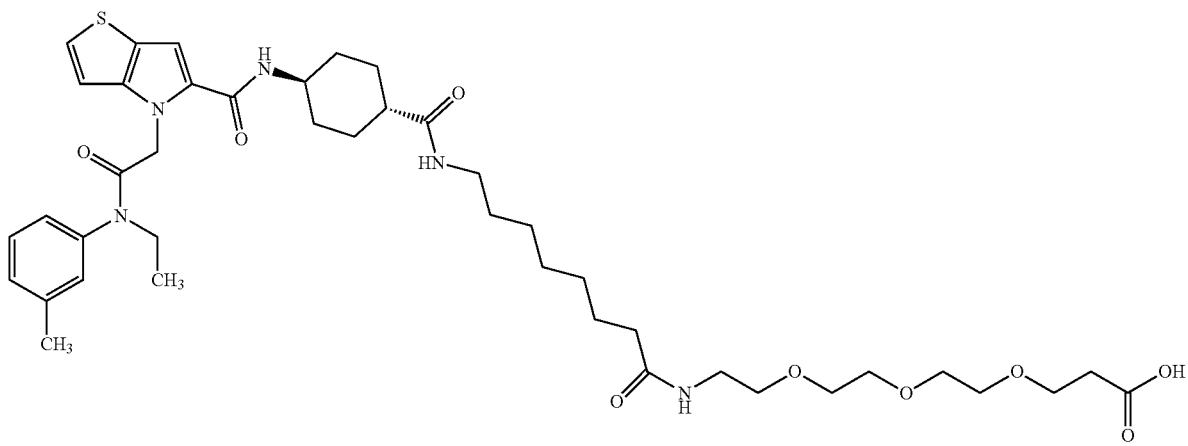 [SMILES: CCN(C(=O)Cn1c(C(=O)N[C@H]2CC[C@H](C(=O)NCCCCCCCC(=O)NCCOCCOCCOCCC(=O)O)CC2)cc2sccc21)c1cccc(C)c1]

To a solution of tert-butyl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oate (51 mg, 0.058 mmol) in DCM (5 mL), TFA (1 mL) was added. The solution stirred at RT for 2 h. The mixture was diluted with toluene, concentrated, resuspended in toluene, and concentrated. This was repeated two times. The crude product was used in the next step. ESI MS m/z 812 [M+H]+.

Step 3. 2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oate (JRW-0545)

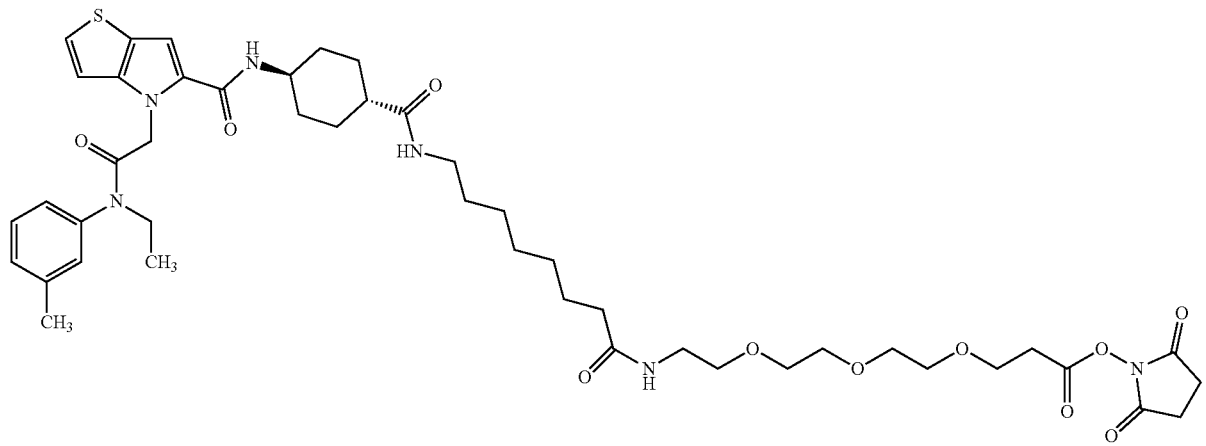 [SMILES: CCN(C(=O)Cn1c(C(=O)N[C@H]2CC[C@H](C(=O)NCCCCCCCC(=O)NCCOCCOCCOCCC(=O)ON3C(=O)CCC3=O)CC2)cc2sccc21)c1cccc(C)c1]

To a solution of 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oic acid (50 mg, 0.061 mmol) in DCM (5 mL), TSTU (28 mg, 0.092 mmol) and diisopropylethylamine (23 mg, 0.18 mmol) was added. The solution stirred at RT for 2 h. The mixture was diluted with DCM and washed with HCl (1 M). The organic layers were combined, dried with sodium sulfate, filtered, concentrated, and purified with silica gel chromatography to afford the desired product (45 mg, 80%) as a white foam. $^1$H NMR (300 MHz, DMSO-$d_6$) δ 7.97-7.87 (m, 1H), 7.87-7.78 (m, 1H), 7.75-7.65 (m, 1H), 7.48-7.37 (m, 2H), 7.36-7.20 (m, 3H), 7.15-7.07 (m, 2H), 4.99 (s, 2H), 3.76-3.58 (m, 5H), 3.57-3.45 (m, 8H), 3.43-3.35 (m, 2H), 3.18 (d, J=5.8, 2H), 3.06-2.97 (s, 2H), 2.93 (t, J=6.0, 2H), 2.81 (s, 4H), 2.39 (s, 3H), 2.11-1.99 (s, 3H), 1.92-1.66 (m, 4H), 1.55-1.13 (m, 14H), 1.10-0.95 (s, 3H); ESI MS m/z 909 [M+H]+; HPLC 96.2% (AUC), $T_R$ 5.78 min; UV (MeOH) λ 288 nm, ε 24195.

Example 13

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oate (JRW-0546)

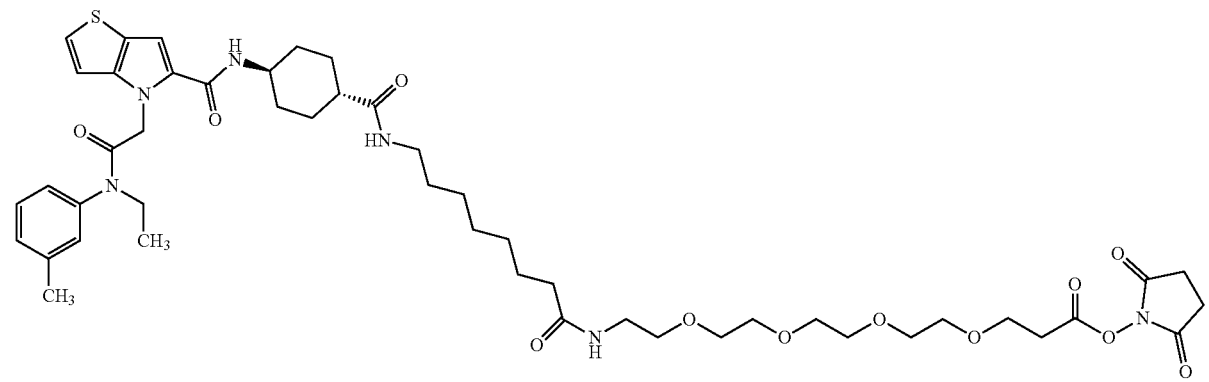 [SMILES: CCN(C(=O)Cn1c(C(=O)N[C@H]2CC[C@H](C(=O)NCCCCCCCC(=O)NCCOCCOCCOCCOCCC(=O)ON3C(=O)CCC3=O)CC2)cc2sccc21)c1cccc(C)c1]

Step 1. tert-butyl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oate (JRW-0539)

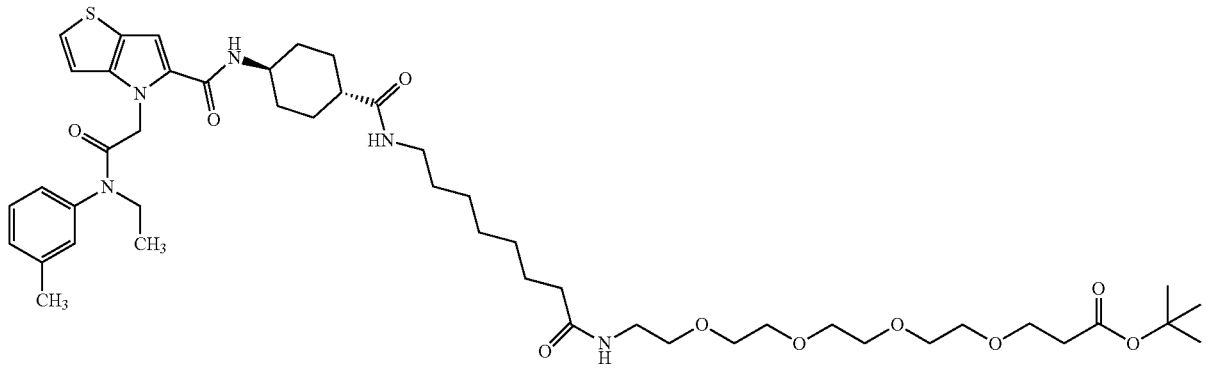 [SMILES: CCN(C(=O)Cn1c(C(=O)N[C@H]2CC[C@H](C(=O)NCCCCCCCC(=O)NCCOCCOCCOCCOCCC(=O)OC(C)(C)C)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (50 mg, 0.082 mmol) in DMF (3 mL), HOBT (25 mg, 0.16 mmol), EDC (31 mg, 0.16 mmol), diisopropyethylamine (31 mg, 0.24 mmol), and tert-butyl 1-amino-3,6,9,12-tetraoxapentadecan-15-oate (39 mg, 0.12 mmol) was added. The solution was heated to 60° C. for 3 h. The mixture was diluted with ethyl acetate and washed with water. The organic layers were combined, dried with sodium sulfate, filtered, concentrated, and purified with silica gel chromatography to afford the desired product (50 mg, 66%) as a clear oil. ESI MS m/z 912 [M+1]+.

Step 2. 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oic acid (JRW-0542)

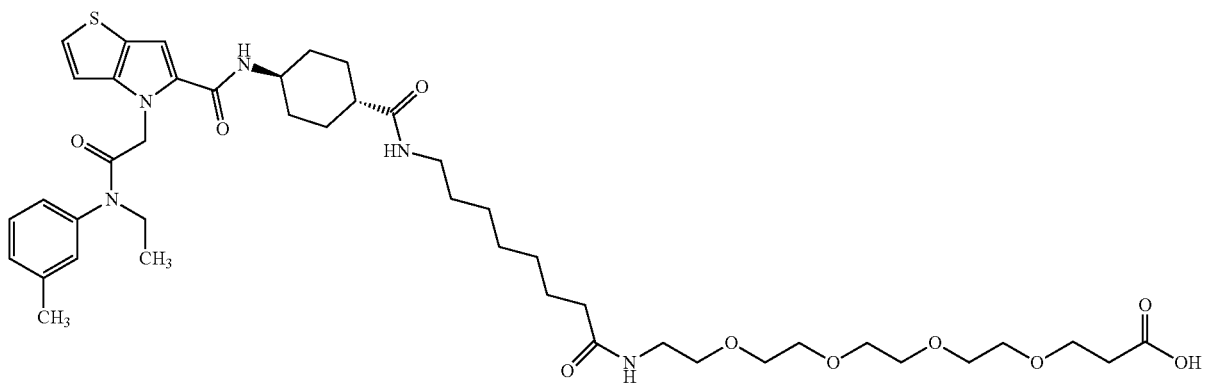 [SMILES: CCN(C(=O)Cn1c(C(=O)N[C@H]2CC[C@H](C(=O)NCCCCCCCC(=O)NCCOCCOCCOCCOCCC(=O)O)CC2)cc2sccc21)c1cccc(C)c1]

To a solution of tert-butyl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oate (50 mg, 0.054 mmol) in DCM (5 mL), TFA (1 mL) was added. The solution stirred at RT for 2 h. The mixture was diluted with toluene, concentrated, resuspended in toluene, and concentrated. This was repeated two times. The crude product was used in the next step. ESI MS m/z 856 [M+H]+.

Step 3. 2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oate (JRW-0546)

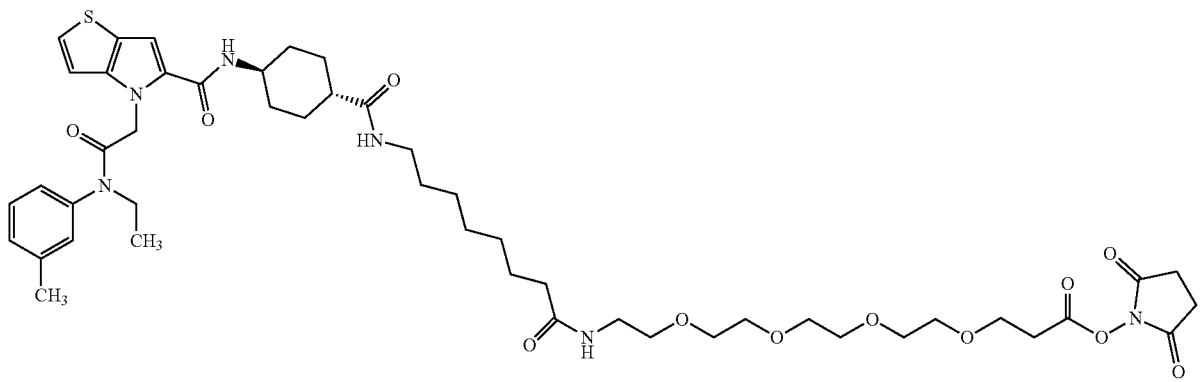 [SMILES: CCN(C(=O)Cn1c(C(=O)N[C@H]2CC[C@H](C(=O)NCCCCCCCC(=O)NCCOCCOCCOCCOCCC(=O)ON3C(=O)CCC3=O)CC2)cc2sccc21)c1cccc(C)c1]

To a solution of 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oic acid (50 mg, 0.058 mmol) in DCM (5 mL), TSTU (26 mg, 0.087 mmol) and diisopropylethylamine (23 mg, 0.18 mmol) was added. The solution stirred at RT for 2 h. The mixture was diluted with DCM and washed with HCl (1 M). The organic layers were combined, dried with sodium sulfate, filtered, concentrated, and purified with silica gel chromatography to afford the desired product (42 mg, 76%) as a white foam. $^1$H NMR (300 MHz, DMSO-$d_6$) δ 7.95-7.88 (m, 1H), 7.88-7.79 (m, 1H), 7.75-7.67 (m, 1H), 7.47-7.36 (m, 2H), 7.36-7.21 (m, 3H), 7.15-7.07 (m, 2H), 4.99 (s, 2H), 3.76-3.57 (m, 5H), 3.56-3.46 (m, 12H), 3.42-3.36 (m, 2H), 3.18 (q, J=5.8, 2H), 3.07-2.97 (m, 2H), 2.93 (t, J=6.0, 2H), 2.81 (s, 4H), 2.39 (s, 3H), 2.11-1.98 (m, 3H), 1.90-1.70 (m, 4H), 1.55-1.14 (m, 14H), 1.08-0.95 (m, 3H); ESI MS m/z 909 [M+H]+; HPLC 96.2% (AUC), $T_R$ 5.78 min; UV (MeOH) λ 288 nm, ε 24195.

Example 14

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oate (JRW-0561)

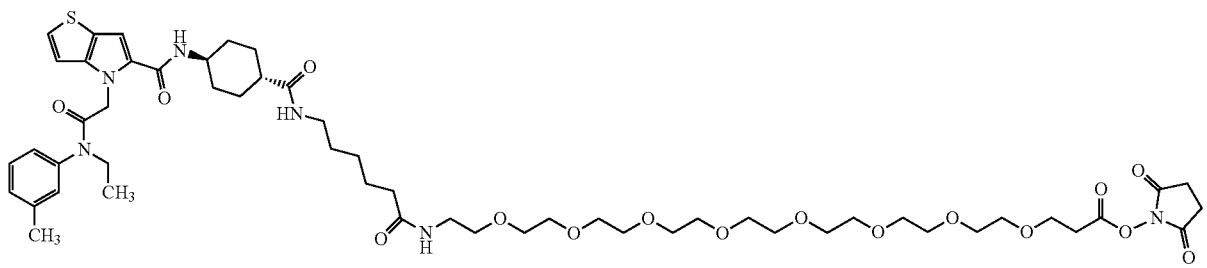 [SMILES: CCN(C(=O)Cn1c(C(=O)N[C@H]2CC[C@H](C(=O)NCCCCCC(=O)NCCOCCOCCOCCOCCOCCOCCOCCOCCC(=O)ON3C(=O)CCC3=O)CC2)cc2sccc21)c1cccc(C)c1]

Step 1. tert-butyl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oate (JRW-0557)

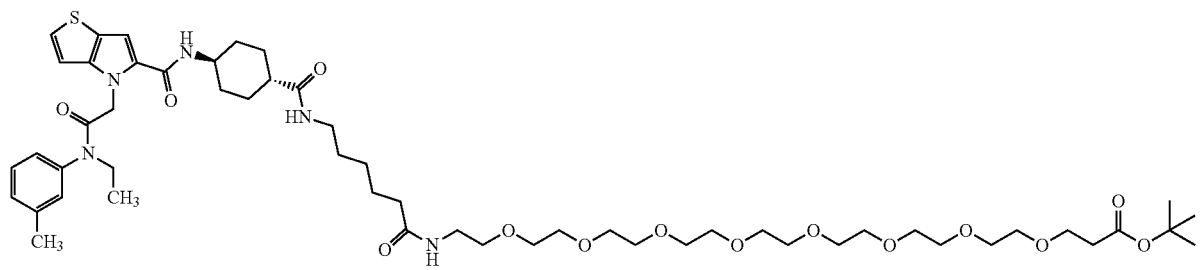 [SMILES: CCN(C(=O)Cn1c(C(=O)N[C@H]2CC[C@H](C(=O)NCCCCCC(=O)NCCOCCOCCOCCOCCOCCOCCOCCOCCC(=O)OC(C)(C)C)CC2)cc2sccc21)c1cccc(C)c1]

To a solution of 6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid (50 mg, 0.086 mmol) in DMF (4 mL), HOBT (26 mg, 0.17 mmol), EDC (33 mg, 0.17 mmol), diisopropyethylamine (33 mg, 0.26 mmol), and tert-butyl 1-amino-3,6,9,12,15,18,21,24-octaoxaheptacosan-27-oate (64 mg, 0.13 mmol) was added. The solution was heated to 60° C. for 2 h. The mixture was diluted with ethyl acetate and washed with water. The organic layers were combined, dried with sodium sulfate, filtered, concentrated, and purified with silica gel chromatography to afford the desired product (66 mg, 72%) as a clear oil. ESI MS m/z 1060 [M+H]+.

Step 2. 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oic acid (JRW-0560)

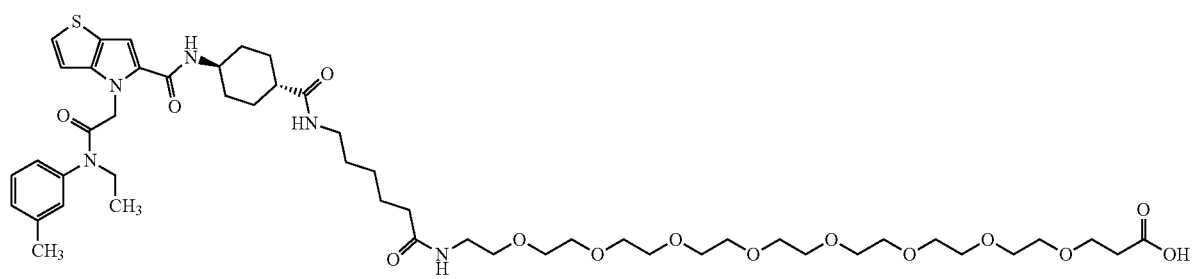 [SMILES: CCN(C(=O)Cn1c(C(=O)N[C@H]2CC[C@H](C(=O)NCCCCCC(=O)NCCOCCOCCOCCOCCOCCOCCOCCOCCC(=O)O)CC2)cc2sccc21)c1cccc(C)c1]

To a solution of tert-butyl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oate (66 mg, 0.062 mmol) in DCM (5 mL), TFA (1 mL) was added. The solution stirred at RT for 2 h. The mixture was diluted with toluene, concentrated, resuspended in toluene, and concentrated. This was repeated two times. The crude product was used in the next step. ESI MS m/z 1004 [M+H]+.

Step 3. 2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oate (JRW-0561)

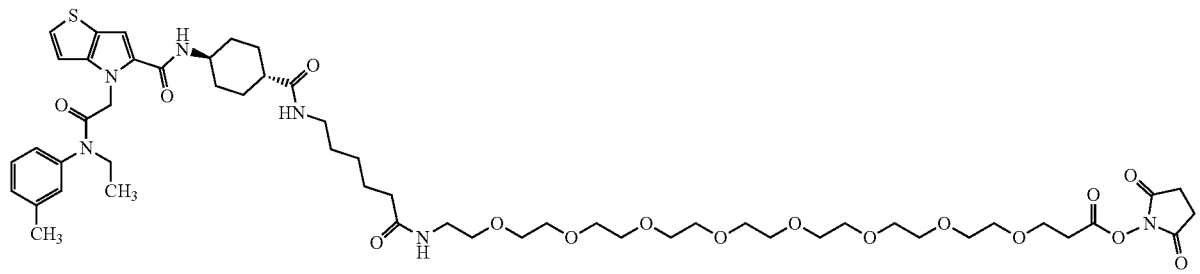 [SMILES: CCN(C(=O)Cn1c(C(=O)N[C@H]2CC[C@H](C(=O)NCCCCCC(=O)NCCOCCOCCOCCOCCOCCOCCOCCOCCC(=O)ON3C(=O)CCC3=O)CC2)cc2sccc21)c1cccc(C)c1]

To a solution of 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oic acid (62 mg, 0.062 mmol) in DCM (10 mL), TSTU (28 mg, 0.093 mmol) and diisopropylethylamine (24 mg, 0.19 mmol) was added. The solution stirred at RT for 2 h. The mixture was diluted with DCM and washed with HCl (1 M). The organic layers were combined, dried with sodium sulfate, filtered, concentrated, and purified with silica gel chromatography to afford the desired product (64 mg, 94%) as a light orange wax. $^1$H NMR (300 MHz, DMSO-$d_6$) δ 7.95-7.83 (m, 1H), 7.83-7.73 (m, 1H), 7.70-7.60 (m, 1H), 7.45-7.34 (m, 2H), 7.33-7.14 (m, 3H), 7.11-7.05 (m, 2H), 4.96 (s, 2H), 3.75-3.55 (s, 5H), 3.55-3.41 (m, 24H), 3.40-3.33 (m, 2H), 3.20-3.12 (m, 2H), 3.03-2.94 (m, 2H), 2.92-2.86 (m, 2H), 2.79 (s, 4H), 2.36 (s, 3H), 2.08-1.94 (m, 3H), 1.88-1.68 (m, 4H), 1.51-1.11 (m, 10H), 1.05-0.95 (m, 3H); ESI MS m/z 1101 [M+H]+; HPLC 94.5% (AUC), $T_R$ 5.93 min; UV (MeOH) λ 288 nm, ε 26186.

Example 15

N-(trans-4-((6-(3-(2,5-dioxo-2,5-dihydro-1H-pyrrol-1-yl)propanamido)hexyl)carbamoyl)cyclohexyl)-4-(2-(ethyl)m-tolyl)amino)-2-oxoethyl)-4H-thieno[3,2-b]pyrrole-5-carboxamide (JRW-0558)

To a solution of N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide (50 mg, 0.088 mmol) in DMF (4 mL), HOBT (27 mg, 0.18 mmol), EDC (34 mg, 0.18 mmol), diisopropylethylamine (34 mg, 0.26 mmol), and 3-(2,5-dioxo-2,5-dihydro-1H-pyrrol-1-yl)propanoic acid (22 mg, 0.13 mmol) was added. The solution was heated to 60° C. for 1 h. The mixture was diluted with ethyl acetate and washed with water. The organic layers were combined, dried with sodium sulfate, filtered, concentrated, and purified with silica gel chromatography to afford the desired product (33 mg, 52%) as a white solid. $^1$N NMR (300 MHz, DMSO-$d_6$) δ 7.95-7.84 (m, 2H), 7.72-7.64 (m, 1H), 7.45-7.34 (m, 2H), 7.33-7.17 (m, 3H), 7.11-7.05 (m, 2H), 6.99 (s, 2H), 4.96 (s, 2H), 3.74-3.48 (m, 5H), 3.05-2.89 (m, 4H), 2.36 (s, 3H), 2.29 (t, J=7.2, 2H), 2.12-1.94 (m, 1H), 1.89-1.68 (m, 4H), 1.52-1.15 (m, 12H), 1.08-0.95 (m, 3H); ESI MS m/z 717 [M+H]+; HPLC 98.5% (AUC), $T_R$ 5.63 min; UV (MeOH) λ 289 nm, ε 25000.

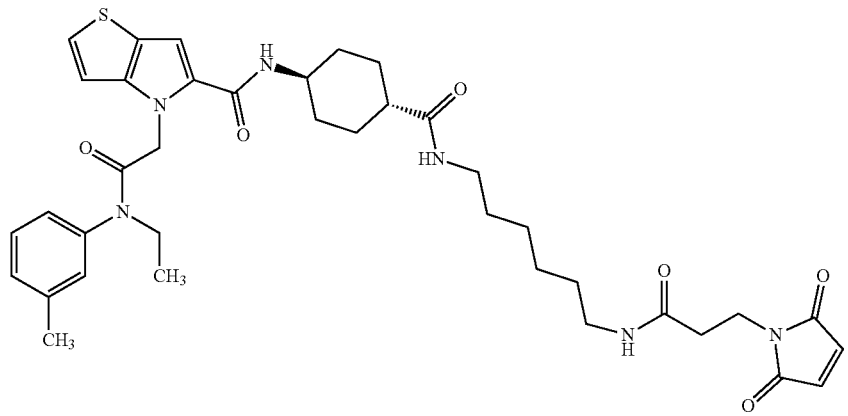 [SMILES: CCN(C(=O)Cn1c(C(=O)N[C@H]2CC[C@H](C(=O)NCCCCCCNC(=O)CCN3C(=O)C=CC3=O)CC2)cc2sccc21)c1cccc(C)c1]

Example 16

N-(trans-4-((1-(2,5-dioxo-2,5-dihydro-1H-pyrrol-1-yl)-3,13-dioxo-7,10-dioxa-4,14-diazaicosan-20-yl)carbamoyl)cyclohexyl)-4-(2-(ethyl)m-tolyl)amino)-2-oxoethyl)-4H-thieno[3,2-b]pyrrole-5-carboxamide (JRW-0559)

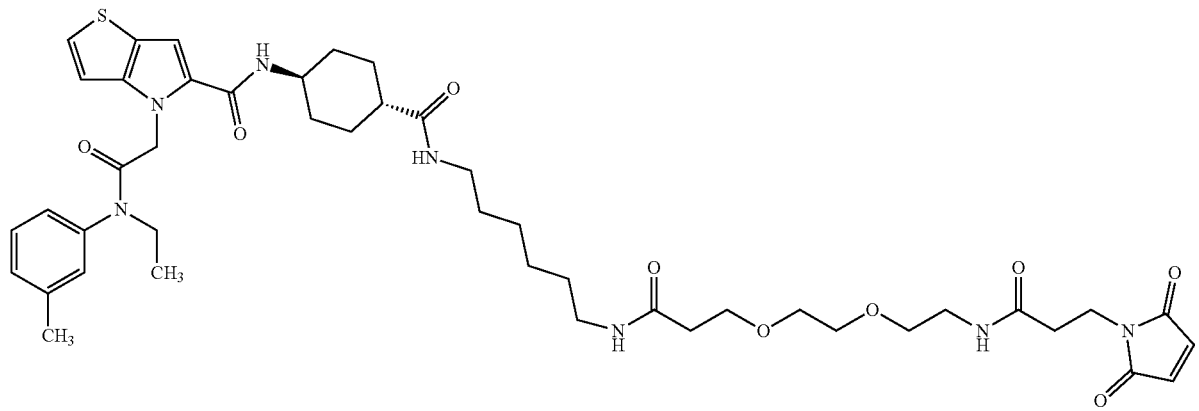 [SMILES: CCN(C(=O)Cn1c(C(=O)N[C@H]2CC[C@H](C(=O)NCCCCCCNC(=O)CCOCCOCCNC(=O)CCN3C(=O)C=CC3=O)CC2)cc2sccc21)c1cccc(C)c1]

To a solution of N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide (50 mg, 0.088 mmol) in DMF (4 mL), HOBT (27 mg, 0.18 mmol), EDC (34 mg, 0.18 mmol), diisopropyethylamine (34 mg, 0.26 mmol), and 3-(2-(2-(3-(2,5-dioxo-2,5-dihydro-1H-pyrrol-1-yl)propanamido)ethoxy)ethoxy)propanoic acid (43 mg, 0.13 mmol) was added. The solution was heated to 60° C. for 1 h. The mixture was diluted with ethyl acetate and washed with water. The organic layers were combined, dried with sodium sulfate, filtered, concentrated, and purified with silica gel chromatography to afford the desired product (32 mg, 41%) as a white foam. $^1$H NMR (300 MHz, DMSO-$d_6$) δ 8.07-7.95 (m, 1H), 7.94-7.84 (m, 1H), 7.84-7.73 (m, 1H), 7.73-7.60 (m, 1H), 7.46-7.35 (m, 2H), 7.33-7.18 (m, 3H), 7.12-7.05 (m, 2H), 6.98 (s, 2H), 4.96 (s, 2H), 3.70-3.53 (m, 7H), 3.47-3.42 (m, 4H), 3.12 (q, J=5.7, 2H), 3.05-2.94 (m, 4H), 2.36 (s, 3H), 2.34-2.23 (m, 4H), 2.11-1.96 (m, 1H), 1.91-1.65 (m, 4H), 1.51-1.15 (m, 12H), 1.05-0.95 (m, 3H); ESI MS m/z 876 [M+H]+; HPLC 87.9% (AUC), $T_R$ 5.23 min; UV (MeOH) λ 288 nm, ε 23840.

Example 17 methyl trans-4-(4-(2-((3-(bromomethyl)phenyl)(ethyl)amino)-2-oxoethyl)-4H-thieno[3,2-b]pyrrole-5-carboxamido)cyclohexane-1-carboxylate (JRW-0466)

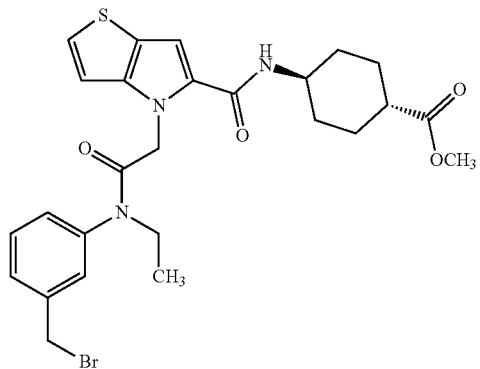 [SMILES: CCN(C(=O)Cn1c(C(=O)N[C@H]2CC[C@H](C(=O)OC)CC2)cc2sccc21)c1cccc(CBr)c1]

The title compound was prepared using the synthesis method described in U.S. patent application Ser. No. 15/192,420, which is incorporated by reference herein in its entirety.

Example 18 methyl trans-4-(4-(2-((3-(3-bromopropyl)phenyl)(ethyl)amino)-2-oxoethyl)-4H-thieno[3,2-b]pyrrole-5-carboxamido)cyclohexane-1-carboxylate (JRW-0548)

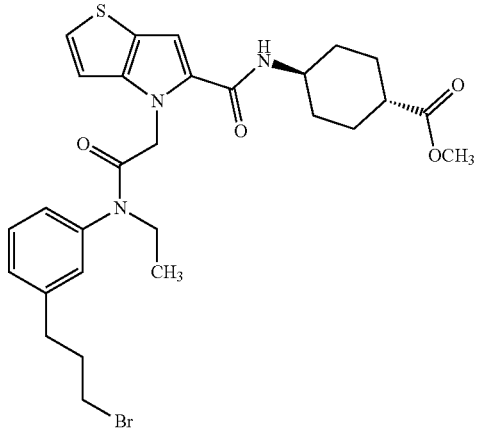 [SMILES: CCN(C(=O)Cn1c(C(=O)N[C@H]2CC[C@H](C(=O)OC)CC2)cc2sccc21)c1cccc(CCCBr)c1]

JRW-0548 may be synthesized according to scheme 3.

Scheme. 3 Synthesis of JRW-0548

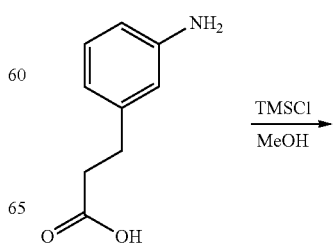

TMSCl / MeOH →

89
-continued
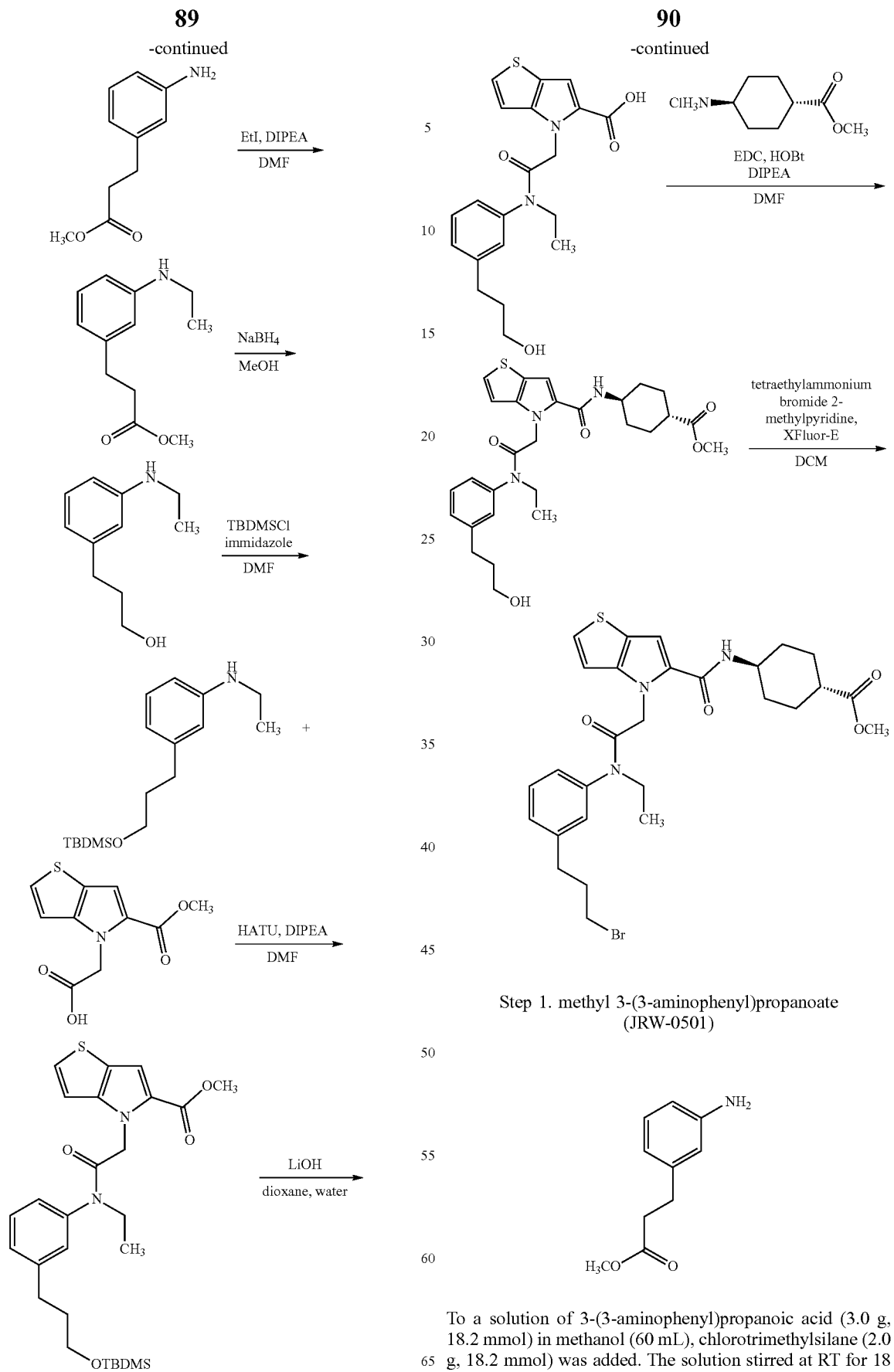
Step 1. methyl 3-(3-aminophenyl)propanoate (JRW-0501)
To a solution of 3-(3-aminophenyl)propanoic acid (3.0 g, 18.2 mmol) in methanol (60 mL), chlorotrimethylsilane (2.0 g, 18.2 mmol) was added. The solution stirred at RT for 18 h. The mixture was concentrated, redissolved in methanol and reconcentrated (2×). The residue was purified with silica gel chromatography to afford the desired product (3.5 g, crude) as a brown solid. ESI MS m/z 180 [M+H]+.

Step 2. methyl 3-(3-(ethylamino)phenyl)propanoate (JRW-0511)

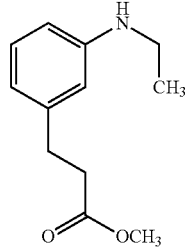

To a solution of methyl 3-(3-aminophenyl)propanoate (1.0 g, 5.6 mmol) in DMF (10 mL), ethyl iodide (0.65 g, 4.2 mmol) and diisopropylamine (2.16 g, 16.7 mmol) was added. The solution was heated to 85° C. in a sealed vessel for 18 h. The mixture was diluted with ethyl acetate and washed with water. The organic layers were combined, dried with sodium sulfate, filtered, concentrated, and purified with silica gel chromatography to afford the desired product (0.48 g, 41%) as a colorless oil. ESI MS m/z 208 [M+H]+.

Step 3. 3-(3-(ethylamino)phenyl)propan-1-ol (JRW-0513)

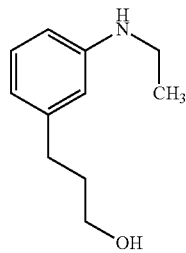

To a solution of methyl 3-(3-(ethylamino)phenyl)propanoate (850 mg, 4.10 mmol) in methanol (10 mL) at 0° C., sodium borohydride (775 mg, 20.5 mmol) was added. The solution stirred at RT for 7 h. The mixture was quenched with NaOH (1 M), diluted with ethyl acetate and washed with water. The organic layers were combined, dried with sodium sulfate, filtered, concentrated, to afford the desired product (750 mg, crude) as a colorless oil. ESI MS m/z 180 [M+H]+.

Step 4. 3-(3-((tert-butyldimethylsilyl)oxy)propyl)-N-ethylaniline (JRW-0514)

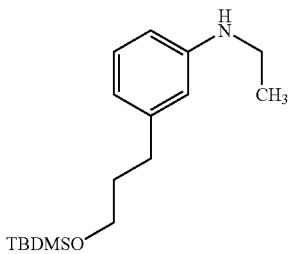 [SMILES: CCNc1cccc(CCCO[Si](C)(C)C(C)(C)C)c1]

To a solution of 3-(3-(ethylamino)phenyl)propan-1-ol (750 mg, 4.2 mmol) in DMF (10 mL) at 0° C., chloro t-butyldimethylsilane (756 mg, 5.0 mmol) and imidazole (561 mg, 8.4 mmol) was added. The solution stirred at RT for 18 h. The mixture was diluted with ethyl acetate and washed with water. The organic layers were combined, dried with sodium sulfate, filtered, concentrated, and purified with silica gel chromatography to afford the desired product (1.02 g, 83%) as a colorless oil. $^1$H NMR (300 MHz, CDCl$_3$) δ 7.03 (t, J=7.4, 1H), 6.49 (d, J=7.8, 1H), 6.43-6.35 (m, 2H), 3.58 (t, J=6.3, 3H), 3.10 (q, J=7.0, 2H), 2.58-2.49 (m, 2H), 1.82-1.70 (m, 2H), 1.25-1.12 (m, 4H), 0.86 (s, 9H), 0.00 (s, 6H); ESI MS m/z 208 [M+H]+.

Step 5. methyl 4-(2-((3-(3-((tert-butyldimethylsilyl)oxy)propyl)phenyl)(ethyl)amino)-2-oxoethyl)-4H-thieno[3,2-b]pyrrole-5-carboxylate (JRW-0516)

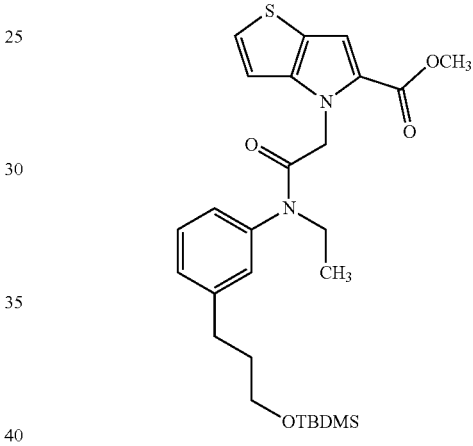

To a solution of 3-(3-((tert-butyldimethylsilyl)oxy)propyl)-N-ethylaniline (135 mg, 0.46 mmol) and 2-(5-(methoxycarbonyl)-4H-thieno[3,2-b]pyrrol-4-yl)acetic acid (100 mg, 0.42 mmol) in DMF (5 mL), HATU (318 mg, 0.84 mmol) and diisopropylethylamine (162 mg, 1.2 mmol) was added. The solution was stirred at 85° C. for 1 h. The mixture was diluted with ethyl acetate and washed with water. The organic layers were combined, dried with sodium sulfate, filtered, concentrated, and purified with silica gel chromatography to afford the desired product (119 mg, 55%) as a light orange solid. $^1$H NMR (300 MHz, CDCl$_3$) δ 7.36-7.28 (m, 1H), 7.25-7.22 (m, 1H), 7.20-7.14 (m, 1H), 7.13-7.05 (m, 3H), 6.74 (d, J=5.4, 1H), 4.91 (s, 2H), 3.81-3.52 (m, 7H), 2.74-2.62 (m, 2H), 1.89-1.73 (m, 2H), 1.06 (t, J=7.1, 3H), 0.85 (s, 9H), 0.00 (s, 6H); ESI MS m/z 515 [M+H]+.

Step 6. 4-(2-(ethyl(3-(3-hydroxypropyl)phenyl) amino)-2-oxoethyl)-4H-thieno[3,2-b]pyrrole-5-carboxylic acid (JRW-0523)

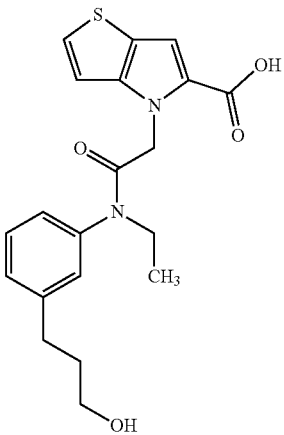 [SMILES: CCN(C(=O)Cn1c(C(=O)O)cc2sccc21)c1cccc(CCCO)c1]

To a solution of methyl 4-(2-((3-(3-((tert-butyldimethylsilyl)oxy)propyl)phenyl)(ethyl)amino)-2-oxoethyl)-4H-thieno[3,2-b]pyrrole-5-carboxylate (110 mg, 0.21 mmol) in dioxane (5 mL) and water (1 mL), lithium hydroxide (26 mg, 1.1 mmol) was added. The mixture stirred at 85° C. for 5 h. The mixture was acidified with HCl (2 M), diluted with ethyl acetate and washed with water. The organic layers were combined, dried with sodium sulfate, filtered, concentrated, to afford the desired product (100 mg, crude) as a light orange glass. ESI MS m/z 387 [M+H]+.

Step 7. methyl trans-4-(4-(2-(ethyl(3-(3-hydroxypropyl)phenyl)amino)-2-oxoethyl)-4H-thieno[3,2-b] pyrrole-5-carboxamido)cyclohexane-1-carboxylate (JRW-0526)

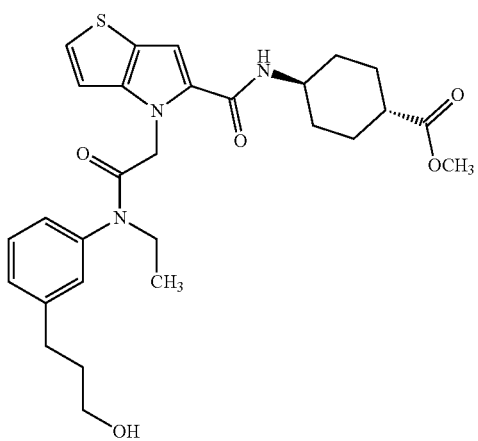 [SMILES: CCN(C(=O)Cn1c(C(=O)N[C@H]2CC[C@H](C(=O)OC)CC2)cc2sccc21)c1cccc(CCCO)c1]

To a solution of 4-(2-(ethyl(3-(3-hydroxypropyl)phenyl) amino)-2-oxoethyl)-4H-thieno[3,2-b]pyrrole-5-carboxylic acid (0.21 mmol) in DMF (5 mL), HOBT (65 mg, 0.43 mmol), EDC (82 mg, 0.43 mmol), diisopropyethylamine (82 mg, 0.64 mmol), and methyl trans-4-aminocyclohexane-1-carboxylate hydrochloride (62 mg, 0.32 mmol) was added. The solution was heated to 65° C. for 18 h. The mixture was diluted with ethyl acetate and washed with water. The organic layers were combined, dried with sodium sulfate, filtered, concentrated, and purified with silica gel chromatography to afford the desired product (110 mg, quant) as a brown foam. ESI MS m/z 526 [M+H]+.

Step 8. methyl trans-4-(4-(2-((3-(3-bromopropyl) phenyl)(ethyl)amino)-2-oxoethyl)-4H-thieno[3,2-b] pyrrole-5-carboxamido)cyclohexane-1-carboxylate (JRW-0548)

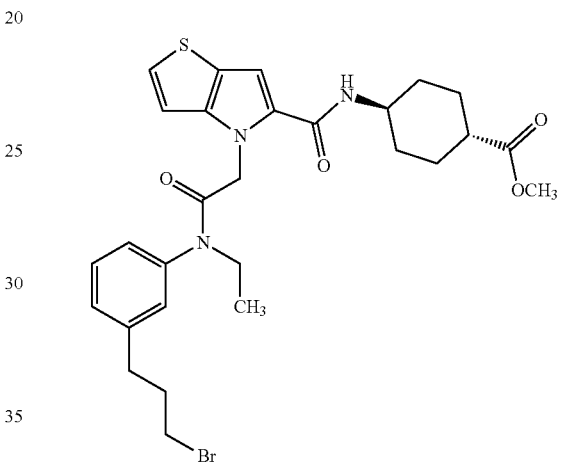

To a solution of methyl trans-4-(4-(2-(ethyl(3-(3-hydroxypropyl)phenyl)amino)-2-oxoethyl)-4H-thieno[3,2-b] pyrrole-5-carboxamido)cyclohexane-1-carboxylate (60 mg, 0.11 mmol) in DCM (5 mL), tetraethylammonium bromide (36 mg, 0.17 mmol), 2-methylpyridine (32 mg, 0.34 mmol), and diethylamino)difluorosulfonium tetrafluoroborate (39 mg, 0.17 mmol) was added. The mixture stirred at RT for 2 h. The mixture was diluted with dichloromethane and washed with slightly basic water, slightly acidic water, water, and brine. The organic layers were combined, dried with sodium sulfate, filtered, concentrated, and purified with silica gel chromatography to afford the desired product (20 mg, 30%) as a white solid. $^1$H NMR (300 MHz, DMSO-$d_6$) δ 7.99-7.89 (m, 1H), 7.52-7.23 (m, 5H), 7.16-7.05 (m, 2H), 4.97 (s, 2H), 3.77-3.48 (m, 7H), 2.88-2.75 (m, 2H), 2.35-2.10 (m, 3H), 2.04-1.78 (m, 4H), 1.55-1.18 (s, 6H), 1.12-0.95 (m, 3H); ESI MS m/z 588 [M+H]+; HPLC 91.7% (AUC), $T_R$ 7.65 min; UV (MeOH) λ 286 nm, ε 17564.

Example 19

2,5-dioxopyrrolidin-1-yl 8-(trans-4-(4-(2-(ethyl)m-tolyl)amino)-2-oxoethyl)-4H-thieno[3,2-b]pyrrole-5-carboxamido)cyclohexane-1-carboxamido)octanoate (JRW-0552)

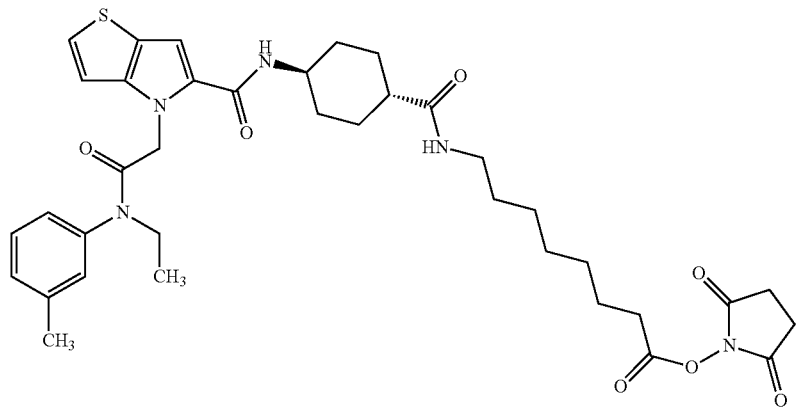 [SMILES: CCN(C(=O)Cn1c(C(=O)N[C@H]2CC[C@H](C(=O)NCCCCCCCC(=O)ON3C(=O)CCC3=O)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (80 mg, 0.13 mmol) in DMF (2 mL), TSTU (59 mg, 0.20 mmol) and diisopropylethylamine (51 mg, 0.39 mmol) was added. The solution stirred at RT for 2 h. The mixture was diluted with DCM and washed with HCl (1 M). The organic layers were combined, dried with sodium sulfate, filtered, concentrated, and purified with silica gel chromatography to afford the desired product (63 mg, 68%) as a white foam. $^1$H NMR (300 MHz, DMSO-$d_6$) δ 7.93-7.84 (m, 1H), 7.72-7.64 (m, 1H), 7.44-7.34 (m, 2H), 7.33-7.17 (m, 3H), 7.12-7.05 (m, 2H), 4.96 (s, 2H), 3.72-3.50 (m, 3H), 3.05-2.94 (m, 2H), 2.79 (s, 4H), 2.64 (t, J=7.2, 2H), 2.36 (s, 3H), 2.10-1.97 (m, 1H), 1.87-1.67 (s, 4H), 1.65-1.54 (m, 2H), 1.51-1.17 (m, 12H), 1.05-0.93 (m, 3H); ESI MS m/z 706 [M+H]+; HPLC 97.6% (AUC), $T_R$ 6.57 min; UV (MeOH) λ 288 nm, ε 19619.

Example 20 methyl 8-(trans-4-(1-(2-(ethyl(3-ethylphenyl)amino)-2-oxoethyl)-1H-indole-2-carboxamido)cyclohexane-1-carboxamido)octanoate (JRW-0597)

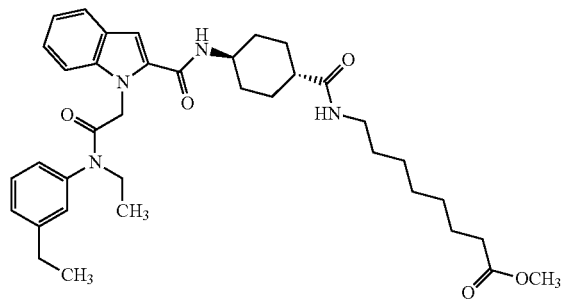 [SMILES: CCc1cccc(N(CC)C(=O)Cn2c(C(=O)N[C@H]3CC[C@H](C(=O)NCCCCCCCC(=O)OC)CC3)cc3ccccc32)c1]

To a solution of trans-4-(1-(2-(ethyl(3-ethylphenyl)amino)-2-oxoethyl)-1H-indole-2-carboxamido)cyclohexane-1-carboxylic acid (100 mg, 0.21 mmol) in DMF (3 mL), HOBT (64 mg, 0.42 mmol), EDC (80 mg, 0.42 mmol), diisopropyethylamine (81 mg, 0.63 mmol), and methyl 8-aminooctanoate-HCl (66 mg, 0.31 mmol) was added. The solution was heated to 60° C. for 1 h. The mixture was diluted with ethyl acetate and washed with water. The organic layers were combined, dried with sodium sulfate, filtered, concentrated, and purified with silica gel chromatography to afford the desired product (90 mg, 68%) as a white foam. $^1$H NMR (300 MHz, DMSO-$d_6$) δ 8.20 (d, J=8.2, 1H), 7.70-7.62 (m, 1H), 7.58 (d, J=7.8, 1H), 7.50-7.15 (m, 6H), 7.12-6.99 (m, 2H), 5.01 (s, 2H), 3.75-3.50 (m, 5H), 3.00 (q, J=6.1, 2H), 2.75-2.61 (m, 2H), 2.27 (t, J=7.4, 2H), 2.15-1.95 (m, 1H), 1.91-1.68 (s, 4H), 1.57-1.15 (m, 17H), 1.08-0.96 (m, 3H); ESI MS m/z 631 [M+H]+; HPLC 99.4% (AUC), $T_R$ 6.32 min; UV (MeOH) λ 291 nm, ε 17858.

Example 21 methyl 6-(trans-4-(1-(2-(ethyl(3-ethylphenyl)amino)-2-oxoethyl)-1H-indole-2-carboxamido)cyclohexane-1-carboxamido)hexanoate (JRW-0598)

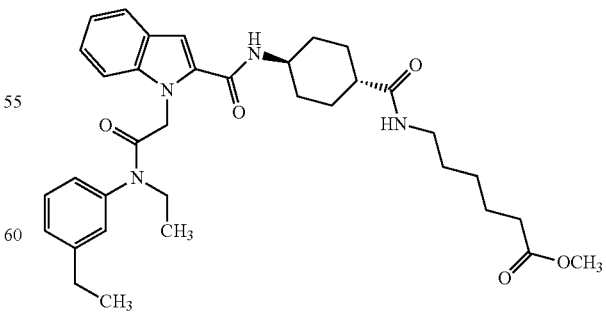

To a solution of trans-4-(1-(2-(ethyl(3-ethylphenyl)amino)-2-oxoethyl)-1H-indole-2-carboxamido)cyclohexane-1-carboxylic acid (100 mg, 0.21 mmol) in DMF (3 mL), HOBT (64 mg, 0.42 mmol), EDC (80 mg, 0.42 mmol), diisopropyethylamine (81 mg, 0.63 mmol), and methyl 8-aminhexanoate-HCl (57 mg, 0.31 mmol) was added. The solution was heated to 60° C. for 2 h. The mixture was diluted with ethyl acetate and washed with water. The organic layers were combined, dried with sodium sulfate, filtered, concentrated, and purified with silica gel chromatography to afford the desired product (125 mg, quant) as a white solid. $^1$H NMR (300 MHz, DMSO-d$_6$) δ 8.20 (d, J=8.1, 1H), 7.71-7.63 (m, 1H), 7.58 (d, J=7.8, 1H), 7.50-7.14 (m, 6H), 7.11-7.02 (m, 2H), 5.01 (s, 2H), 3.75-3.53 (m, 5H), 3.00 (q, J=6.0, 2H), 2.74-2.61 (m, 2H), 2.27 (t, J=7.4, 2H), 2.12-1.98 (m, 1H), 1.91-1.68 (m, 4H), 1.56-1.19 (m, 15H), 1.08-0.95 (m, 3H); ESI MS m/z 603 [M+H]+; HPLC >99% (AUC), T$_R$ 5.91 min; UV (MeOH) λ 291 nm, ε 16816.

Example 22

2,5-dioxopyrrolidin-1-yl 8-(trans-4-(1-(2-(ethyl(3-ethylphenyl)amino)-2-oxoethyl)-1H-indole-2-carboxamido)cyclohexane-1-carboxamido)octanoate (JRW-0600)

Example 23

2,5-dioxopyrrolidin-1-yl 6-(trans-4-(1-(2-(ethyl(3-ethylphenyl)amino)-2-oxoethyl)-1H-indole-2-carboxamido)cyclohexane-1-carboxamido)hexanoate (JRW-0604)

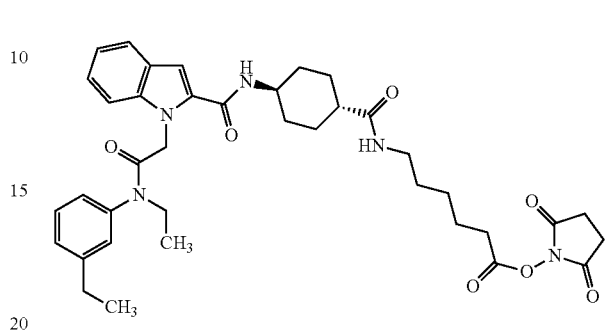

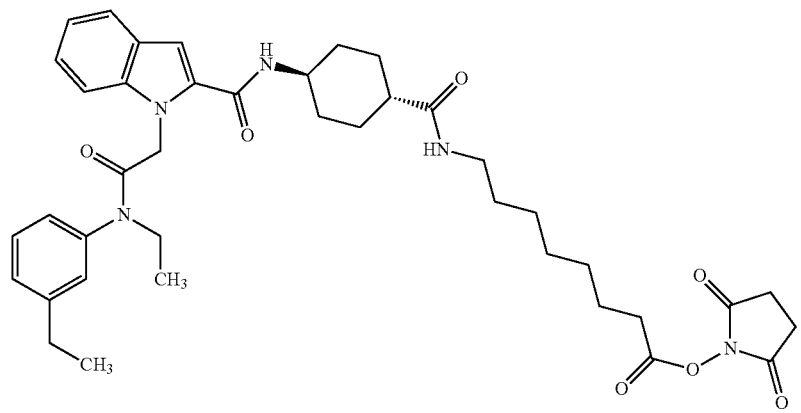 [SMILES: CCc1cccc(N(CC)C(=O)Cn2c(C(=O)N[C@H]3CC[C@H](C(=O)NCCCCCCCC(=O)ON4C(=O)CCC4=O)CC3)cc3ccccc32)c1]

To a solution of 8-(trans-4-(1-(2-(ethyl(3-ethylphenyl)amino)-2-oxoethyl)-1H-indole-2-carboxamido)cyclohexane-1-carboxamido)octanoic acid (40 mg, 0.064 mmol) in DCM (5 mL), TSTU (29 mg, 0.097 mmol) and diisopropylethylamine (25 mg, 0.19 mmol) was added. The solution stirred at RT for 1 h. The mixture was diluted with DCM and washed with HCl (1 M). The organic layers were combined, dried with sodium sulfate, filtered, concentrated, and purified with silica gel chromatography to afford the desired product (42 mg, 91%) as a white solid. $^1$H NMR (300 MHz, DMSO-d$_6$) δ 8.28-8.11 (m, 1H), 7.70-7.62 (m, 1H), 7.61-7.55 (d, J=7.7, 1H), 7.50-7.15 (m, 6H), 7.12-7.02 (m, 2H), 5.01 (s, 2H), 3.89-3.43 (m, 3H), 3.05-2.95 (m, 2H), 2.79 (s, 4H), 2.74-2.55 (m, 2H), 2.12-1.96 (m, 1H), 1.92-1.68 (m, 4H), 1.60 (s, 2H), 1.53-1.18 (m, 15H), 1.07-0.95 (m, 3H); ESI MS m/z 714 [M+H]+; HPLC 97.2% (AUC), T$_R$ 5.99 min; UV (MeOH) λ 291 nm, ε 16810.

To a solution of 6-(trans-4-(1-(2-(ethyl(3-ethylphenyl)amino)-2-oxoethyl)-1H-indole-2-carboxamido)cyclohexane-1-carboxamido)hexanoic acid (45 mg, 0.076 mmol) in DCM (10 mL), TSTU (34 mg, 0.11 mmol) and diisopropylethylamine (29 mg, 0.22 mmol) was added. The solution stirred at RT for 4 h. The mixture was diluted with DCM and washed with HCl (1 M). The organic layers were combined, dried with sodium sulfate, filtered, concentrated, and purified with silica gel chromatography to afford the desired product (50 mg, 96%) as a white solid. $^1$H NMR (300 MHz, DMSO-d$_6$) δ 8.26-8.13 (m, 1H), 7.72-7.64 (m, 1H), 7.58 (d, J=7.9, 1H), 7.50-7.15 (m, 6H), 7.12-7.01 (m, 2H), 5.02 (s, 2H), 3.78-3.46 (m, 3H), 3.05-2.95 (m, 2H), 2.79 (s, 4H), 2.75-2.60 (m, 4H), 2.12-1.98 (m, 1H), 1.90-1.70 (m, 4H), 1.67-1.55 (m, 2H), 1.542-1.18 (m, 13H), 1.07-0.94 (m, 3H); ESI MS m/z 686 [M+H]+; HPLC 99.2% (AUC), T$_R$ 5.69 min; UV (MeOH) λ 291 nm, ε 15593.

Example 24 phenyl 8-(trans-4-(1-(2-(ethyl(3-ethylphenyl)amino)-2-oxoethyl)-1H-indole-2-carboxamido)cyclohexane-1-carboxamido)octanoate (JRW-0605)

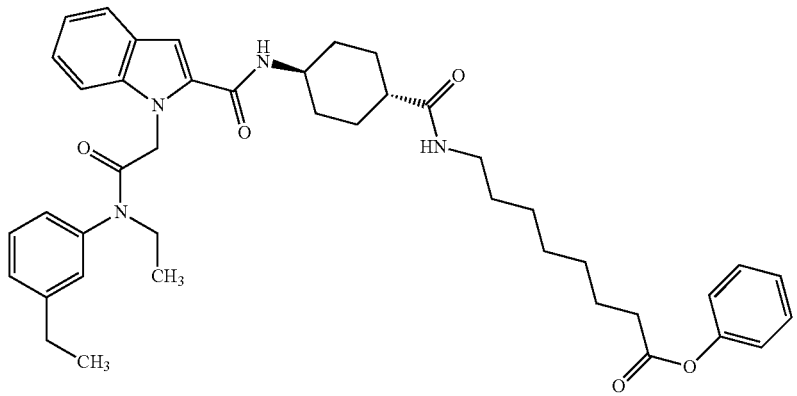 [SMILES: CCc1cccc(N(CC)C(=O)Cn2c(C(=O)N[C@H]3CC[C@H](C(=O)NCCCCCCCC(=O)Oc4ccccc4)CC3)cc3ccccc32)c1]

To a solution of 8-(trans-4-(1-(2-(ethyl(3-ethylphenyl)amino)-2-oxoethyl)-1H-indole-2-carboxamido)cyclohexane-1-carboxamido)octanoic acid (45 mg, 0.073 mmol) in DCM (10 mL), N,N'-dicyclohexylcarbodiimide (22 mg, 0.11 mmol), DMAP (2 mg, cat.), and phenol (14 mg, 0.15 mmol) was added. The solution stirred at RT for 18 h. The mixture was diluted with DCM and washed with HCl (1 M). The organic layers were combined, dried with sodium sulfate, filtered, concentrated, and purified with silica gel chromatography to afford the desired product (38 mg, 76%) as a white solid. $^1$H NMR (300 MHz, DMSO-$d_6$) δ 7.75-7.64 (m, 1H), 7.60-7.51 (m, 1H), 7.46-7.14 (m, 10H), 7.07-7.00 (m, 4H), 4.97 (s, 2H), 3.81-3.46 (m, 3H), 3.07-2.95 (m, 2H), 2.75-2.58 (m, 2H), 2.57-2.50 (m, 2H), 2.18-1.96 (m, 1H), 1.93-1.68 (m, 4H), 1.68-1.54 (m, 2H), 1.55-1.18 (m, 15H), 1.09-0.94 (m, 3H); ESI MS m/z 693 [M+H]+; HPLC >99% (AUC), $T_R$ 6.69 min; UV (MeOH) λ 291 nm, ε 20943.

Example 25 phenyl 6-(trans-4-(1-(2-(ethyl(3-ethylphenyl)amino)-2-oxoethyl)-1H-indole-2-carboxamido)cyclohexane-1-carboxamido)hexanoate (JRW-0606)

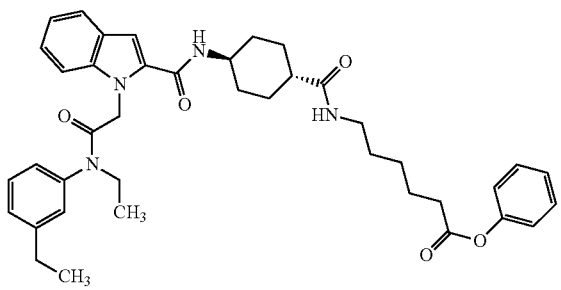 [SMILES: CCc1cccc(N(CC)C(=O)Cn2c(C(=O)N[C@H]3CC[C@H](C(=O)NCCCCCC(=O)Oc4ccccc4)CC3)cc3ccccc32)c1]

To a solution of 6-(trans-4-(1-(2-(ethyl(3-ethylphenyl)amino)-2-oxoethyl)-1H-indole-2-carboxamido)cyclohexane-1-carboxamido)hexanoic acid (64 mg, 0.11 mmol) in DCM (5 mL), N,N'-dicyclohexylcarbodiimide (33 mg, 0.16 mmol), DMAP (2 mg, cat.), and phenol (20 mg, 0.22 mmol) was added. The solution stirred at RT for 18 h. The mixture was diluted with DCM and washed with HCl (1 M). The organic layers were combined, dried with sodium sulfate, filtered, concentrated, and purified with silica gel chromatography to afford the desired product (63 mg, 87%) as a white solid. $^1$H NMR (300 MHz, DMSO-$d_6$) δ 8.25-8.13 (m, 1H), 7.79-7.67 (m, 1H), 7.60-7.54 (m, 1H), 7.47-7.14 (m, 10H), 7.11-7.00 (m, 4H), 4.99 (s, 2H), 3.79-3.51 (m, 3H), 3.08-2.98 (m, 2H), 2.73-2.60 (m, 2H), 2.58-2.50 (m, 2H), 2.12-1.98 (m, 1H), 1.88-1.69 (m, 4H), 1.68-1.55 (m, 2H), 1.52-1.15 (m, 13H), 1.08-0.93 (m, 3H); ESI MS m/z 665 [M+H]+; HPLC >99% (AUC), $T_R$ 6.39 min; UV (MeOH) λ 291 nm, ε 17018.

Example 26

1-(2-(ethyl(3-ethylphenyl)amino)-2-oxoethyl)-N-(trans-4-((6-iodohexyl)carbamoyl)cyclohexyl)-1H-indole-2-carboxamide (JRW-0622)

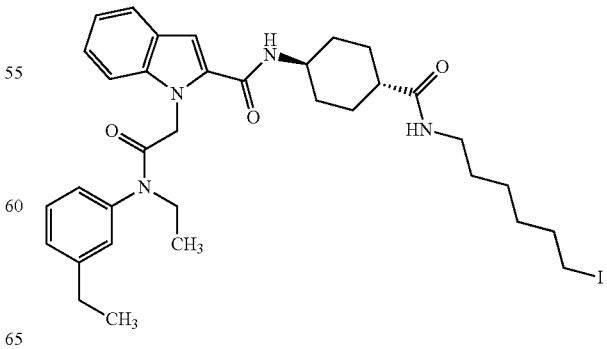

A solution of imidazole (35 mg, 0.52 mmol), triphenylphosphine (137 mg, 0.52 mmol), and iodine (132 mg, 0.52 mmol) in THF (10 mL) stirred at RT for 10 min. 1-(2-(ethyl (3-ethylphenyl)amino)-2-oxoethyl)-N-(trans-4-((6-hydroxyhexyl)carbamoyl)cyclohexyl)-1H-indole-2-carboxamide (100 mg, 0.17 mmol) dissolved in THF (5 mL) was added. The solution stirred at RT for 1 h. The reaction was diluted with ethyl acetate and quenched with a 10% $Na_2S_2O_3$ solution. The mixture was diluted with ethyl acetate and water, and the layers were separated. The organic layer was washed with a 10% $Na_2S_2O_3$ solution and brine, dried over anhydrous sodium sulfate, filtered, and concentrated. The residue was purified by column chromatography to afford desired product (77 mg, 64%) as a white solid. $^1$H NMR (300 MHz, DMSO-$d_6$) δ 8.26-8.18 (m, 1H), 7.75-7.65 (m, 1H), 7.58 (d, J=7.7, 1H), 7.50-7.15 (m, 6H), 7.12-7.03 (m, 2H), 5.01 (s, 2H), 3.75-3.52 (m, 3H), 3.25 (t, J=6.9, 2H), 3.05-2.94 (m, 2H), 2.75-2.60 (m, 2H), 2.14-1.94 (m, 1H), 1.90-1.68 (m, 6H), 1.51-1.16 (m, 13H), 1.08-0.92 (m, 3H); ESI MS m/z 685 [M+H]+; HPLC 97.5% (AUC), $T_R$ 6.84 min; UV (MeOH) λ 290 nm, ε 16990.

Example 27

N-(trans-4-((6-bromohexyl)carbamoyl)cyclohexyl)-1-(2-(ethyl(3-ethylphenyl)amino)-2-oxoethyl)-1H-indole-2-carboxamide (JRW-0626)

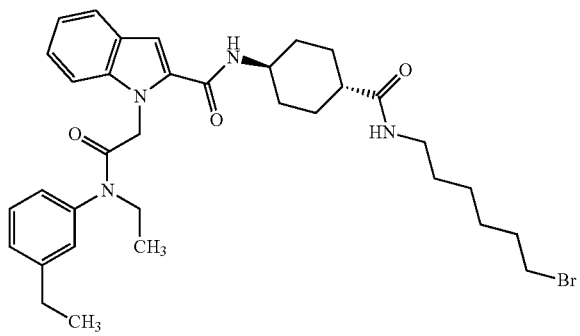 [SMILES: CCc1cccc(N(CC)C(=O)Cn2c(C(=O)N[C@H]3CC[C@H](C(=O)NCCCCCCBr)CC3)cc3ccccc32)c1]

A solution of carbon tetrabromide (207 mg, 0.63 mmol) and triphenylphosphine (164 mg, 0.63 mmol) in DCM (2 mL) was stirred at RT for 5 min. 1-(2-(Ethyl(3-ethylphenyl) amino)-2-oxoethyl)-N-(trans-4-((6-hydroxyhexyl)carbamoyl)cyclohexyl)-1H-indole-2-carboxamide (120 mg, 0.21 mmol) in DCM (2 mL) was added. The solution stirred at RT for 5 h. The mixture was diluted with ethyl acetate and water, and the layers were separated. The organic layers were combined, dried with sodium sulfate, filtered, concentrated, and purified with silica gel chromatography to afford the desired product (62 mg, 46%) as a white foam. $^1$H NMR (300 MHz, DMSO-$d_6$) δ 8.26-8.18 (m, 1H), 7.84-7.76 (m, 1H), 7.56 (d, J=7.9, 1H), 7.48-7.35 (m, 1H), 7.35-7.15 (m, 5H), 7.09-7.00 (m, 2H), 4.91 (s, 2H), 3.72-3.48 (m, 3H), 3.44 (t, J=6.6, 2H), 3.04-2.92 (m, 2H), 2.70-2.56 (s, 2H), 2.18-1.93 (m, 1H), 1.88-1.65 (m, 6H), 1.55-1.05 (m, 13H), 1.03-0.90 (m, 3H); ESI MS m/z 637 [M+H]+; HPLC >99% (AUC), $T_R$ 6.67 min; UV (MeOH) λ 291 nm, ε 16866.

Example 28

1-(2-(ethyl(3-ethylphenyl)amino)-2-oxoethyl)-N-(trans-4-((8-iodooctyl)carbamoyl)cyclohexyl)-1H-indole-2-carboxamide (JRW-0660)

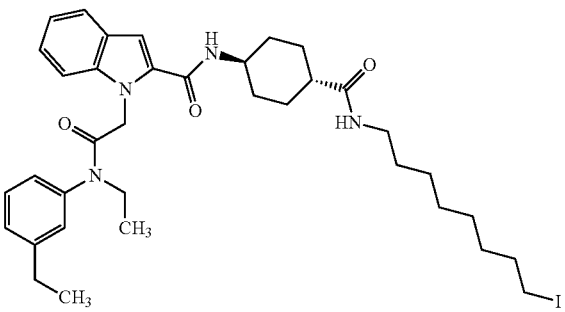 [SMILES: CCc1cccc(N(CC)C(=O)Cn2c(C(=O)N[C@H]3CC[C@H](C(=O)NCCCCCCCCI)CC3)cc3ccccc32)c1]

A solution of imidazole (38 mg, 0.56 mmol), triphenylphosphine (147 mg, 0.56 mmol), and iodine (142 mg, 0.56 mmol) in THF (10 mL) stirred at RT for 10 min. 1-(2-(ethyl (3-ethylphenyl)amino)-2-oxoethyl)-N-(trans-4-((8-hydroxyoctyl)carbamoyl)cyclohexyl)-1H-indole-2-carboxamide (113 mg, 0.19 mmol) dissolved in THF (5 mL) was added. The solution stirred at RT for 30 min. The reaction was diluted with ethyl acetate and quenched with a 10% $Na_2S_2O_3$ solution. The mixture was diluted with ethyl acetate and water, and the layers were separated. The organic layer was washed with a 10% $Na_2S_2O_3$ solution and brine, dried over anhydrous sodium sulfate, filtered, and concentrated. The residue was purified by column chromatography to afford desired product (101 mg, 75%) as a white solid. $^1$H NMR (300 MHz, DMSO-$d_6$) δ 8.33-8.12 (m, 1H), 7.76-7.56 (m, 2H), 7.56-7.01 (m, 8H), 5.04 (m, 2H), 3.84-3.48 (m, 3H), 3.11-2.93 (m, 2H), 2.84-2.62 (m, 2H), 2.18-1.98 (m, 1H), 1.95-1.68 (s, 6H), 1.58-1.15 (m, 17H), 1.14-0.91 (m, 3H); ESI MS m/z 713 [M+H]+; HPLC >99% (AUC), $T_R$ 7.00 min; UV (MeOH) λ 291 nm, ε 18958.

Example 29

4-fluorophenyl 8-(trans-4-(4-(2-(ethyl)m-tolyl)amino)-2-oxoethyl)-4H-thieno[3,2-b]pyrrole-5-carboxamido)cyclohexane-1-carboxamido)octanoate (JRW-0831)

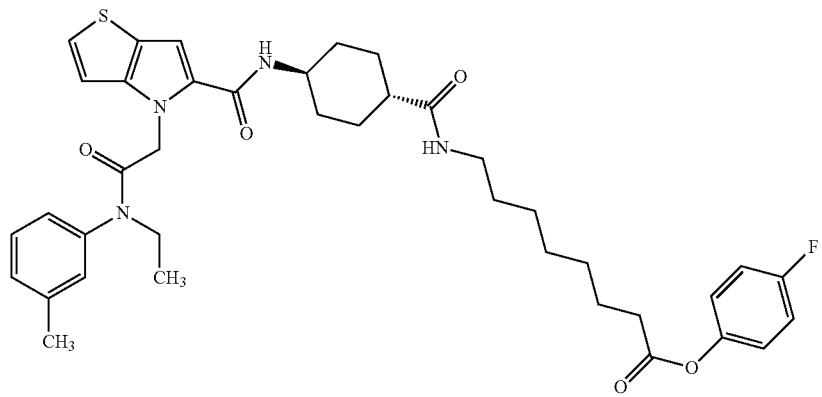 [SMILES: CCN(C(=O)Cn1c(C(=O)N[C@H]2CC[C@H](C(=O)NCCCCCCCC(=O)Oc3ccc(F)cc3)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (50 mg, 0.082 mmol) in DCM (5 mL), N,N'-dicyclohexylcarbodiimide (25 mg, 0.12 mmol), DMAP (2 mg, cat.), and 4-fluorophenol (18 mg, 0.16 mmol) was added. The solution stirred at RT for 18 h. The mixture was diluted with DCM and washed with HCl (1 M). The organic layers were combined, dried with sodium sulfate, filtered, concentrated, and purified with silica gel chromatography to afford the desired product (68 mg, crude) as a white solid. ESI MS m/z 703 [M+H]+.

Example 30

3,5-difluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate (JRW-0833)

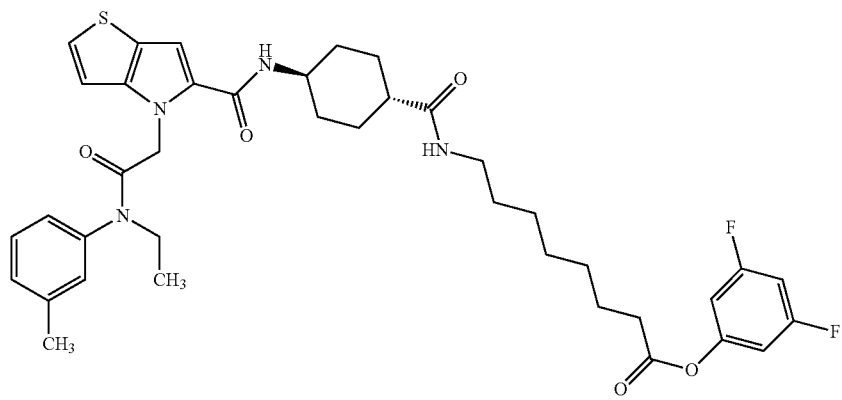 [SMILES: CCN(C(=O)Cn1c(C(=O)N[C@H]2CC[C@H](C(=O)NCCCCCCCC(=O)Oc3cc(F)cc(F)c3)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (50 mg, 0.082 mmol) in DCM (5 mL), N,N'-dicyclohexylcarbodiimide (25 mg, 0.12 mmol), DMAP (2 mg, cat.), and 3,5-difluorophenol (21 mg, 0.16 mmol) was added. The solution stirred at RT for 5 h. The mixture was diluted with DCM and washed with HCl (1 M). The organic layers were combined, dried with sodium sulfate, filtered, concentrated, and purified with silica gel chromatography to afford the desired product (44 mg, 74%) as a white solid. ESI MS m/z 721 [M+H]+.

Example 31

4-cyanophenyl 8-(trans-4-(4-(2-(ethyl(m-tolyl) amino)-2-oxoethyl)-4H-thieno[3,2-b]pyrrole-5-carboxamido)cyclohexane-1-carboxamido)octanoate (JRW-0834)

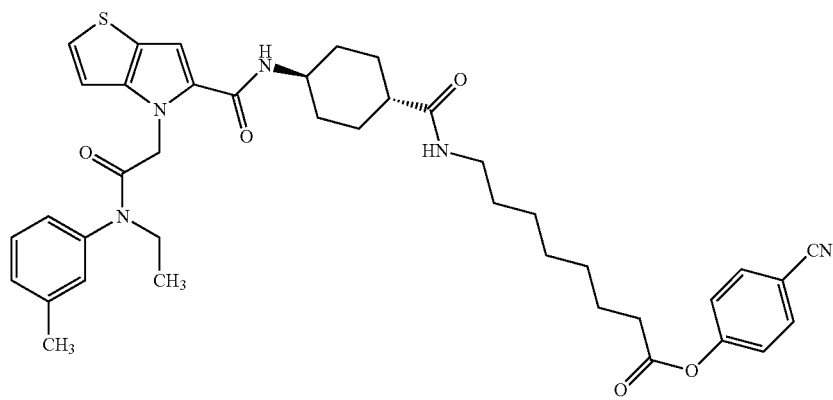 [SMILES: CCN(C(=O)Cn1c(C(=O)N[C@H]2CC[C@H](C(=O)NCCCCCCCC(=O)Oc3ccc(C#N)cc3)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (66 mg, 0.11 mmol) in DCM (5 mL), N,N'-dicyclohexylcarbodiimide (34 mg, 0.16 mmol), DMAP (2 mg, cat.), and 4-hydroxybenzonitrile (25 mg, 0.22 mmol) was added. The solution stirred at RT for 3 h. The mixture was diluted with DCM and washed with HCl (1 M). The organic layers were combined, dried with sodium sulfate, filtered, concentrated, and purified with silica gel chromatography to afford the desired product (70 mg, 90%) as a white solid. ESI MS m/z 710 [M+H]+.

Example 32 sodium 1-((8-(trans-4-(4-(2-(ethyl(m-tolyl)amino)-2-oxoethyl)-4H-thieno[3,2-b]pyrrole-5-carboxamido) cyclohexane-1-carboxamido)octanoyl)oxy)-2,5-dioxopyrrolidine-3-sulfonate (JRW-0830)

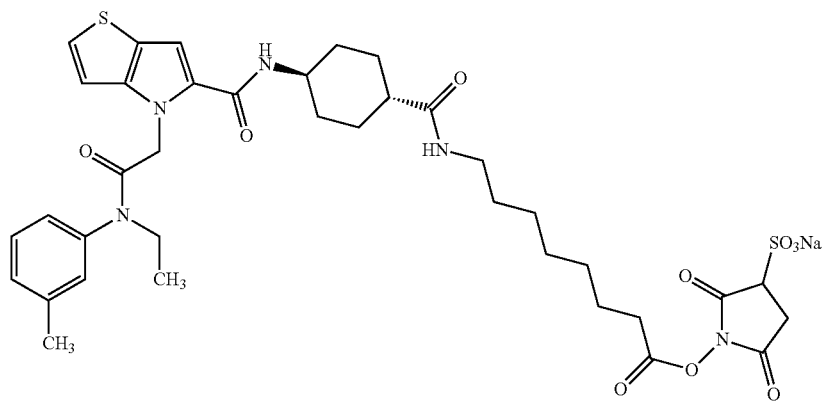

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (50 mg, 0.082 mmol) in DMF (1 mL), HATU (46 mg, 0.12 mmol), sodium 1-hydroxy-2,5-dioxopyrrolidine-3-sulfonate (21 mg, 0.099 mmol) and diisopropylethylamine (32 mg, 0.25 mmol) was added. The solution was stirred at 85° C. for 2 h. The mixture was diluted dichloromethane, poured onto celite, concentrated, and purified with silica gel chromatography to afford the desired product (30 mg, 45%) as a light brown solid. ESI MS m/z 786 [M−Na+H]+.

Example 33

N-(trans-4-((5-(2-chloroacetamido)pentyl)carbamoyl)cyclohexyl)-4-(2-(ethyl(m-tolyl)amino)-2-oxoethyl)-4H-thieno[3,2-b]pyrrole-5-carboxamide (JRW-0844)

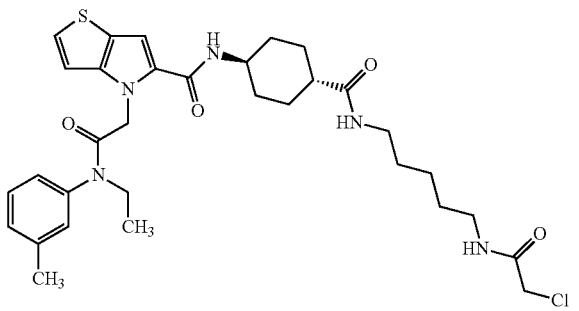 [SMILES: CCN(C(=O)Cn1c(C(=O)N[C@H]2CC[C@H](C(=O)NCCCCCNC(=O)CCl)CC2)cc2sccc21)c1cccc(C)c1]

To a solution of N-(trans-4-((5-aminopentyl)carbamoyl)cyclohexyl)-4-(2-(ethyl(m-tolyl)amino)-2-oxoethyl)-4H-thieno[3,2-b]pyrrole-5-carboxamide (70 mg, 0.13 mmol) in ethyl acetate/water (10/2 mL) chilled with an ice bath, 2-chloroacetyl chloride (21 mg, 0.19 mmol) and potassium hydroxide (21 mg, 0.38 mmol) was added. The solution stirred at RT for 1 h. The mixture was diluted with ethyl acetate and water. The organic layers were combined, dried with sodium sulfate, filtered, concentrated, and purified with silica gel chromatography to afford the desired product (22 mg, 27%) as a white solid. ESI MS m/z 628 [M+H]+.

Example 34

N-(trans-4-((6-(2-chloroacetamido)hexyl)carbamoyl)cyclohexyl)-4-(2-(ethyl(m-tolyl)amino)-2-oxoethyl)-4H-thieno[3,2-b]pyrrole-5-carboxamide (JRW-0846)

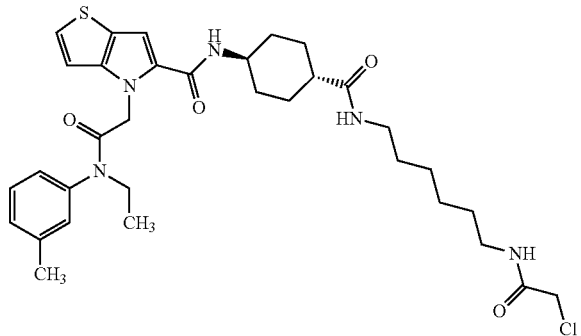 [SMILES: CCN(C(=O)Cn1c(C(=O)N[C@H]2CC[C@H](C(=O)NCCCCCCNC(=O)CCl)CC2)cc2sccc21)c1cccc(C)c1]

To a solution of N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide (60 mg, 0.11 mmol) in ethyl acetate/water (10/2 mL) chilled with an ice bath, 2-chloroacetyl chloride (18 mg, 0.16 mmol) and potassium hydroxide (18 mg, 0.32 mmol) was added. The solution stirred at RT for 1 h. The mixture was diluted with ethyl acetate and water. The organic layers were combined, dried with sodium sulfate, filtered, concentrated, and purified with silica gel chromatography to afford the desired product (18 mg, 26%) as a white solid. ESI MS m/z 642 [M+H]+.

Example 35

2,3,5,6-tetrafluorophenyl 8-(trans-4-(4-(2-(ethyl)m-tolyl)amino)-2-oxoethyl)-4H-thieno[3,2-b]pyrrole-5-carboxamido)cyclohexane-1-carboxamido)octanoate (JRW-0847)

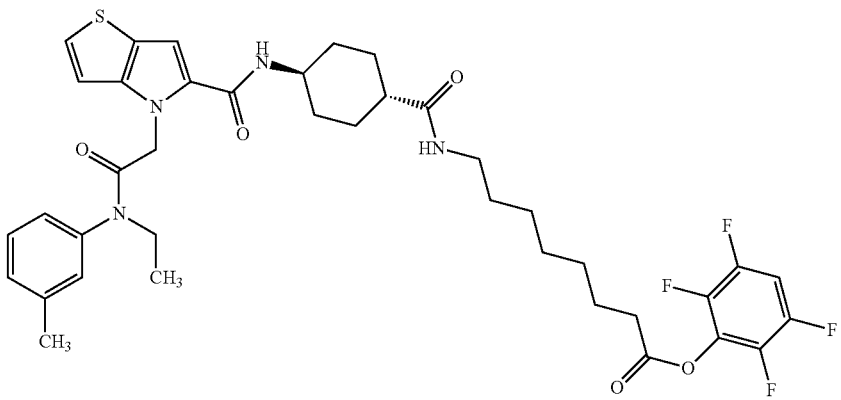 [SMILES: CCN(C(=O)Cn1c(C(=O)N[C@H]2CC[C@H](C(=O)NCCCCCCCC(=O)Oc3c(F)c(F)cc(F)c3F)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (54 mg, 0.089 mmol) in DCM (5 mL), N,N'-dicyclohexylcarbodiimide (27 mg, 0.13 mmol), DMAP (2 mg, cat.), and 2,3,5,6-tetrafluorophenol (29 mg, 0.18 mmol) was added. The solution stirred at RT for 1.5 h. The mixture was diluted with DCM and washed with HCl (1 M). The organic layers were combined, dried with sodium sulfate, filtered, concentrated, and purified with silica gel chromatography to afford the desired product (52 mg, 77%) as a white solid. ESI MS m/z 757 [M+H]+.

Example 36

N-(trans-4-((5-(2-bromoacetamido)pentyl)carbamoyl)cyclohexyl)-4-(2-(ethyl(m-tolyl)amino)-2-oxoethyl)-4H-thieno[3,2-b]pyrrole-5-carboxamide (JRW-0870)

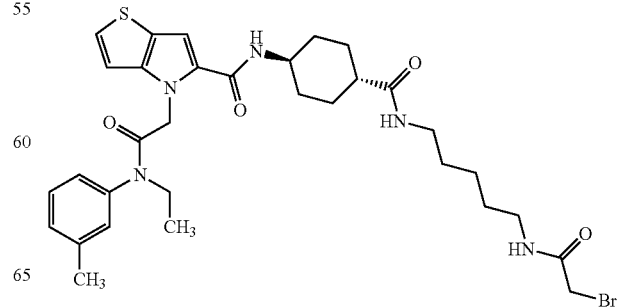

To a solution of N-(trans-4-((5-aminopentyl)carbamoyl) cyclohexyl)-4-(2-(ethyl(m-tolyl)amino)-2-oxoethyl)-4H-thieno[3,2-b]pyrrole-5-carboxamide (220 mg, 0.11 mmol) in ethyl acetate/water (10/2 mL) chilled with an ice bath, 2-bromoacetyl bromide (120 mg, 0.60 mmol) and potassium hydroxide (67 mg, 1.2 mmol) was added. The solution stirred at RT for 6 h. The mixture was diluted with ethyl acetate and water. The organic layers were combined, dried with sodium sulfate, filtered, concentrated, and purified with silica gel chromatography to afford the desired product (20 mg, 7%) as a white solid. ESI MS m/z 672 [M+H]+.

Example 37

N-(trans-4-((1-(4-(6-((5-((2-chloro-6-methylphenyl) carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl)m-tolyl)amino)-2-oxoethyl)-4H-thieno[3,2-b] pyrrole-5-carboxamide (JRW-0577)

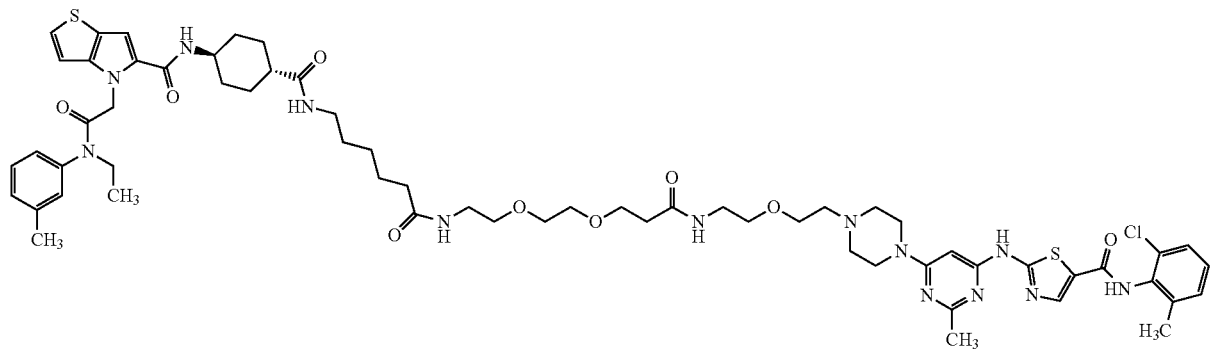 [SMILES: CCN(C(=O)Cn1c(C(=O)N[C@H]2CC[C@H](C(=O)NCCCCCC(=O)NCCOCCOCCC(=O)NCCOCCN3CCN(c4cc(Nc5ncc(C(=O)Nc6c(C)cccc6Cl)s5)nc(C)n4)CC3)CC2)cc2sccc21)c1cccc(C)c1]

To a solution of 2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oate (5 mg, 0.0060 mmol) in DCM (3 mL), 2-((6-(4-(2-(2-aminoethoxy)ethyl)piperazin-1-yl)-2-methylpyrimidin-4-yl)amino)-N-(2-chloro-6-methylphenyl) thiazole-5-carboxamide (3 mg, 0.0060 mmol) and diisopropylethylamine (1 drop) was added. The solution stirred at RT for 3 h. The mixture was purified with silica gel chromatography to afford the desired product (5 mg, 70%) as a brown solid. ESI MS m/z 1252 [M−Na+H]+; HPLC 91.0% (AUC), $T_R$ 4.31 min; UV (MeOH) λ 302 nm, ε 24164.

Example 38

N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,18-trioxo-12,15,22-trioxa-2,9,19-triazatetracosan-24-yl)piperazin-1-yl)-2-methylpyrimidin-4-yl)amino)thiazole-5-carboxamide (JRW-0588)

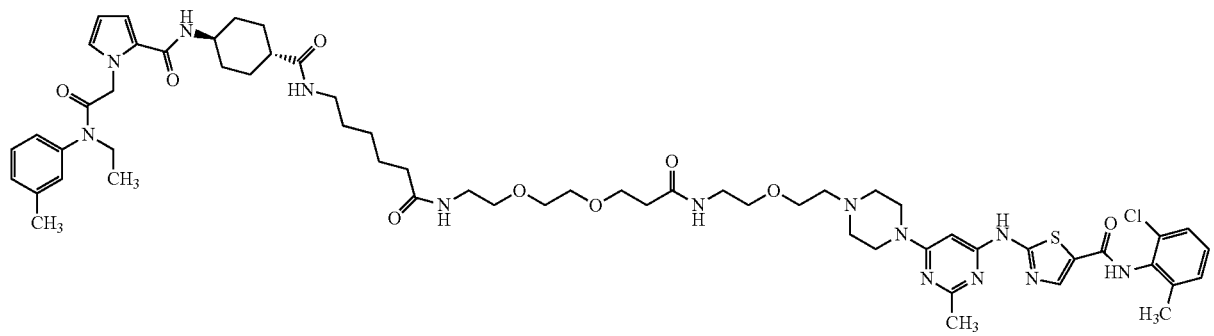 [SMILES: CCN(C(=O)Cn1cccc1C(=O)N[C@H]1CC[C@H](C(=O)NCCCCCC(=O)NCCOCCOCCC(=O)NCCOCCN2CCN(c3cc(Nc4ncc(C(=O)Nc5c(C)cccc5Cl)s4)nc(C)n3)CC2)CC1)c1cccc(C)c1]

Step 1. trans-4-(1-(2-(ethyl(m-tolyl)amino)-2-oxo-ethyl)-1H-pyrrole-2-carboxamido)cyclohexane-1-carboxylic acid (JRW-0579)

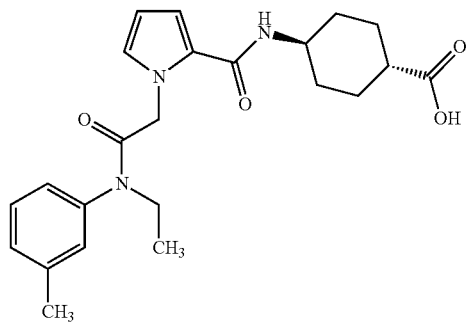 [SMILES: CCN(C(=O)Cn1cccc1C(=O)N[C@H]1CC[C@H](C(=O)O)CC1)c1cccc(C)c1]

To a suspension of methyl trans-4-(1-(2-(ethyl(m-tolyl)amino)-2-oxoethyl)-1H-pyrrole-2-carboxamido)cyclohexane-1-carboxylate (500 mg, 1.2 mmol) in dioxane (20 mL) and water (5 mL), lithium hydroxide (140 mg, 5.9 mmol) was added. The suspension was stirred at 60° C. for 18 h. The mixture was acidified with HCl (2 M), diluted with ethyl acetate and washed with water. The organic layers were combined, dried with sodium sulfate, filtered, concentrated, to afford the desired product (500 mg, crude) as a white foam. ESI MS m/z 412 [M+H]+.

Step 2. methyl 6-(trans-4-(1-(2-(ethyl(m-tolyl)amino)-2-oxoethyl)-1H-pyrrole-2-carboxamido)cyclohexane-1-carboxamido)hexanoate (JRW-0580)

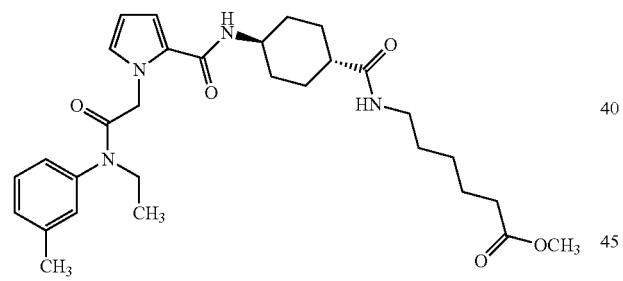

To a solution of trans-4-(1-(2-(ethyl(m-tolyl)amino)-2-oxoethyl)-1H-pyrrole-2-carboxamido)cyclohexane-1-carboxylic acid (260 mg, 0.63 mmol) in DMF (10 mL), HOBT (193 mg, 1.3 mmol), EDC (242 mg, 1.3 mmol), diisopropyethylamine (245 mg, 1.9 mmol), and methyl 6-aminohexanoate hydrochloride (172 mg, 0.95 mmol) was added. The solution was heated to 65° C. for 1 h. The mixture was diluted with ethyl acetate and washed with water. The organic layers were combined, dried with sodium sulfate, filtered, concentrated, and purified with silica gel chromatography to afford the desired product (282 mg, 83%) as a light brown oil. ESI MS m/z 539 [M+H]+.

Step 3. 6-(trans-4-(1-(2-(ethyl(m-tolyl)amino)-2-oxoethyl)-1H-pyrrole-2-carboxamido)cyclohexane-1-carboxamido)hexanoic acid (JRW-0582)

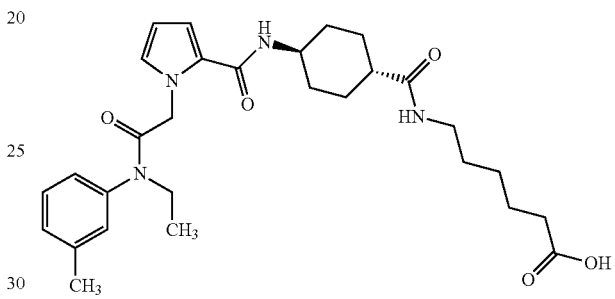

To a suspension of methyl 6-(trans-4-(1-(2-(ethyl(m-tolyl)amino)-2-oxoethyl)-1H-pyrrole-2-carboxamido)cyclohexane-1-carboxamido)hexanoate (280 mg, 0.52 mmol) in dioxane (10 mL) and water (2 mL), lithium hydroxide (62 mg, 2.6 mmol) was added. The suspension was stirred at 60° C. for 2 h. The mixture was acidified with HCl (2 M), diluted with ethyl acetate, and washed with water. The organic layers were combined, dried with sodium sulfate, filtered, concentrated, to afford the desired product (205 mg, crude) as a white foam. ESI MS m/z 525 [M+H]+.

Step 4. tert-butyl 1-(trans-4-(1-(2-(ethyl(m-tolyl)amino)-2-oxoethyl)-1H-pyrrole-2-carboxamido)cyclohexyl)-1,8-dioxo-12,15-dioxa-2,9-diazaoctadecan-18-oate (JRW-0583)

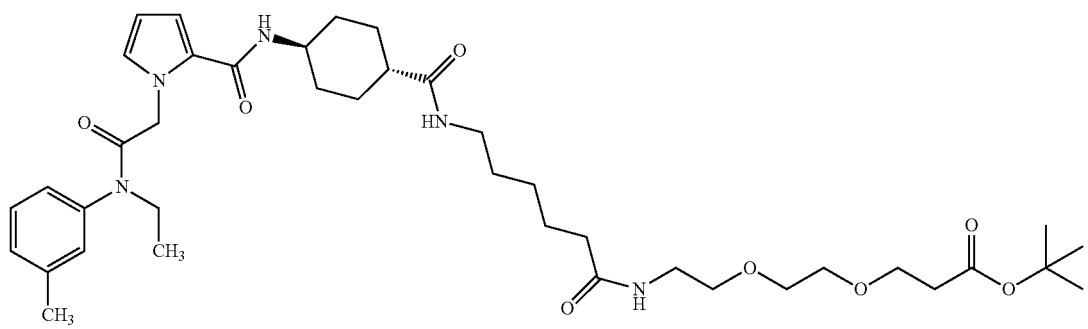 [SMILES: CCN(C(=O)Cn1cccc1C(=O)N[C@H]1CC[C@H](C(=O)NCCCCCC(=O)NCCOCCOCCC(=O)OC(C)(C)C)CC1)c1cccc(C)c1]

To a solution of 6-(trans-4-(1-(2-(ethyl(m-tolyl)amino)-2-oxoethyl)-1H-pyrrole-2-carboxamido)cyclohexane-1-carboxamido)hexanoic acid (50 mg, 0.095 mmol) in DMF (3 mL), HOBT (29 mg, 0.19 mmol), EDC (26 mg, 0.19 mmol), diisopropyethylamine (37 mg, 0.28 mmol), and tert-butyl 3-(2-(2-aminoethoxy)ethoxy)propanoate (33 mg, 0.14 mmol) was added. The solution was heated to 60° C. for 18 h. The mixture was diluted with ethyl acetate and washed with water. The organic layers were combined, dried with sodium sulfate, filtered, concentrated, and purified with silica gel chromatography to afford the desired product (84 mg, crude) as a white solid. ESI MS m/z 740 [M+H]+.

Step 5. 1-(trans-4-(1-(2-(ethyl(m-tolyl)amino)-2-oxoethyl)-1H-pyrrole-2-carboxamido)cyclohexyl)-1,8-dioxo-12,15-dioxa-2,9-diazaoctadecan-18-oic acid (JRW-0586)

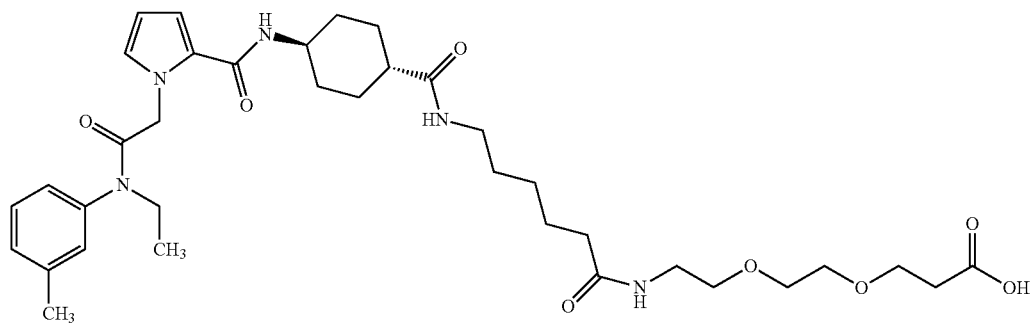 [SMILES: CCN(C(=O)Cn1cccc1C(=O)N[C@H]1CC[C@H](C(=O)NCCCCCC(=O)NCCOCCOCCC(=O)O)CC1)c1cccc(C)c1]

To a solution of tert-butyl 1-(trans-4-(1-(2-(ethyl(m-tolyl)amino)-2-oxoethyl)-1H-pyrrole-2-carboxamido)cyclohexyl)-1,8-dioxo-12,15-dioxa-2,9-diazaoctadecan-18-oate (80 mg, 0.11 mmol) in DCM (5 mL), TFA (1 mL) was added. The solution stirred at RT for 3 h. The mixture was diluted with toluene, concentrated, resuspended in toluene, and concentrated. This was repeated two times. The crude product (75 mg) was used in the next step. ESI MS m/z 684 [M+H]+.

Step 6. N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,18-trioxo-12,15,22-trioxa-2,9,19-triazatetracosan-24-yl)piperazin-1-yl)-2-methylpyrimidin-4-yl)amino)thiazole-5-carboxamide (JRW-0588)

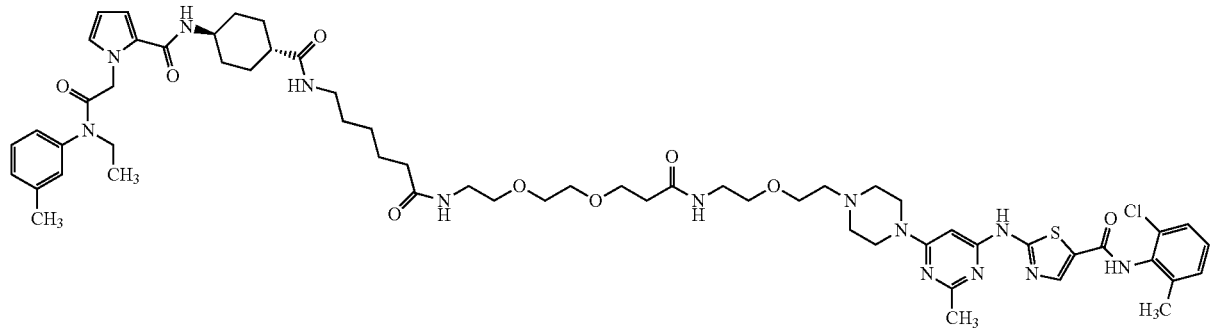 [SMILES: CCN(C(=O)Cn1cccc1C(=O)N[C@H]1CC[C@H](C(=O)NCCCCCC(=O)NCCOCCOCCC(=O)NCCOCCN2CCN(c3cc(Nc4ncc(C(=O)Nc5c(C)cccc5Cl)s4)nc(C)n3)CC2)CC1)c1cccc(C)c1]

To a solution of 1-(trans-4-(1-(2-(ethyl(m-tolyl)amino)-2-oxoethyl)-1H-pyrrole-2-carboxamido)cyclohexyl)-1,8-dioxo-12,15-dioxa-2,9-diazaoctadecan-18-oic acid (10 mg, 0.015 mmol) in DMF (2 mL), HOBT (4 mg, 0.029 mmol), EDC (5 mg, 0.029 mmol), diisopropyethylamine (5 mg, 0.044 mmol), and 2-((6-(4-(2-(2-aminoethoxy)ethyl)piperazin-1-yl)-2-methylpyrimidin-4-yl)amino)-N-(2-chloro-6-methylphenyl)thiazole-5-carboxamide (11 mg, 0.022 mmol) was added. The solution was heated to 60° C. for 3 h. The mixture was diluted with ethyl acetate and washed with water. The organic layers were combined, dried with sodium sulfate, filtered, concentrated, and purified with silica gel chromatography to afford the desired product (11 mg, 64%) as a light red solid. $^1$H NMR (300 MHz, DMSO-d$_6$) δ 11.44 (s, 1H), 9.84 (s, 1H), 8.19 (s, 1H), 7.92-7.83 (m, 1H), 7.83-7.74 (m, 1H), 7.69-7.56 (m, 2H), 7.42-7.33 (m, 2H), 7.30-7.15 (m, 5H), 6.80-6.72 (m, 2H), 6.03 (s, 1H), 5.96-5.91 (m, 1H), 4.74 (s, 2H), 3.65-3.43 (m, 16H), 3.37 (q, J=5.6, 4H), 3.24-3.10 (m, 4H), 3.04-2.92 (m, 2H), 2.38 (s, 3H), 2.34 (s, 3H), 2.32-2.25 (m, 2H), 2.22 (s, 3H), 2.07-1.99 (m, 3H), 1.84-1.66 (m, 4H), 1.53-1.15 (m, 10H), 1.05-0.93 (m, 3H); ESI MS m/z 1196 [M+H]+; HPLC 97.6% (AUC), T$_R$ 4.73 min; UV (MeOH) λ 322 nm, ε 28287.

Example 39

N-(trans-4-((1-(4-(6-((5-((2-chloro-6-methylphenyl)carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl(3-ethylphenyl)amino)-2-oxoethyl)-4H-thieno[3,2-b]pyrrole-5-carboxamide (JRW-0589)

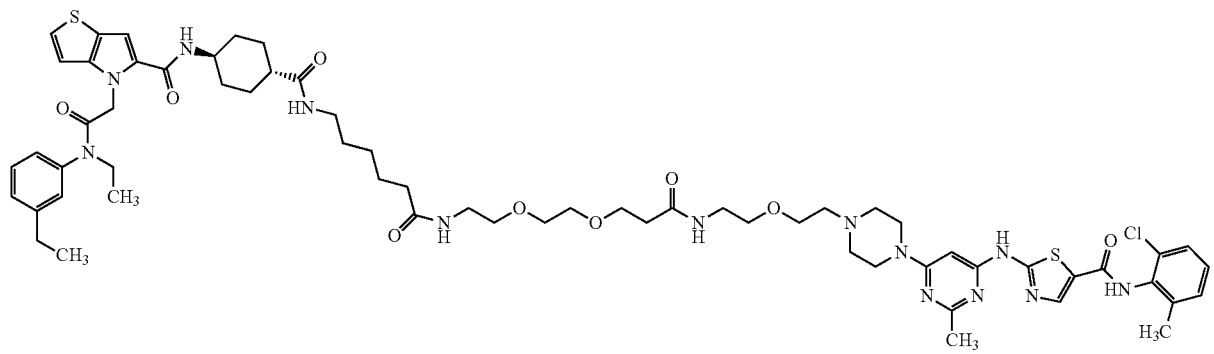 [SMILES: CCc1cccc(N(CC)C(=O)Cn2c(C(=O)N[C@H]3CC[C@H](C(=O)NCCCCCC(=O)NCCOCCOCCC(=O)NCCOCCN4CCN(c5cc(Nc6ncc(C(=O)Nc7c(C)cccc7Cl)s6)nc(C)n5)CC4)CC3)cc3sccc32)c1]

Step 1. tert-butyl 1-(trans-4-(4-(2-(ethyl(3-ethylphenyl)amino)-2-oxoethyl)-4H-thieno[3,2-b]pyrrole-5-carboxamido)cyclohexyl)-1,8-dioxo-12,15-dioxa-2,9-diazaoctadecan-18-oate (JRW-0585)

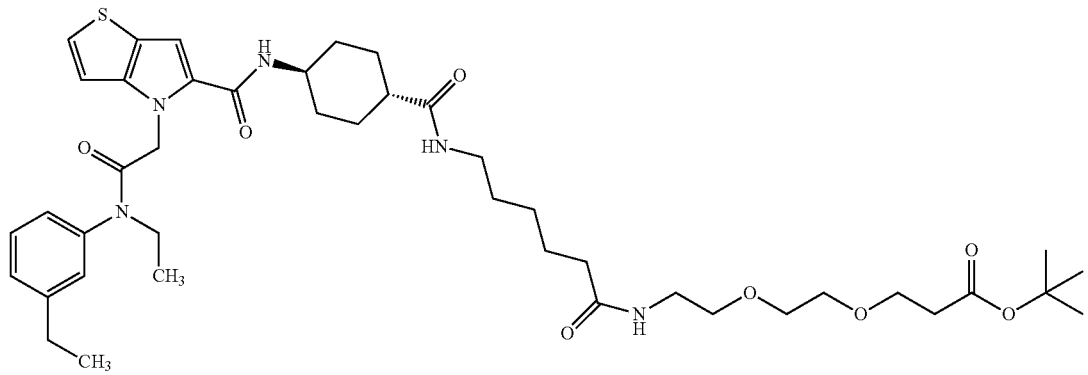 [SMILES: CCc1cccc(N(CC)C(=O)Cn2c(C(=O)N[C@H]3CC[C@H](C(=O)NCCCCCC(=O)NCCOCCOCCC(=O)OC(C)(C)C)CC3)cc3sccc32)c1]

To a solution of 6-(trans-4-(4-(2-(ethyl(3-ethylphenyl)amino)-2-oxoethyl)-4H-thieno[3,2-b]pyrrole-5-carboxamido)cyclohexane-1-carboxamido)hexanoic acid (50 mg, 0.084 mmol) in DMF (3 mL), HOBT (25 mg, 0.17 mmol), EDC (32 mg, 0.17 mmol), diisopropyethylamine (32 mg, 0.25 mmol), and tert-butyl 3-(2-(2-aminoethoxy)ethoxy)propanoate (29 mg, 0.13 mmol) was added. The solution was heated to 60° C. for 2 h. The mixture was diluted with ethyl acetate and washed with water. The organic layers were combined, dried with sodium sulfate, filtered, concentrated, and purified with silica gel chromatography to afford the desired product (45 mg, 66%) as a white foam. ESI MS m/z 810 [M+H]+.

Step 2. 1-(trans-4-(4-(2-(ethyl(3-ethylphenyl)amino)-2-oxoethyl)-4H-thieno[3,2-b]pyrrole-5-carboxamido)cyclohexyl)-1,8-dioxo-12,15-dioxa-2,9-diazaoctadecan-18-oic acid (JRW-0587)

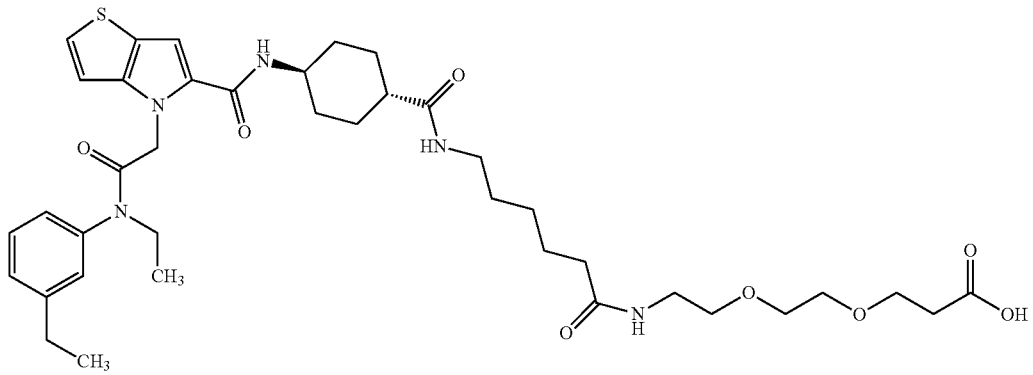 [SMILES: CCc1cccc(N(CC)C(=O)Cn2c(C(=O)N[C@H]3CC[C@H](C(=O)NCCCCCC(=O)NCCOCCOCCC(=O)O)CC3)cc3sccc32)c1]

To a solution of tert-butyl 1-(trans-4-(4-(2-(ethyl(3-ethylphenyl)amino)-2-oxoethyl)-4H-thieno[3,2-b]pyrrole-5-carboxamido)cyclohexyl)-1,8-dioxo-12,15-dioxa-2,9-diazaoctadecan-18-oate (45 mg, 0.055 mmol) in DCM (5 mL), TFA (1 mL) was added. The solution stirred at RT for 18 h. The mixture was diluted with toluene, concentrated, resuspended in toluene, and concentrated. This was repeated two times. The crude product (42 mg) was used in the next step. ESI MS m/z 754 [M+H]+.

Step 3. N-(trans-4-((1-(4-(6-((5-((2-chloro-6-methylphenyl)carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl(3-ethylphenyl)amino)-2-oxoethyl)-4H-thieno[3,2-b]pyrrole-5-carboxamide (JRW-0589)

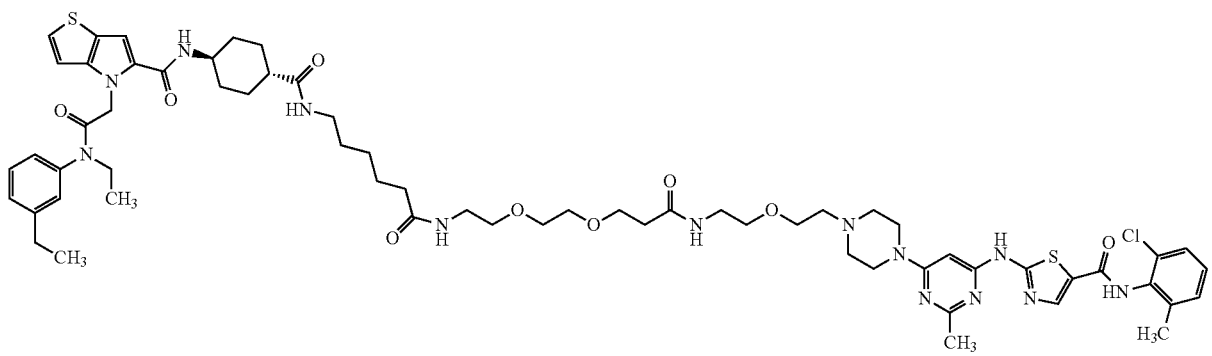 [SMILES: CCc1cccc(N(CC)C(=O)Cn2c(C(=O)N[C@H]3CC[C@H](C(=O)NCCCCCC(=O)NCCOCCOCCC(=O)NCCOCCN4CCN(c5cc(Nc6ncc(C(=O)Nc7c(C)cccc7Cl)s6)nc(C)n5)CC4)CC3)cc3sccc32)c1]

To a solution of 1-(trans-4-(4-(2-(ethyl(3-ethylphenyl)amino)-2-oxoethyl)-4H-thieno[3,2-b]pyrrole-5-carboxamido)cyclohexyl)-1,8-dioxo-12,15-dioxa-2,9-diazaoctadecan-18-oic acid (10 mg, 0.013 mmol) in DMF (2 mL), HOBT (4 mg, 0.026 mmol), EDC (5 mg, 0.026 mmol), diisopropyethylamine (5 mg, 0.040 mmol), and 2-((6-(4-(2-(2-aminoethoxy)ethyl)piperazin-1-yl)-2-methylpyrimidin-4-yl)amino)-N-(2-chloro-6-methylphenyl)thiazole-5-carboxamide (10 mg, 0.020 mmol) was added. The solution was heated to 60° C. for 6 h. The mixture was diluted with ethyl acetate and washed with water. The organic layers were combined, dried with sodium sulfate, filtered, concentrated, and purified with silica gel chromatography to afford the desired product (10 mg, 60%) as a white solid. $^1$H NMR (300 MHz, DMSO-$d_6$) δ 11.43 (s, 1H), 9.84 (s, 1H), 8.20 (s, 1H), 7.93-7.83 (m, 2H), 7.83-7.73 (m, 1H), 7.71-7.61 (m, 1H), 7.45-7.18 (m, 8H), 7.12-7.04 (m, 2H), 6.03 (s, 1H), 4.95 (s, 2H), 3.70-3.42 (m, 15H), 3.37 (q, J=4.7, 5H), 3.23-3.10 (m, 4H), 3.04-2.92 (m, 2H), 2.76-2.59 (m, 3H), 2.38 (s, 3H), 2.33-2.26 (m, 2H), 2.22 (s, 3H), 2.10-1.97 (m, 3H), 1.90-1.66 (m, 4H), 1.53-1.13 (m, 15H), 1.07-0.94 (m, 3H); ESI MS m/z 1266 [M+H]+; HPLC 97.2% (AUC), $T_R$ 5.34 min; UV (MeOH) λ 322 nm, ε 37053.

Example 40

N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,24-trioxo-12,15,18,21,28-pentaoxa-2,9,25-triazatriacontan-30-yl)piperazin-1-yl)-2-methylpyrimidin-4-yl)amino)thiazole-5-carboxamide (JRW-0593)

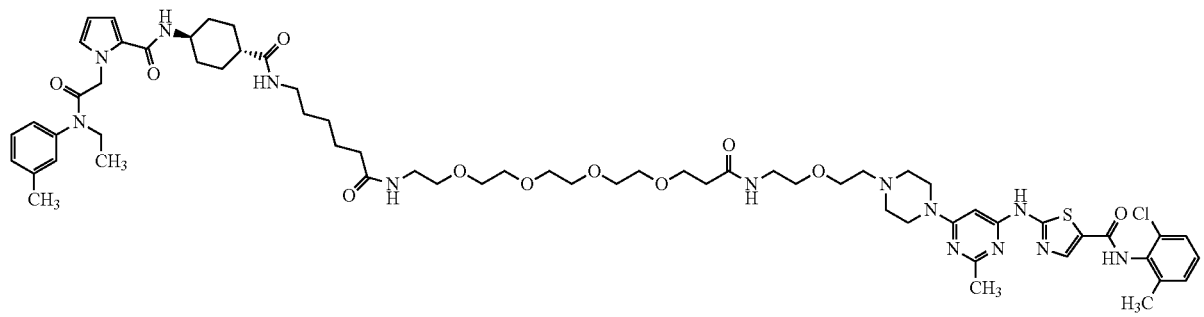 [SMILES: CCN(C(=O)Cn1cccc1C(=O)N[C@H]1CC[C@H](C(=O)NCCCCCC(=O)NCCOCCOCCOCCOCCC(=O)NCCOCCN2CCN(c3cc(Nc4ncc(C(=O)Nc5c(C)cccc5Cl)s4)nc(C)n3)CC2)CC1)c1cccc(C)c1]

Step 1. tert-butyl 1-(trans-4-(1-(2-(ethyl(m-tolyl)amino)-2-oxoethyl)-1H-pyrrole-2-carboxamido)cyclohexyl)-1,8-dioxo-12,15,18,21-tetraoxa-2,9-diazatetracosan-24-oate (JRW-0590)

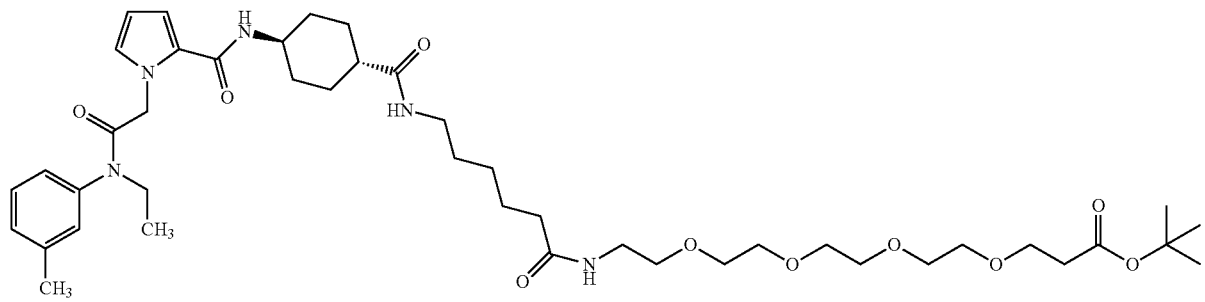 [SMILES: CCN(C(=O)Cn1cccc1C(=O)N[C@H]1CC[C@H](C(=O)NCCCCCC(=O)NCCOCCOCCOCCOCCC(=O)OC(C)(C)C)CC1)c1cccc(C)c1]

To a solution of 6-(trans-4-(1-(2-(ethyl(m-tolyl)amino)-2-oxoethyl)-1H-pyrrole-2-carboxamido)cyclohexane-1-carboxamido)hexanoic acid (50 mg, 0.095 mmol) in DMF (3 mL), HOBT (29 mg, 0.19 mmol), EDC (36 mg, 0.19 mmol), diisopropyethylamine (37 mg, 0.28 mmol), and tert-butyl 1-amino-3,6,9,12-tetraoxapentadecan-15-oate (46 mg, 0.14 mmol) was added. The solution was heated to 60° C. for 2 h. The mixture was diluted with ethyl acetate and washed with water. The organic layers were combined, dried with sodium sulfate, filtered, concentrated, and purified with silica gel chromatography to afford the desired product (45 mg, 56%) as an oil. ESI MS m/z 828 [M+H]+.

Step 2. 1-(trans-4-(1-(2-(ethyl(m-tolyl)amino)-2-oxoethyl)-1H-pyrrole-2-carboxamido)cyclohexyl)-1,8-dioxo-12,15,18,21-tetraoxa-2,9-diazatetracosan-24-oic acid (JRW-0592)

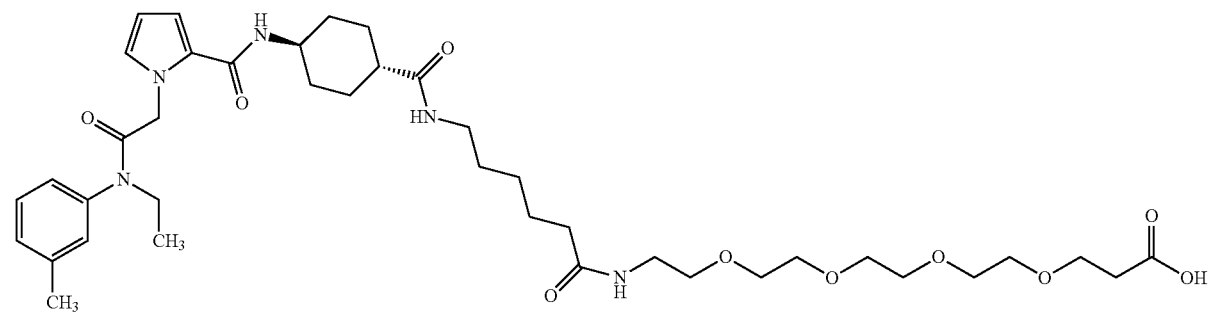 [SMILES: CCN(C(=O)Cn1cccc1C(=O)N[C@H]1CC[C@H](C(=O)NCCCCCC(=O)NCCOCCOCCOCCOCCC(=O)O)CC1)c1cccc(C)c1]

To a solution of tert-butyl 1-(trans-4-(1-(2-(ethyl(m-tolyl)amino)-2-oxoethyl)-1H-pyrrole-2-carboxamido)cyclohexyl)-1,8-dioxo-12,15,18,21-tetraoxa-2,9-diazatetracosan-24-oate (45 mg, 0.054 mmol) in DCM (5 mL), TFA (1 mL) was added. The solution stirred at RT for 18 h. The mixture was diluted with toluene, concentrated, resuspended in toluene, and concentrated. This was repeated two times. The crude product (47 mg) was used in the next step. ESI MS m/z 772 [M+H]+.

Step 3. N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,24-trioxo-12,15,18,21,28-pentaoxa-2,9,25-triazatriacontan-30-yl)piperazin-1-yl)-2-methylpyrimidin-4-yl)amino)thiazole-5-carboxamide (JRW-0593)

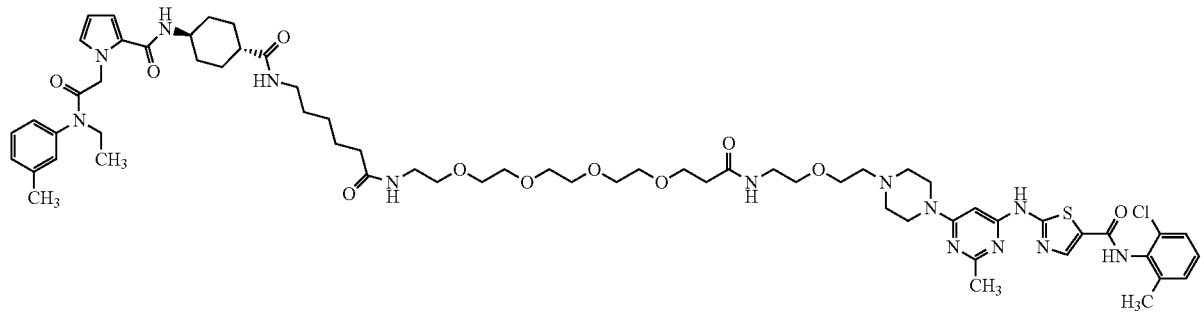 [SMILES: CCN(C(=O)Cn1cccc1C(=O)N[C@H]1CC[C@H](C(=O)NCCCCCC(=O)NCCOCCOCCOCCOCCC(=O)NCCOCCN2CCN(c3cc(Nc4ncc(C(=O)Nc5c(C)cccc5Cl)s4)nc(C)n3)CC2)CC1)c1cccc(C)c1]

To a solution of 1-(trans-4-(1-(2-(ethyl(m-tolyl)amino)-2-oxoethyl)-1H-pyrrole-2-carboxamido)cyclohexyl)-1,8-dioxo-12,15,18,21-tetraoxa-2,9-diazatetracosan-24-oic acid (12 mg, 0.015 mmol) in DMF (3 mL), HOBT (5 mg, 0.031 mmol), EDC (6 mg, 0.031 mmol), diisopropyethylamine (6 mg, 0.046 mmol), and 2-((6-(4-(2-(2-aminoethoxy)ethyl)piperazin-1-yl)-2-methylpyrimidin-4-yl)amino)-N-(2-chloro-6-methylphenyl)thiazole-5-carboxamide (12 mg, 0.023 mmol) was added. The solution was heated to 60° C. for 18 h. The mixture was diluted with ethyl acetate and washed with water. The organic layers were combined, dried with sodium sulfate, filtered, concentrated, and purified with silica gel chromatography to afford the desired product (10 mg, 50%) as a white solid. $^1$H NMR (300 MHz, DMSO-$d_6$) δ 11.44 (s, 1H), 9.84 (s, 1H), 8.19 (s, 1H), 7.91-7.82 (m, 1H), 7.82-7.75 (m, 1H), 7.69-7.57 (m, 2H), 7.42-7.33 (m, 2H), 7.30-7.15 (m, 5H), 6.79-6.72 (s, 2H), 6.03 (s, 1H), 5.96-5.93 (m, 1H), 4.78 (s, 2H), 3.66-3.43 (m, 23H), 3.43-3.34 (m, 4H), 3.23-3.12 (m, 4H), 3.05-2.92 (m, 2H), 2.38 (s, 3H), 2.34 (s, 3H), 2.33-2.23 (s, 2H), 2.22 (s, 3H), 2.07-1.97 (m, 3H), 1.87-1.66 (m, 4H), 1.52-1.10 (s, 14H), 1.05-0.93 (m, 3H); ESI MS m/z 1284 [M+H]+; HPLC 99.1% (AUC), $T_R$ 3.94 min; UV (MeOH) λ 322 nm, ε 37166.

Example 41

N-(trans-4-((1-(4-(6-((5-((2-chloro-6-methylphenyl)carbamoyl)thiazol-2-yl)amino)-2-methylpyrimidin-4-yl)piperazin-1-yl)-7,23-dioxo-3,10,13,16,19-pentaoxa-6,22-diazaoctacosan-28-yl)carbamoyl)cyclohexyl)-4-(2-(ethyl(3-ethylphenyl)amino)-2-oxoethyl)-4H-thieno[3,2-b]pyrrole-5-carboxamide (JRW-0595)

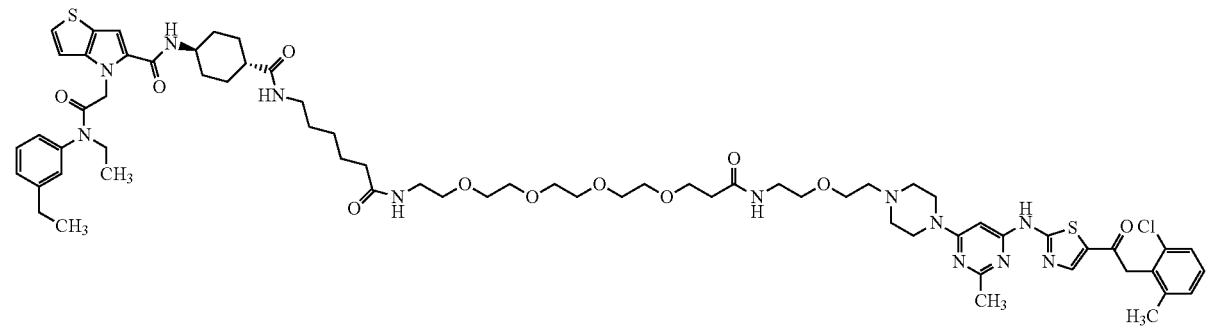 [SMILES: CCc1cccc(N(CC)C(=O)Cn2c(C(=O)N[C@H]3CC[C@H](C(=O)NCCCCCC(=O)NCCOCCOCCOCCOCCC(=O)NCCOCCN4CCN(c5cc(Nc6ncc(C(=O)Cc7c(C)cccc7Cl)s6)nc(C)n5)CC4)CC3)cc3sccc32)c1]

Step 1. tert-butyl 1-(trans-4-(4-(2-(ethyl(3-ethylphenyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate (JRW-0591)

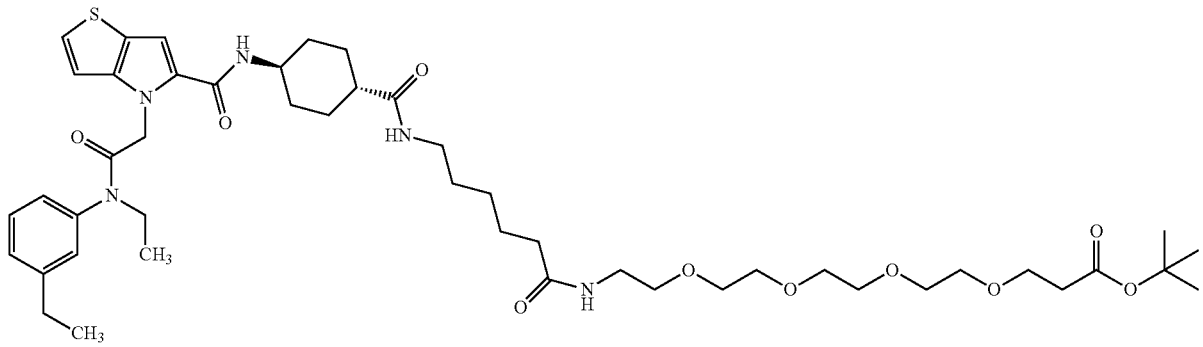 [SMILES: CCc1cccc(N(CC)C(=O)Cn2c(C(=O)N[C@H]3CC[C@H](C(=O)NCCCCCC(=O)NCCOCCOCCOCCOCCC(=O)OC(C)(C)C)CC3)cc3sccc32)c1]

To a solution of 6-(trans-4-(4-(2-(ethyl(3-ethylphenyl)amino)-2-oxoethyl)-4H-thieno[3,2-b]pyrrole-5-carboxamido)cyclohexane-1-carboxamido)hexanoic acid (50 mg, 0.084 mmol) in DMF (3 mL), HOBT (25 mg, 0.16 mmol), EDC (32 mg, 0.16 mmol), diisopropyethylamine (33 mg, 0.25 mmol), and tert-butyl 1-amino-3,6,9,12-tetraoxapentadecan-15-oate (40 mg, 0.13 mmol) was added. The solution was heated to 60° C. for 18 h. The mixture was diluted with ethyl acetate and washed with water. The organic layers were combined, dried with sodium sulfate, filtered, concentrated, and purified with silica gel chromatography to afford the desired product (62 mg, 82%) as a white foam. ESI MS m/z 898 [M+H]+.

Step 2. 1-(trans-4-(4-(2-(ethyl(3-ethylphenyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oic acid (JRW-0594)

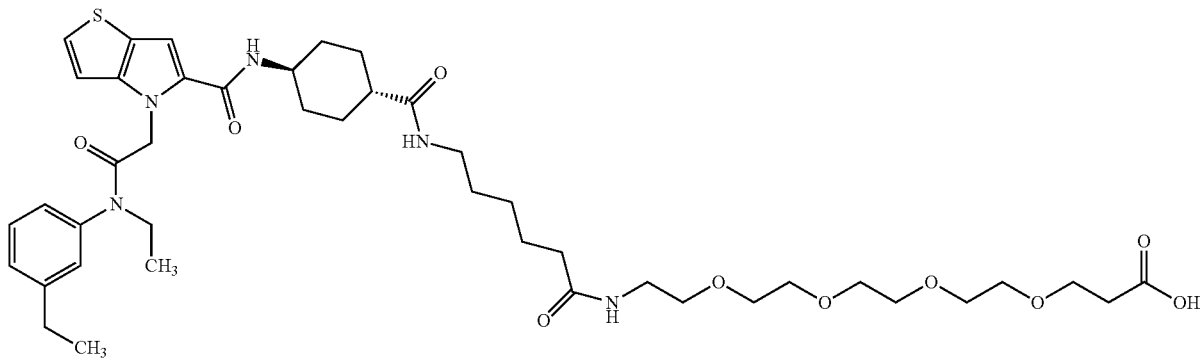 [SMILES: CCc1cccc(N(CC)C(=O)Cn2c(C(=O)N[C@H]3CC[C@H](C(=O)NCCCCCC(=O)NCCOCCOCCOCCOCCC(=O)O)CC3)cc3sccc32)c1]

To a solution of tert-butyl 1-(trans-4-(4-(2-(ethyl(3-ethylphenyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate (62 mg, 0.069 mmol) in DCM (5 mL), TFA (1 mL) was added. The solution stirred at RT for 2 h. The mixture was diluted with toluene, concentrated, resuspended in toluene, and concentrated. This was repeated two times. The crude product (65 mg) was used in the next step. ESI MS m/z 842 [M+H]+.

Step 3. N-(trans-4-((1-(4-(6-((5-((2-chloro-6-methylphenyl)carbamoyl)thiazol-2-yl)amino)-2-methylpyrimidin-4-yl)piperazin-1-yl)-7,23-dioxo-3,10,13,16,19-pentaoxa-6,22-diazaoctacosan-28-yl)carbamoyl)cyclohexyl)-4-(2-(ethyl(3-ethylphenyl)amino)-2-oxoethyl)-4H-thieno[3,2-b]pyrrole-5-carboxamide (JRW-0595)

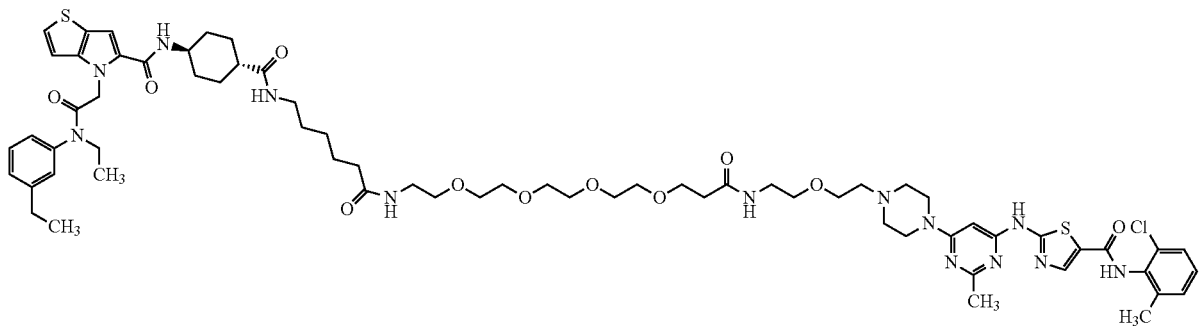 [SMILES: CCc1cccc(N(CC)C(=O)Cn2c(C(=O)N[C@H]3CC[C@H](C(=O)NCCCCCC(=O)NCCOCCOCCOCCOCCC(=O)NCCOCCN4CCN(c5cc(Nc6ncc(C(=O)Nc7c(C)cccc7Cl)s6)nc(C)n5)CC4)CC3)cc3sccc32)c1]

To a solution of 1-(trans-4-(4-(2-(ethyl(3-ethylphenyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oic acid (15 mg, 0.018 mmol) in DMF (3 mL), HOBT (5 mg, 0.035 mmol), EDC (7 mg, 0.035 mmol), diisopropyethylamine (7 mg, 0.053 mmol), and 2-((6-(4-(2-(2-aminoethoxy)ethyl)piperazin-1-yl)-2-methylpyrimidin-4-yl)amino)-N-(2-chloro-6-methylphenyl)thiazole-5-carboxamide (14 mg, 0.027 mmol) was added. The solution was heated to 60° C. for 18 h. The mixture was diluted with ethyl acetate and washed with water. The organic layers were combined, dried with sodium sulfate, filtered, concentrated, and purified with silica gel chromatography to afford the desired product (14 mg, 58%) as a white solid. $^1$H NMR (300 MHz, DMSO-$d_6$) δ 11.43 (s, 1H), 9.84 (m, 1H), 8.19 (s, 1H), 7.92-7.75 (s, 3H), 7.72-7.58 (m, 1H), 7.50-7.17 (m, 7H), 7.12-7.05 (m, 2H), 6.03 (s, 1H), 4.95 (s, 2H), 3.72-3.43 (m, 22H), 3.41-3.34 (m, 4H), 3.23-3.12 (m, 4H), 3.03-2.93 (m, 2H), 2.73-2.60 (m, 2H), 2.38 (s, 3H), 2.34-2.26 (m, 2H), 2.22 (s, 3H), 2.10-1.97 (m, 3H), 1.90-1.67 (m, 4H), 1.51-1.12 (m, 15H), 1.05-0.95 (m, 3H); ESI MS m/z 1354 [M+H]+; HPLC 98.5% (AUC), T$_R$ 4.51 min; UV (MeOH) λ 322 nm, ε 37048.

Example 42

N-(trans-4-((6-(3',6'-dihydroxy-3-oxo-3H-spiro[isobenzofuran-1,9'-xanthene]-5-carboxamido)hexyl)carbamoyl)cyclohexyl)-4-(2-(ethyl(m-tolyl)amino)-2-oxoethyl)-4H-thieno[3,2-b]pyrrole-5-carboxamide (JRW-0200)

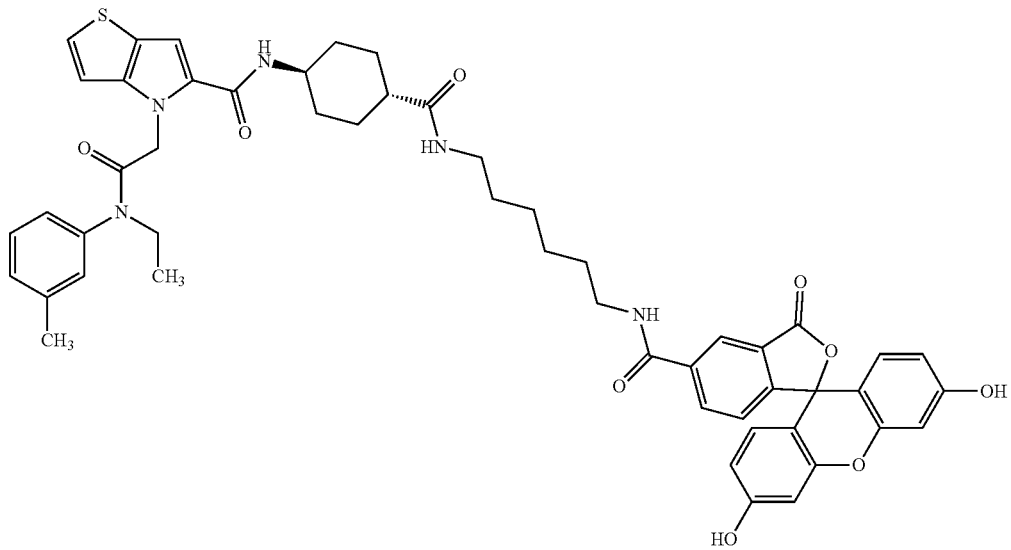

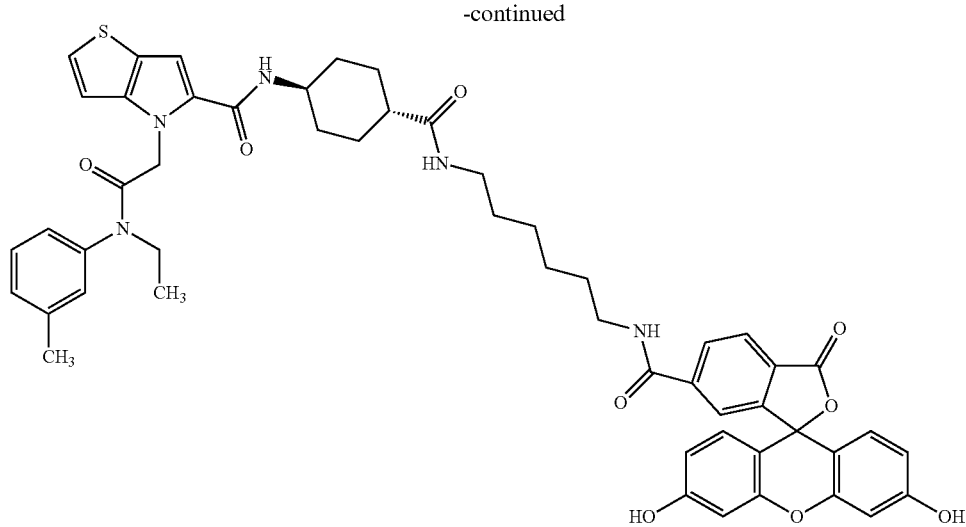
The title compound was prepared using the synthesis method described in U.S. patent application Ser. No. 15/192,420, which is incorporated by reference herein in its entirety.
Example 43
5-((6-(trans-4-(1-(2-(ethyl(3-ethylphenyl)amino)-2-oxoethyl)-1H-indole-2-carboxamido)cyclohexane-1-carboxamido)hexyl)carbamoyl)-3-oxo-3H-spiro[isobenzofuran-1,9'-xanthene]-3',6'-diyl diacetate (JRW-0650)
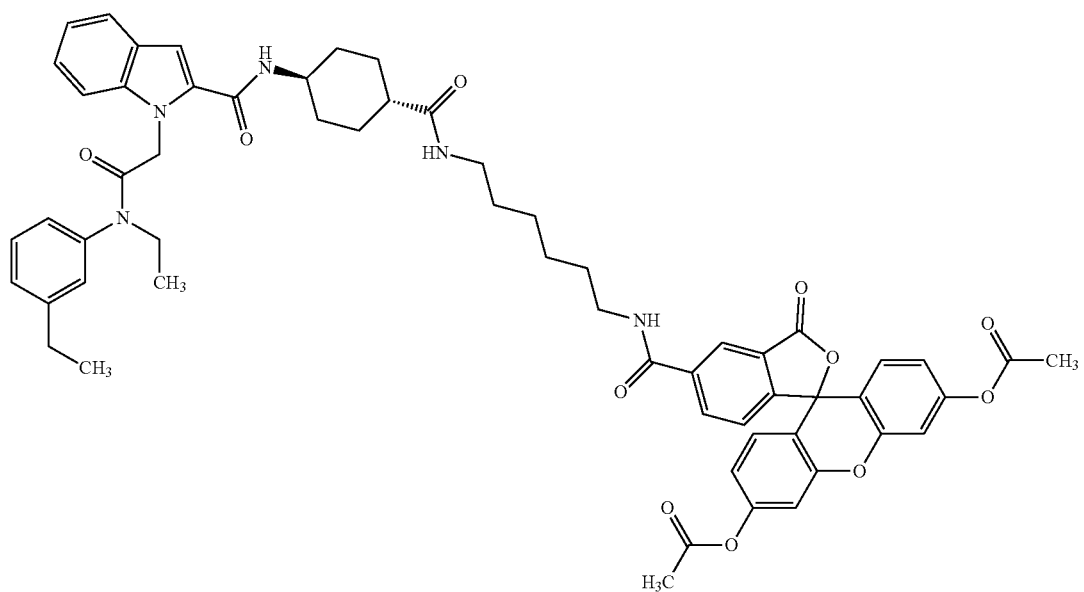

-continued

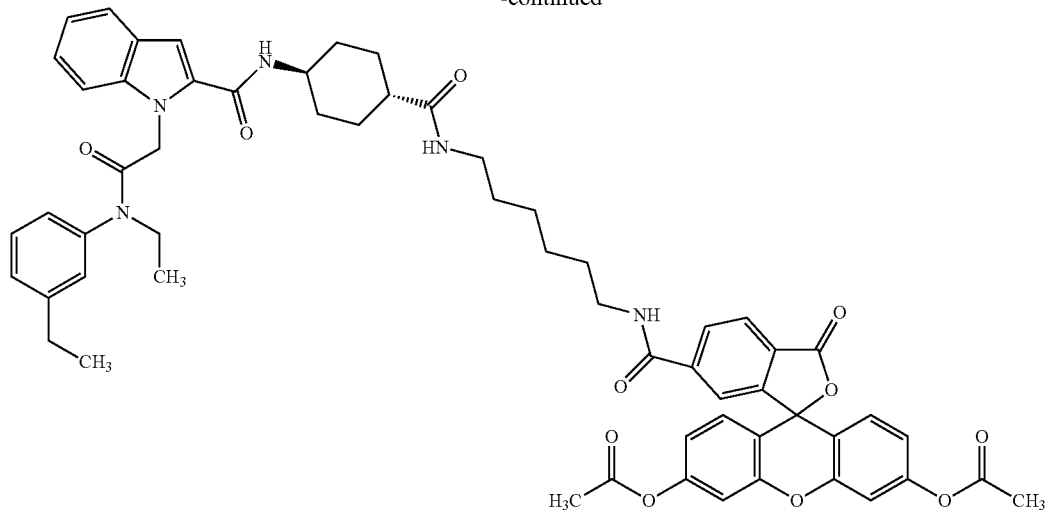

Step 1. tert-butyl (6-(trans-4-(1-(2-(ethyl(3-ethyl-phenyl)amino)-2-oxoethyl)-1H-indole-2-carbox-amido)cyclohexane-1-carboxamido)hexyl)carbamate (JRW-0647)

Step 2. N-(trans-4-((6-aminohexyl)carbamoyl)cyclo-hexyl)-1-(2-(ethyl(3-ethylphenyl)amino)-2-oxo-ethyl)-1H-indole-2-carboxamide (JRW-0648)

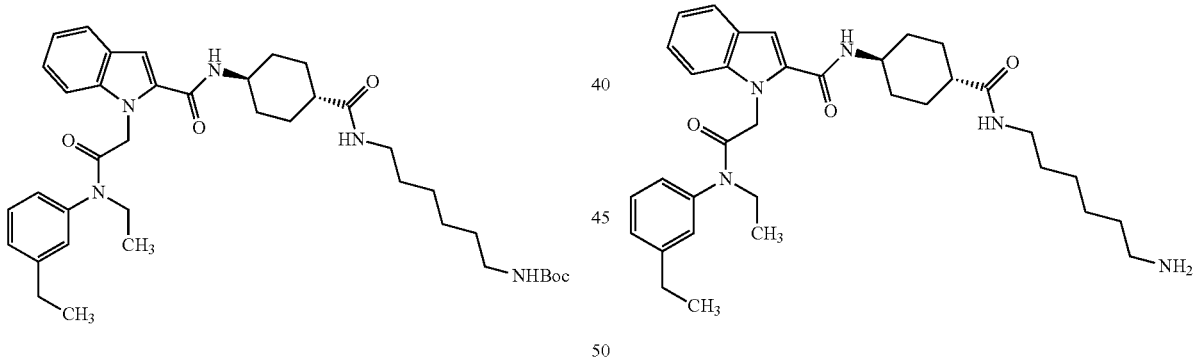

To a solution of trans-4-(1-(2-(ethyl(3-ethylphenyl)amino)-2-oxoethyl)-1H-indole-2-carboxamido)cyclo-hexane-1-carboxylic acid (100 mg, 0.21 mmol) in DMF (3 mL), HOBT (64 mg, 0.42 mmol), EDC (80 mg, 0.42 mmol), diisopropyethylamine (81 mg, 0.63 mmol), and tert-butyl (6-aminohexyl)carbamate (68 mg, 0.31 mmol) was added. The solution was heated to 60° C. for 18 h. The mixture was diluted with ethyl acetate and washed with water. The organic layers were combined, dried with sodium sulfate, filtered, concentrated, and purified with silica gel chromatography to afford the desired product (150 mg, crude) as an oil. ESI MS m/z 674 [M+H]+.

To a solution of tert-butyl (6-(trans-4-(1-(2-(ethyl(3-ethylphenyl)amino)-2-oxoethyl)-1H-indole-2-carboxamido) cyclohexane-1-carboxamido)hexyl)carbamate (150 mg, 0.22 mmol) in DCM (10 mL), TFA (1 mL) was added. The solution stirred at RT for 2 h. The mixture was diluted with toluene, concentrated, resuspended in toluene, and concentrated. This was repeated two times. The crude product (140 mg) was used in the next step. ESI MS m/z 574 [M+H]+.

Step 3. 5-((6-(trans-4-(1-(2-(ethyl(3-ethylphenyl)amino)-2-oxoethyl)-1H-indole-2-carboxamido)cyclohexane-1-carboxamido)hexyl)carbamoyl)-3-oxo-3H-spiro[isobenzofuran-1,9'-xanthene]-3',6'-diyl diacetate (JRW-0650)

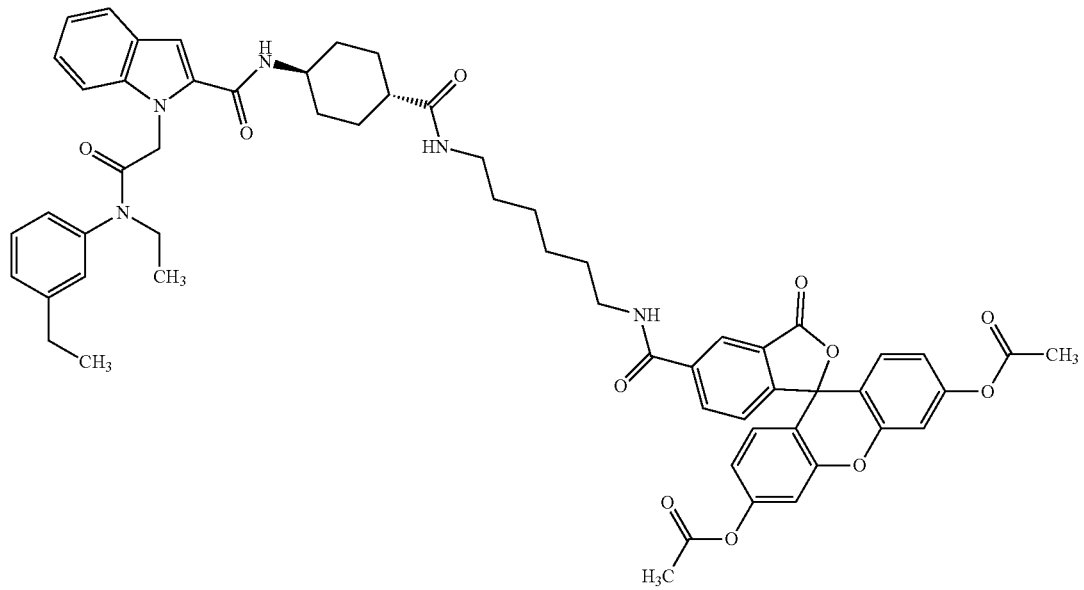

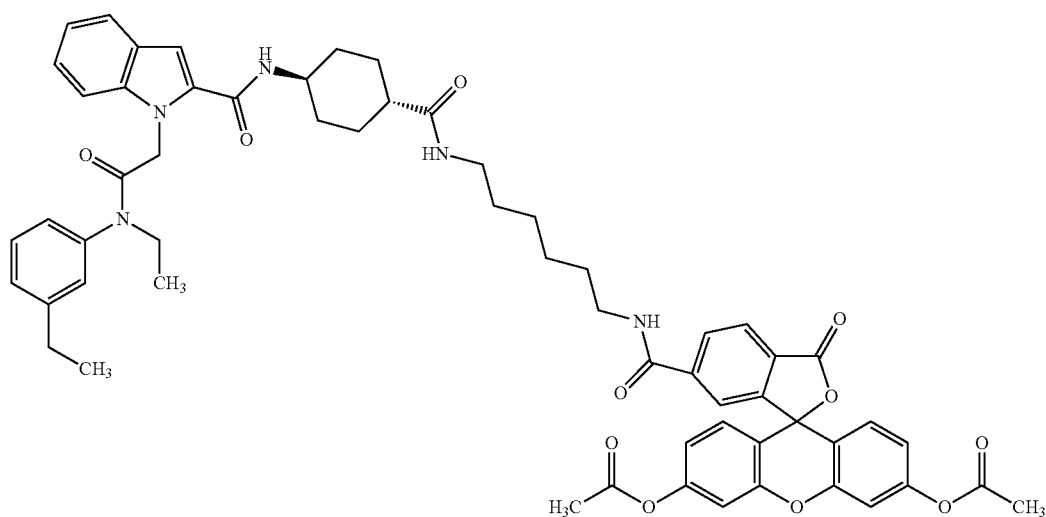

To a solution of N-(trans-4-(((6-aminohexyl)carbamoyl)cyclohexyl)-1-(2-(ethyl(3-ethylphenyl)amino)-2-oxoethyl)-1H-indole-2-carboxamide (0.22 mmol) in DCM (10 mL), a mixture of 5- and 6-((2,5-dioxopyrrolidin-1-yl)oxy)carbonyl)-3-oxo-3H-spiro[isobenzofuran-1,9'-xanthene]-3',6'-diyl diacetate (148 mg, 0.26 mmol) and diisopropylethylamine (115 mg, 0.89 mmol) was added. The solution was stirred at RT for 1 h. The mixture was diluted with DCM and washed with HCl (1 M). The organic layers were combined, dried with sodium sulfate, filtered, concentrated, and purified with silica gel chromatography to afford the desired product (125 mg, 56%) as a white solid. $^1$H NMR (300 MHz, DMSO-$d_6$) δ 8.87-8.73 (m, 1H, isomer A), 8.72-8.58 (m, 1H, isomer B), 8.51 (s, 1H, isomer A), 8.30-8.09 (m, 2H), 7.79 (s, 1H, isomer B), 7.74-7.14 (m, 10H), 7.12-7.00 (m, 2H), 6.99-6.87 (m, 4H), 5.02 (s, 2H), 3.82-3.50 (m, 3H), 3.22-3.13 (m, 1H), 3.10-2.90 (m, 2H), 2.75-2.62 (m, 2H), 2.27 (s, 6H), 2.12-1.98 (m, 2H), 1.91-1.65 (m, 4H), 1.61-1.18 (m, 15H), 1.10-0.94 (m, 3H); ESI MS m/z 1016 [M+H]+; HPLC 87.8% (AUC), $T_R$ 6.56 min; UV (MeOH) λ 290 nm, ε 23397.

Example 44

N-(trans-4-((6-(3',6'-dihydroxy-3-oxo-3H-spiro[isobenzofuran-1,9'-xanthene]-5-carboxamido)hexyl)carbamoyl)cyclohexyl)-1-(2-(ethyl(3-ethylphenyl)amino)-2-oxoethyl)-1H-indole-2-carboxamide (JRW-0818)

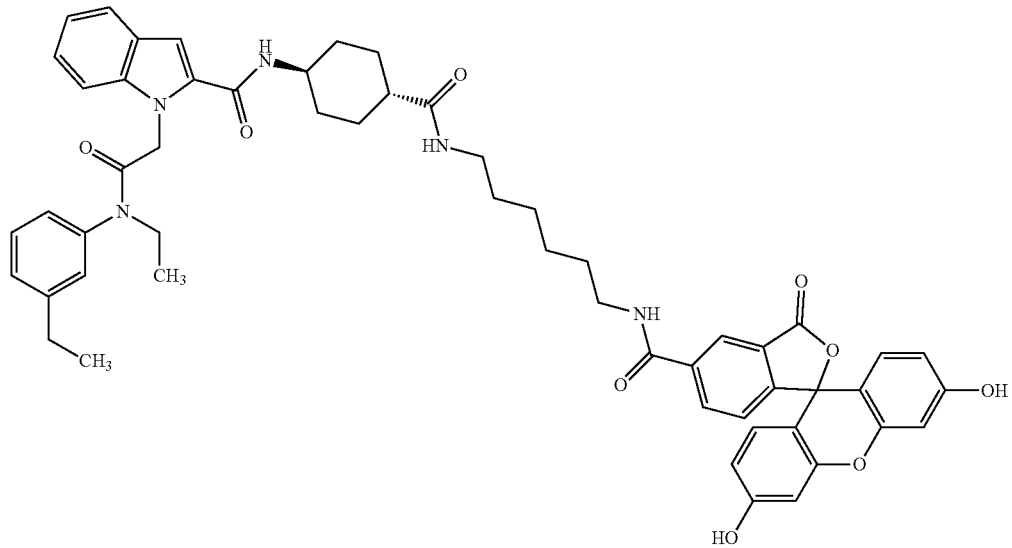

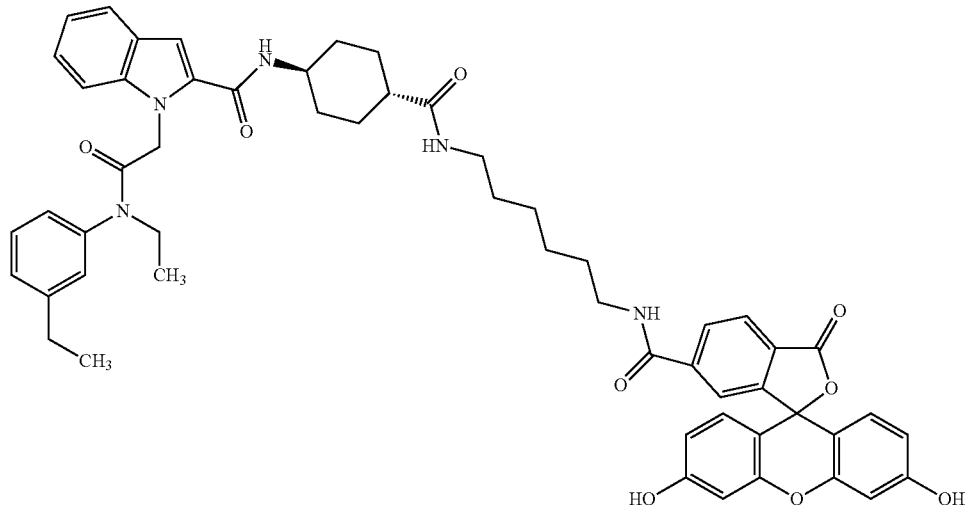

To a solution of 5-((6-(trans-4-(1-(2-(ethyl(3-ethylphenyl)amino)-2-oxoethyl)-1H-indole-2-carboxamido)cyclohexane-1-carboxamido)hexyl)carbamoyl)-3-oxo-3H-spiro[isobenzofuran-1,9'-xanthene]-3',6'-diyl diacetate (50 mg, 0.049 mmol) in methanol (5 mL), potassium carbonate (34 mg, 0.25 mmol) was added. The reaction stirred at RT for 30 min. The mixture was diluted with ethyl acetate and washed with HCl (1 M). The organic layers were combined, dried with sodium sulfate, filtered, concentrated, and purified with silica gel chromatography to afford the desired product (42 mg, 91%) as an orange solid. $^1$H NMR (300 MHz, DMSO-$d_6$) δ 10.18 (s, 2H), 8.86-8.72 (m, 1H, isomer A), 8.72-8.57 (m, 1H, isomer B), 8.45 (s, 1H, isomer A), 8.25-8.13 (m, 2H), 8.11-8.00 (m, 1H, isomer B), 7.77-7.15 (m, 9H), 7.12-7.02 (m, 2H), 6.67 (s, 2H), 6.63-6.49 (m, 4H), 5.02 (s, 2H), 3.84-3.46 (m, 3H), 3.21-3.13 (m, 1H), 3.09-2.90 (m, 2H), 2.76-2.60 (m, 2H), 2.14-1.96 (m, 1H), 1.91-1.68 (m, 4H), 1.62-1.18 (m, 15H), 1.08-0.95 (m, 3H); ESI MS m/z 930 [M−H]−; HPLC >99% (AUC), $T_R$ 6.44 min; UV (MeOH) λ 288 nm, ε 20392.

Example 45

N-(trans-4-((6-(3',6'-bis(dimethylamino)-3-oxo-3H-spiro[isobenzofuran-1,9'-xanthene]-6-carboxamido)hexyl)carbamoyl)cyclohexyl)-1-(2-(ethyl(3-ethylphenyl)amino)-2-oxoethyl)-1H-indole-2-carboxamide (JRW-0822)

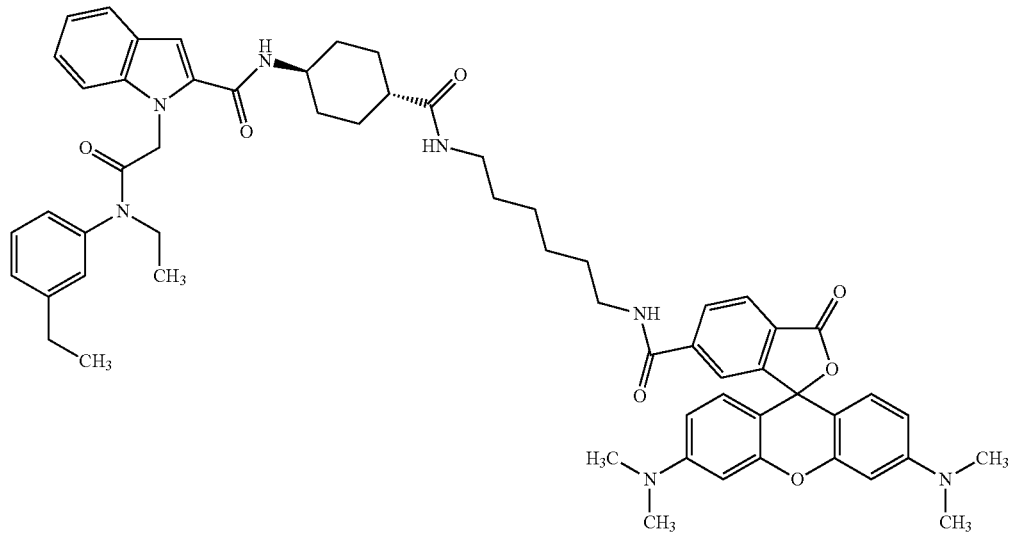 [SMILES: CCc1cccc(N(CC)C(=O)Cn2c(C(=O)N[C@H]3CC[C@H](C(=O)NCCCCCCNC(=O)c4ccc5c(c4)C4(OC5=O)c5ccc(N(C)C)cc5Oc5cc(N(C)C)ccc54)CC3)cc3ccccc32)c1]

To a solution of N-(trans-4-((6-aminohexyl)carbamoyl)cyclohexyl)-1-(2-(ethyl(3-ethylphenyl)amino)-2-oxoethyl)-1H-indole-2-carboxamide (35 mg. 0.061 mmol) in DCM (5 mL), a mixture of 2,5-dioxopyrrolidin-1-yl 3',6'-bis(dimethylamino)-3-oxo-3H-spiro[isobenzofuran-1,9'-xanthene]-6-carboxylate (32 mg, 0.061 mmol) and diisopropylethylamine (31 mg, 0.24 mmol) was added. The solution was stirred at RT for 2 h. The mixture was diluted with DCM and water. The aqueous layer was extracted with a mixture of CHCl$_3$/isopropanol (3:1), the organic layers were combined, dried with sodium sulfate, filtered, concentrated, and purified with silica gel chromatography to afford the desired product (41 mg, 68%) as a purple black solid. $^1$H NMR (300 MHz, DMSO-d$_6$) δ 9.36 (s, 1H), 8.81-8.71 (m, 1H), 8.25-8.18 (m, 3H), 7.82 (s, 1H), 7.75-7.65 (m, 1H), 7.62-7.53 (m, 1H), 7.49-7.00 (m, 8H), 7.00-6.74 (m, 5H), 5.01 (s, 2H), 3.72-3.50 (m, 5H), 3.25-3.05 (s, 14H), 3.04-2.92 (m, 2H), 2.76-2.59 (m, 2H), 2.12-1.95 (m, 1H), 1.89-1.64 (m, 4H), 1.55-1.18 (m, 15H), 1.05-0.95 (m, 3H); ESI MS m/z 986 [M+H]+; HPLC 95.5% (AUC), T$_R$ 5.78 min; UV (MeOH) λ 546 nm, ε 85005.

Example 46

N-(trans-4-((6-(3',6'-bis(dimethylamino)-3-oxo-3H-spiro[isobenzofuran-1,9'-xanthene]-6-carboxamido)hexyl)carbamoyl)cyclohexyl)-4-(2-(ethyl)m-tolyl)amino)-2-oxoethyl)-4H-thieno[3,2-b]pyrrole-5-carboxamide (JRW-0824)

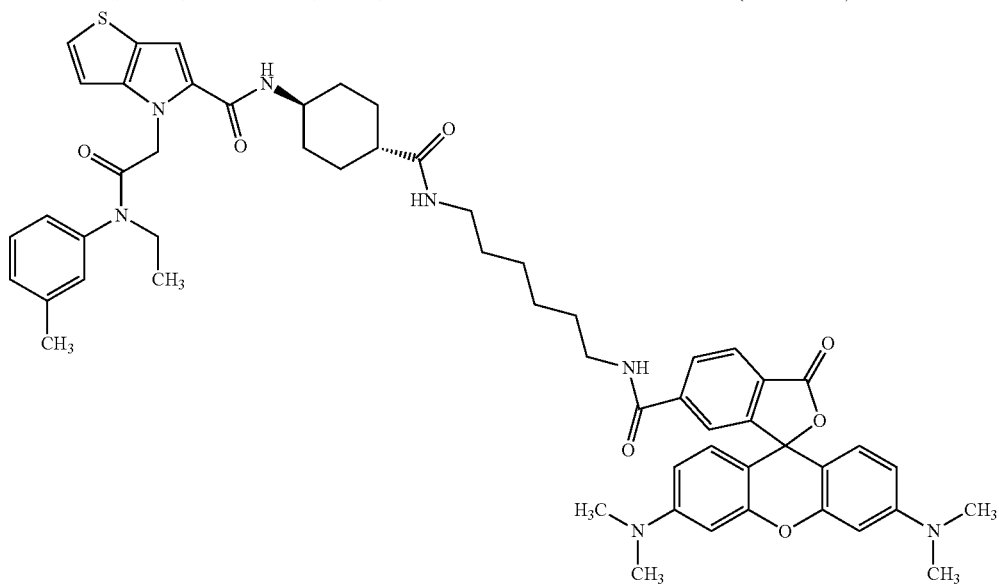

To a solution of N-(trans-4-(((6-aminohexyl)carbamoyl)cyclohexyl)-4-(2-(ethyl(m-tolyl)amino)-2-oxoethyl)-4H-thieno[3,2-b]pyrrole-5-carboxamide (35 mg. 0.062 mmol) in DCM (5 mL), a mixture of 2,5-dioxopyrrolidin-1-yl 3',6'-bis(dimethylamino)-3-oxo-3H-spiro[isobenzofuran-1, 9'-xanthene]-6-carboxylate (33 mg, 0.062 mmol) and diisopropylethylamine (32 mg, 0.25 mmol) was added. The solution was stirred at RT for 1 h. The mixture was diluted with methanol, added to celite, and purified with silica gel chromatography to afford the desired product (36 mg, 60%) as a purple black solid. $^1$H NMR (300 MHz, DMSO-d$_6$) δ 8.68-8.60 (m, 1H), 8.16-8.12 (m, 1H), 8.06-8.02 (m, 1H), 7.91-7.85 (m, 1H), 7.68-7.59 (m, 2H), 7.44-7.33 (m, 2H), 7.31-7.16 (m, 3H), 7.12-7.05 (m, 2H), 6.55-6.44 (m, 6H), 4.97 (s, 2H), 3.70-3.54 (m, 3H), 3.22-3.15 (m, 2H), 3.01-2.88 (m, 14H), 2.36 (s, 3H), 2.09-1.93 (m, 1H), 1.89-1.65 (m, 4H), 1.53-1.18 (m, 12H), 1.10-0.94 (m, 3H); ESI MS m/z 978 [M+H]+; HPLC 91.9% (AUC), T$_R$ 5.52 min.

Example 47

N-(trans-4-((6-(3-(5,5-difluoro-7,9-dimethyl-5H-514,614-dipyrrolo[1,2-c:2',1'-f][1,3,2]diazaborinin-3-yl)propanamido)hexyl)carbamoyl)cyclohexyl)-1-(2-(ethyl(3-ethylphenyl)amino)-2-oxoethyl)-1H-indole-2-carboxamide (JRW-0827)

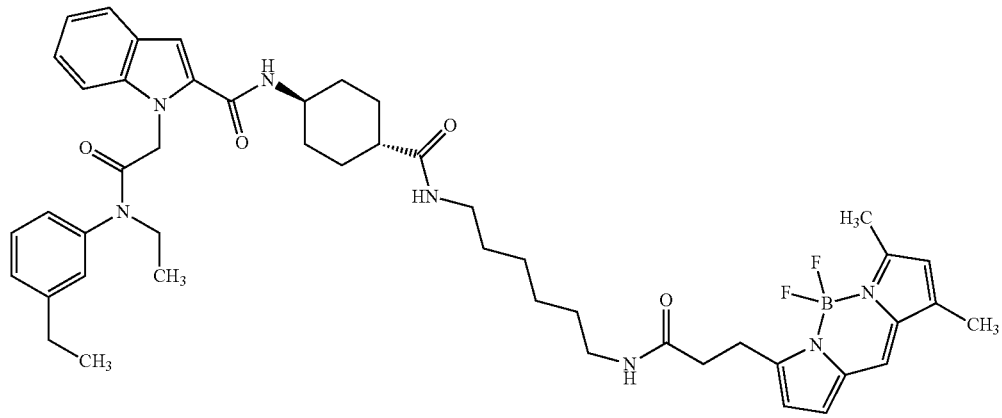

To a solution of N-(trans-4-(((6-aminohexyl)carbamoyl)cyclohexyl)-1-(2-(ethyl(3-ethylphenyl)amino)-2-oxoethyl)-1H-indole-2-carboxamide (20 mg. 0.035 mmol) in DCM (5 mL), a mixture of 2,5-dioxopyrrolidin-1-yl 3-(5,5-difluoro-7,9-dimethyl-5H-514,614-dipyrrolo[1,2-c:2',1'-f][1,3,2]diazaborinin-3-yl)propanoate (10 mg, 0.027 mmol) and diisopropylethylamine (22 mg, 0.17 mmol) was added. The solution was stirred at RT for 18 h. The mixture was diluted with DCM and purified with silica gel chromatography to afford the desired product (21 mg, 70%) as a red solid. $^1$H NMR (300 MHz, DMSO-d$_6$) δ 8.28-8.12 (m, 1H), 7.98-7.80 (m, 1H), 7.72-7.64 (m, 2H), 7.63-7.53 (m, 1H), 7.50-7.15 (m, 6H), 7.13-7.03 (m, 3H), 6.36-6.30 (m, 1H), 6.27 (s, 1H), 5.02 (s, 2H), 3.77-3.52 (m, 3H), 3.11-2.95 (m, 6H), 2.74-2.60 (m, 2H), 2.44 (s, 3H), 2.23 (s, 3H), 2.13-1.92 (m, 1H), 1.92-1.69 (m, 4H), 1.55-1.18 (m, 15H), 1.09-0.95 (m, 3H); ESI MS m/z 848 [M+H]+; HPLC>99% (AUC), T$_R$ 6.84 min; UV (MeOH) λ 504 nm, ε 79275.

Example 48

N-(trans-4-((6-(3-(5,5-difluoro-7,9-dimethyl-5H-5l4,6l4-dipyrrolo[1,2-c:2',1'-f][1,3,2]diazaborinin-3-yl)propanamido)hexyl)carbamoyl)cyclohexyl)-4-(2-(ethyl(m-tolyl)amino)-2-oxoethyl)-4H-thieno[3,2-b]pyrrole-5-carboxamide (JRW-0829)

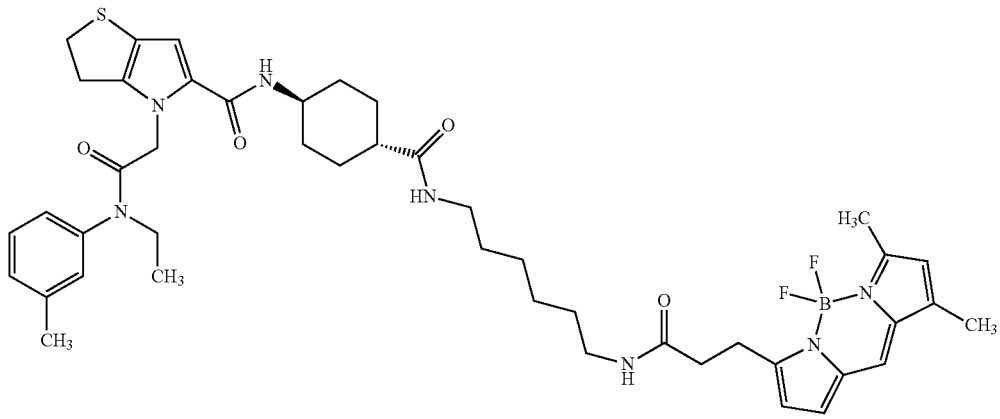

To a solution of N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide (20 mg, 0.035 mmol) in DCM (5 mL), a mixture of 2,5-dioxopyrrolidin-1-yl 3-(5,5-difluoro-7,9-dimethyl-5H-5l4,6l4-dipyrrolo[1,2-c:2',1'-f][1,3,2]diazaborinin-3-yl)propanoate (11 mg, 0.028 mmol) and diisopropylethylamine (22 mg, 0.17 mmol) was added. The solution was stirred at RT for 2 h. The mixture was diluted with DCM and purified with silica gel chromatography to afford the desired product (20 mg, 67%) as a red solid. $^1$H NMR (300 MHz, DMSO-$d_6$) δ 7.91-7.80 (m, 2H), 7.72-7.62 (m, 2H), 7.44-7.33 (m, 2H), 7.32-7.18 (m, 3H), 7.12-7.05 (m, 3H), 6.33 (d, J=4.0, 1H), 6.27 (s, 1H), 4.96 (s, 2H), 3.72-3.54 (s, 3H), 3.11-2.95 (m, 6H), 2.44 (s, 3H), 2.36 (s, 3H), 2.23 (s, 3H), 2.12-1.89 (m, 1H), 1.90-1.68 (s, 4H), 1.55-1.20 (m, 15H), 1.10-0.94 (m, 3H); ESI MS m/z 840 [M+H]+; HPLC 99.7% (AUC), $T_R$ 6.63 min; UV (MeOH) λ 504 nm, ε 85909.

Example 49

N-(trans-4-((6-(3',6'-diamino-3-oxo-3H-spiro[isobenzofuran-1,9'-xanthene]-5,6-carboxamido)hexyl)carbamoyl)cyclohexyl)-1-(2-(ethyl(3-ethylphenyl)amino)-2-oxoethyl)-1H-indole-2-carboxamide (JRW-0859)

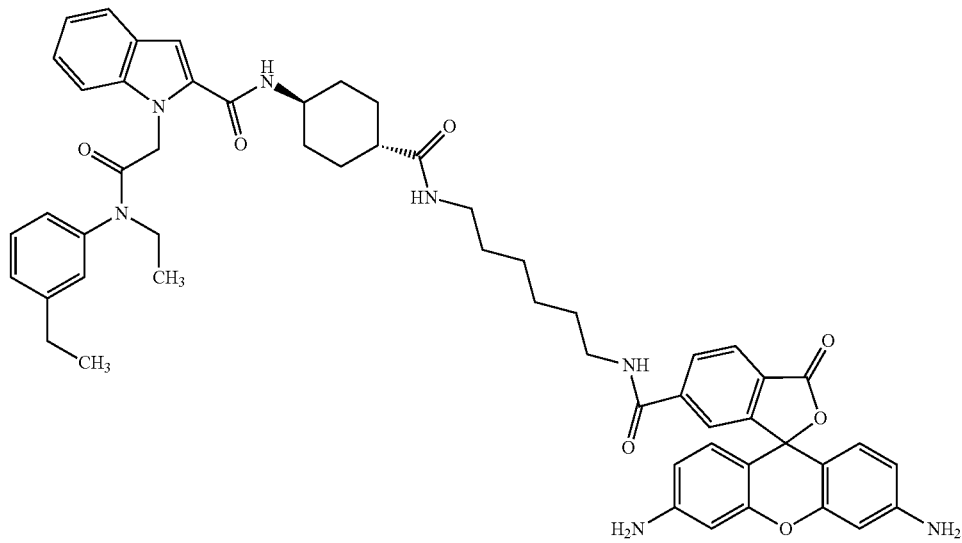

-continued
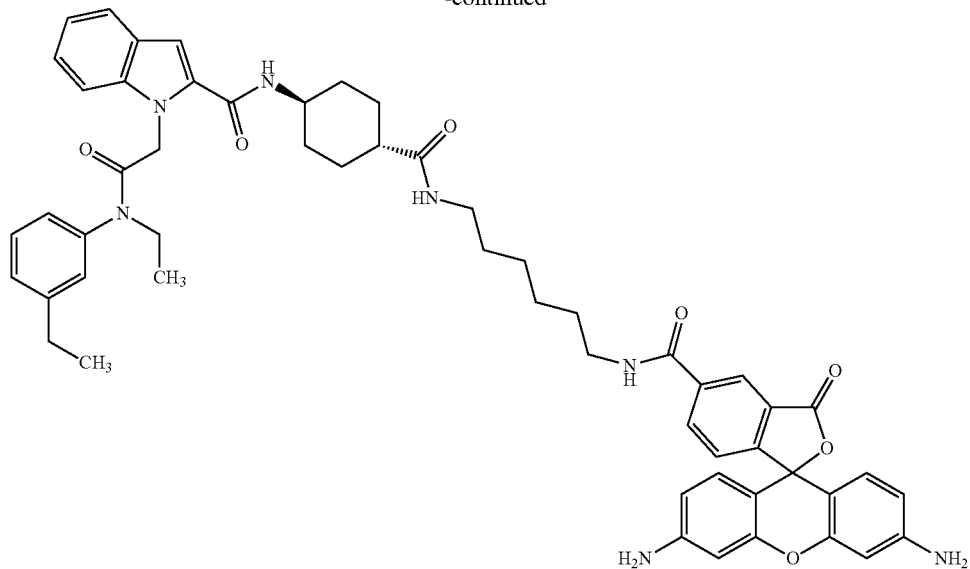
Step 1. N,N'-(5,6-((6-(trans-4-(1-(2-(ethyl(3-ethyl-phenyl)amino)-2-oxoethyl)-1H-indole-2-carbox-amido)cyclohexane-1-carboxamido)hexyl)carbam-oyl)-3-oxo-3H-spiro[isobenzofuran-1,9'-xanthene]-3',6'-diyl)bis(2,2,2-trifluoroacetamide) (JRW-0858)
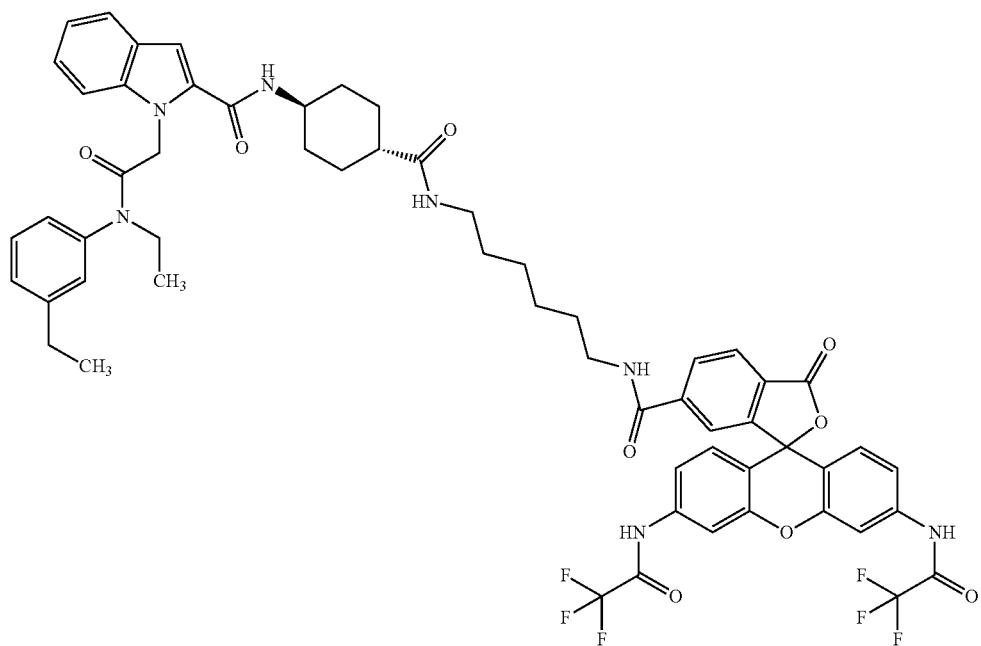

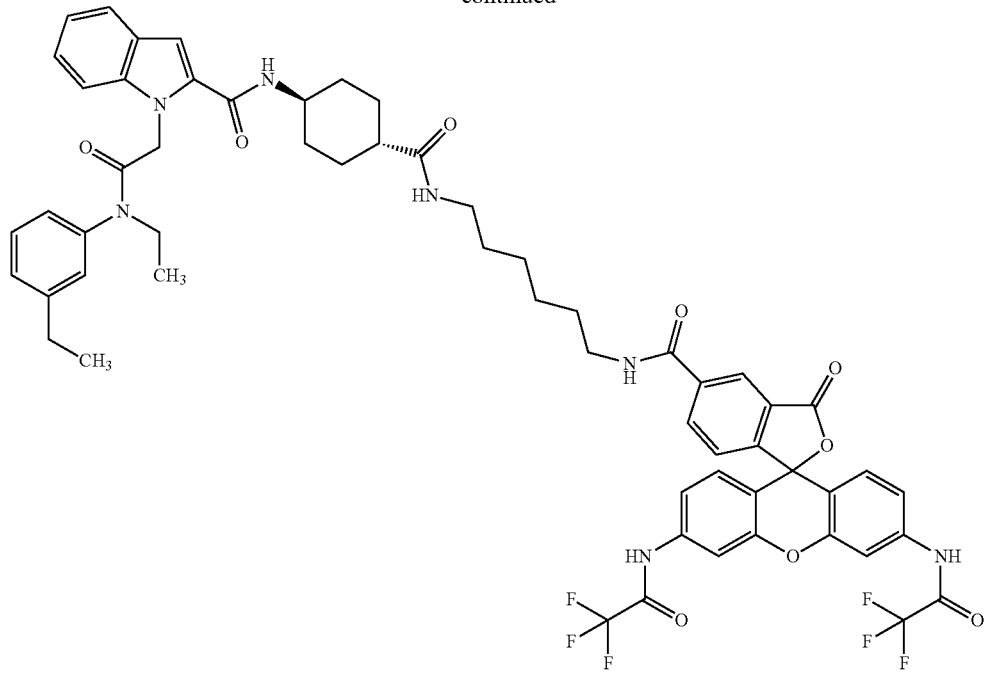

To a solution of N-(trans-4-((6-aminohexyl)carbamoyl)cyclohexyl)-1-(2-(ethyl(3-ethylphenyl)amino)-2-oxoethyl)-1H-indole-2-carboxamide (50 mg, 0.087 mmol) in DCM (5 mL), a mixture of 2,5-dioxopyrrolidin-1-yl 3-oxo-3',6'-bis(2,2,2-trifluoroacetamido)-3H-spiro[isobenzofuran-1,9'-xanthene]-5,6-carboxylate (115 mg, 0.17 mmol) and diisopropylethylamine (45 mg, 0.35 mmol) was added. The solution was stirred at RT for 18 h. The mixture was diluted with DCM and celite, concentrated, and purified with silica gel chromatography to afford crude product (65 mg) as a light red solid. ESI MS m/z 1122 [M+H]+.

Step 2. N-(trans-4-((6-(3',6'-diamino-3-oxo-3H-spiro[isobenzofuran-1,9'-xanthene]-5,6-carboxamido)hexyl)carbamoyl)cyclohexyl)-1-(2-(ethyl(3-ethylphenyl)amino)-2-oxoethyl)-1H-indole-2-carboxamide (JRW-0859)

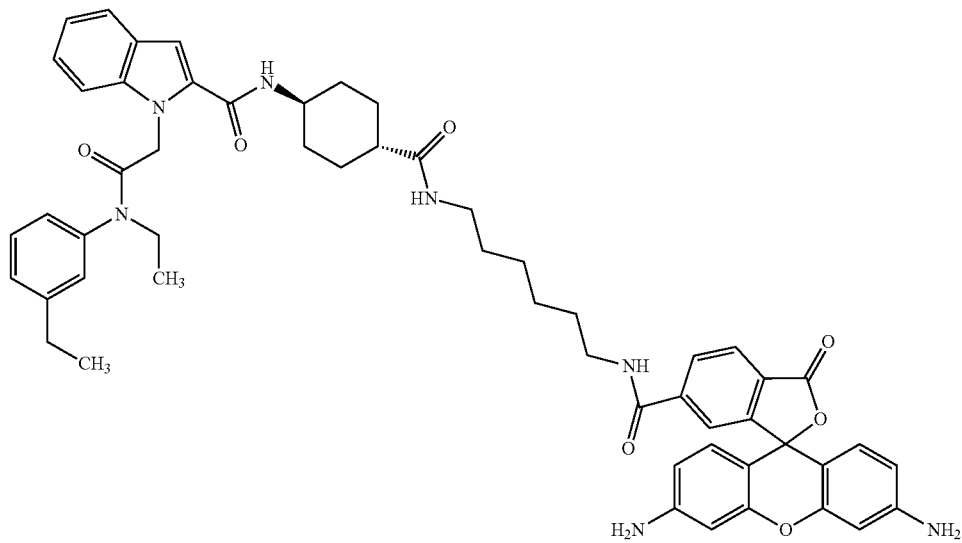

-continued

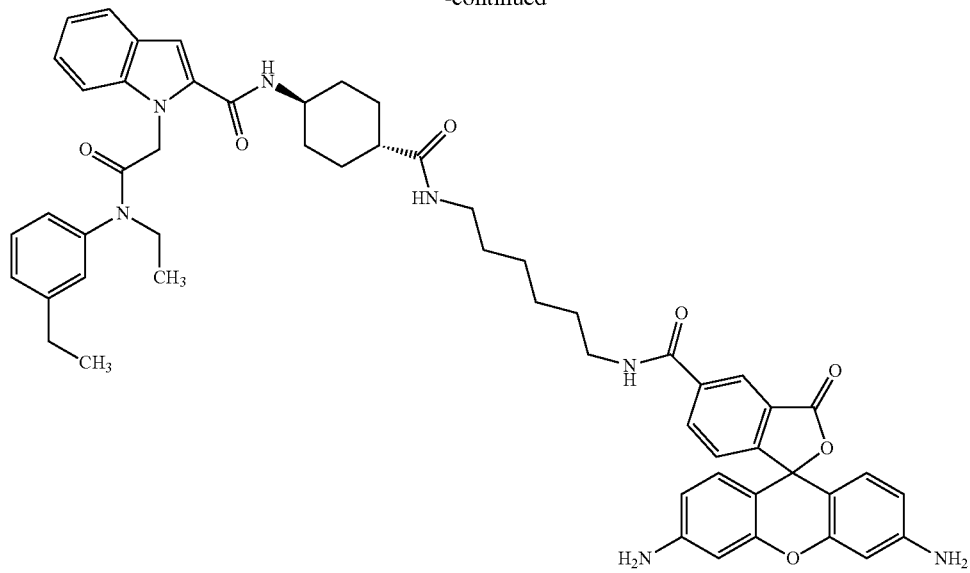

To a solution of N,N'-(5,6((6-(trans-4-(1-(2-(ethyl(3-ethylphenyl)amino)-2-oxoethyl)-1H-indole-2-carboxamido)cyclohexane-1-carboxamido)hexyl)carbamoyl)-3-oxo-3H-spiro[isobenzofuran-1,9'-xanthene]-3',6'-diyl)bis(2,2,2-trifluoroacetamide) (0.087 mmol) in methanol (5 mL) and water (0.1 mL) was added potassium carbonate (24 mg, 0.17 mmol). The reaction stirred at RT for 30 min. The mixture was acidified (2M HCl), diluted with DCM, and celite, concentrated, and purified with silica gel chromatography to afford the desired product (30 mg, 37%) as a red solid. ESI MS m/z 930 [M+H]+.

Example 50

N-(trans-4-((6-(3',6'-diamino-3-oxo-3H-spiro[isobenzofuran-1,9'-xanthene]-6-carboxamido)hexyl)carbamoyl)cyclohexyl)-4-(2-(ethyl)m-tolyl)amino)-2-oxoethyl)-4H-thieno[3,2-b]pyrrole-5,6-carboxamide (JRW-0863)

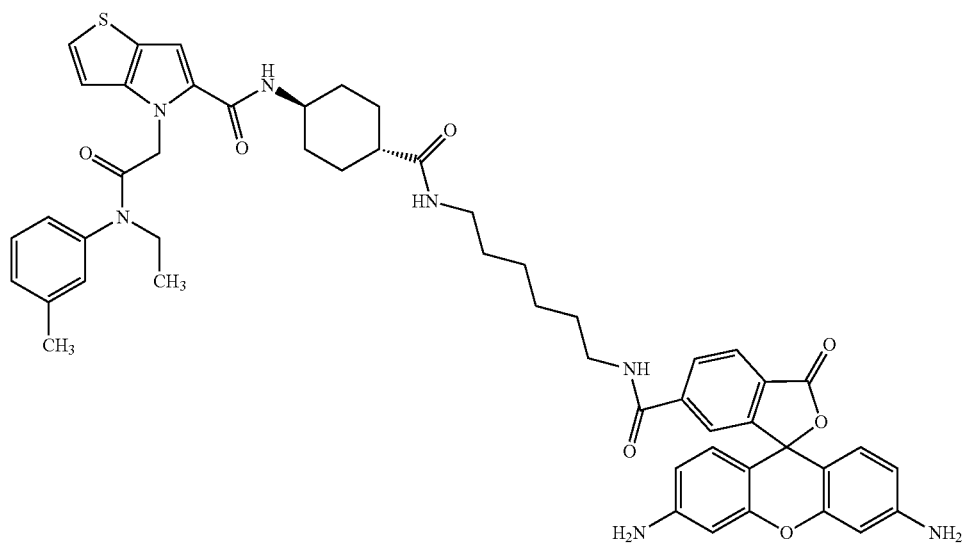

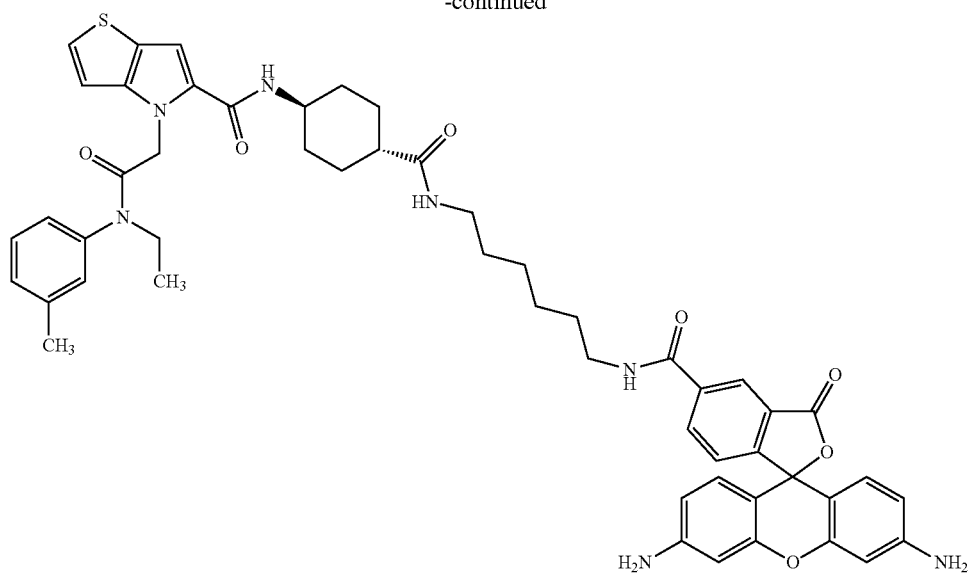
Step 1. N,N'-(5,6-(((6-(trans-4-(4-(2-(ethyl(m-tolyl)amino)-2-oxoethyl)-4H-thieno[3,2-b]pyrrole-5-carboxamido)cyclohexane-1-carboxamido)hexyl)carbamoyl)-3-oxo-3H-spiro[isobenzofuran-1,9'-xanthene]-3',6'-diyl)bis(2,2,2-trifluoroacetamide) (JRW-0862)
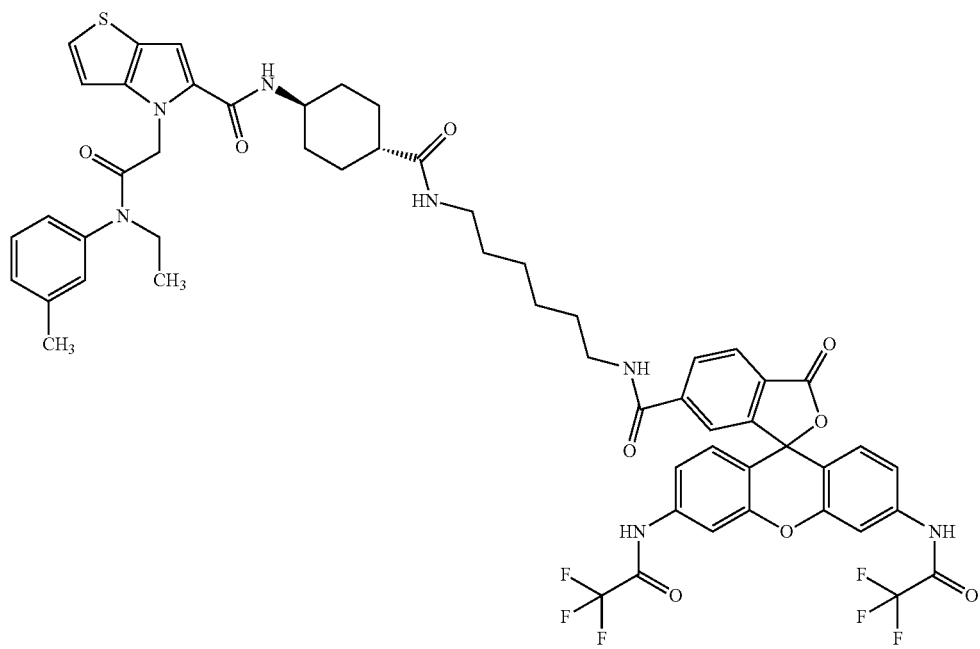

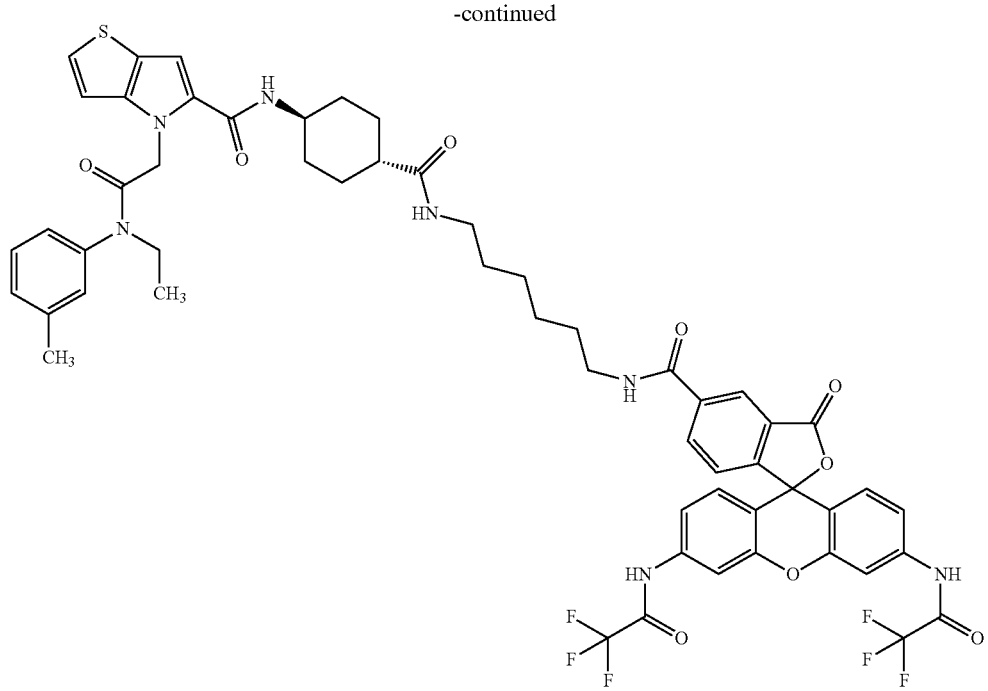

To a solution of N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide (45 mg, 0.080 mmol) in DCM (10 mL), a mixture of 2,5-dioxopyrrolidin-1-yl3-oxo-3',6'-bis(2,2,2-trifluoroacetamido)-3H-spiro[isobenzofuran-1,9'-xanthene]-5,6-carboxylate (53 mg, 0.080 mmol) and diisopropylethylamine (30 mg, 0.24 mmol) was added. The solution was stirred at RT for 18 h. The mixture was diluted with DCM and celite, concentrated, and purified with silica gel chromatography to afford crude product (86 mg) as an orange oil. ESI MS m/z 1114 [M+H]+.

Step 2. N-(trans-4-((6-(3',6'-diamino-3-oxo-3H-spiro[isobenzofuran-1,9'-xanthene]-6-carboxamido)hexyl)carbamoyl)cyclohexyl)-4-(2-(ethyl(m-tolyl)amino)-2-oxoethyl)-4H-thieno[3,2-b]pyrrole-5,6-carboxamide (JRW-0863)

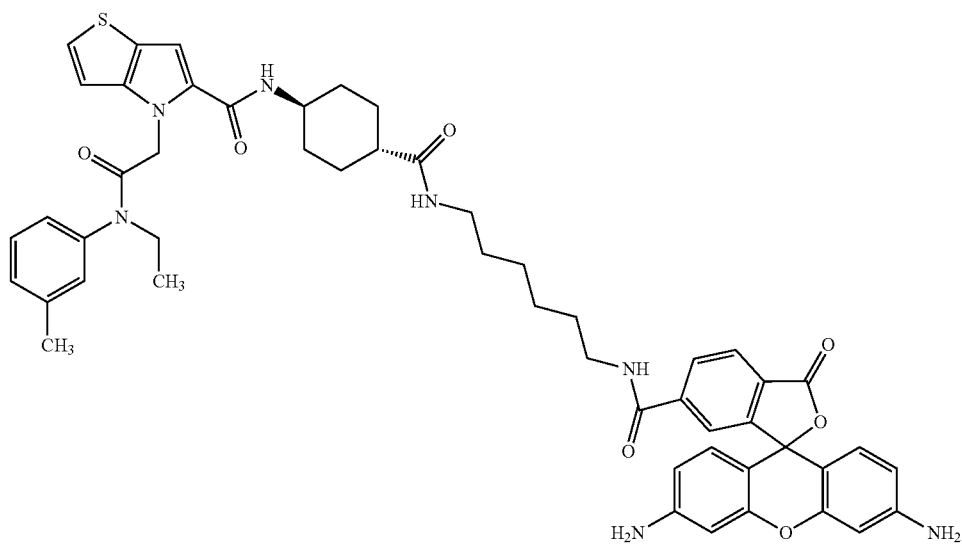

-continued

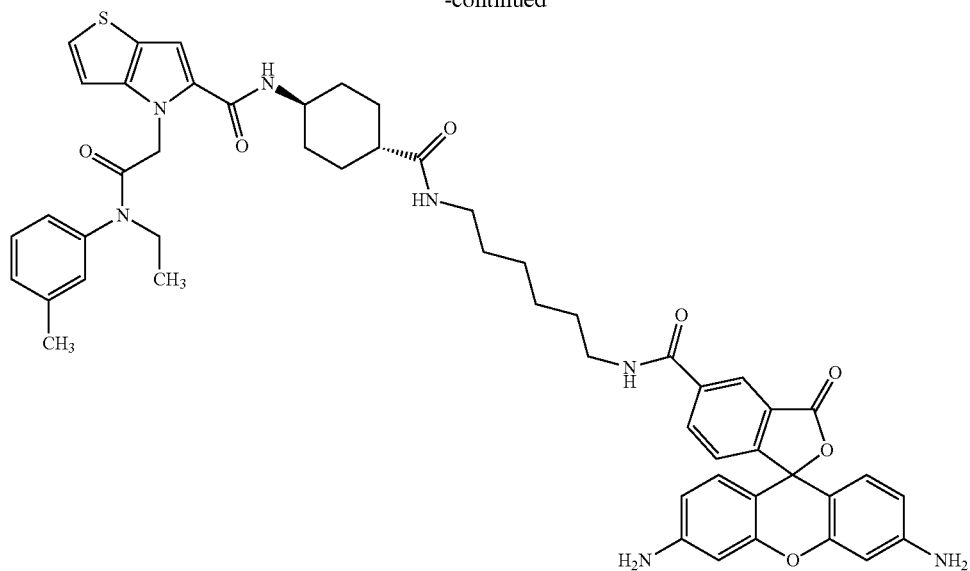

To a solution of N,N'-(5,6-((6-(trans-4-(4-(2-(ethyl(m-tolyl)amino)-2-oxoethyl)-4H-thieno[3,2-b]pyrrole-5-carboxamido)cyclohexane-1-carboxamido)hexyl)carbamoyl)-3-oxo-3H-spiro[isobenzofuran-1,9'-xanthene]-3',6'-diyl)bis(2,2,2-trifluoroacetamide) (0.080 mmol) in methanol (5 mL) and water (0.1 mL) was added potassium carbonate (32 mg, 0.23 mmol). The reaction stirred at RT for 30 min. The mixture was acidified (2M HCl), diluted with DCM and celite, concentrated, and purified with silica gel chromatography to afford the desired product (22 mg, 30%) as a red solid. ESI MS m/z 922 [M+H]+.

Example 51

N-(trans-4-((8-(3',6'-dihydroxy-3-oxo-3H-spiro[isobenzofuran-1,9'-xanthene]-5-carboxamido)octyl)carbamoyl)cyclohexyl)-1-(2-(ethyl(3-ethylphenyl)amino)-2-oxoethyl)-1H-indole-2-carboxamide (JRW-0882)

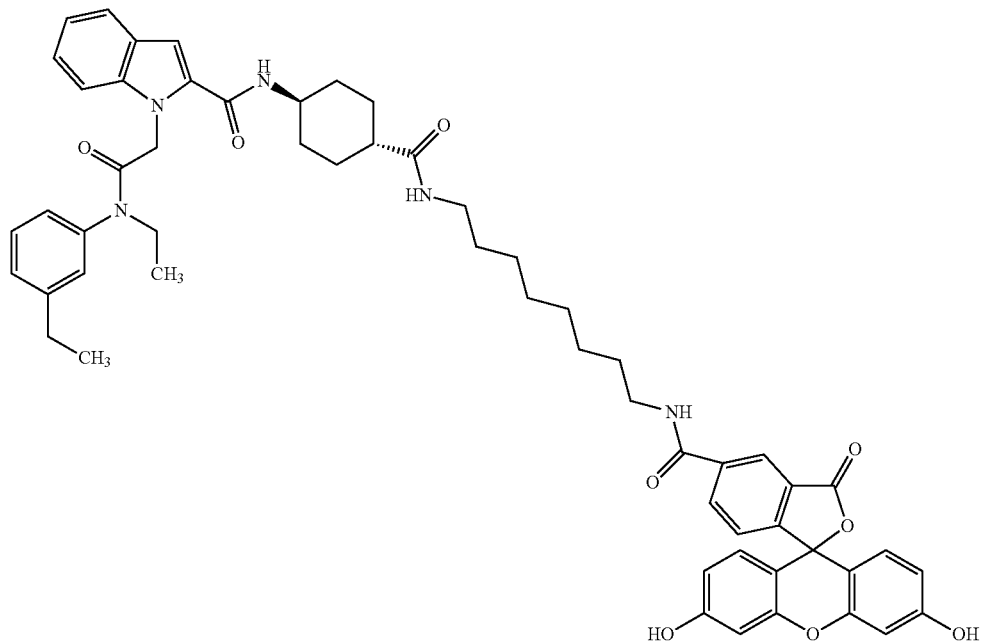 [SMILES: CCc1cccc(N(CC)C(=O)Cn2c(C(=O)N[C@H]3CC[C@H](C(=O)NCCCCCCCCNC(=O)c4ccc5c(c4)C(=O)OC54c5ccc(O)cc5Oc5cc(O)ccc54)CC3)cc3ccccc32)c1]

To a solution of N-(trans-4-((8-aminooctyl)carbamoyl)cyclohexyl)-1-(2-(ethyl(3-ethylphenyl)amino)-2-oxoethyl)-1H-indole-2-carboxamide (200 mg, 0.33 mmol) in DMF (10 mL), 2,5-dioxopyrrolidin-1-yl 3',6'-dihydroxy-3-oxo-3H-spiro[isobenzofuran-1,9'-xanthene]-5-carboxylate (472 mg, 1.0 mmol) and diisopropylethylamine (129 mg, 1.0 mmol) was added. The solution was stirred at RT for 18 h. The mixture was diluted with ethyl acetate and washed with water. Celite was added to the organic layer, concentrated, and purified with silica gel chromatography to afford desired product (32 mg, 10%) as a yellow solid. ESI MS m/z 961 [M+H]+.

Example 52

N-(trans-4-((8-(3',6'-dihydroxy-3-oxo-3H-spiro[isobenzofuran-1,9'-xanthene]-5-carboxamido)octyl)carbamoyl)cyclohexyl)-4-(2-(ethyl)m-tolyl)amino)-2-oxoethyl)-4H-thieno[3,2-b]pyrrole-5-carboxamide (JRW-0883)

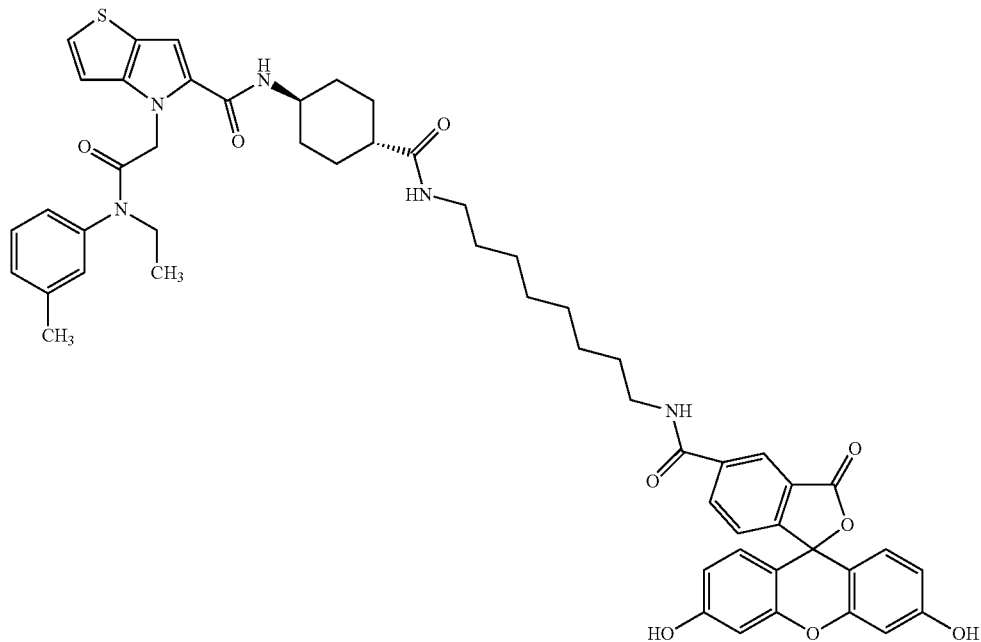 [SMILES: CCN(C(=O)Cn1c(C(=O)N[C@H]2CC[C@H](C(=O)NCCCCCCCCNC(=O)c3ccc4c(c3)C(=O)OC43c4ccc(O)cc4Oc4cc(O)ccc43)CC2)cc2sccc21)c1cccc(C)c1]

To a solution of N-(trans-4-((8-aminooctyl)carbamoyl)cyclohexyl)-4-(2-(ethyl(m-tolyl)amino)-2-oxoethyl)-4H-thieno[3,2-b]pyrrole-5-carboxamide (180 mg, 0.30 mmol) in DMF (10 mL), 2,5-dioxopyrrolidin-1-yl 3',6'-dihydroxy-3-oxo-3H-spiro[isobenzofuran-1,9'-xanthene]-5-carboxylate (430 mg, 0.91 mmol) and diisopropylethylamine (118 mg, 0.91 mmol) was added. The solution was stirred at RT for 18 h. The mixture was diluted with ethyl acetate and washed with water. Celite was added to the organic layer, concentrated, and purified with silica gel chromatography to afford desired product (45 mg, 15%) as a yellow solid. ESI MS m/z 952 [M+H]+.

Example 53
N-(trans-4-((8-(3',6'-diamino-3-oxo-3H-spiro[isobenzofuran-1,9'-xanthene]-5,6-carboxamido)octyl)carbamoyl)cyclohexyl)-1-(2-(ethyl(3-ethylphenyl)amino)-2-oxoethyl)-1H-indole-2-carboxamide (JRW-0886)
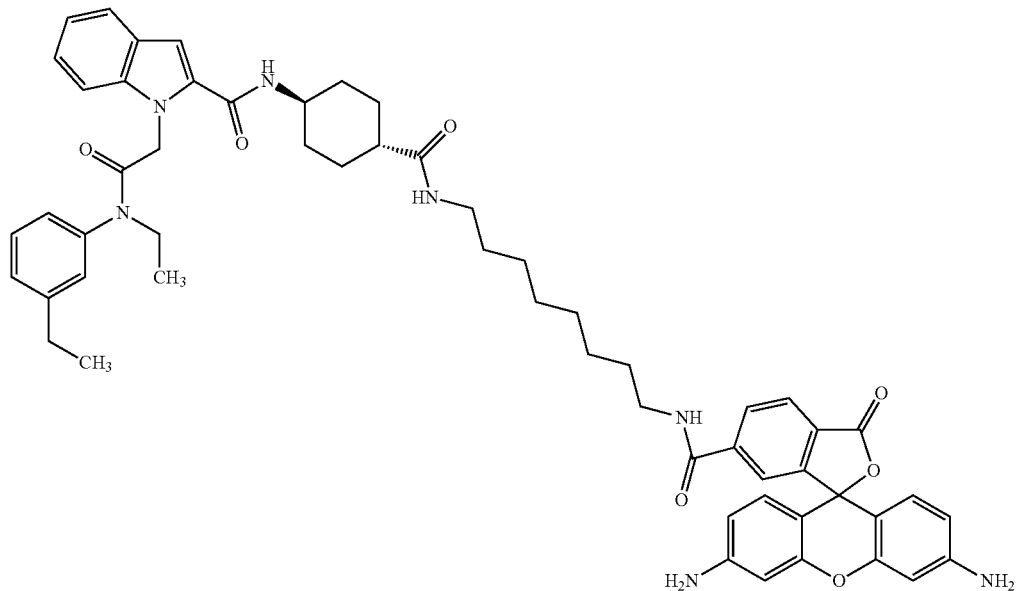
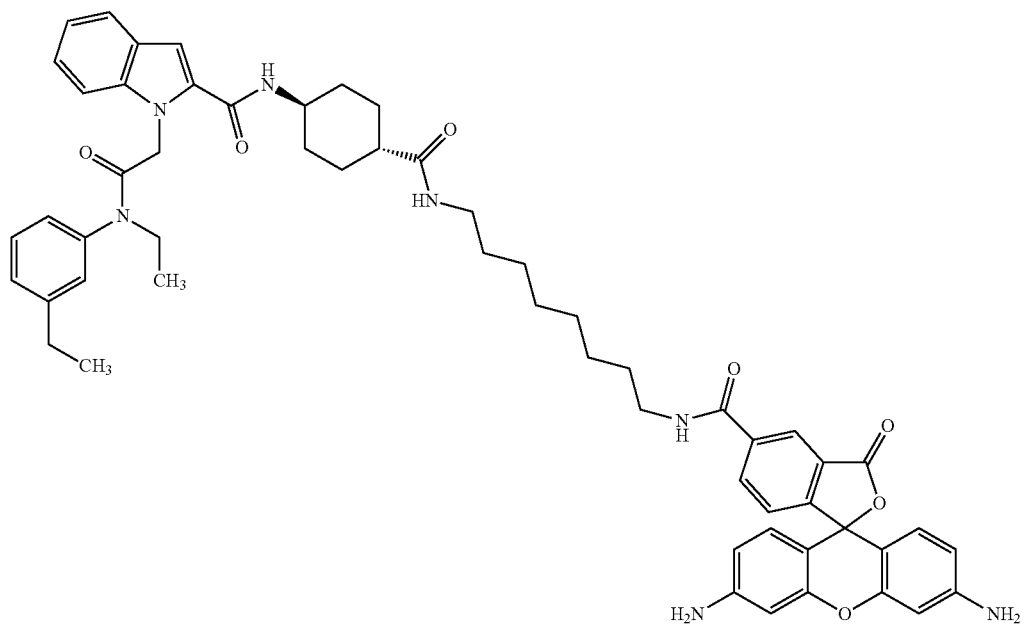

Step 1. N,N'-(5,6-((8-(trans-4-(1-(2-(ethyl(3-ethyl-phenyl)amino)-2-oxoethyl)-1H-indole-2-carbox-amido)cyclohexane-1-carboxamido)octyl)carbam-oyl)-3-oxo-3H-spiro[isobenzofuran-1,9'-xanthene]-3',6'-diyl)bis(2,2,2-trifluoroacetamide) (JRW-0884)

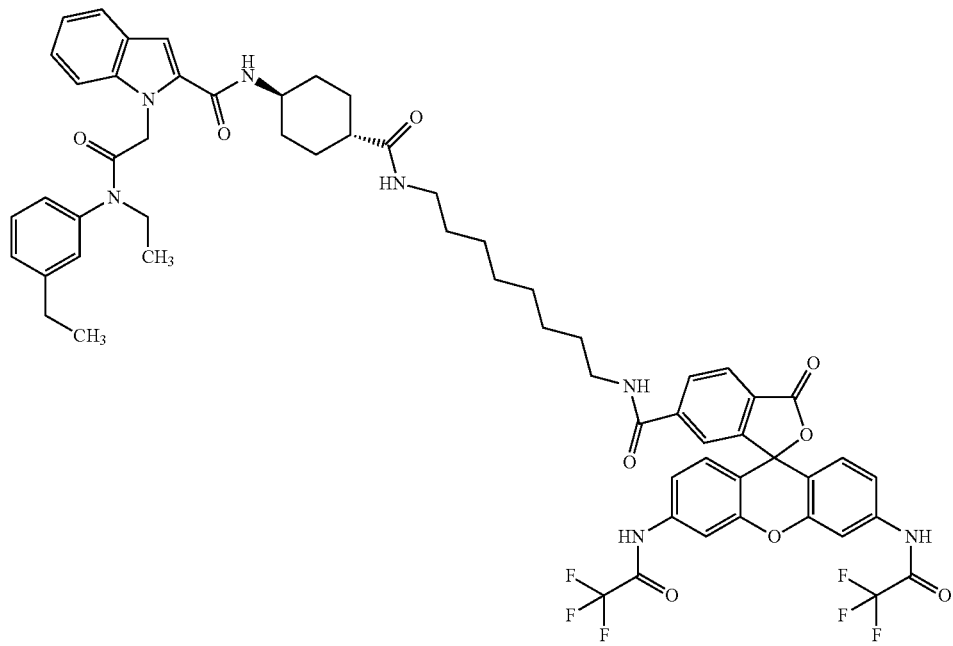

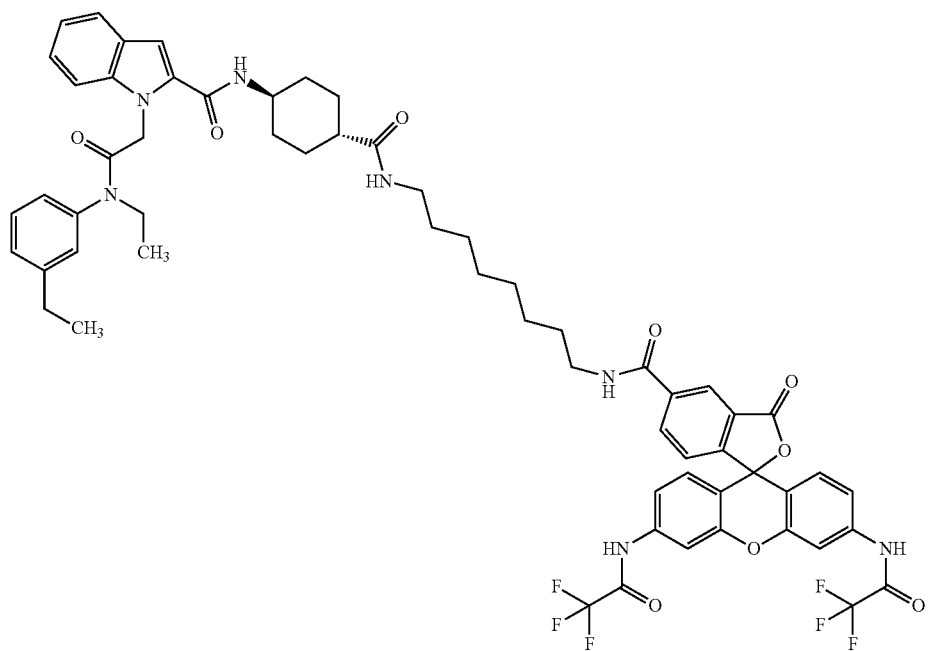

To a solution of N-(trans-4-((8-aminooctyl)carbamoyl)cyclohexyl)-1-(2-(ethyl(3-ethylphenyl)amino)-2-oxoethyl)-1H-indole-2-carboxamide (75 mg, 0.12 mmol) in DMF (10 mL), a mixture of 2,5-dioxopyrrolidin-1-yl 3-oxo-3',6'-bis(2,2,2-trifluoroacetamido)-3H-spiro[isobenzofuran-1,9'-xanthene]-5,6-carboxylate (124 mg, 0.19 mmol) and diisopropylethylamine (48 mg, 0.37 mmol) was added. The solution was stirred at RT for 1 h. The mixture was diluted with ethyl acetate and washed with water. Celite was added to the organic layer, concentrated, and purified with silica gel chromatography to afford crude product (120 mg) as a white solid. ESI MS m/z 1150 [M+H]+.

Step 2. N-(trans-4-((8-(3',6'-diamino-3-oxo-3H-spiro[isobenzofuran-1,9'-xanthene]-5,6-carboxamido)octyl)carbamoyl)cyclohexyl)-1-(2-(ethyl(3-ethylphenyl)amino)-2-oxoethyl)-1H-indole-2-carboxamide (JRW-0886)

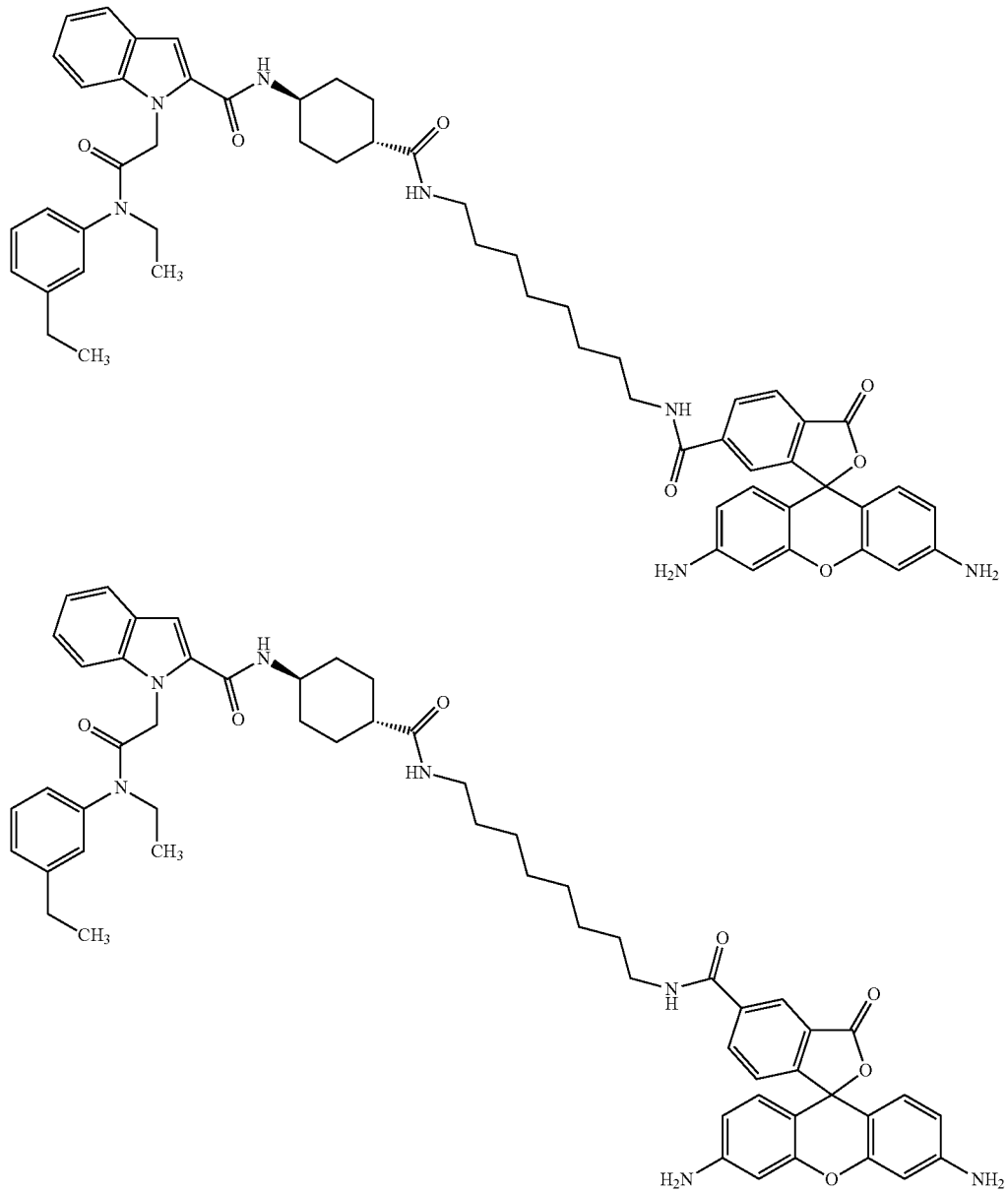

N,N'-(5,6-((8-(trans-4-(1-(2-(ethyl(3-ethylphenyl)amino)-2-oxoethyl)-1H-indole-2-carboxamido)cyclohexane-1-carboxamido)octyl)carbamoyl)-3-oxo-3H-spiro[isobenzofuran-1,9'-xanthene]-3',6'-diyl)bis(2,2,2-trifluoroacetamide) (0.12 mmol) in methanol (5 mL) and water (1 mL) was added potassium carbonate (43 mg, 0.31 mmol). The reaction stirred at RT for 2 h. The mixture was acidified (2M HCl), diluted with DCM and celite, concentrated, and purified with silica gel chromatography to afford the desired product (96 mg, 83%) as a red solid. ESI MS m/z 958 [M+H]+.

Example 54
N-(trans-4-((8-(3',6'-diamino-3-oxo-3H-spiro[isobenzofuran-1,9'-xanthene]-5-carboxamido)octyl)carbamoyl)cyclohexyl)-4-(2-(ethyl)m-tolyl)amino)-2-oxoethyl)-4H-thieno[3,2-b]pyrrole-5,6-carboxamide (JRW-0887)
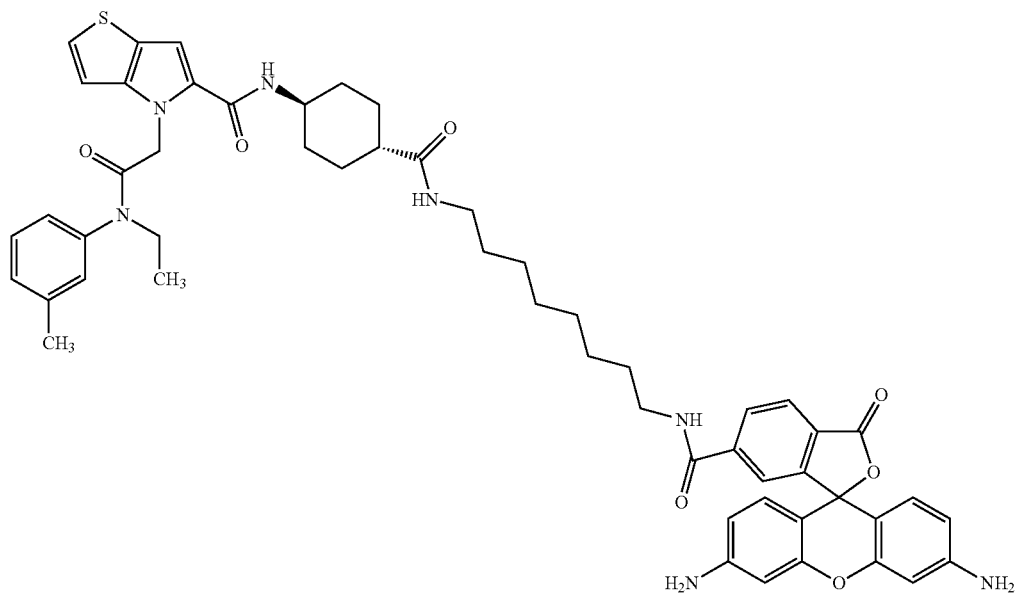
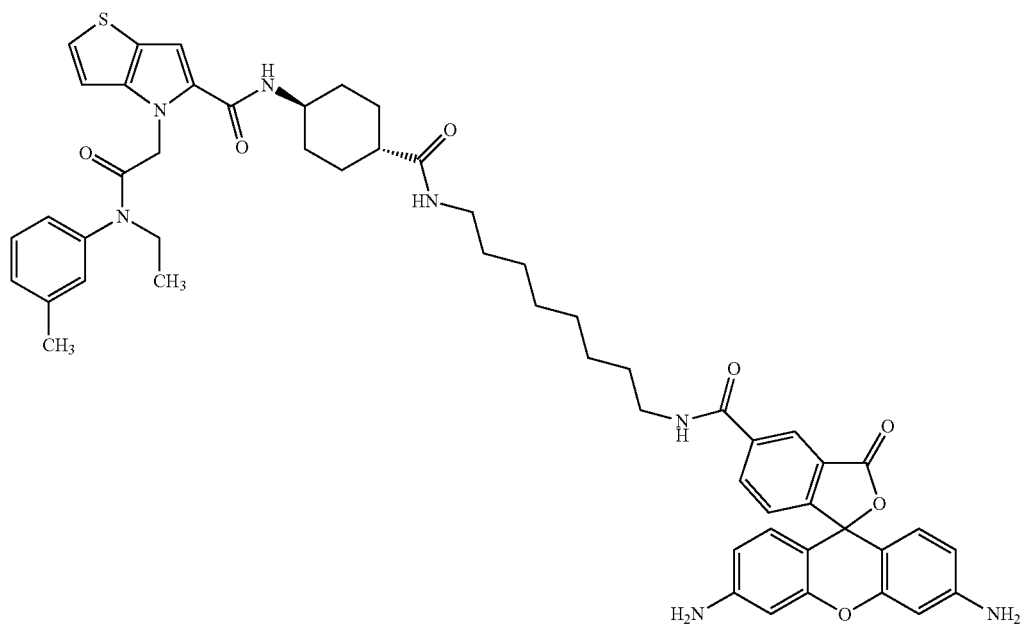

Step 1. N,N'-(5,6-((8-(trans-4-(4-(2-(ethyl(m-tolyl)amino)-2-oxoethyl)-4H-thieno[3,2-b]pyrrole-5-carboxamido)cyclohexane-1-carboxamido)octyl)carbamoyl)-3-oxo-3H-spiro[isobenzofuran-1,9'-xanthene]-3',6'-diyl)bis(2,2,2-trifluoroacetamide) (JRW-0885)

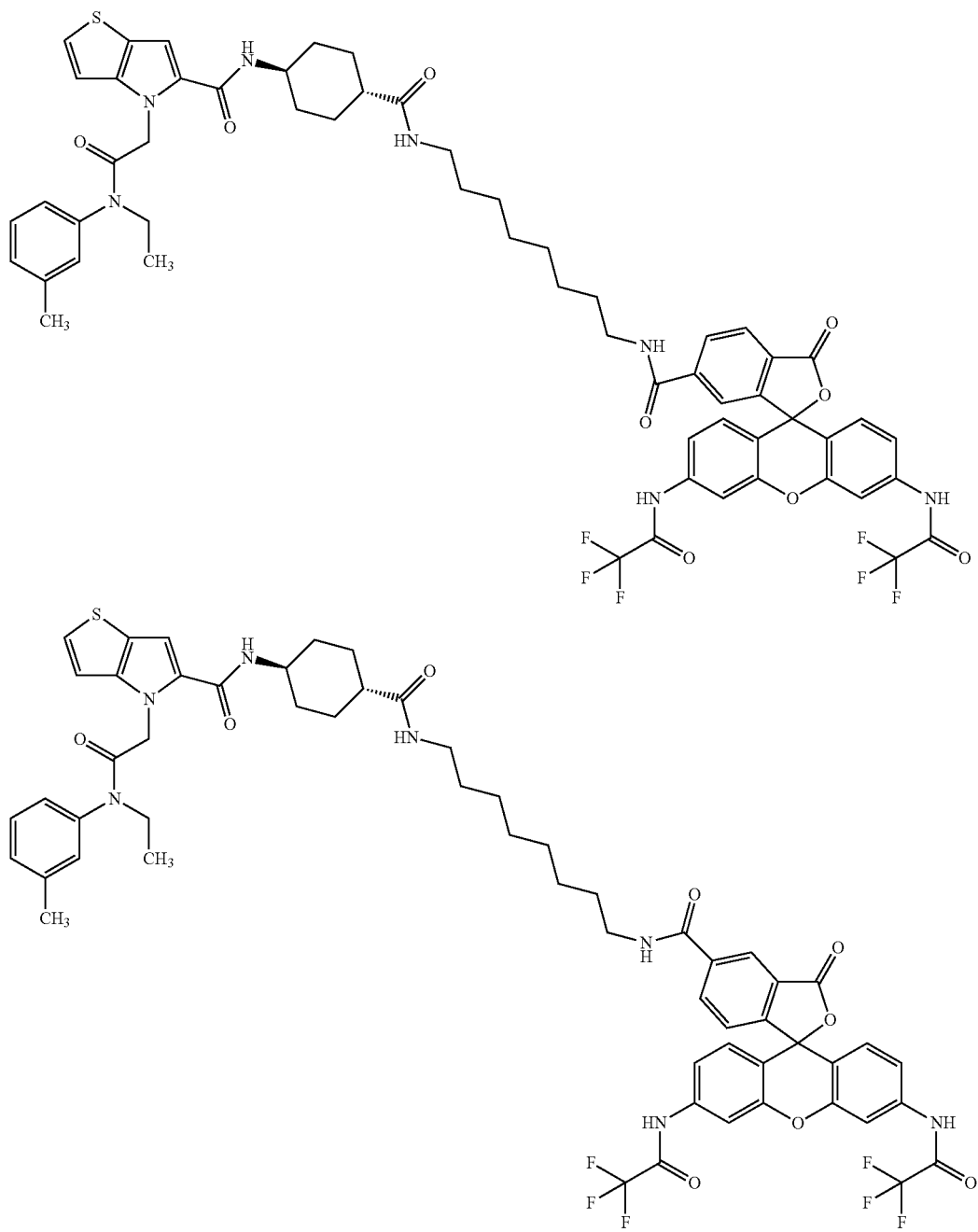

To a solution of N-(trans-4-((8-aminooctyl)carbamoyl)cyclohexyl)-4-(2-(ethyl(m-tolyl)amino)-2-oxoethyl)-4H-thieno[3,2-b]pyrrole-5-carboxamide (75 mg, 0.13 mmol) in DMF (10 mL), a mixture of 2,5-dioxopyrrolidin-1-yl3-oxo-3',6'-bis(2,2,2-trifluoroacetamido)-3H-spiro[isobenzofuran-1,9'-xanthene]-5,6-carboxylate (126 mg, 0.19 mmol) and diisopropylethylamine (49 mg, 0.38 mmol) was added. The solution was stirred at RT for 3 h. The mixture was diluted with ethyl acetate and washed with water. Celite was added to the organic layer, concentrated, and purified with silica gel chromatography to afford crude product (115 mg) as a white solid. ESI MS m/z 1142 [M+H]+.

Step 2. N-(trans-4-((8-(3',6'-diamino-3-oxo-3H-spiro[isobenzofuran-1,9'-xanthene]-5-carboxamido)octyl)carbamoyl)cyclohexyl)-4-(2-(ethyl(m-tolyl)amino)-2-oxoethyl)-4H-thieno[3,2-b]pyrrole-5,6-carboxamide (JRW-0887)

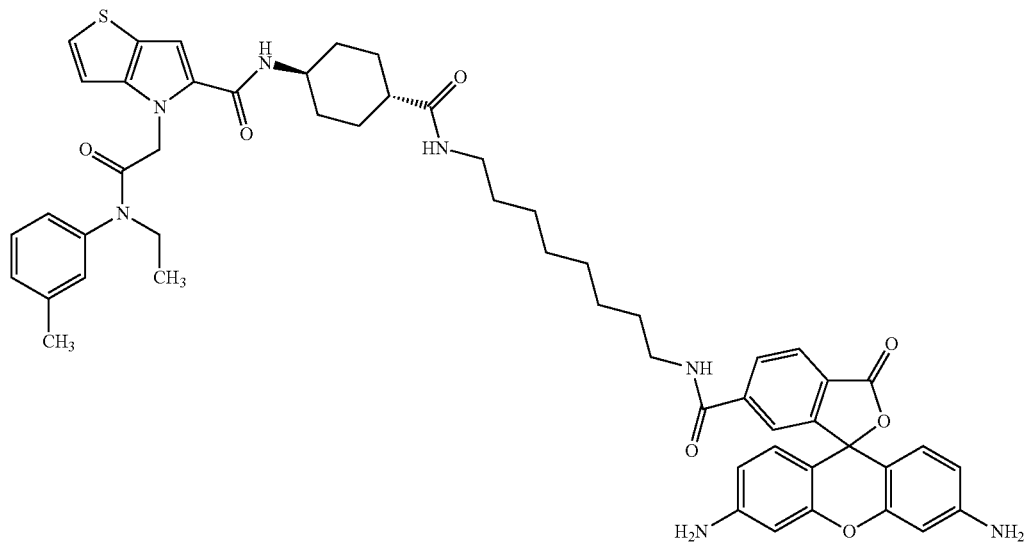

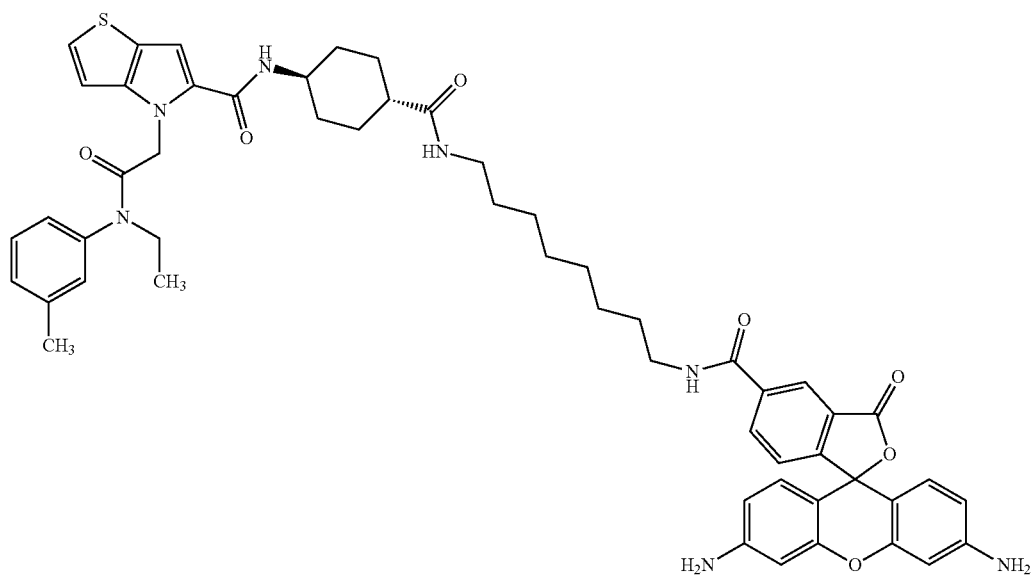

N,N'-(5,6-((8-(trans-4-(4-(2-(ethyl(m-tolyl)amino)-2-oxoethyl)-4H-thieno[3,2-b]pyrrole-5-carboxamido)cyclohexane-1-carboxamido)octyl)carbamoyl)-3-oxo-3H-spiro[isobenzofuran-1,9'-xanthene]-3',6'-diyl)bis(2,2,2-trifluoroacetamide) (0.13 mmol) in methanol (5 mL) and water (1 mL) was added potassium carbonate (42 mg, 0.30 mmol). The reaction stirred at RT for 2 h. The mixture was acidified (2M HCl), diluted with DCM and celite, concentrated, and purified with silica gel chromatography to afford the desired product (100 mg, 81%) as a red solid. ESI MS m/z 950 [M+H]+.

Example 55

N-(trans-4-((8-(3-(5,5-difluoro-7,9-dimethyl-5H-5λ4,6λ4-dipyrrolo[1,2-c:2',1'-f][1,3,2]diazaborinin-3-yl)propanamido)octyl)carbamoyl)cyclohexyl)-1-(2-(ethyl(3-ethylphenyl)amino)-2-oxoethyl)-1H-indole-2-carboxamide (JRW-0888)

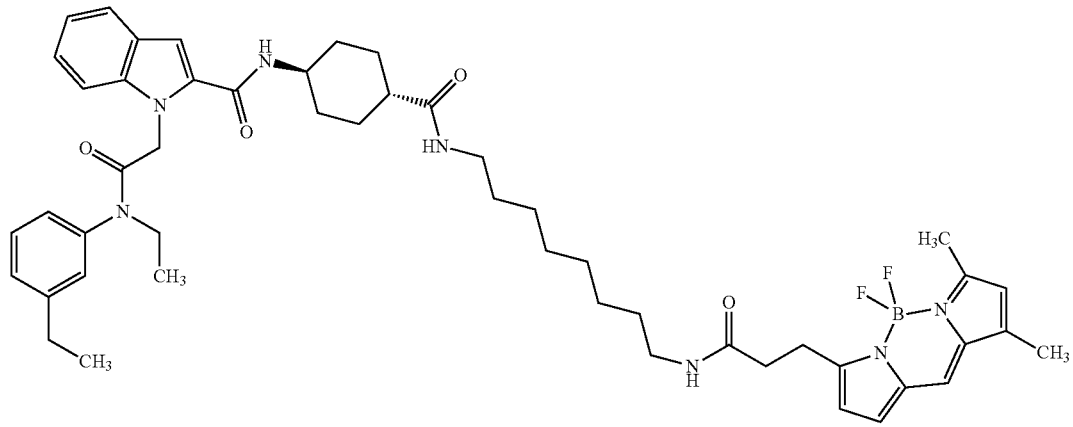

To a solution of N-(trans-4-((8-aminooctyl)carbamoyl)cyclohexyl)-1-(2-(ethyl(3-ethylphenyl)amino)-2-oxoethyl)-1H-indole-2-carboxamide (20 mg, 0.033 mmol) in DCM (5 mL), 2,5-dioxopyrrolidin-1-yl 3-(5,5-difluoro-7,9-dimethyl-5H-5λ4,6λ4-dipyrrolo[1,2-c:2',1'-f][1,3,2]diazaborinin-3-yl)propanoate (10 mg, 0.026 mmol) and diisopropylethylamine (13 mg, 0.1 mmol) was added. The solution was stirred at RT for 4 h. The mixture was concentrated and purified with silica gel chromatography to afford desired product (27 mg, 93%) as a red solid. ESI MS m/z 876 [M+H]+.

Example 56

N-(trans-4-((8-(3-(5,5-difluoro-7,9-dimethyl-5H-5λ4,6λ4-dipyrrolo[1,2-c:2',1'-f][1,3,2]diazaborinin-3-yl)propanamido)octyl)carbamoyl)cyclohexyl)-4-(2-(ethyl(m-tolyl)amino)-2-oxoethyl)-4H-thieno[3,2-b]pyrrole-5-carboxamide (JRW-0889)

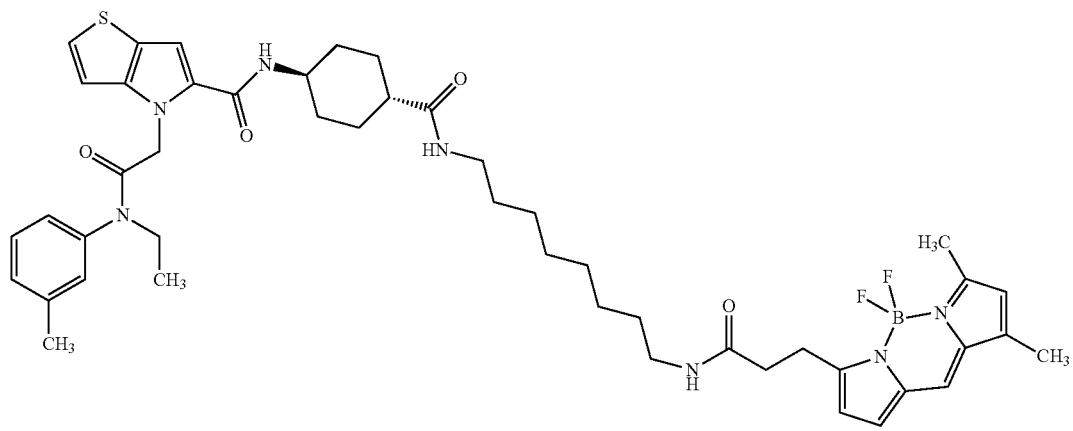

To a solution of N-(trans-4-((8-aminooctyl)carbamoyl)cyclohexyl)-4-(2-(ethyl(m-tolyl)amino)-2-oxoethyl)-4H-thieno[3,2-b]pyrrole-5-carboxamide (20 mg, 0.034 mmol) in DCM (5 mL), 2,5-dioxopyrrolidin-1-yl 3-(5,5-difluoro-7,9-dimethyl-5H-5λ4,6λ4-dipyrrolo[1,2-c:2',1'-f][1,3,2]diazaborinin-3-yl)propanoate (11 mg, 0.027 mmol) and diisopropylethylamine (13 mg, 0.1 mmol) was added. The solution was stirred at RT for 4 h. The mixture was concentrated and purified with silica gel chromatography to afford desired product (22 mg, 75%) as a red solid. ESI MS m/z 868 [M+H]+.

Example 57

N-(trans-4-((1-(3',6'-bis(dimethylamino)-3-oxo-3H-spiro[isobenzofuran-1,9'-xanthen]-6-yl)-1,11-dioxo-5,8-dioxa-2,12-diazaoctadecan-18-yl)carbamoyl)cyclohexyl)-1-(2-(ethyl(3-ethylphenyl)amino)-2-oxoethyl)-1H-indole-2-carboxamide (JRW-0915)

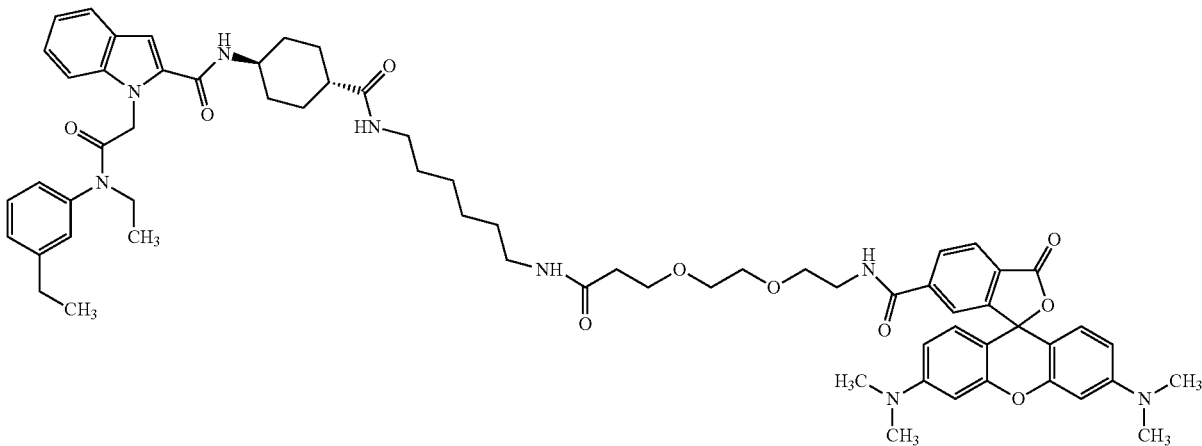 [SMILES: CCc1cccc(N(CC)C(=O)Cn2c(C(=O)N[C@H]3CC[C@H](C(=O)NCCCCCCNC(=O)CCOCCOCCNC(=O)c4ccc5c(c4)C4(OC5=O)c5ccc(N(C)C)cc5Oc5cc(N(C)C)ccc54)CC3)cc3ccccc32)c1]

To a solution of N-(trans-4-((6-(3-(2-(2-aminoethoxy)ethoxy)propanamido)hexyl)carbamoyl)cyclohexyl)-1-(2-(ethyl(3-ethylphenyl)amino)-2-oxoethyl)-1H-indole-2-carboxamide (30 mg, 0.041 mmol) in DCM (5 mL), 2,5-dioxopyrrolidin-1-yl 3',6'-bis(dimethylamino)-3-oxo-3H-spiro[isobenzofuran-1,9'-xanthene]-6-carboxylate (24 mg, 0.045 mmol) and diisopropylethylamine (16 mg, 0.12 mmol) was added. The solution was stirred at RT for 18 h. The mixture was concentrated and purified by preparative HPLC to afford desired product (30 mg, 63%) as a black solid. ESI MS m/z 1145 [M+H]+.

Example 58

N-(trans-4-((1-(3',6'-dihydroxy-3-oxo-3H-spiro[isobenzofuran-1,9'-xanthen]-5,6-yl)-1,11-dioxo-5,8-dioxa-2,12-diazaicosan-20-yl)carbamoyl)cyclohexyl)-1-(2-(ethyl(3-ethylphenyl)amino)-2-oxoethyl)-1H-indole-2-carboxamide (JRW-0921)

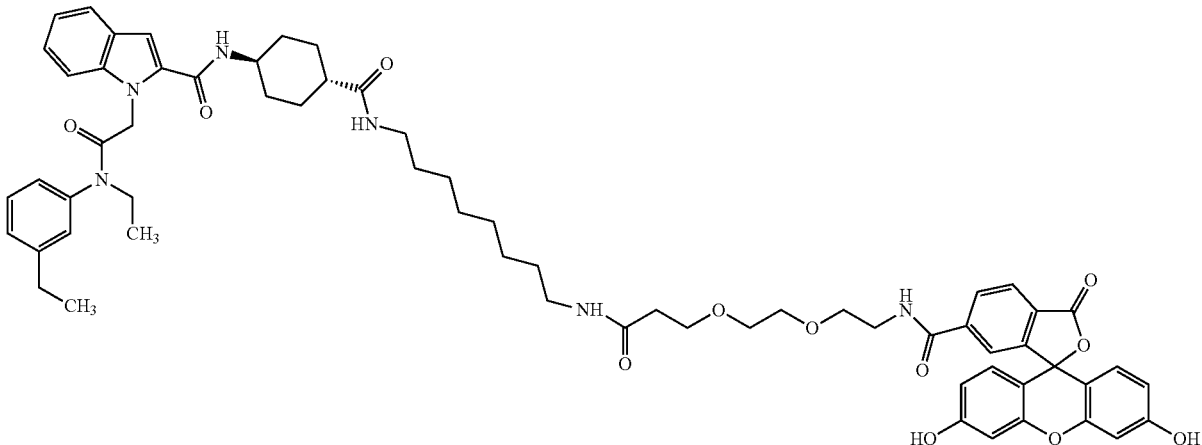

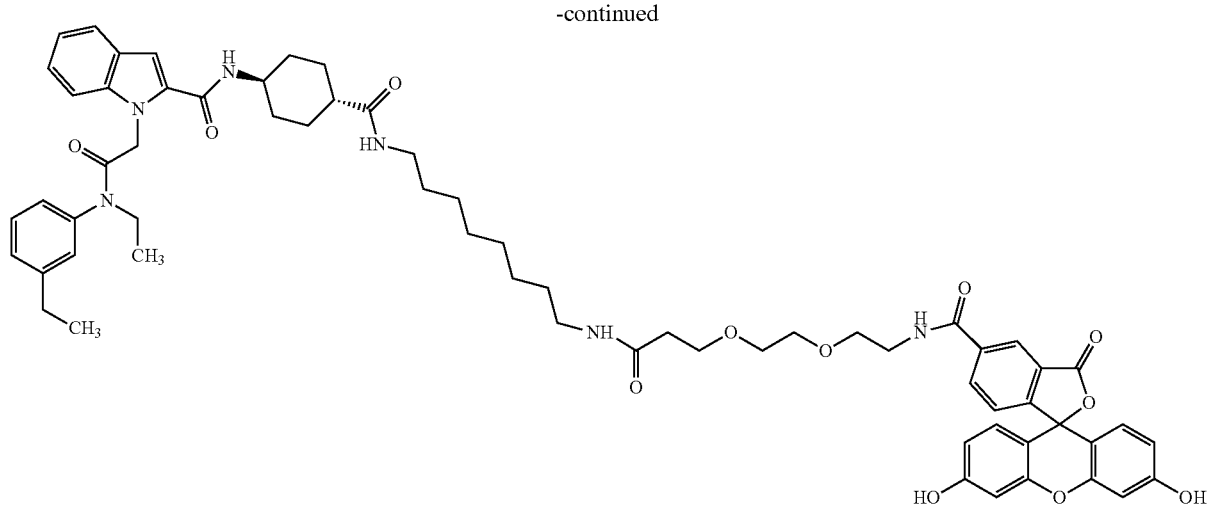

To a solution of N-(trans-4-((8-(3-(2-(2-aminoethoxy)ethoxy)propanamido)octyl)carbamoyl)cyclohexyl)-1-(2-(ethyl(3-ethylphenyl)amino)-2-oxoethyl)-1H-indole-2-carboxamide (50 mg, 0.066 mmol) in DCM (5 mL), 2,5-dioxopyrrolidin-1-yl 3',6'-dihydroxy-3-oxo-3H-spiro[isobenzofuran-1,9'-xanthene]-5,6-carboxylate (37 mg, 0.079 mmol) and diisopropylethylamine (25 mg, 0.20 mmol) was added. The solution was stirred at RT for 3 h. The mixture was concentrated with celite and purified by silica gel chromatography to afford desired product (67 mg, 90%) as a yellow solid. ESI MS m/z 1119 [M+H]+.

Example 59

N-(trans-4-((1-(3',6'-bis(dimethylamino)-3-oxo-3H-spiro[isobenzofuran-1,9'-xanthen]-6-yl)-1,11-dioxo-5,8-dioxa-2,12-diazaicosan-20-yl)carbamoyl)cyclohexyl)-1-(2-(ethyl(3-ethylphenyl)amino)-2-oxoethyl)-1H-indole-2-carboxamide (JRW-0920)

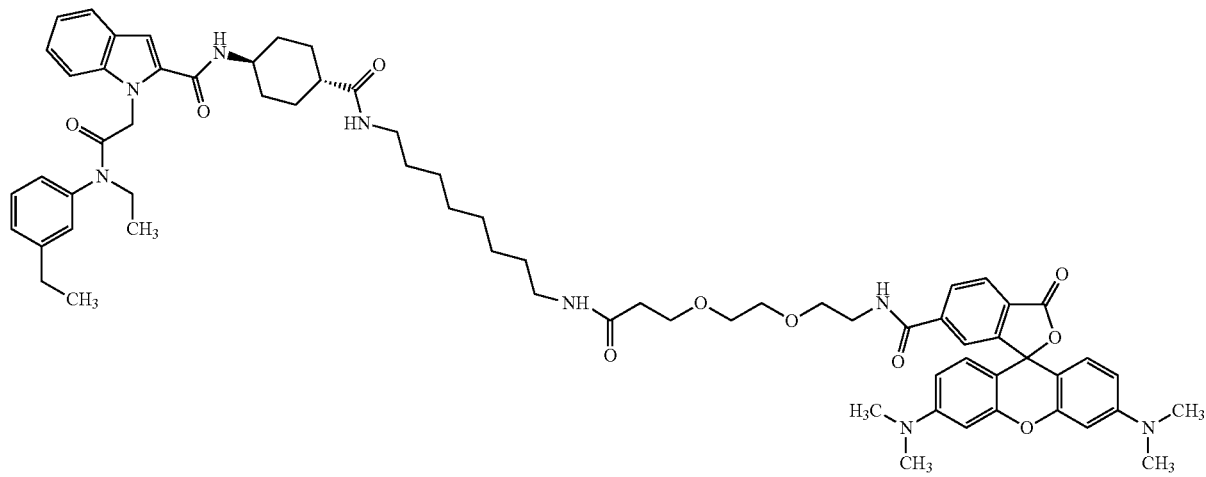 [SMILES: CCc1cccc(N(CC)C(=O)Cn2c(C(=O)N[C@H]3CC[C@H](C(=O)NCCCCCCCCNC(=O)CCOCCOCCNC(=O)c4ccc5c(c4)C4(OC5=O)c5ccc(N(C)C)cc5Oc5cc(N(C)C)ccc54)CC3)cc3ccccc32)c1]

To a solution of 3',6'-bis(dimethylamino)-3-oxo-3H-spiro[isobenzofuran-1,9'-xanthene]-6-carboxylic acid (25 mg, 0.058 mmol) in DCM/DMF (3/1 mL) was added TSTU (19 mg, 0.064 mmol) and diisopropylethylamine (30 mg, 0.23 mmol). The solution stirred for 10 min and N-(trans-4-((8-(3-(2-(2-aminoethoxy)ethoxy)propanamido)octyl)carbamoyl)cyclohexyl)-1-(2-(ethyl(3-ethylphenyl)amino)-2-oxoethyl)-1H-indole-2-carboxamide (44 mg, 0.058 mmol) in DCM (2 mL) was added. The solution stirred at RT for 18 h. The mixture was concentrated with celite and purified by reverse phase silica gel chromatography to afford desired product (34 mg, 50%) as a red solid. ESI MS m/z 1173 [M+H]+.

Example 60

N-(trans-4-((8-(6-((Z)-2-((E)-3-(1,1-dimethyl-1,4,5,6-tetrahydro-3λ4-pyrrolo[3,2,1-ij]quinolin-2-yl)allylidene)-1-methyl-1,2,5,6-tetrahydro-4H-pyrrolo[3,2,1-ij]quinolin-1-yl)hexanamido)octyl)carbamoyl)cyclohexyl)-1-(2-(ethyl(3-ethylphenyl)amino)-2-oxoethyl)-1H-indole-2-carboxamide (JRW-0958)

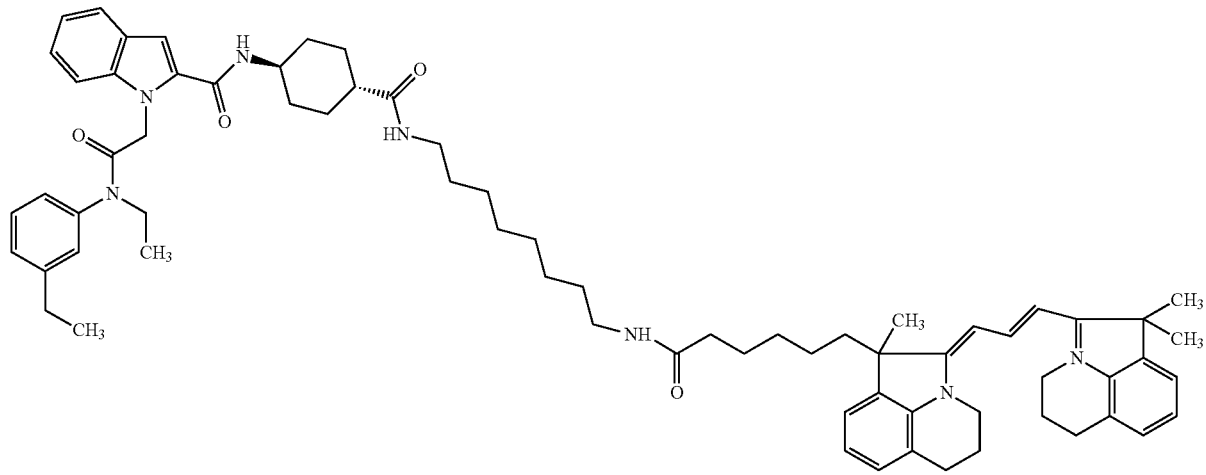

To a solution of N-(trans-4-((8-aminooctyl)carbamoyl)cyclohexyl)-1-(2-(ethyl(3-ethylphenyl)amino)-2-oxoethyl)-1H-indole-2-carboxamide (75 mg, 0.12 mmol) in DMF (5 mL), 2,5-dioxopyrrolidin-1-yl 6-((Z)-2-((E)-3-(1,1-dimethyl-1,4,5,6-tetrahydro-3λ4-pyrrolo[3,2,1-ij]quinolin-2-yl)allylidene)-1-methyl-1,2,5,6-tetrahydro-4H-pyrrolo[3,2,1-ij]quinolin-1-yl)hexanoate (75 mg, 0.12 mmol) and diisopropylethylamine (48 mg, 0.37 mmol) was added. The solution was stirred at RT for 3.5 h. The mixture was diluted with ethyl acetate and washed with water. Celite was added to the organic layer, concentrated, and purified with silica gel chromatography to afford desired product (35 mg, 25%) as a red black solid. ESI MS m/z 1192 [M]+.

Example 61

N-(trans-4-((8-(4',5'-dichloro-3',6'-dihydroxy-2',7'-dimethoxy-3-oxo-3H-spiro[isobenzofuran-1,9'-xanthene]-5,6-carboxamido)octyl)carbamoyl)cyclohexyl)-1-(2-(ethyl(3-ethylphenyl)amino)-2-oxoethyl)-1H-indole-2-carboxamide (JRW-0964)

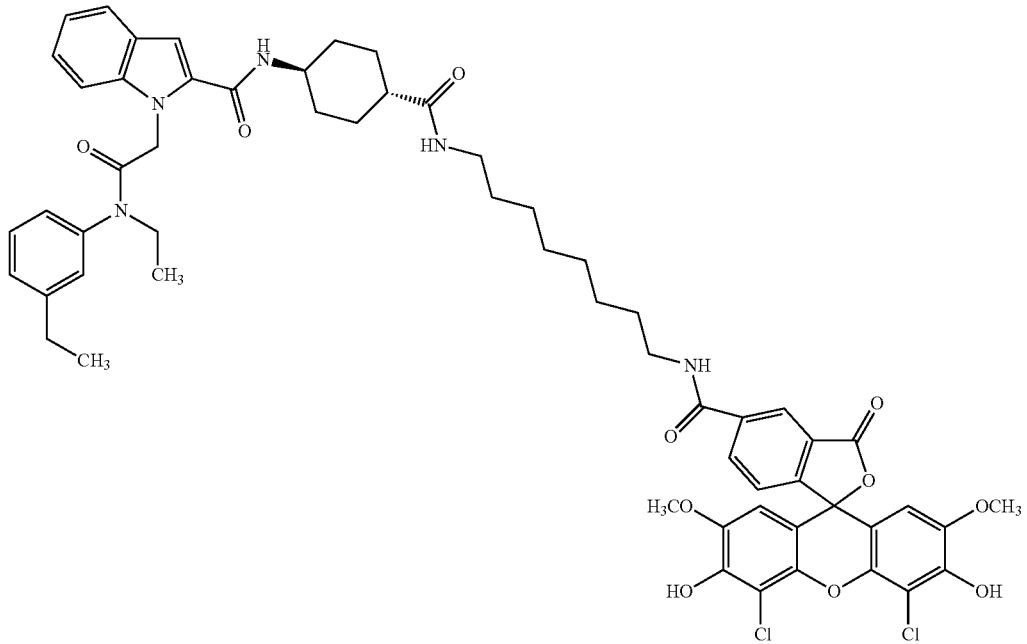

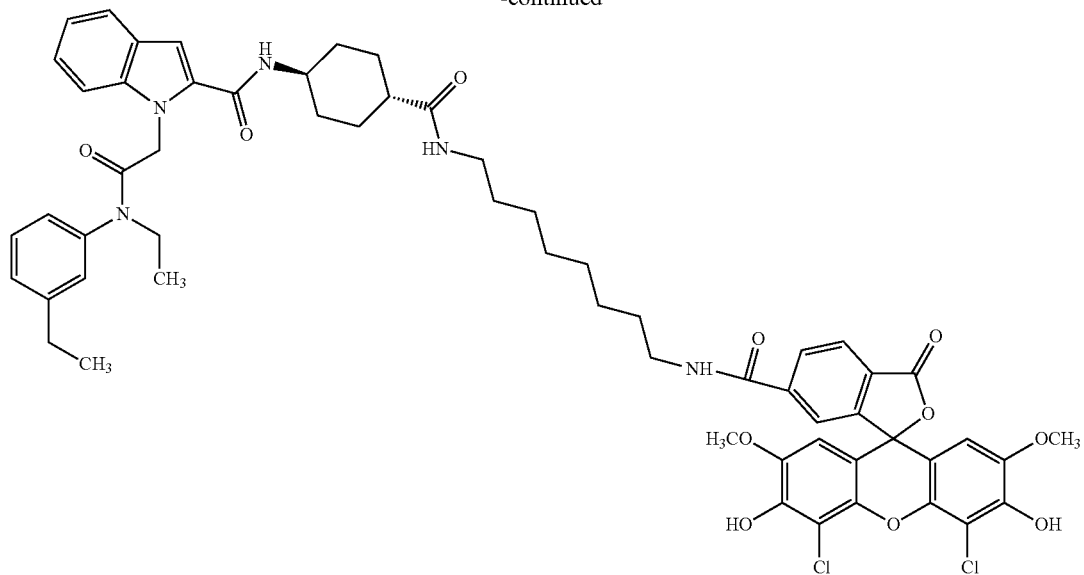

To a solution of N-(trans-4-((8-aminooctyl)carbamoyl)cyclohexyl)-1-(2-(ethyl(3-ethylphenyl)amino)-2-oxoethyl)-1H-indole-2-carboxamide (50 mg, 0.083 mmol) in DMF (5 mL), 2,5-dioxopyrrolidin-1-yl 4',5'-dichloro-3',6'-dihydroxy-2',7'-dimethoxy-3-oxo-3H-spiro[isobenzofuran-1,9'-xanthene]-5,6-carboxylate (75 mg, 0.12 mmol) and diisopropylethylamine (32 mg, 0.25 mmol) was added. The solution was stirred at RT for 1 h. The mixture was diluted with ethyl acetate and washed with water. The aqueous layer was extracted with CHCl$_3$/isopropanol (3:1). Celite was added to the organic layers, concentrated, and purified with silica gel chromatography to afford desired product (49 mg, 25%) as a dark red solid. ESI MS m/z 1088 [M]+H.

Example 62

N1-(2-(5,5-difluoro-1,3-dimethyl-5H-5λ4,6λ4-dipyrrolo[1,2-c:2',1'-f][1,3,2]diazaborinin-10-yl)ethyl)-N4-(1-(trans-4-(1-(2-(ethyl(3-ethylphenyl)amino)-2-oxoethyl)-1H-indole-2-carboxamido)cyclohexyl)-1,10-dioxo-13,16-dioxa-2,9-diazaoctadecan-18-yl)succinamide (JRW-1082)

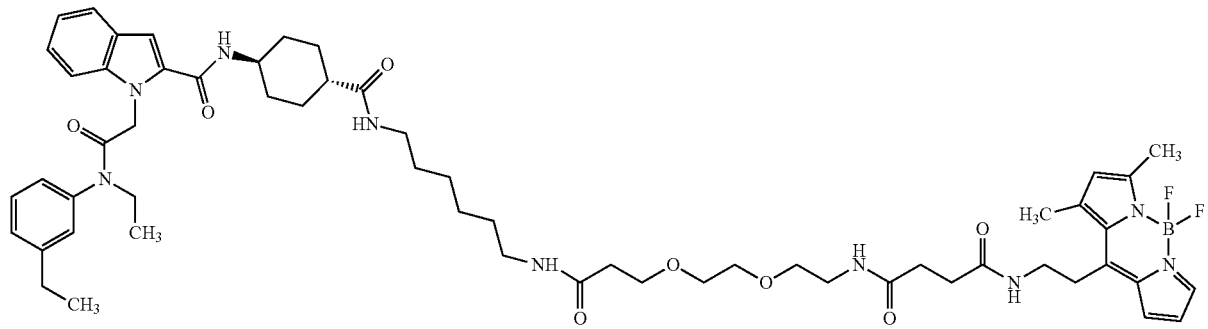

To a solution of N-(trans-4-((6-(3-(2-(2-aminoethoxy)ethoxy)propanamido)hexyl)carbamoyl)cyclohexyl)-1-(2-(ethyl(3-ethylphenyl)amino)-2-oxoethyl)-1H-indole-2-carboxamide (30 mg, 0.041 mmol) in DMF (3 mL), HOBT (12 mg, 0.082 mmol), EDC (16 mg, 0.082 mmol), diisopropylethylamine (15 mg, 0.12 mmol), and 4-((2-(5,5-difluoro-1,3-dimethyl-5H-5λ4,6λ4-dipyrrolo[1,2-c:2',1'-f][1,3,2]diazaborinin-10-yl)ethyl)amino)-4-oxobutanoic acid (22 mg, 0.061 mmol) was added. The solution was heated to 40° C. for 2 h. The mixture was diluted with ethyl acetate and washed with water. The organic layers were combined, dried with sodium sulfate, filtered, concentrated, and purified with silica gel chromatography to afford the desired product (20 mg, 45%) as a brown solid. ESI MS m/z 1078 [M+H]+.

Example 63

N1-(2-(5,5-difluoro-1,3-dimethyl-5H-5λ4,6λ4-dipyrrolo[1,2-c:2',1'-f][1,3,2]diazaborinin-10-yl)ethyl)-N4-(8-(trans-4-(1-(2-(ethyl(3-ethylphenyl)amino)-2-oxoethyl)-1H-indole-2-carboxamido)cyclohexane-1-carboxamido)octyl)succinamide (JRW-1081)

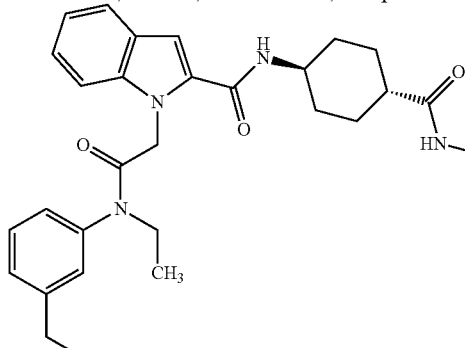
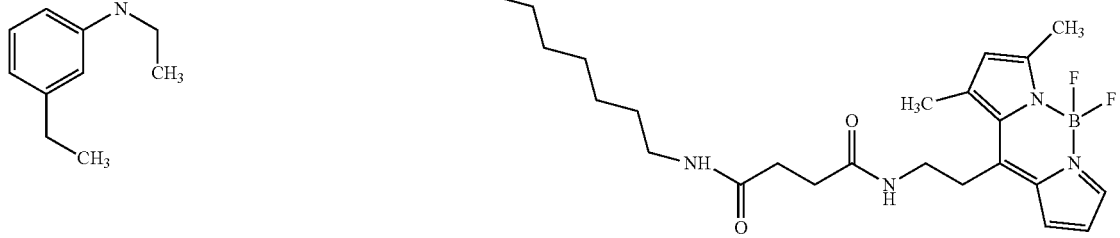

To a solution of N-(trans-4-((8-aminooctyl)carbamoyl)cyclohexyl)-1-(2-(ethyl(3-ethylphenyl)amino)-2-oxoethyl)-1H-indole-2-carboxamide (33 mg, 0.054 mmol) in DMF (3 mL), HOBT (17 mg, 0.11 mmol), EDC (21 mg, 0.11 mmol), diisopropyethylamine (21 mg, 0.16 mmol), and 4-((2-(5,5-difluoro-1,3-dimethyl-5H-5λ4,6λ4-dipyrrolo[1,2-c:2',1'-f][1,3,2]diazaborinin-10-yl)ethyl)amino)-4-oxobutanoic acid (30 mg, 0.082 mmol) was added. The solution was heated to 40° C. for 2 h. The mixture was diluted with ethyl acetate and washed with water. The organic layers were combined, dried with sodium sulfate, filtered, concentrated, and purified with silica gel chromatography to afford the desired product (23 mg, 44%) as a brown solid. ESI MS m/z 947 [M+H]+.

Example 64

N1-(2-(5,5-difluoro-1,3-dimethyl-5H-5λ4,6λ4-dipyrrolo[1,2-c:2',1'-f][1,3,2]diazaborinin-10-yl)ethyl)-N4-(1-(trans-4-(1-(2-(ethyl(3-ethylphenyl)amino)-2-oxoethyl)-1H-indole-2-carboxamido)cyclohexyl)-1,12-dioxo-15,18-dioxa-2,11-diazaicosan-20-yl)succinamide (JRW-1083)

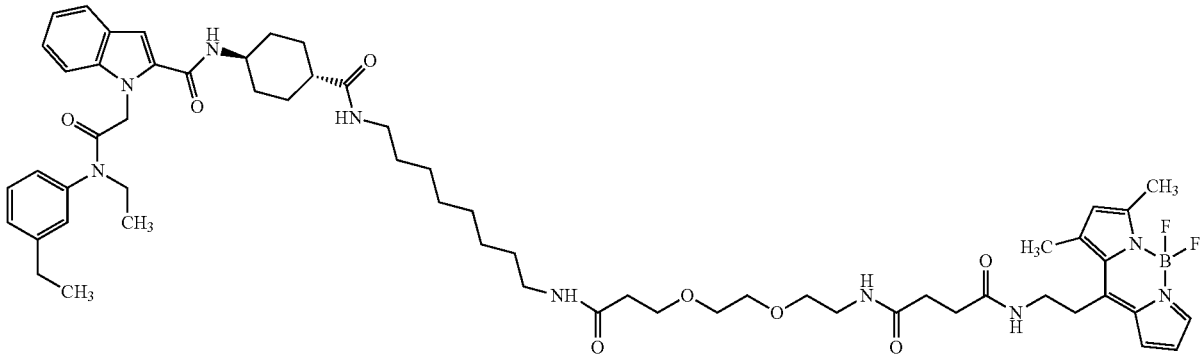

To a solution of N-(trans-4-((8-(3-(2-(2-aminoethoxy)ethoxy)propanamido)octyl)carbamoyl)cyclohexyl)-1-(2-(ethyl(3-ethylphenyl)amino)-2-oxoethyl)-1H-indole-2-carboxamide (42 mg, 0.055 mmol) in DMF (3 mL), HOBT (17 mg, 0.11 mmol), EDC (21 mg, 0.11 mmol), diisopropyethylamine (21 mg, 0.16 mmol), and 4-((2-(5,5-difluoro-1,3-dimethyl-5H-5λ4,6λ4-dipyrrolo[1,2-c:2',1'-f][1,3,2]diazaborinin-10-yl)ethyl)amino)-4-oxobutanoic acid (30 mg, 0.082 mmol) was added. The solution was heated to 40° C. for 2 h. The mixture was diluted with ethyl acetate and washed with water. The organic layers were combined, dried with sodium sulfate, filtered, concentrated, and purified with silica gel chromatography to afford the desired product (27 mg, 44%) as a brown solid. ESI MS m/z 1106 [M+H]+.

Example 65

4-(2-(ethyl(m-tolyl)amino)-2-oxoethyl)-N-(trans-4-((8-((7-nitrobenzo[c][1,2,5]oxadiazol-4-yl)oxy)octyl)carbamoyl)cyclohexyl)-4H-thieno[3,2-b]pyrrole-5-carboxamide (JRW-1181)

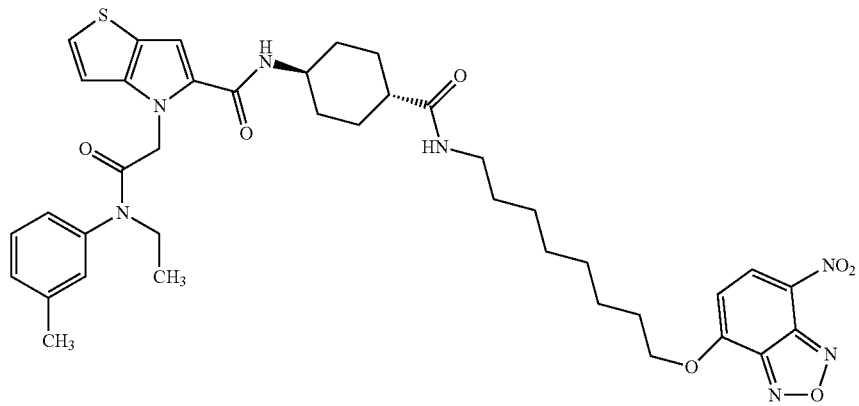 [SMILES: CCN(C(=O)Cn1c(C(=O)N[C@H]2CC[C@H](C(=O)NCCCCCCCCOc3ccc([N+](=O)[O-])c4nonc34)CC2)cc2sccc21)c1cccc(C)c1]

To a solution of 4-(2-(ethyl(m-tolyl)amino)-2-oxoethyl)-N-(trans-4-((8-hydroxyoctyl)carbamoyl)cyclohexyl)-4H-thieno[3,2-b]pyrrole-5-carboxamide (53 mg, 0.089 mmol) in DCM (5 mL), 4-fluoro-7-nitrobenzo[c][1,2,5]oxadiazole (16 mg, 0.089 mmol) and diisopropylethylamine (23 mg, 0.18 mmol) was added. The solution was stirred at RT for 18 h. The mixture was concentrated and purified with silica gel chromatography to afford desired product (32 mg, 47%) as a green brown solid. ESI MS m/z 758 [M]+H.

Example 66

4-(2-(ethyl(m-tolyl)amino)-2-oxoethyl)-N-(trans-4-((6-((7-nitrobenzo[c][1,2,5]oxadiazol-4-yl)oxy)hexyl)carbamoyl)cyclohexyl)-4H-thieno[3,2-b]pyrrole-5-carboxamide (JRW-1184)

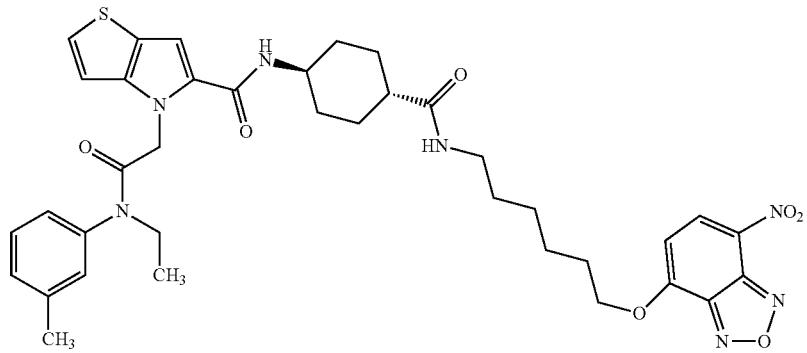 [SMILES: CCN(C(=O)Cn1c(C(=O)N[C@H]2CC[C@H](C(=O)NCCCCCCOc3ccc([N+](=O)[O-])c4nonc34)CC2)cc2sccc21)c1cccc(C)c1]

To a solution of 4-(2-(ethyl(m-tolyl)amino)-2-oxoethyl)-N-(trans-4-((6-hydroxyhexyl)carbamoyl)cyclohexyl)-4H-thieno[3,2-b]pyrrole-5-carboxamide (55 mg, 0.097 mmol) in DCM (5 mL), 4-fluoro-7-nitrobenzo[c][1,2,5]oxadiazole (21 mg, 0.12 mmol) and diisopropylethylamine (25 mg, 0.19 mmol) was added. The solution was stirred at RT for 24 h. The mixture was concentrated and purified with silica gel chromatography to afford desired product (56 mg, 80%) as a green brown solid. ESI MS m/z 730 [M]+H.

Example 67

1-(2-(ethyl(3-ethylphenyl)amino)-2-oxoethyl)-N-(trans-4-((8-((7-nitrobenzo[c][1,2,5]oxadiazol-4-yl)oxy)octyl)carbamoyl)cyclohexyl)-1H-indole-2-carboxamide (JRW-1185)

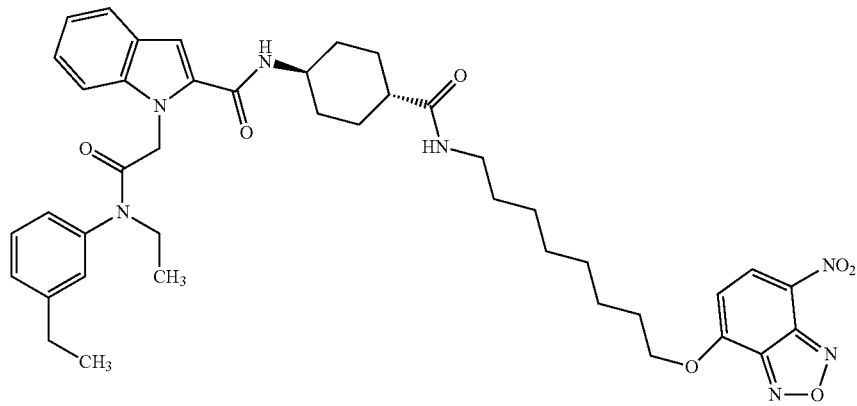 [SMILES: CCc1cccc(N(CC)C(=O)Cn2c(C(=O)N[C@H]3CC[C@H](C(=O)NCCCCCCCCOc4ccc([N+](=O)[O-])c5nonc45)CC3)cc3ccccc32)c1]

To a solution of 1-(2-(ethyl(3-ethylphenyl)amino)-2-oxoethyl)-N-((trans-4-((8-hydroxyoctyl)carbamoyl)cyclohexyl)-1H-indole-2-carboxamide (53 mg, 0.088 mmol) in DCM (5 mL), 4-fluoro-7-nitrobenzo[c][1,2,5]oxadiazole (19 mg, 0.11 mmol) and diisopropylethylamine (34 mg, 0.26 mmol) was added. The solution was stirred at RT for 18 h. The mixture was concentrated and purified with silica gel chromatography to afford desired product (13 mg, 19%) as a dark green solid. ESI MS m/z 766 [M]+H.

Example 68

1-(2-(ethyl(3-ethylphenyl)amino)-2-oxoethyl)-N-(trans-4-((6-((7-nitrobenzo[c][1,2,5]oxadiazol-4-yl)oxy)hexyl)carbamoyl)cyclohexyl)-1H-indole-2-carboxamide (JRW-1187)

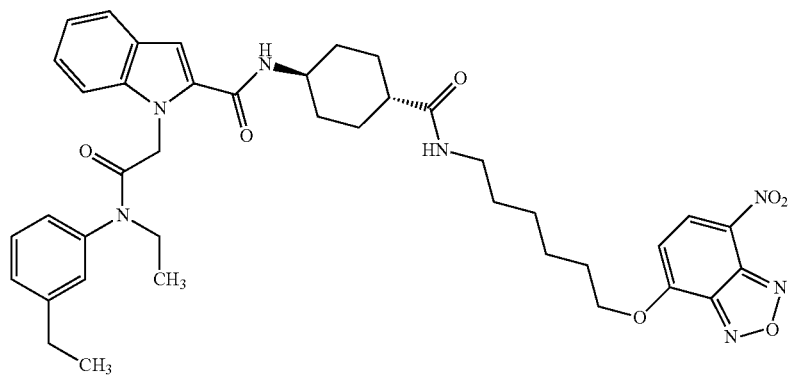 [SMILES: CCc1cccc(N(CC)C(=O)Cn2c(C(=O)N[C@H]3CC[C@H](C(=O)NCCCCCCOc4ccc([N+](=O)[O-])c5nonc45)CC3)cc3ccccc32)c1]

To a solution of 1-(2-(ethyl(3-ethylphenyl)amino)-2-oxoethyl)-N-(trans-4-((6-hydroxyhexyl)carbamoyl)cyclohexyl)-1H-indole-2-carboxamide (53 mg, 0.092 mmol) in DCM (5 mL), 4-fluoro-7-nitrobenzo[c][1,2,5]oxadiazole (20 mg, 0.11 mmol) and diisopropylethylamine (35 mg, 0.27 mmol) was added. The solution was stirred at RT for 18 h. The mixture was concentrated and purified with silica gel chromatography to afford desired product (47 mg, 69%) as a brown solid. ESI MS m/z 738 [M]+H.

Example 69

4-(2-(ethyl(m-tolyl)amino)-2-oxoethyl)-N-(trans-4-(((R)-3-((3S,4R)-3-hydroxy-4-((4-(4-methylthiazol-5-yl)benzyl)carbamoyl)pyrrolidine-1-carbonyl)-2,2-dimethyl-5,18-dioxo-8,11,14-trioxa-4,17-diazatricosan-23-yl)carbamoyl)cyclohexyl)-4H-thieno[3,2-b]pyrrole-5-carboxamide (JRW-1216)

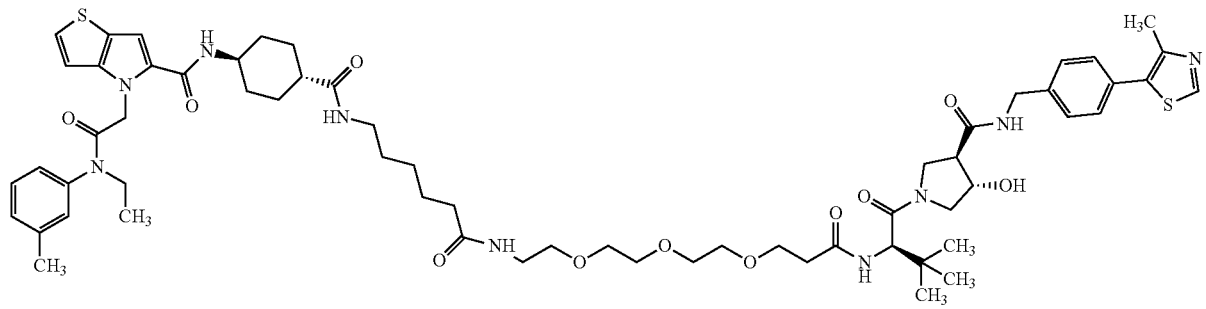 [SMILES: CCN(C(=O)Cn1c(C(=O)N[C@H]2CC[C@H](C(=O)NCCCCCC(=O)NCCOCCOCCOCCC(=O)N[C@@H](C(=O)N3C[C@@H](O)[C@H](C(=O)NCc4ccc(-c5scnc5C)cc4)C3)C(C)(C)C)CC2)cc2sccc21)c1cccc(C)c1]

To a solution of 6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid (18 mg, 0.031 mmol) in DMF (3 mL), HOBT (9 mg, 0.062 mmol), EDC (12 mg, 0.062 mmol), diisopropyethylamine (12 mg, 0.093 mmol), and (3R,4S)-1-((R)-1-amino-14-(tert-butyl)-12-oxo-3,6,9-trioxa-13-azapentadecan-15-oyl)-4-hydroxy-N-(4-(4-methylthiazol-5-yl)benzyl)pyrrolidine-3-carboxamide (20 mg, 0.031 mmol) was added. The solution was heated to 60° C. for 18 h. The mixture was diluted with ethyl acetate and washed with water. The organic layers were combined, dried with sodium sulfate, filtered, concentrated, and purified with silica gel chromatography to afford the desired product (5 mg, 13%) as a colorless film. ESI MS m/z 1196 [M+H]+.

Example 70

4-(2-(ethyl(m-tolyl)amino)-2-oxoethyl)-N-(trans-4-(((R)-3-((3S,4R)-3-hydroxy-4-((4-(4-methylthiazol-5-yl)benzyl)carbamoyl)pyrrolidine-1-carbonyl)-2,2-dimethyl-5,21-dioxo-8,11,14,17-tetraoxa-4,20-diazahexacosan-26-yl)carbamoyl)cyclohexyl)-4H-thieno[3,2-b]pyrrole-5-carboxamide (JRW-1217)

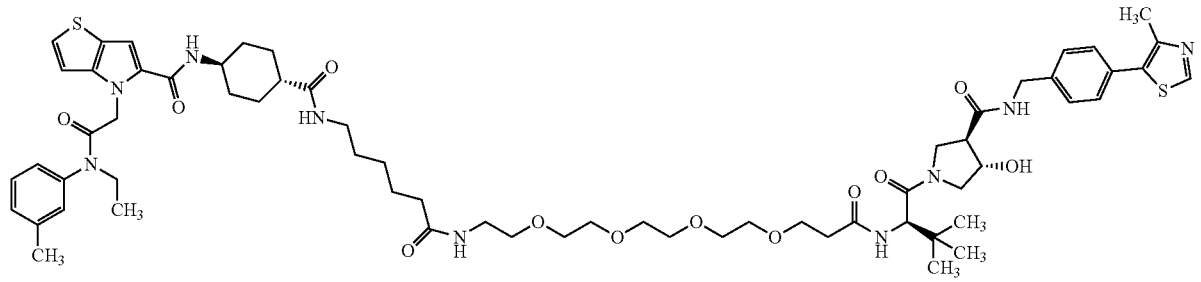 [SMILES: CCN(C(=O)Cn1c(C(=O)N[C@H]2CC[C@H](C(=O)NCCCCCC(=O)NCCOCCOCCOCCOCCC(=O)N[C@@H](C(=O)N3C[C@@H](O)[C@H](C(=O)NCc4ccc(-c5scnc5C)cc4)C3)C(C)(C)C)CC2)cc2sccc21)c1cccc(C)c1]

To a solution of 6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid (18 mg, 0.031 mmol) in DMF (3 mL), HOBT (9 mg, 0.062 mmol), EDC (12 mg, 0.062 mmol), diisopropyethylamine (12 mg, 0.093 mmol), and (3R,4S)-1-((R)-1-amino-17-(tert-butyl)-15-oxo-3,6,9,12-tetraoxa-16-azaoctadecan-18-oyl)-4-hydroxy-N-(4-(4-methylthiazol-5-yl)benzyl)pyrrolidine-3-carboxamide (21 mg, 0.031 mmol) was added. The solution was heated to 60° C. for 18 h. The mixture was diluted with ethyl acetate and washed with water. The organic layers were combined, dried with sodium sulfate, filtered, concentrated, and purified with silica gel chromatography to afford the desired product (8 mg, 21%) as a colorless film. ESI MS m/z 1240 [M+H]+.

Example 71

4-(2-(ethyl(m-tolyl)amino)-2-oxoethyl)-N-(trans-4-(((R)-3-((3S,4R)-3-hydroxy-4-((4-(4-methylthiazol-5-yl)benzyl)carbamoyl)pyrrolidine-1-carbonyl)-2,2-dimethyl-5,18-dioxo-8,11,14-trioxa-4,17-diazapentacosan-25-yl)carbamoyl)cyclohexyl)-4H-thieno[3,2-b]pyrrole-5-carboxamide (JRW-1219)

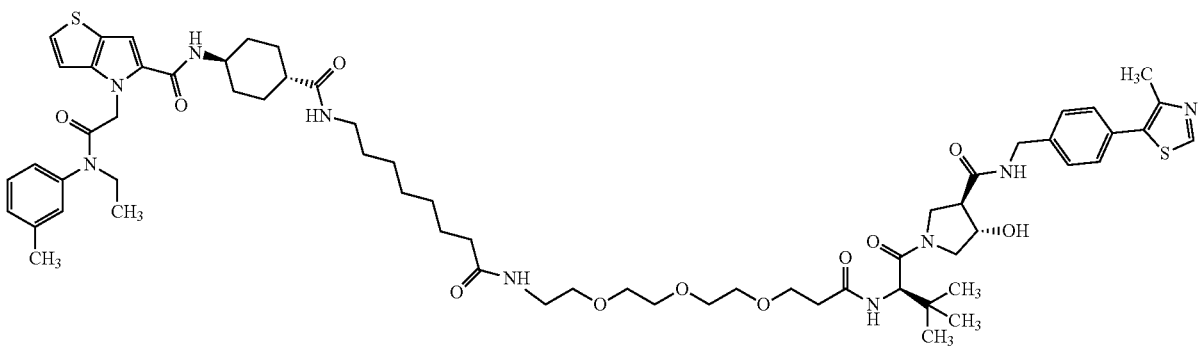 [SMILES: CCN(C(=O)Cn1c(C(=O)N[C@H]2CC[C@H](C(=O)NCCCCCCCC(=O)NCCOCCOCCOCCC(=O)N[C@@H](C(=O)N3C[C@@H](O)[C@H](C(=O)NCc4ccc(-c5scnc5C)cc4)C3)C(C)(C)C)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (20 mg, 0.032 mmol) in DMF (3 mL), HOBT (10 mg, 0.066 mmol), EDC (13 mg, 0.066 mmol), diisopropyethylamine (13 mg, 0.098 mmol), and (3R,4S)-1-((R)-1-amino-14-(tert-butyl)-12-oxo-3,6,9-trioxa-13-azapentadecan-15-oyl)-4-hydroxy-N-(4-(4-methylthiazol-5-yl)benzyl)pyrrolidine-3-carboxamide (21 mg, 0.033 mmol) was added. The solution was heated to 60° C. for 3 h. The mixture was diluted with ethyl acetate and washed with water. The organic layers were combined, dried with sodium sulfate, filtered, concentrated, and purified with silica gel chromatography to afford the desired product (5 mg, 13%) as a colorless film. ESI MS m/z 1224 [M+H]+.

Example 72

4-(2-(ethyl(m-tolyl)amino)-2-oxoethyl)-N-(trans-4-(((R)-3-((3S,4R)-3-hydroxy-4-((4-(4-methylthiazol-5-yl)benzyl)carbamoyl)pyrrolidine-1-carbonyl)-2,2-dimethyl-5,21-dioxo-8,11,14,17-tetraoxa-4,20-diazaoctacosan-28-yl)carbamoyl)cyclohexyl)-4H-thieno[3,2-b]pyrrole-5-carboxamide (JRW-1220)

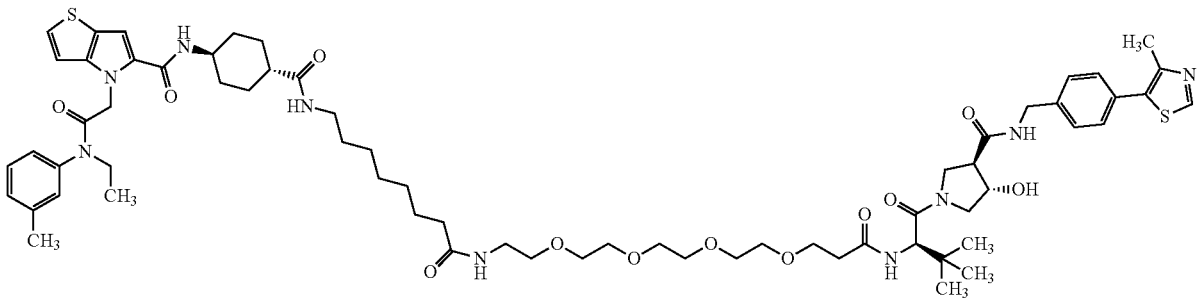 [SMILES: CCN(C(=O)Cn1c(C(=O)N[C@H]2CC[C@H](C(=O)NCCCCCCCC(=O)NCCOCCOCCOCCOCCC(=O)N[C@@H](C(=O)N3C[C@@H](O)[C@H](C(=O)NCc4ccc(-c5scnc5C)cc4)C3)C(C)(C)C)CC2)cc2sccc21)c1cccc(C)c1]

To a solution of 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (18 mg, 0.030 mmol) in DMF (3 mL), HOBT (9 mg, 0.060 mmol), EDC (11 mg, 0.060 mmol), diisopropyethylamine (11 mg, 0.089 mmol), and (3R,4S)-1-((R)-1-amino-17-(tert-butyl)-15-oxo-3,6,9,12-tetraoxa-16-azaoctadecan-18-oyl)-4-hydroxy-N-(4-(4-methylthiazol-5-yl)benzyl)pyrrolidine-3-carboxamide (20 mg, 0.030 mmol) was added. The solution was heated to 60° C. for 4 h. The mixture was diluted with ethyl acetate and washed with water. The organic layers were combined, dried with sodium sulfate, filtered, concentrated, and purified with silica gel chromatography to afford the desired product (9 mg, 24%) as a colorless film. ESI MS m/z 1268 [M+H]+.

Example 73

Inhibition of Nluc Luciferase

The following example provides a use for an inhibitor appended to a chloroalkane to potently inhibit an Nluc-HT fusion protein. Nluc, Nluc-HaloTag (HT), and Nluc-HT-TMR (Nluc-HT conjugated to TMR chloroalkane) were diluted to a final concentration of 0.05 nM in PBS/0.05% BSA and incubated with the indicated concentration of JRW-0308 for 2 hours at room temperature. Samples were analyzed after addition of furimazine (10 µM final concentration) using a BMG Clariostar plate reader. FIG. 1 demonstrates that JRW-0308 potently inhibits the Nluc-HT fusion protein, whereas higher concentrations are required to inhibit Nluc alone and Nluc-HT-TMR. TMR itself contains a chloroalkane group, such that it competes with the chloroalkane group of the JRW-0308 for binding to HT. As such, higher concentrations of JRW-0308 are required in order to inhibit the Nluc-HT-TMR fusion protein.

Inhibition of Nluc Luciferase in Cells

Figure 2A:
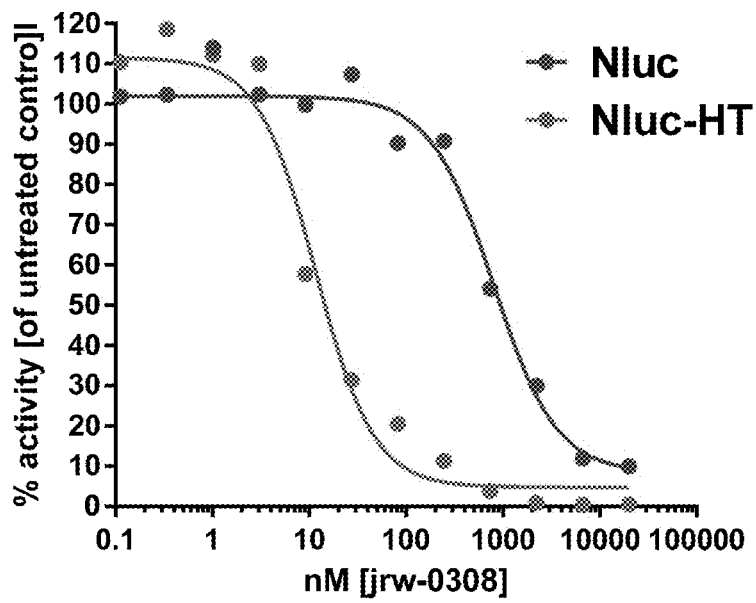
FIG. 2A and FIG. 2B show the inhibition of Nluc by JRW-0308 in cells. HeLa cells were reverse transfected with expression constructs for Nluc or Nluc-HT, plated (20,000 cells/100 μL growth medium) and incubated for 24 hours. Growth medium was then replaced with 50 μL, OptiMEM (optionally including 500 nM NanoBRET™ 618 ligand (Nluc-HT-618)), followed by incubation for 30 min at 37° C. The cells were then treated with a serial dilution of JRW-0308 in 50 μL, OptiMEM for 2 hours at 37° C. Luciferase activity was measured after addition of furimazine to a final concentration of 190 μM in 50 μL, OptiMEM using a BMG Clariostar plate reader.
Figure 2B:
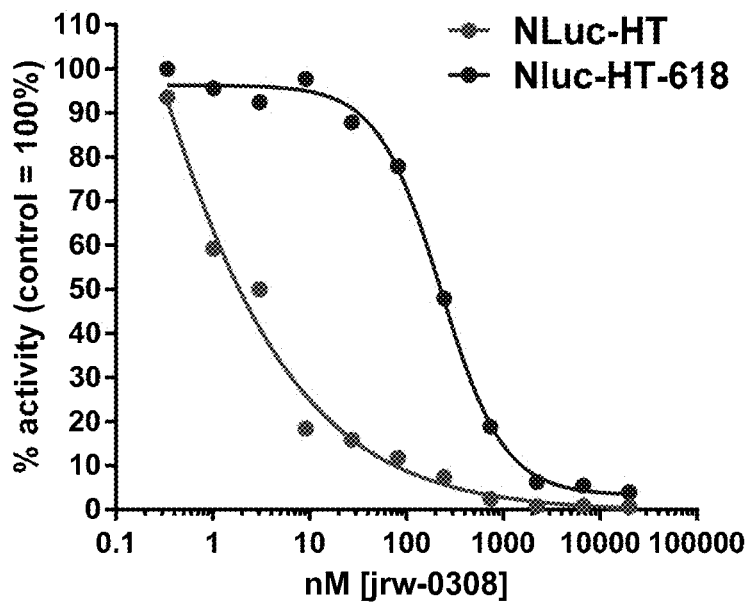

HeLa cells were reverse transfected with expression constructs for Nluc or Nluc-HT, plated (20,000 cells/100 µL growth medium), and incubated for 24 hours. Growth medium was then replaced with 50 µL, OptiMEM (optionally including 500 nM NanoBRET™ 618 ligand (Nluc-HT-618)), followed by incubation for 30 min at 37° C. The cells were then treated with a serial dilution of JRW-0308 in 50 µL, OptiMEM for 2 hours at 37° C. Luciferase activity was measured after addition of furimazine to a final concentration of 190 µM in 504, OptiMEM using a BMG Clariostar plate reader. FIG. 2A shows that JRW-0308 potently inhibits the Nluc-HT fusion protein, whereas higher concentrations are required to inhibit Nluc. FIG. 2B shows inhibition of Nluc-HT and Nluc-HT-618. The NanoBRET™ 618 ligand also contains a chloralkane group which competes with JRW-0308 for the binding to HT. As such, higher concentrations of JRW-0308 are necessary to inhibit Nluc-HT-618.

Example 74

Measuring Caspase Activity

Figure 3:
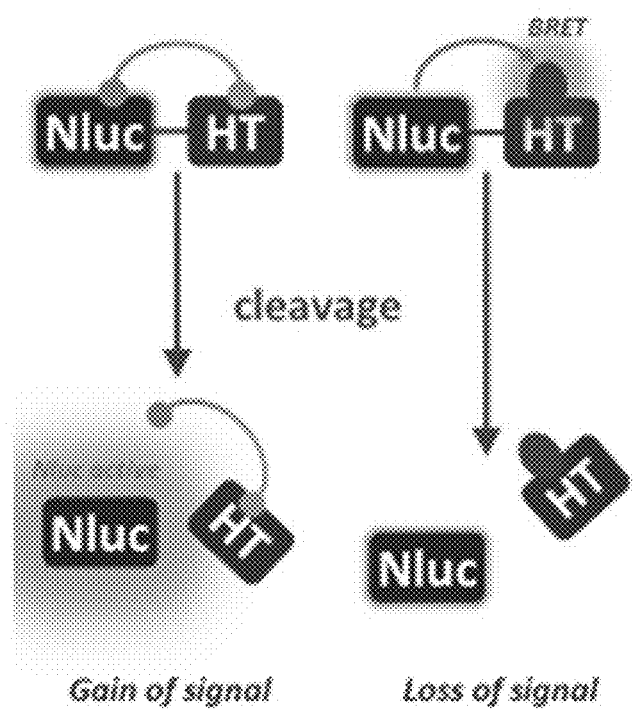
FIG. 3 shows two principle approaches for measuring caspase activity using the same Nluc-DEVD-HT fusion protein. The graphic on the left shows a luminescence-intensity based approach. An increase of caspase activity leads to the cleavage of the Nluc-DEVD-HT fusion protein and consequently to the dissociation of Nluc inhibitor and Nluc, which in turn results in increased luminescence. The figure on the right depicts a BRET based sensor in which a BRET occurs between Nluc and a HT-dye conjugate. The BRET signal is at its maximum in the uncleaved state. Upon activation of caspase the Nluc-DEVD-HT fusion is cleaved, which results in a decrease of BRET.
Figure 4:
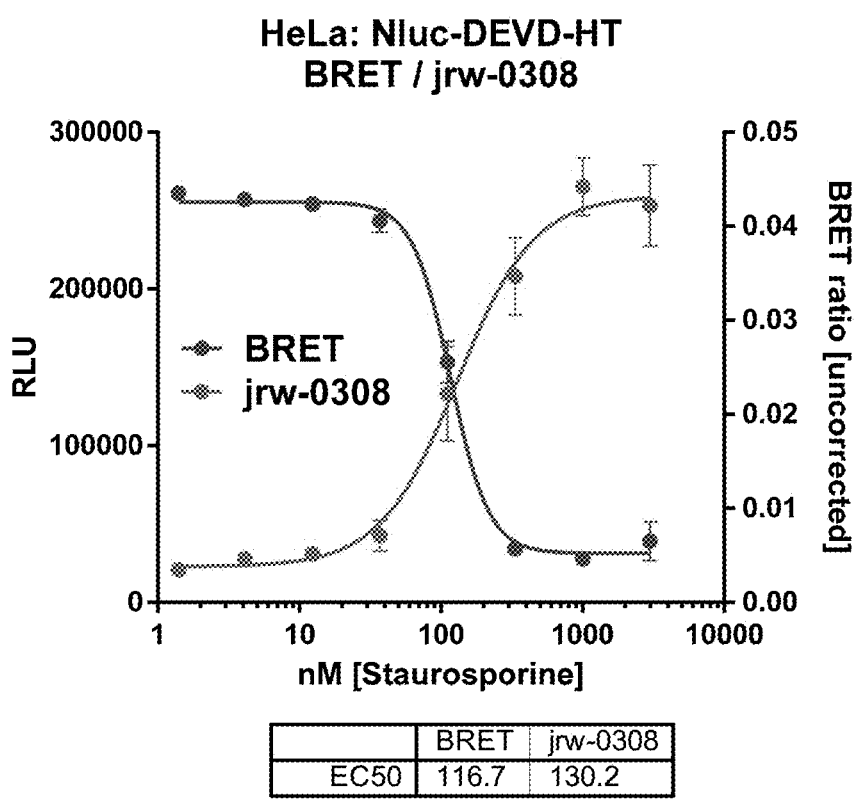
FIG. 4 shows comparison between the intensity based assay and the BRET based assay described in FIG. 3. HeLa cells were reverse transfected with Nluc-DEVD-HT, plated, and incubated overnight. Labeling was performed by replacement of growth medium with OptiMEM including the indicating concentration of JRW-0308 (shown in green) or 500 nM NanoBRET™ 618 ligand (shown in red) followed by incubation for 90 min at 37° C. Caspase activity was induced by adding 50 μL OptiMEM containing a serial dilution of staurosporine and incubation for 7 h at 37° C. Plates were read following addition of furimazine (10 μM final concentration) using a BMG Clariostar. Similar EC50 values for staurosporine were calculated for both approaches.

Two principle approaches for measuring caspase activity using the same Nluc-DEVD-HT fusion protein have been tested. These approaches are shown in FIG. 3. The graphic on the left shows a luminescence-intensity based approach. In the luminescence-intensity based approach, Nluc bioluminescence is inhibited when the fusion protein is intact. An increase of caspase activity leads to the cleavage of the Nluc-DEVD-HT fusion protein and consequently to the dissociation of Nluc inhibitor and Nluc. This increase in caspase activity thereby disinhibits Nluc, increasing the bioluminescence emitted. The figure on the right depicts a BRET based sensor in which a BRET occurs between Nluc and a HT-dye conjugate. The BRET signal is at its maximum in when caspase is not activated and the fusion protein exists in the uncleaved state. Upon activation of caspase the Nluc-DEVD-HT fusion will be cleaved, which will result in a decrease of BRET. FIG. 4 shows comparison between the intensity based assay and the BRET based assay described in FIG. 3. HeLa cells were reverse transfected with Nluc-DEVD-HT, plated, and incubated overnight. Labeling was performed by replacement of growth medium with OptiMEM including the indicating concentration of JRW-0308 (shown in green) or 500 nM NanoBRET™ 618 ligand (shown in red) followed by incubation for 90 min at 37° C. Caspase activity was induced by adding 50 µL, OptiMEM containing a serial dilution of staurosporine and incubation for 7 h at 37° C. Plates were read following addition of furimazine (10 µM final concentration) using a BMG Clariostar. Similar $EC_{50}$ values for staurosporine were calculated for both approaches.

Example 75

Modeling Protein-Protein Interactions

Figure 5A:
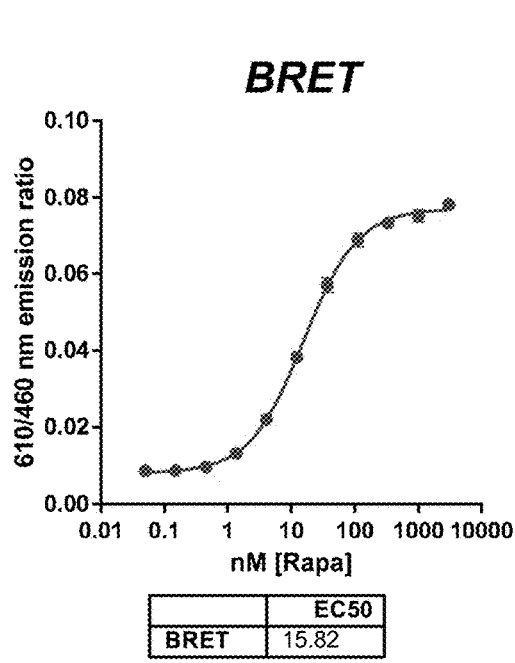
FIG. 5A, FIG. 5B and FIG. 5C show two principle approaches for modeling protein-protein interactions. HeLa cells were reverse transfected with Frb-NL/FKBP-HT (1:4DNA ratio), plated, and incubated overnight. Labeling was performed by replacement of growth medium with OptiMEM including 500 nM NanoBRET™ 618 ligand (FIG. 5A) or the indicated concentration of JRW-0308 (FIG. 5B) followed by incubation for 90 min at 37° C. Plates were read 10 minutes following addition of a serial dilution of rapamycin and furimazine (10 μM final concentration) using a BMG Clariostar.
Figure 5B:
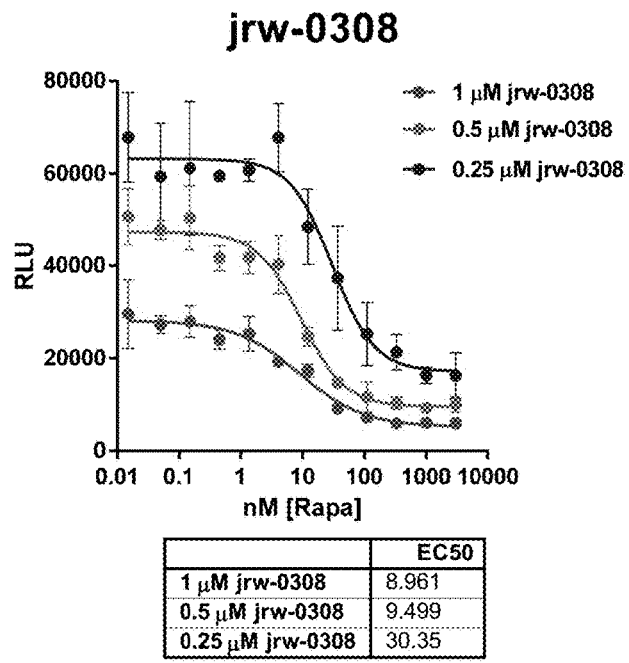
Figure 5C:
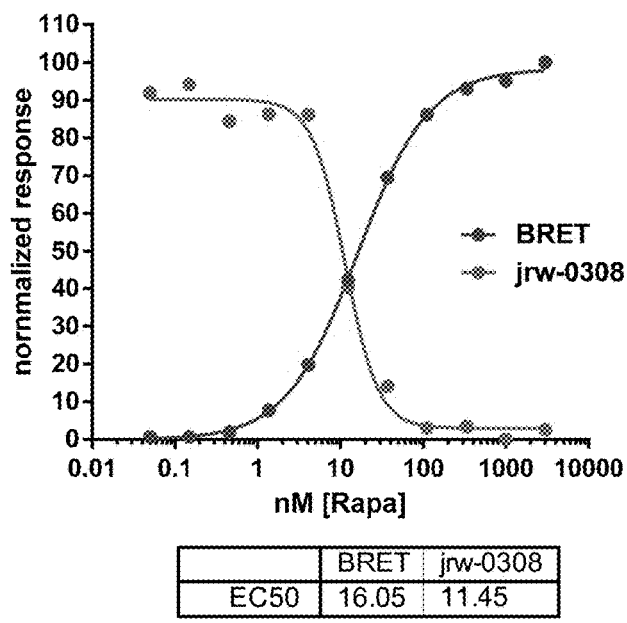

Protein-protein interactions were measured using an Frb/FKBP association/dissociation model. HeLa cells were reverse transfected with expression constructs for Frb-NL/FKBP-HT (1:4DNA ratio) fusions, plated, and incubated overnight. Labeling was performed by replacement of growth medium with OptiMEM including 500 nM NanoBRET™ 618 ligand, or the indicated concentration of JRW-0308, followed by incubation for 90 min at 37° C. Plates were read 10 minutes following addition of a serial dilution of rapamycin and furimazine (10 µM final concentration) using a BMG Clariostar. FIG. 5A shows a BRET based Frb/FKBP interaction assay under conditions without inhibitor present. FKBP-HT binds to FRB-NL in the presence of rapamycin, bringing Nluc into close proximity to the HT-NanoBRET™ 618 ligand complex and enabling BRET. Under these conditions, the BRET ratio increases with increasing concentrations of rapamycin, increasing the ratio of 610 nm:460 nm light emitted. FIG. 5B shows the same Frb/FKBP interaction model in the presence of JRW-0308. In conditions with low concentrations of rapamycin present, FKB does not bind to FRB and Nluc remains unbound from the HT-JRW-0308 complex. The addition of rapamycin induces FKB-HT/FRB-HT interaction, which brings the HT-inhibitor complex into contact with the Nluc causing decreased signal. FIG. 5C shows that rapamycin displays a similar $EC_{50}$ for both of the above described models.

Example 76

Suicide Inhibition

Figure 6:
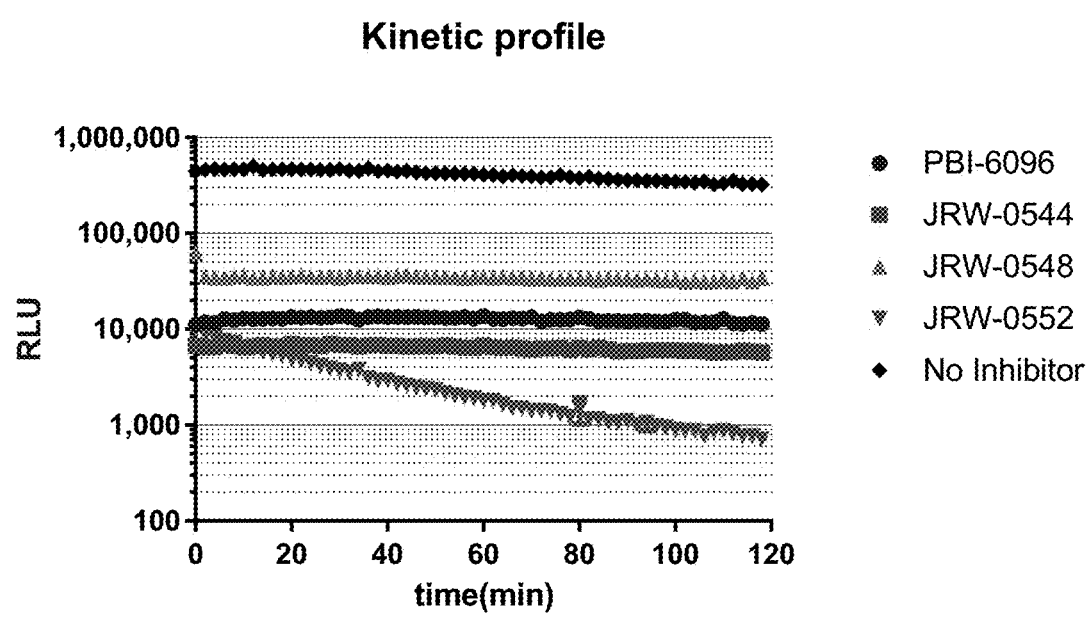
FIG. 6 shows Nluc inhibition by exemplary succinate (JRW-0552, JRW-0544) or bromide (JRW-0549) functionalized inhibitors tested. Inhibitors were diluted to 3 uM into OptiMEM+0.1% FBS. NanoLuc was diluted to 0.4 ng/ml into NanoGlo® buffer+100 uM furimazine. 50 ul of each inhibitor was added to 50 ul of the NanoLuc/furimazine/NanoGlo® solution. Samples were immediately placed in a GloMax Multi+ set to read in kinetic mode at two minute intervals. JRW-0552 showed irreversible inhibition. JRW-0259 was used as a control (reversible inhibitor).

Nluc inhibitory activity of exemplary succinate or bromide functionalized inhibitors was tested. Inhibitors were diluted to 3 uM into OptiMEM+0.1% FBS. NanoLuc was diluted to 0.4 ng/ml into NanoGlo® buffer+100 uM furimazine. 50 ul of each inhibitor was added to 50 ul of the NanoLuc/furimazine/NanoGlo® solution. Samples were immediately placed in a GloMax® Multi+ set to read in kinetic mode at two minute intervals. FIG. 6 shows a kinetic measurement of light output of NanoLuc/furimazine (black diamonds). In the presence of reversible inhibitors (JRW-0347), inhibition over time remains the same. Alkyl bromide (JRW-0548) shows steady state inhibition. Succinate ester JRW-0544 also shows steady state binding while succinate ester JRW-0552 unexpectedly shows time dependent inhibition. This indicates JRW-0552 is an irreversible inhibitor.

Figure 7:
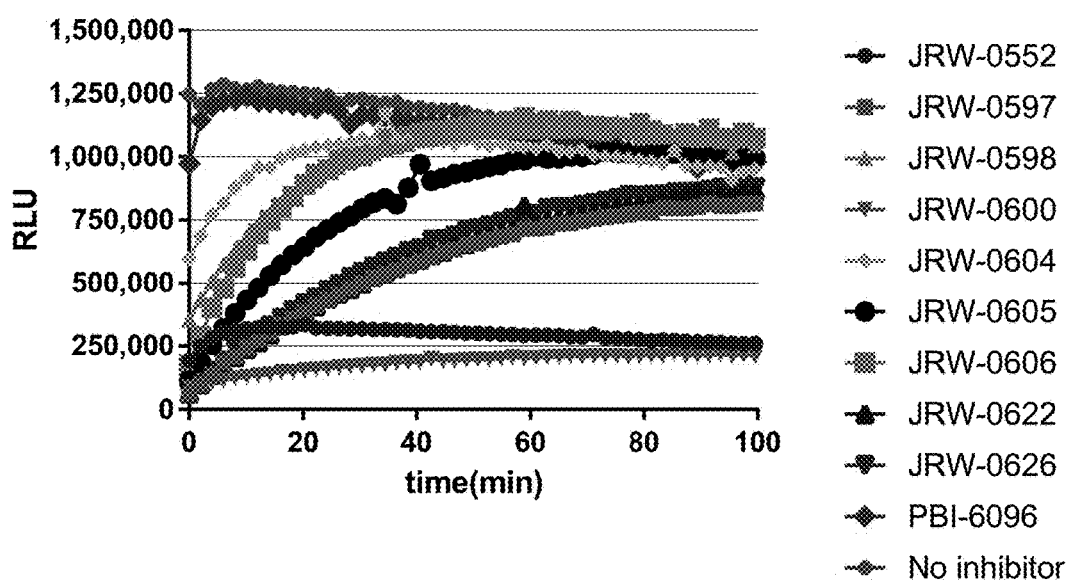
FIG. 7 shows Nluc inhibition by exemplary succinate (JRW-0552, JRW-0600, JRW-0604), ester (JRW-0597, JRW-0598, JRW-0605, JRW-0606), halo (JRW-0622, JRW-0626) functionalized inhibitors. 10 µM Nluc was incubated with 10 µM inhibitor in OptiMEM+0.1% FBS and incubated for 30 minutes at RT. The mixture was then diluted 10×10⁶ fold (10 pM NanoLuc and inhibitor). Following dilution, 50 ul of the dilution was combined with 50 ul of NanoGlo® assay buffer. Final furimazine concentration was 10 uM. Only succinates with a C8 linker (JRW-0552, JRW-0600) showed irreversible inhibition; succinate with a C6 linker (JRW-0604) did not show irreversible inhibition which indicates the specificity for this interaction. Other functionalized inhibitors (bromide, iodide, ester) were eventually displaced by furimazine (indicated by the convergence of RLU's over time)

FIG. 7 shows a kinetic read of light output of NanoLuc/furimazine in the presence or absence of inhibitor. The experiment was designed to show which inhibitors can or cannot be displaced by furimazine upon dilution. 10 µM Nluc was incubated with 10 µM inhibitor in OptiMEM+ 0.1% FBS and incubated for 30 minutes at RT. The mixture was then diluted 10×10$^6$ fold (10 pM NanoLuc and inhibitor). Following dilution, 50 ul of the dilution was combined with 50 ul of NanoGlo® assay buffer. Final furimazine concentration was 10 uM. JRW-0347 shows rapid displacement by furimazine; JRW-0598, JRW-0604, JRW-0650, and JRW-0606 are slower; and JRW-0597, JRW-0622, and JRW-0626 are even slower to be displaced by furimazine. JRW-0552 and JRW-0600 were not displaced by furimazine and irreversibly inhibit NanoLuc affectively in a 1:1 molar ratio.

FIG. 8A, FIG. 8B and FIG. 8C show a comparison of succinate ester functionalized inhibitors and a potent reversible inhibitor using an EGFR/Cetuximab binding assay. FIG. 8A shows a schematic illustrating the concept of the binding assay. Cetuximab is appended to a HT-NLuc fusion protein (Cetux-Fab-Nluc) and added to an EGFR plate. Under control conditions, Cetuximab binds EGFR and the Nluc signal is high. The addition of inhibitor diminishes the Nluc signal. FIG. 8B shows the Nluc inhibitory activity of JRW-0552, JRW-0597, and JRW-0600. An EGFR coated plate was treated with 3 µg/ml Cetux-Fab-Nluc. The plate was treated with the indicated concentration of inhibitors. Plates were read following addition of furimazine (10 µM final concentration) using a BMG Clariostar. FIG. 8C shows the % inhibition of the tested compounds relative to control.

Figure 9A:
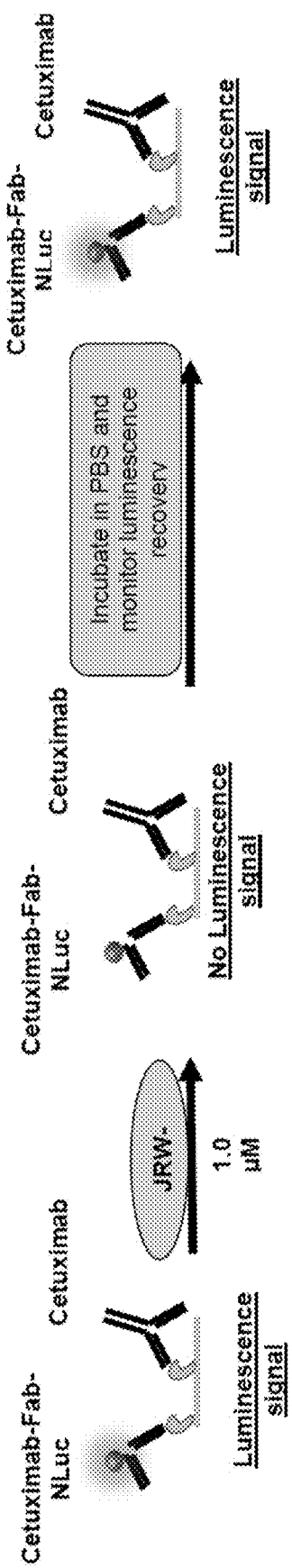
FIG. 9A and FIG. 9B show that inhibition by the succinate ester functionalized inhibitor JRW-0552 is irreversible. A schematic for the experimental design is shown in FIG. 9A. Cetux-Fab-Nluc competes with Cetuximab for binding of EGFR. Plates were read following addition of furimazine (10 µM final concentration) using a BMG Clariostar. Following the first reading, 1 µM inhibitor is added for a period of 5 minutes or 30 minutes. The plates were subsequently washed with PBS for 0, 10, 30, or 60 minutes. A second signal reading is then taken following addition of furimazine (10 µM final concentration) using a BMG Clariostar. The results are shown in FIG. 9B.
Figure 9B:
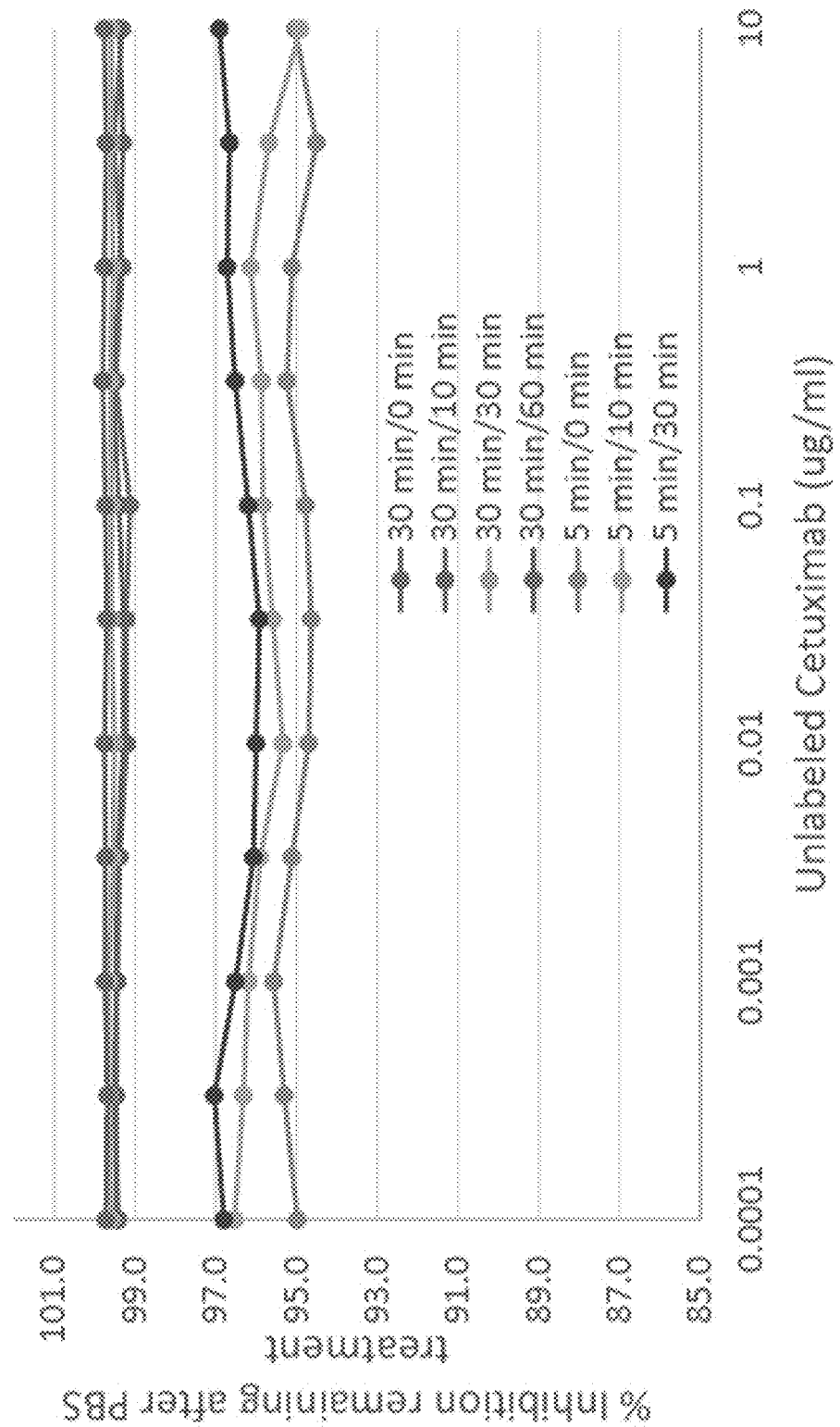
Figure 10A:
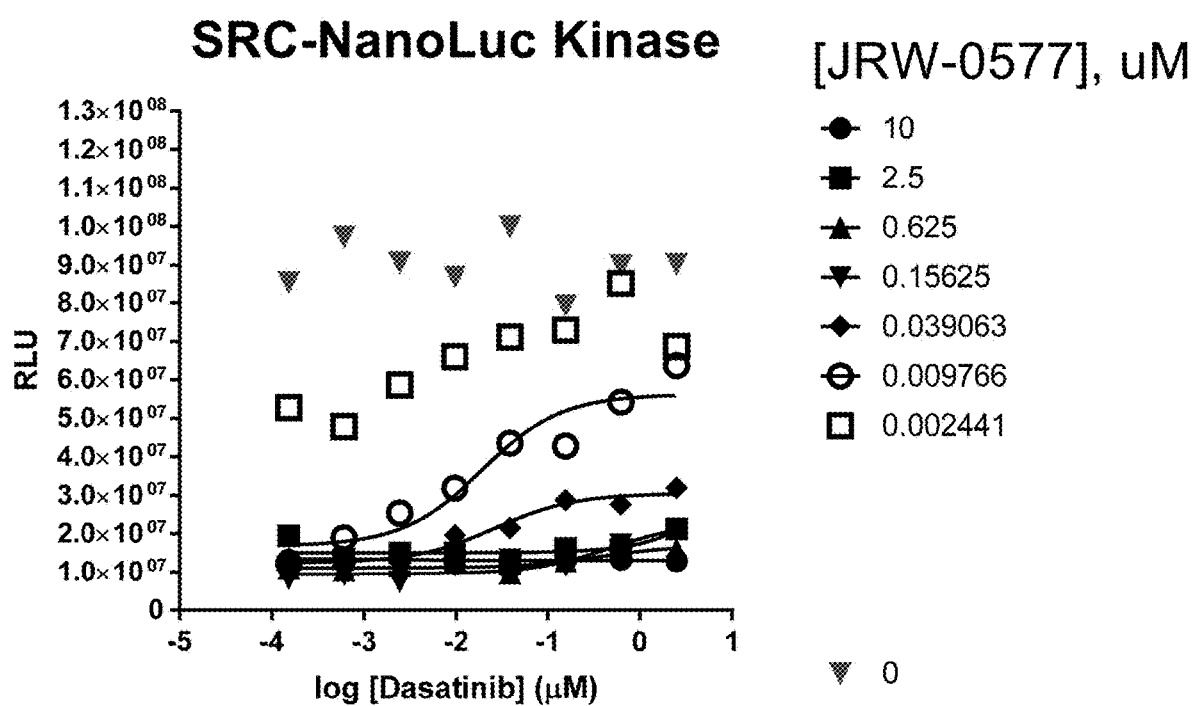
In FIG. 10A, FIG. 10B, FIG. 10C and FIG. 10D, HEK293 cells were transfected with DNA encoding a fusion of SRC kinase and NanoLuc. Cells were transfected with a 1:3 ratio of DNA:Fugene HD. Following 24 hours of expression, cells were lysed with 50 ug/mL of digitonin in OptiMEM and treated with varying concentrations of dasatinib-linked NanoLuc® inhibitors (JRW-0577, -0589, -0593, -0595, FIG. 10A, FIG. 10B, FIG. 10C and FIG. 10D, respectively). Cells were co-treated with serially diluted unmodified dasatinib. After 2 hours of incubation at room temperature, furimazine (10 uM) was added, and luminescence was measured on a GloMax® luminometer. Binding of dasatinib is evident as a dose-dependent increase in luminescence.
Figure 10B:
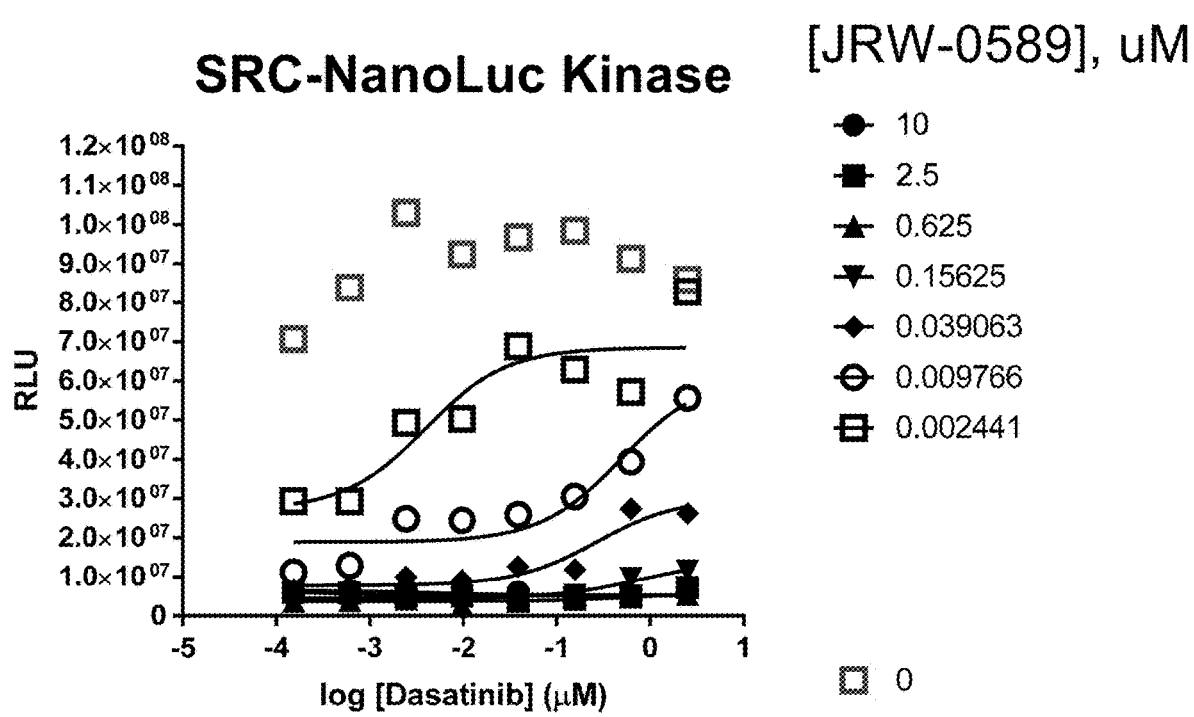
Figure 10C:
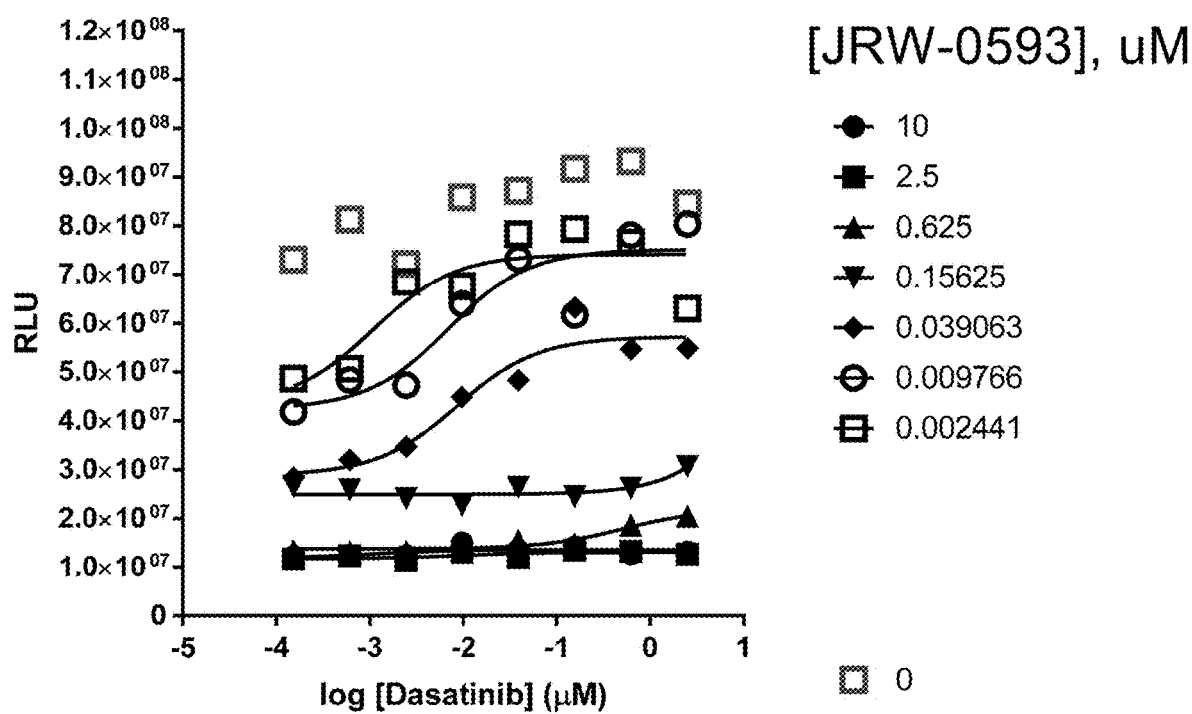
Figure 10D:
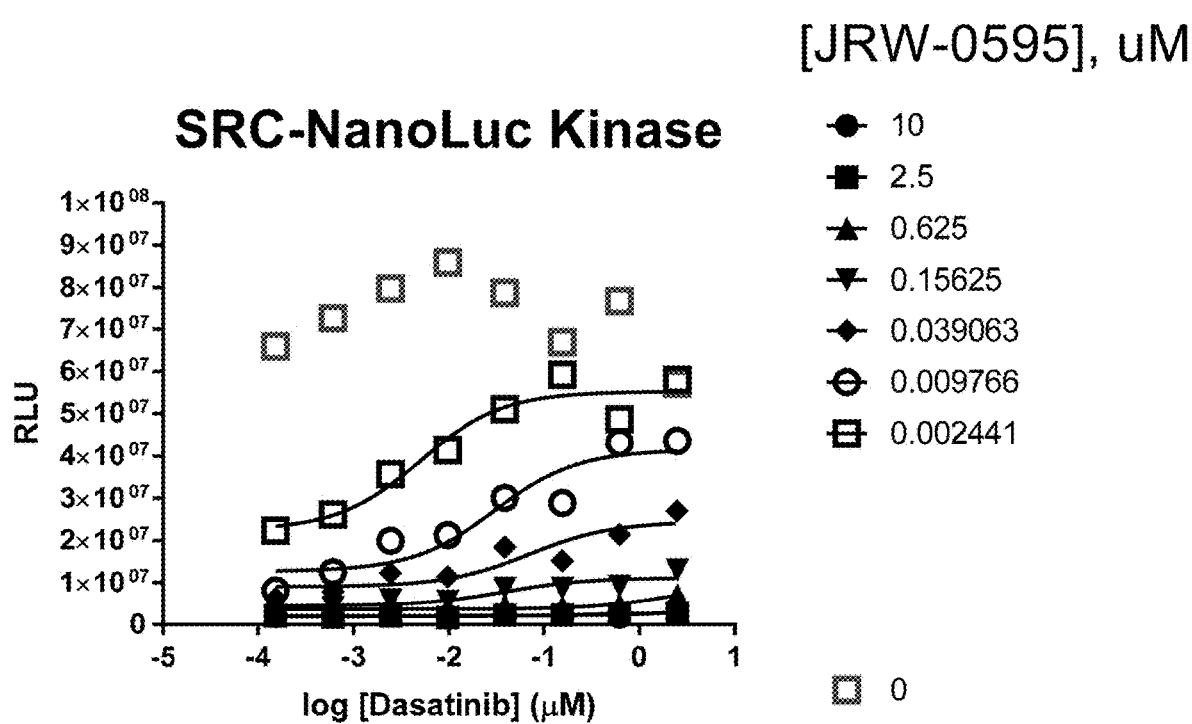

FIG. 9A and FIG. 9B show that inhibition by the succinate ester functionalized inhibitor JRW-0552 is irreversible. A schematic for the experimental design is shown in FIG. 9A. Cetux-Fab-Nluc competes with Cetuximab for binding of EGFR. Plates were read following addition of furimazine (10 µM final concentration) using a BMG Clariostar. Following the first reading, 1 µM inhibitor is added for a period of 5 minutes or 30 minutes. The plates were subsequently washed with PBS for 0, 10, 30, or 60 minutes. A second signal reading is then taken following addition of furimazine (10 µM final concentration) using a BMG Clariostar. Results from the above described experiment are shown in FIG. 9B.

Example 77

Inhibitor IC$_{50}$ Determination

The following example provides the IC$_{50}$ values for the compounds disclosed herein. The results are shown in Table 1. NANOLUC® enzyme was diluted to 0.4 ng/ml in CO$_2$ independent media+10% FBS to make the detection reagent. A 3× dilution series of each inhibitor was then made in the detection reagent. A "no inhibitor" control was also made for each sample. 50 ul of each inhibitor dilution was mixed with 50 ul of NanoGlo® buffer containing 20 µM furimazine (final furimazine concentration is 10 µM, which is at Km.), and luminescence was measured. Each sample was normalized to the "no inhibitor" control. The IC$_{50}$ values were then determined using GraphPad Prism (log[inhibitor] vs. normalized response).

TABLE 1

| Identifier | IC$_{50}$ (µM) |
|---|---|
| JRW-0200 | 0.049 |
| JRW-0308 | 0.022 |
| JRW-0466 | 0.0021 |
| JRW-0520 | 0.094 |
| JRW-0525 | 0.084 |
| JRW-0533 | 0.092 |
| JRW-0544 | 0.013 |
| JRW-0548 | 0.099 |
| JRW-0552 | 0.0029 |
| JRW-0559 | 0.033 |
| JRW-0597 | 0.00016 (5 h pre-incubation) |
| JRW-0598 | 0.00040 (5 h pre-incubation) |
| JRW-0600 | ND |
| JRW-0604 | 0.0027 (5 h pre-incubation) |
| JRW-0605 | 0.00012 (5 h pre-incubation) |
| JRW-0606 | 0.0041 (5 h pre-incubation) |
| JRW-0622 | 0.00014 (5 h pre-incubation) |
| JRW-0626 | 0.0002 (5 h pre-incubation) |
| JRW-0660 | ND |
| JRW-0818 | 0.0012 |
| JRW-822 | 0.0033 |
| JRW-0824 | 0.18 |
| JRW-0827 | 0.0027 |
| JRW-0829 | 0.48 |
| JRW-0831 | 0.32 |
| JRW-0833 | 0.02 |
| JRW-0830 | 0.0042 |
| JRW-0834 | 0.0033 |
| JRW-0844 | 0.041 |
| JRW-0846 | 0.016 |
| JRW-0847 | 0.0003 (60 min pre-incub) |
| JRW-0859 | 0.002 |
| JRW-0863 | 0.036 |
| JRW-0870 | 0.042 |
| JRW-0882 | 0.0011 |
| JRW-0883 | 0.0054 |
| JRW-0886 | 0.0037 |
| JRW-0887 | 0.0063 |
| JRW-0888 | 0.026 |
| JRW-0889 | 0.28 |
| JRW-0915 | 0.0052 |
| JRW-0921 | 0.0011 |
| JRW-0920 | 0.0017 |
| JRW-0958 | 0.016 |
| JRW-0964 | 0.012 |
| JRW-1082 | 0.0033 |
| JRW-1081 | 0.006 |
| JRW-1083 | 0.0018 |

Example 78

Binding of Dasatinib-Linked NanoLuc® Inhibitors

HEK293 cells were transfected with DNA encoding a fusion of SRC kinase and NanoLuc. Cells were transfected with a 1:3 ratio of DNA:Fugene HD. Following 24 hours of expression, cells were lysed with 50 ug/mL of digitonin in OptiMEM and treated with varying concentrations of dasatinib-linked NanoLuc® inhibitors (JRW-0577, -0589, -0593, -0595, results shown in FIG. 10A, FIG. 10B, FIG. 10C and FIG. 10D, respectively). Cells were co-treated with serially diluted unmodified dasatinib. After 2 hours of incubation at room temperature, furimazine (10 uM) was added, and luminescence was measured on a GloMax® luminometer. Binding of dasatinib is evident as a dose-dependent increase in luminescence.

Example 79

Multiplexing Luciferases with the same Wavelength

The following solutions were prepared in TBS+20 uM furimazine: 1) 0.4 ng/ml NanoLuc, 2) 0.4 ng/ml NanoLuc+ 0.2 nM HaloTag-HiBiT, 3) 0.4 ng/ml NanoLuc+200 nM LgBiT. 50 ul of each solution was combined in triplicate with a solution containing 100 uM JRW-0552 diluted into NanoGlo® buffer. Samples were immediately placed in a GloMax®⁻ luminometer and read in kinetic mode at two minute intervals for 50 minutes.

Figure 11:
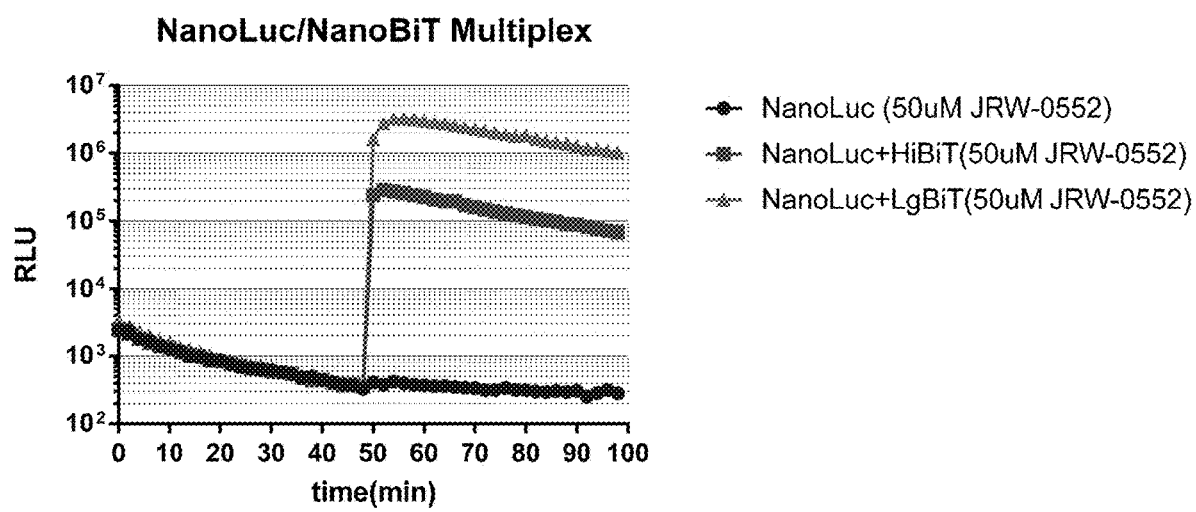
FIG. 11 shows light output under conditions when NanoLuc is incubated with a NanoLuc® specific inhibitor, one that can preferentially block NanoLuc® activity, but allow a functional NanoBiT™ enzyme system. Three conditions are represented in this figure: 1) NanoLuc with JRW-0552; 2) NanoLuc and HiBiT with JRW-0552; and 3) NanoLuc and LgBiT with JRW-0552. At the 50 minute mark, an addition is done in each condition: 1) furimazine; 2) furimazine; and 3) LgBiT, furimazine, and HiBiT, respectively. As demonstrated, the signal for NanoLuc remains inhibited while the two NanoBiT configurations are operational and results in a large signal increase.

After 50 minutes, 100 ul of the following solutions were added to the corresponding samples: 1) NanoGlo® buffer+ 50 uM furimazine, 2) NanoGlo® buffer+50 uM furimazine+ 200 nM LgBiT, 3) NanoGlo® buffer+50 uM furimazine+0.2 nM HaloTag-HiBiT. Samples were immediately placed in a GloMax® Multi+luminometer and read in kinetic mode at two minute intervals for another 50 minutes. As shown in FIG. 11, JRW-0552 selectively inhibits the signal for Nano-Luc while the two NanoBiT configurations remain operational.

Further examples of uses for inhibitors of *Oplophorus* luciferase are described in, for example, U.S. patent application Ser. No. 15/192,420, which is incorporated herein by reference.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the present disclosure are set out in the following numbered clauses:

Clause 1. A compound of formula (I), or a salt thereof:

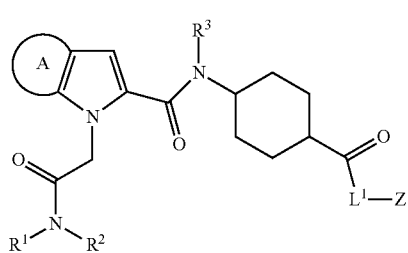

(I)

wherein:

A is absent, an optionally substituted phenyl ring, or an optionally substituted thienyl ring;

$L^1$ is absent or —$(CR^{a1}R^{a2})_{m1}$—, wherein m1 is 1 to 100, optionally wherein one or more $CR^{a1}R^{a2}$ groups are replaced by a heteroatom or heteroatom group selected from the group consisting of O, N($R^{a3}$), S(=O), and S(=O)$_2$, optionally wherein one or more $CR^{a1}R^{a2}$ groups are replaced by C(=O), optionally wherein two adjacent $CR^{a1}R^{a2}$ groups form $CR^{a1}$=$CR^{a1}$, and optionally wherein one or more $CR^{a1}R^{a2}$ groups are replaced by a -Cy- group, wherein each Cy is independently selected from the group consisting of aryl, heteroaryl, cycloalkyl, cycloalkenyl, and heterocycle; wherein $R^{a1}$, $R^{a2}$, and $R^{a3}$ are independently selected from the group consisting of hydrogen and $C_1$-$C_4$-alkyl;

Z is $C_1$-$C_{10}$ haloalkyl, a leaving group Y, a bioactive agent, or a dye, wherein the leaving group Y is selected from the group consisting of $OR^4$, halogen, heteroaryl, and heterocyclyl;

$R^1$ is hydrogen or $C_1$-$C_8$ alkyl;

$R^2$ is selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;

$R^3$ is hydrogen or $C_1$-$C_8$ alkyl; and $R^4$ is selected from the group consisting of optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl.

Clause 2. The compound of clause 1, wherein A is an optionally substituted phenyl ring.

Clause 3. The compound of clause 1, wherein A is an optionally substituted thienyl ring.

Clause 4. The compound of any of clauses 1-3, wherein $R^1$ is selected from the group consisting of hydrogen, $C_1$-$C_8$ alkyl, halo-$C_1$-$C_8$-alkyl, alkoxyalkoxyalkyl and arylalkyl.

Clause 5. The compound of any of clause 1-4, wherein $R^2$ is optionally substituted aryl.

Clause 6. The compound of any of clauses 1-5, wherein $R^2$ is phenyl substituted with at least one substituent selected from the group consisting of $C_1$-$C_4$ alkyl, cyano, amido, $C_1$-$C_4$ alkoxy, $C_1$-$C_4$ haloalkyl, and hydroxyalkyl.

Clause 7. The compound of any of clauses 1-6, wherein $R^3$ is hydrogen.

Clause 8. The compound of clause 1, wherein the compound has formula (Ia):

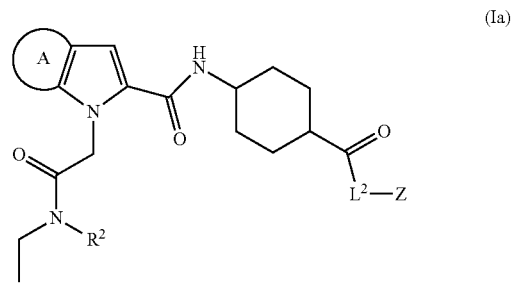

(Ia)

wherein:

A is absent, a phenyl ring, or a thienyl ring;

$R^2$ is phenyl substituted with at least one $C_1$-$C_4$ alkyl or $C_1$-$C_4$ haloalkyl; and $L^2$ is absent or —$(CR^{a1}R^{a2})_{m2}$—, wherein m2 is 1 to 90, and wherein each $CR^{a1}R^{a2}$ is as defined in clause 1.

Clause 9. The compound of clause 1, wherein the compound has formula (Ib):

(Ib)

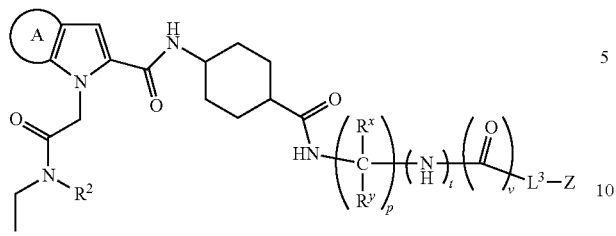

wherein:
A is absent, a phenyl ring, or a thienyl ring;
$R^2$ is phenyl substituted with at least one $C_1$-$C_4$ alkyl or $C_1$-$C_4$ haloalkyl;
$R^x$ and $R^y$ at each occurrence is independently hydrogen or $C_1$-$C_4$ alkyl;
p is 4, 5, 6, 7, 8, 9, or 10;
t is 0 or 1;
v is 0 or 1; and
$L^3$ is absent or —$(CR^{a1}R^{a2})_{m3}$—, wherein m3 is 1 to 80, and wherein each $CR^{a1}R^{a2}$ is as defined in clause 1.

Clause 10. The compound of clause 9, wherein $L^3$ is —$(CR^{a1}R^{a2})_{m3}$—, wherein m3 is 1-20, and $R^{a1}$ and $R^{a2}$, at each occurrence are independently hydrogen or $C_1$-$C_4$ alkyl.

Clause 11. The compound of clause 9, wherein $L^3$ is -$Q^1$-$(CH_2$—$CH_2$—$O)_{k1}$-$Q^2$-$(CH_2$—$CH_2$—$O)_{k2}$-$Q^3$-$(CH_2$—$CH_2$—$O)_{k3}$—, wherein:
$Q^1$ is absent, O, or NH;
$Q^2$ is absent,

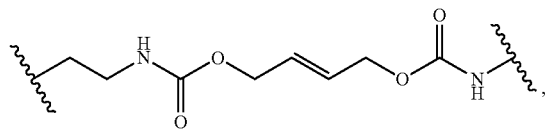 [SMILES: *CCNC(=O)OC/C=C/COC(=O)N*]

—CO—NH—, —$CH_2$—$CH_2$—CO—, —$CH_2$—$CH_2$—NH—CO, or —$CH_2$—$CH_2$—CO—NH—
$Q^3$ is absent, —CO—NH—, or —$CH_2$—$CH_2$—;
k1 is 1-10;
k2 is 0-10; and
k3 is 0-10.

Clause 12. The compound of clause 9, wherein $L^3$ is selected from the group consisting of:

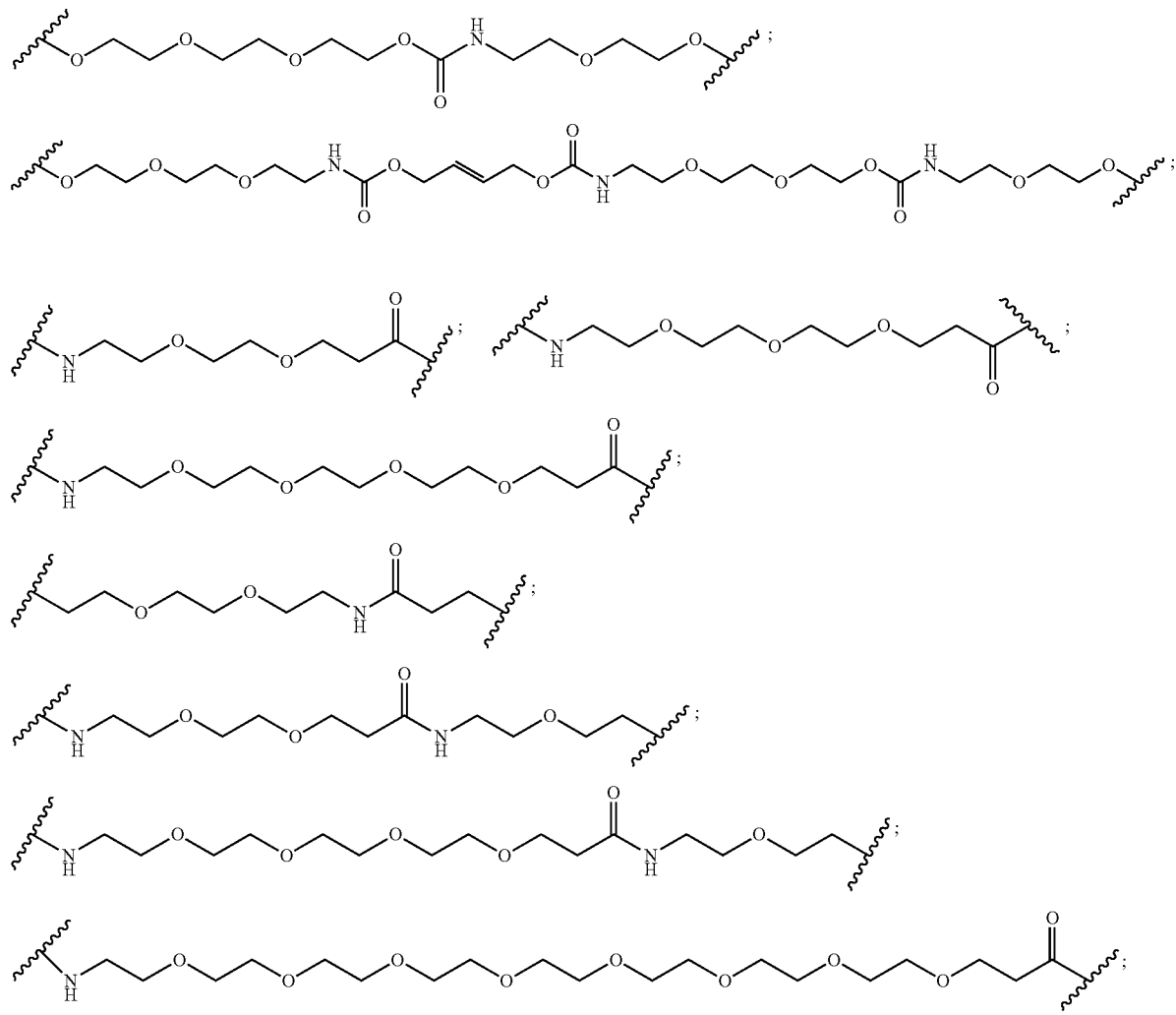

-continued

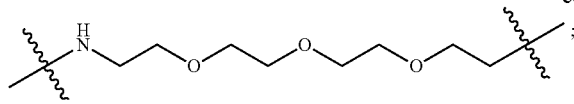

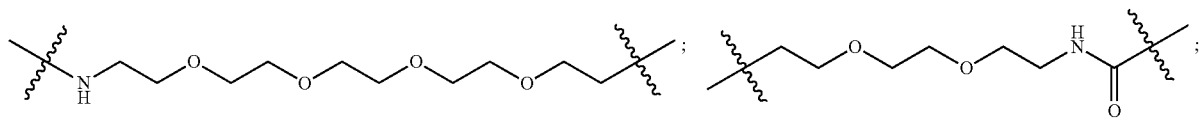

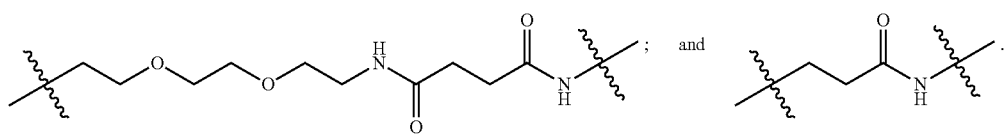

Clause 13. The compound of any of clauses 1, 8, and 9, wherein Z is $C_1$-$C_{10}$ haloalkyl.

Clause 14. The compound of clause 13 wherein the compound has formula (Ic):

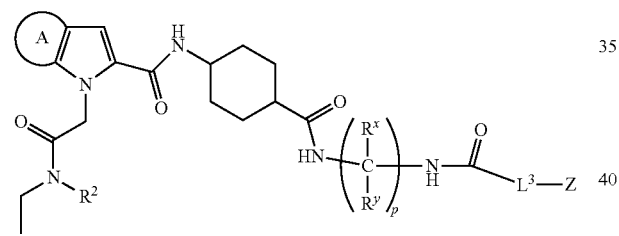

(Ic)

wherein:
A is a phenyl ring or thienyl ring;
$R^2$ is phenyl substituted with one methyl or ethyl group;
$R^x$ and $R^y$ at each occurrence is independently hydrogen or $C_1$-$C_4$ alkyl;
p is 4, 5, 6, 7, 8, 9, or 10; and
$L^3$ is

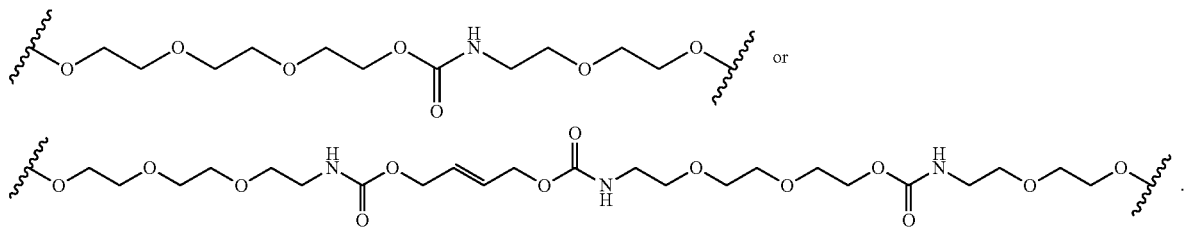

Clause 15. The compound of any of clauses 13-14, wherein Z is —(CH$_2$)$_6$—Cl.

Clause 16. The compound of any of clauses 1, 8, and 9, wherein Z is a leaving group Y selected from the group consisting of $OR^4$, halogen, heteroaryl, and heterocyclyl.

Clause 17. The compound of clause 16, wherein the compound has formula (Id):

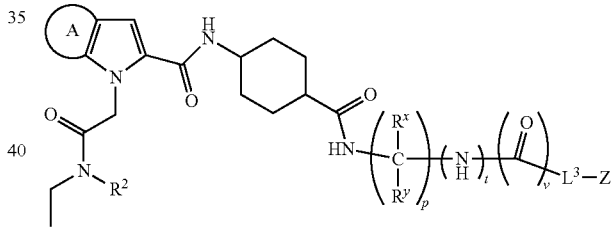

(Id)

wherein:
A is a phenyl ring or a thienyl ring;
$R^2$ is phenyl substituted with one substituent selected from the group consisting of methyl, ethyl, —CH$_2$Br, and —CH$_2$CH$_2$CH$_2$Br;
$R^x$ and $R^y$ at each occurrence is independently hydrogen or $C_1$-$C_4$ alkyl;
p is 4, 5, 6, 7, 8, 9, or 10;
t is 0 or 1;
v is 0 or 1; and
$L^3$ is absent, $C_1$-$C_4$ alkylene,

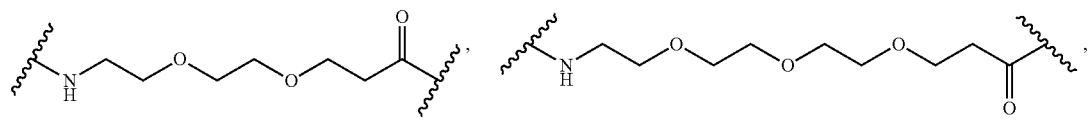
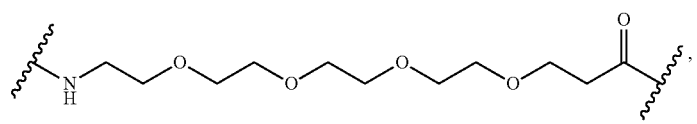
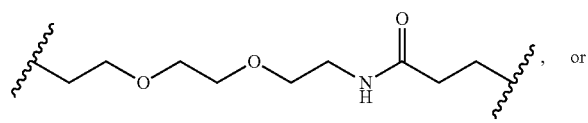, or
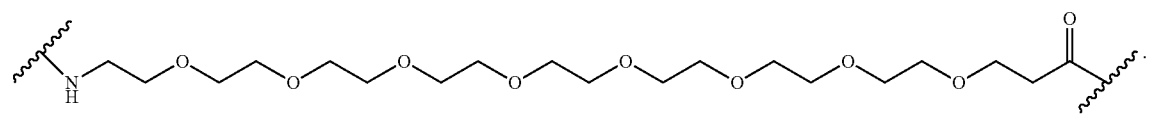
Clause 18. The compound of any of clauses 16-17, wherein Z is chloro, bromo, iodo, $C_1$-$C_4$ alkoxy, phenoxy,
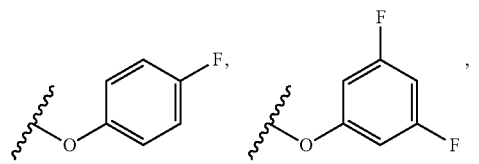
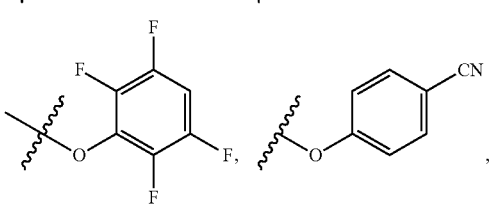,
-continued
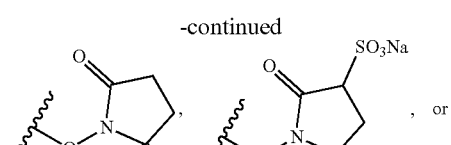, or
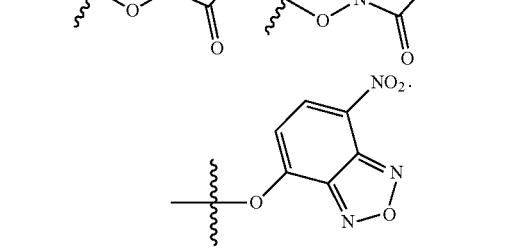
Clause 19. The compound of any of clauses 16-17, wherein
$L^3$ is absent,
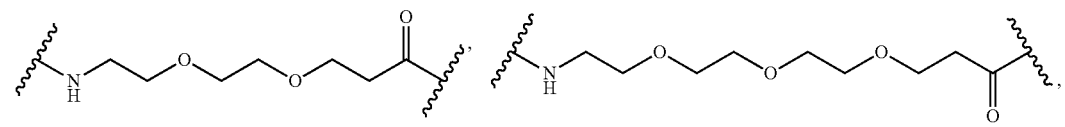
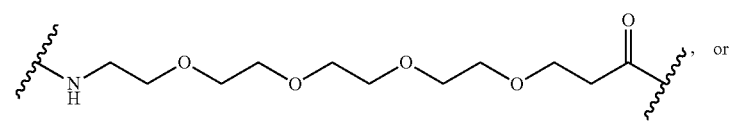, or
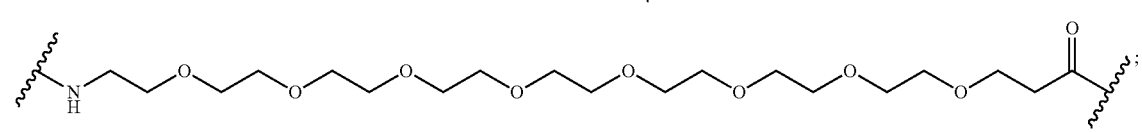;

and

Z is $C_1$-$C_4$ alkoxy, phenoxy,

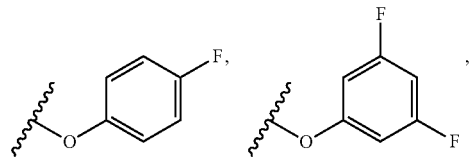

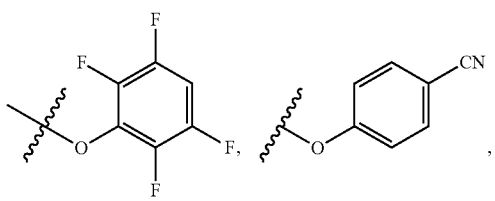

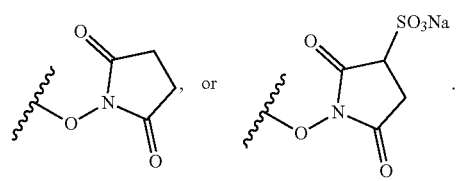

, or

Clause 20. The compound of any of clauses 16-17, wherein $L^3$ is —$CH_2$—$CH_2$—, or

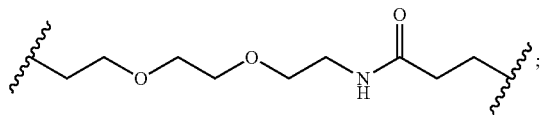 [SMILES: *CCOCCOCCNC(=O)CC*]

and Z is

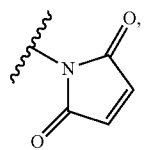 [SMILES: *N1C(=O)C=CC1=O]

or $L^3$ is $C_1$-$C_4$ alkylene; and Z is chloro, bromo, or iodo.

Clause 21. The compound of any of clauses 16-17, wherein, t is 0;

v is 0;

$L^3$ is absent; and

Z is bromo, iodo, or

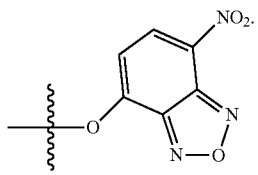 [SMILES: *Oc1ccc([N+](=O)[O-])c2nonc12]

Clause 22. The compound of any of clauses 1, 8, and 9, wherein Z is a bioactive agent selected from the group consisting of an enzyme inhibitor, a receptor inhibitor, and a moiety which induces protein degradation.

Clause 23. The compound of clause 22, wherein Z is a kinase inhibitor.

Clause 24. The compound of any of clauses 22-23, wherein the compound has formula (Ie):

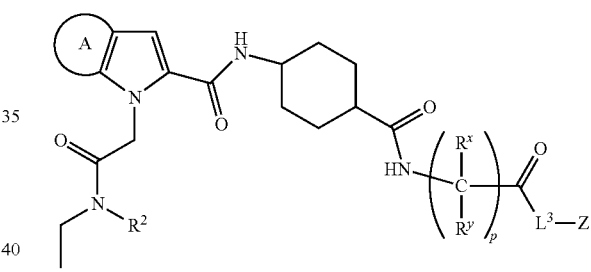

(Ie)

wherein:

A is absent, a phenyl ring or a thienyl ring;

$R^2$ is phenyl substituted with one methyl or ethyl group;

$R^x$ and $R^y$ at each occurrence is independently hydrogen or $C_1$-$C_4$ alkyl;

p is 4, 5, 6, 7, 8, 9, or 10;

$L^3$ is

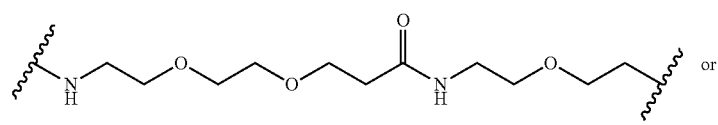 or

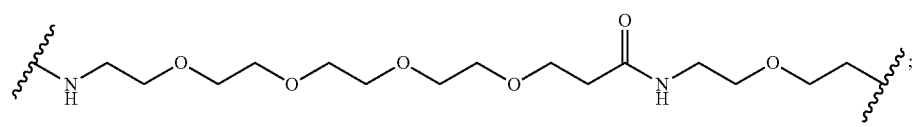;

and
Z is
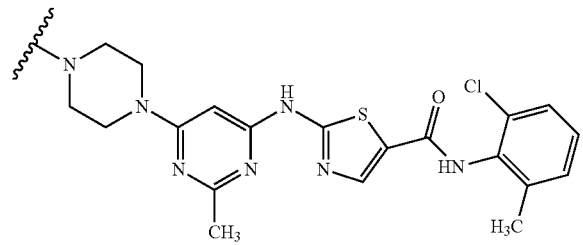 [SMILES: *N1CCN(c2cc(Nc3ncc(C(=O)Nc4c(C)cccc4Cl)s3)nc(C)n2)CC1]
or
L³ is
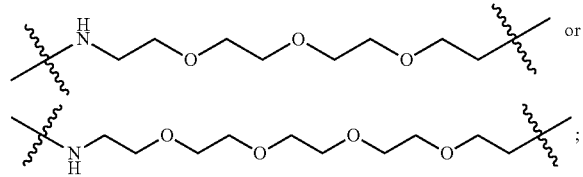
and
Z is
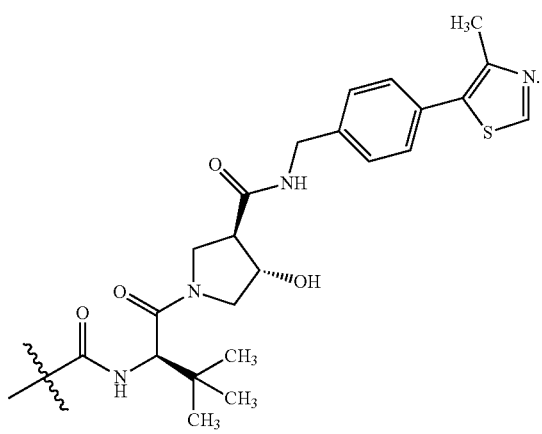 [SMILES: *C(=O)N[C@@H](C(=O)N1C[C@@H](O)[C@H](C(=O)NCc2ccc(-c3scnc3C)cc2)C1)C(C)(C)C]
Clause 25. The compound of any of clauses 1, 8, and 9, wherein Z is a dye.
Clause 26. The compound of clause 25, wherein the compound has formula (If'):
(If')
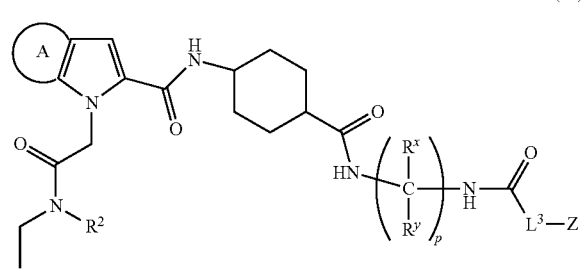
wherein:
A is a phenyl ring or thienyl ring;
R² is phenyl substituted with one methyl or ethyl group;
$R^x$ and $R^y$ at each occurrence is independently hydrogen or $C_1$-$C_4$ alkyl;
p is 4, 5, 6, 7, 8, 9, or 10;
L³ is absent,
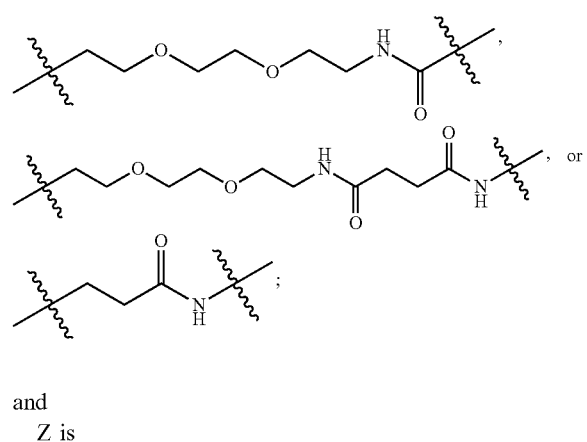
and
Z is
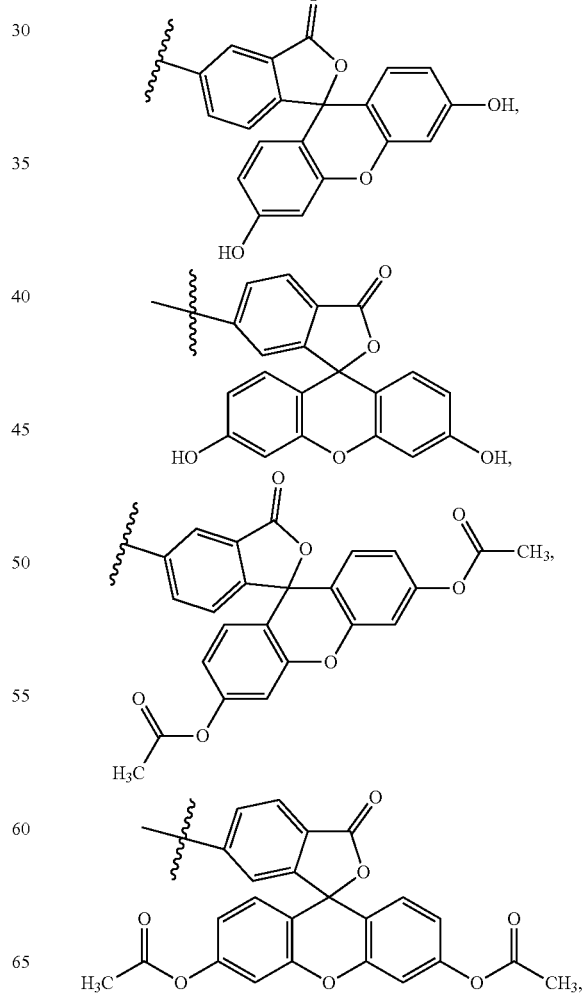

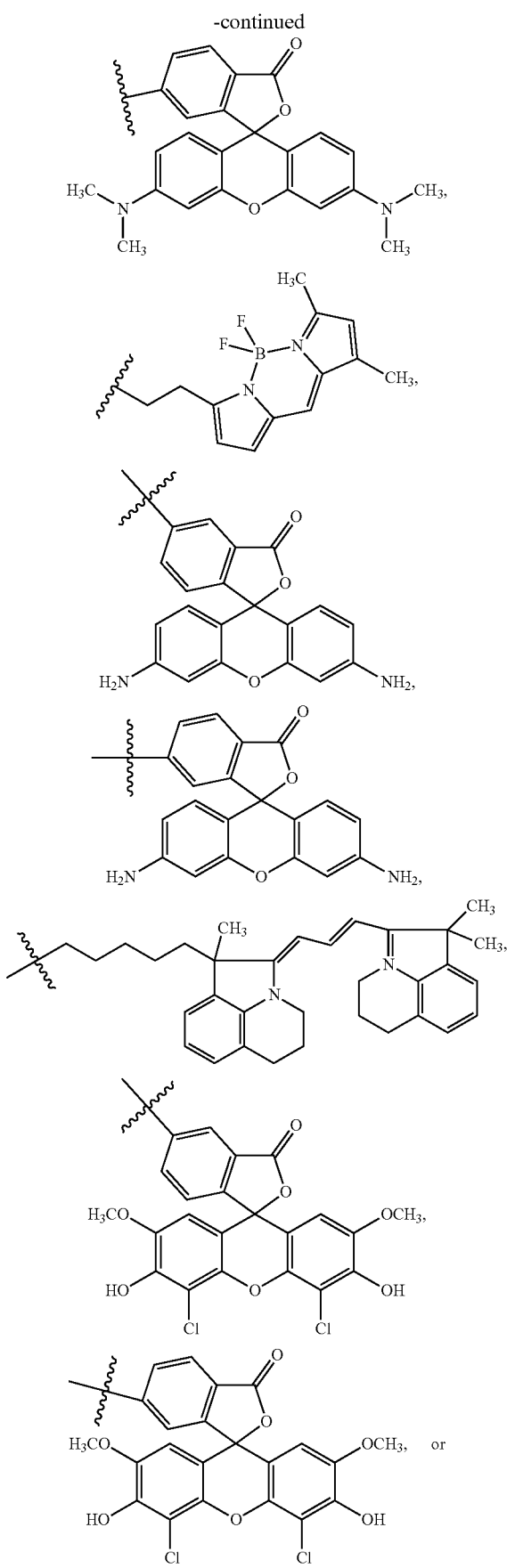
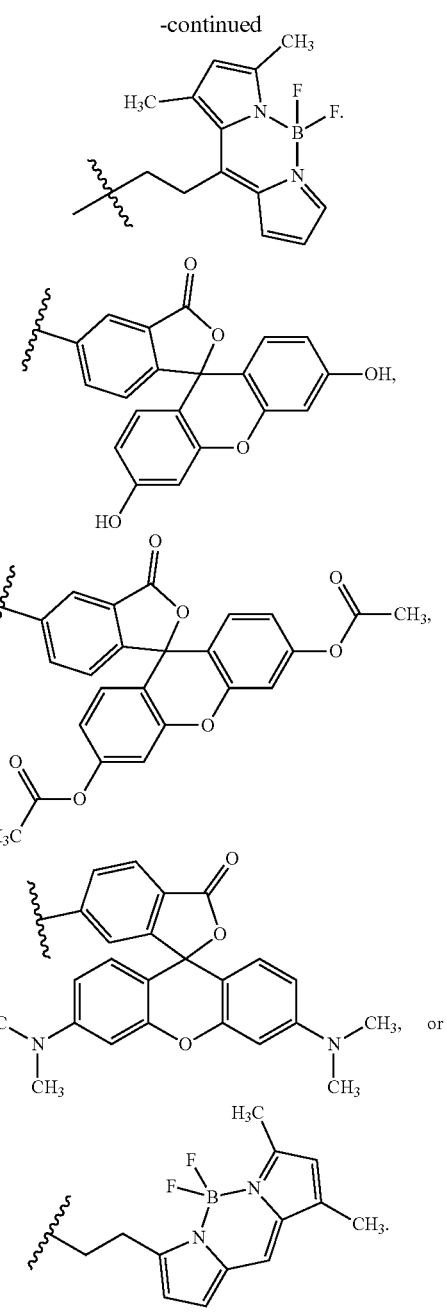

Clause 27. The compound of clause 1, wherein the compound is selected from the group consisting of:

1-(trans-4-(4-(2-(ethyl(m-tolyl)amino)-2-oxoethyl)-4H-thieno[3,2-b]pyrrole-5-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

[(E)-30-chloro-6,17-dioxo-5,10,13,16,21,24-hexaoxa-7,18-diazatriacont-2-en-1-yl (1-(trans-4-(4-(2-(ethyl(3-ethyl-phenyl)amino)-2-oxoethyl)-4H-thieno[3,2-b]pyrrole-5-carboxamido)cyclohexyl)-1,10-dioxo-11,14,17-trioxa-2,9-diazanonadecan-19-yl)carbamate;

[(E)-30-chloro-6,17-dioxo-5,10,13,16,21,24-hexaoxa-7,18-diazatriacont-2-en-1-yl (1-(trans-4-(1-(2-(ethyl(3-ethyl-phenyl)amino)-2-oxoethyl)-1H-indole-2-carboxamido)cyclohexyl)-1,10-dioxo-11,14,17-trioxa-2,9-diazanonadecan-19-yl)carbamate;

1-(trans-4-(4-(2-(ethyl(3-ethylphenyl)amino)-2-oxoethyl)-4H-thieno[3,2-b]pyrrole-5-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

1-(trans-4-(1-(2-(ethyl(3-ethylphenyl)amino)-2-oxoethyl)-1H-indole-2-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oate;

2,5-dioxopyrrolidin-1-yl 1-((1r,4r)-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oate;

N-(trans-4-((6-(3-(2,5-dioxo-2,5-dihydro-1H-pyrrol-1-yl)propanamido)hexyl)carbamoyl)cyclohexyl)-4-(2-(ethyl(m-tolyl)amino)-2-oxoethyl)-4H-thieno[3,2-b]pyrrole-5-carboxamide;

N-(trans-4-((1-(2,5-dioxo-2,5-dihydro-1H-pyrrol-1-yl)-3,13-dioxo-7,10-dioxa-4,14-diazaicosan-20-yl)carbamoyl)cyclohexyl)-4-(2-(ethyl(m-tolyl)amino)-2-oxoethyl)-4H-thieno[3,2-b]pyrrole-5-carboxamide;

methyl trans-4-(4-(2-((3-(bromomethyl)phenyl)(ethyl)amino)-2-oxoethyl)-4H-thieno[3,2-b]pyrrole-5-carboxamido)cyclohexane-1-carboxylate;

methyl trans-4-(4-(2-((3-(3-bromopropyl)phenyl)(ethyl)amino)-2-oxoethyl)-4H-thieno[3,2-b]pyrrole-5-carboxamido)cyclohexane-1-carboxylate;

2,5-dioxopyrrolidin-1-yl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

methyl 8-(trans-4-(1-(2-(ethyl(3-ethylphenyl)amino)-2-oxoethyl)-1H-indole-2-carboxamido)cyclohexane-1-carboxamido)octanoate;

methyl 6-(trans-4-(1-(2-(ethyl(3-ethylphenyl)amino)-2-oxoethyl)-1H-indole-2-carboxamido)cyclohexane-1-carboxamido)hexanoate;

2,5-dioxopyrrolidin-1-yl 8-(trans-4-(1-(2-(ethyl(3-ethylphenyl)amino)-2-oxoethyl)-1H-indole-2-carboxamido)cyclohexane-1-carboxamido)octanoate;

2,5-dioxopyrrolidin-1-yl 6-(trans-4-(1-(2-(ethyl(3-ethylphenyl)amino)-2-oxoethyl)-1H-indole-2-carboxamido)cyclohexane-1-carboxamido)hexanoate;

phenyl 8-(trans-4-(1-(2-(ethyl(3-ethylphenyl)amino)-2-oxoethyl)-1H-indole-2-carboxamido)cyclohexane-1-carboxamido)octanoate;

phenyl 6-(trans-4-(1-(2-(ethyl(3-ethylphenyl)amino)-2-oxoethyl)-1H-indole-2-carboxamido)cyclohexane-1-carboxamido)hexanoate;

1-(2-(ethyl(3-ethylphenyl)amino)-2-oxoethyl)-N-(trans-4-((6-iodohexyl)carbamoyl)cyclohexyl)-1H-indole-2-carboxamide;

N-(trans-4-((6-bromohexyl)carbamoyl)cyclohexyl)-1-(2-(ethyl(3-ethylphenyl)amino)-2-oxoethyl)-1H-indole-2-carboxamide;

1-(2-(ethyl(3-ethylphenyl)amino)-2-oxoethyl)-N-(trans-4-((8-iodooctyl)carbamoyl)cyclohexyl)-1H-indole-2-carboxamide;

4-fluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

3,5-difluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

4-cyanophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

sodium 1-((8-(trans-4-(4-(2-(ethyl(m-tolyl)amino)-2-oxoethyl)-4H-thieno[3,2-b]pyrrole-5-carboxamido)cyclohexane-1-carboxamido)octanoyl)oxy)-2,5-dioxopyrrolidine-3-sulfonate;

N-(trans-4-((5-(2-chloroacetamido)pentyl)carbamoyl)cyclohexyl)-4-(2-(ethyl(m-tolyl)amino)-2-oxoethyl)-4H-thieno[3,2-b]pyrrole-5-carboxamide;

N-(trans-4-((6-(2-chloroacetamido)hexyl)carbamoyl)cyclohexyl)-4-(2-(ethyl(m-tolyl)amino)-2-oxoethyl)-4H-thieno[3,2-b]pyrrole-5-carboxamide;

2,3,5,6-tetrafluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

N-(trans-4-((5-(2-bromoacetamido)pentyl)carbamoyl)cyclohexyl)-4-(2-(ethyl(m-tolyl)amino)-2-oxoethyl)-4H-thieno[3,2-b]pyrrole-5-carboxamide;

N-(trans-4-((1-(4-(6-((5-((2-chloro-6-methylphenyl)carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl(m-tolyl)amino)-2-oxoethyl)-4H-thieno[3,2-b]pyrrole-5-carboxamide;

N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,18-trioxo-12,15,22-trioxa-2,9,19-triazatetracosan-24-yl)piperazin-1-yl)-2-methylpyrimidin-4-yl)amino)thiazole-5-carboxamide;

N-(trans-4-((1-(4-(6-((5-((2-chloro-6-methylphenyl)carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl(3-ethylphenyl)amino)-2-oxoethyl)-4H-thieno[3,2-b]pyrrole-5-carboxamide;

N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,24-trioxo-12,15,18,21,28-pentaoxa-2,9,25-triazatriacontan-30-yl)piperazin-1-yl)-2-methylpyrimidin-4-yl)amino)thiazole-5-carboxamide;

N-(trans-4-((1-(4-(6-((5-((2-chloro-6-methylphenyl)carbamoyl)thiazol-2-yl)amino)-2-methylpyrimidin-4-yl)piperazin-1-yl)-7,23-dioxo-3,10,13,16,19-pentaoxa-6,22-diazaoctacosan-28-yl)carbamoyl)cyclohexyl)-4-(2-(ethyl (3-ethylphenyl)amino)-2-oxoethyl)-4H-thieno[3,2-b] pyrrole-5-carboxamide;

N-(trans-4-((6-(3',6'-dihydroxy-3-oxo-3H-spiro[isobenzofuran-1,9'-xanthene]-5-carboxamido)hexyl)carbamoyl) cyclohexyl)-4-(2-(ethyl(m-tolyl)amino)-2-oxoethyl)-4H-thieno[3,2-b]pyrrole-5-carboxamide;

5-((6-(trans-4-(1-(2-(ethyl(3-ethylphenyl)amino)-2-oxoethyl)-1H-indole-2-carboxamido)cyclohexane-1-carboxamido)hexyl)carbamoyl)-3-oxo-3H-spiro[isobenzofuran-1,9'-xanthene]-3',6'-diyl diacetate;

N-(trans-4-((6-(3',6'-dihydroxy-3-oxo-3H-spiro[isobenzofuran-1,9'-xanthene]-5-carboxamido)hexyl)carbamoyl) cyclohexyl)-1-(2-(ethyl(3-ethylphenyl)amino)-2-oxoethyl)-1H-indole-2-carboxamide;

N-(trans-4-((6-(3',6'-bis(dimethylamino)-3-oxo-3H-spiro [isobenzofuran-1,9'-xanthene]-6-carboxamido)hexyl)carbamoyl)cyclohexyl)-1-(2-(ethyl(3-ethylphenyl)amino)-2-oxoethyl)-1H-indole-2-carboxamide;

N-(trans-4-((6-(3',6'-bis(dimethylamino)-3-oxo-3H-spiro [isobenzofuran-1,9'-xanthene]-6-carboxamido)hexyl)carbamoyl)cyclohexyl)-4-(2-(ethyl(m-tolyl)amino)-2-oxoethyl)-4H-thieno[3,2-b]pyrrole-5-carboxamide;

N-(trans-4-((6-(3-(5,5-difluoro-7,9-dimethyl-5H-5λ4,6λ4-dipyrrolo[1,2-c:2',1'-f][1,3,2]diazaborinin-3-yl)propanamido)hexyl)carbamoyl)cyclohexyl)-1-(2-(ethyl(3-ethylphenyl)amino)-2-oxoethyl)-1H-indole-2-carboxamide;

N-(trans-4-((6-(3-(5,5-difluoro-7,9-dimethyl-5H-5λ4,6λ4-dipyrrolo[1,2-c:2',1'-f][1,3,2]diazaborinin-3-yl)propanamido)hexyl)carbamoyl)cyclohexyl)-4-(2-(ethyl(m-tolyl) amino)-2-oxoethyl)-4H-thieno[3,2-b]pyrrole-5-carboxamide;

N-(trans-4-((6-(3',6'-diamino-3-oxo-3H-spiro[isobenzofuran-1,9'-xanthene]-5,6-carboxamido)hexyl)carbamoyl) cyclohexyl)-1-(2-(ethyl(3-ethylphenyl)amino)-2-oxoethyl)-1H-indole-2-carboxamide;

N-(trans-4-((6-(3',6'-diamino-3-oxo-3H-spiro[isobenzofuran-1,9'-xanthene]-6-carboxamido)hexyl)carbamoyl) cyclohexyl)-4-(2-(ethyl(m-tolyl)amino)-2-oxoethyl)-4H-thieno[3,2-b]pyrrole-5,6-carboxamide;

N-(trans-4-((8-(3',6'-dihydroxy-3-oxo-3H-spiro[isobenzofuran-1,9'-xanthene]-5-carboxamido)octyl)carbamoyl) cyclohexyl)-1-(2-(ethyl(3-ethylphenyl)amino)-2-oxoethyl)-1H-indole-2-carboxamide;

N-(trans-4-((8-(3',6'-dihydroxy-3-oxo-3H-spiro[isobenzofuran-1,9'-xanthene]-5-carboxamido)octyl)carbamoyl) cyclohexyl)-4-(2-(ethyl(m-tolyl)amino)-2-oxoethyl)-4H-thieno[3,2-b]pyrrole-5-carboxamide;

N-(trans-4-((8-(3',6'-diamino-3-oxo-3H-spiro[isobenzofuran-1,9'-xanthene]-5,6-carboxamido)octyl)carbamoyl) cyclohexyl)-1-(2-(ethyl(3-ethylphenyl)amino)-2-oxoethyl)-1H-indole-2-carboxamide;

N-(trans-4-((8-(3',6'-diamino-3-oxo-3H-spiro[isobenzofuran-1,9'-xanthene]-5-carboxamido)octyl)carbamoyl) cyclohexyl)-4-(2-(ethyl(m-tolyl)amino)-2-oxoethyl)-4H-thieno[3,2-b]pyrrole-5,6-carboxamide;

N-(trans-4-((8-(3-(5,5-difluoro-7,9-dimethyl-5H-5λ4,6λ4-dipyrrolo[1,2-c:2',1'-f][1,3,2]diazaborinin-3-yl)propanamido)octyl)carbamoyl)cyclohexyl)-1-(2-(ethyl(3-ethylphenyl)amino)-2-oxoethyl)-1H-indole-2-carboxamide;

N-(trans-4-((8-(3-(5,5-difluoro-7,9-dimethyl-5H-5λ4,6λ4-dipyrrolo[1,2-c:2',1'-f][1,3,2]diazaborinin-3-yl)propanamido)octyl)carbamoyl)cyclohexyl)-4-(2-(ethyl(m-tolyl) amino)-2-oxoethyl)-4H-thieno[3,2-b]pyrrole-5-carboxamide;

N-(trans-4-((1-(3',6'-bis(dimethylamino)-3-oxo-3H-spiro [isobenzofuran-1,9'-xanthen]-6-yl)-1,11-dioxo-5,8-dioxa-2,12-diazaoctadecan-18-yl)carbamoyl)cyclohexyl)-1-(2-(ethyl(3-ethylphenyl)amino)-2-oxoethyl)-1H-indole-2-carboxamide;

N-(trans-4-((1-(3',6'-dihydroxy-3-oxo-3H-spiro[isobenzofuran-1,9'-xanthen]-5,6-yl)-1,11-dioxo-5,8-dioxa-2,12-diazaicosan-20-yl)carbamoyl)cyclohexyl)-1-(2-(ethyl(3-ethylphenyl)amino)-2-oxoethyl)-1H-indole-2-carboxamide;

N-(trans-4-((1-(3',6'-bis(dimethylamino)-3-oxo-3H-spiro [isobenzofuran-1,9'-xanthen]-6-yl)-1,11-dioxo-5,8-dioxa-2,12-diazaicosan-20-yl)carbamoyl)cyclohexyl)-1-(2-(ethyl(3-ethylphenyl)amino)-2-oxoethyl)-1H-indole-2-carboxamide;

N-(trans-4-((8-(6-((Z)-2-((E)-3-(1,1-dimethyl-1,4,5,6-tetrahydro-3λ4-pyrrolo[3,2,1-ij]quinolin-2-yl)allylidene)-1-methyl-1,2,5,6-tetrahydro-4H-pyrrolo[3,2,1-ij]quinolin-1-yl)hexanamido)octyl)carbamoyl)cyclohexyl)-1-(2-(ethyl(3-ethylphenyl)amino)-2-oxoethyl)-1H-indole-2-carboxamide;

N-(trans-4-((8-(4',5'-dichloro-3',6'-dihydroxy-2',7'-dimethoxy-3-oxo-3H-spiro[isobenzofuran-1,9'-xanthene]-5,6-carboxamido)octyl)carbamoyl)cyclohexyl)-1-(2-(ethyl(3-ethylphenyl)amino)-2-oxoethyl)-1H-indole-2-carboxamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(1-(trans-4-(1-(2-(ethyl(3-ethylphenyl)amino)-2-oxoethyl)-1H-indole-2-carboxamido)cyclohexyl)-1,10-dioxo-13,16-dioxa-2,9-diazaoctadecan-18-yl)succinamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(8-(trans-4-(1-(2-(ethyl(3-ethylphenyl)amino)-2-oxoethyl)-1H-indole-2-carboxamido)cyclohexane-1-carboxamido)octyl) succinamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(1-(trans-4-(1-(2-(ethyl(3-ethylphenyl)amino)-2-oxoethyl)-1H-indole-2-carboxamido)cyclohexyl)-1,12-dioxo-15,18-dioxa-2,11-diazaicosan-20-yl)succinamide;

4-(2-(ethyl(m-tolyl)amino)-2-oxoethyl)-N-(trans-4-((8-((7-nitrobenzo[c][1,2,5]oxadiazol-4-yl)oxy)octyl)carbamoyl) cyclohexyl)-4H-thieno[3,2-b]pyrrole-5-carboxamide;

4-(2-(ethyl(m-tolyl)amino)-2-oxoethyl)-N-(trans-4-((6-((7-nitrobenzo[c][1,2,5]oxadiazol-4-yl)oxy)hexyl)carbamoyl)cyclohexyl)-4H-thieno[3,2-b]pyrrole-5-carboxamide;

1-(2-(ethyl(3-ethylphenyl)amino)-2-oxoethyl)-N-(trans-4-((8-((7-nitrobenzo[c][1,2,5]oxadiazol-4-yl)oxy)octyl)carbamoyl)cyclohexyl)-1H-indole-2-carboxamide;

1-(2-(ethyl(3-ethylphenyl)amino)-2-oxoethyl)-N-(trans-4-((6-((7-nitrobenzo[c][1,2,5]oxadiazol-4-yl)oxy)hexyl) carbamoyl)cyclohexyl)-1H-indole-2-carboxamide;

4-(2-(ethyl(m-tolyl)amino)-2-oxoethyl)-N-(trans-4-((R)-3-((3S,4R)-3-hydroxy-4-((4-(4-methylthiazol-5-yl)benzyl) carbamoyl)pyrrolidine-1-carbonyl)-2,2-dimethyl-5,18-dioxo-8,11,14-trioxa-4,17-diazatricosan-23-yl)carbamoyl) cyclohexyl)-4H-thieno[3,2-b]pyrrole-5-carboxamide;

4-(2-(ethyl(m-tolyl)amino)-2-oxoethyl)-N-(trans-4-(((R)-3-((3 S,4R)-3-hydroxy-4-((4-(4-methylthiazol-5-yl)benzyl) carbamoyl)pyrrolidine-1-carbonyl)-2,2-dimethyl-5,21-dioxo-8,11,14,17-tetraoxa-4,20-diazahexacosan-26-yl) carbamoyl)cyclohexyl)-4H-thieno[3,2-b]pyrrole-5-carboxamide;

4-(2-(ethyl(m-tolyl)amino)-2-oxoethyl)-N-(trans-4-(((R)-3-((3 S,4R)-3-hydroxy-4-((4-(4-methylthiazol-5-yl)benzyl) carbamoyl)pyrrolidine-1-carbonyl)-2,2-dimethyl-5,18-dioxo-8,11,14-trioxa-4,17-diazapentacosan-25-yl) carbamoyl)cyclohexyl)-4H-thieno[3,2-b]pyrrole-5-carboxamide; and 4-(2-(ethyl(m-tolyl)amino)-2-oxoethyl)-N-(trans-4-(((R)-3-((3 S,4R)-3-hydroxy-4-((4-(4-methylthiazol-5-yl)benzyl) carbamoyl)pyrrolidine-1-carbonyl)-2,2-dimethyl-5,21-dioxo-8,11,14,17-tetraoxa-4,20-diazaoctacosan-28-yl) carbamoyl)cyclohexyl)-4H-thieno[3,2-b]pyrrole-5-carboxamide, or a salt thereof.

Clause 28. A method of inhibiting an *Oplophorus*-derived luciferase the method comprising contacting the *Oplophorus*-derived luciferase with a compound of any of clauses 1-27.

Clause 29. The method of clause 28, wherein the *Oplophorus*-derived luciferase comprises a polypeptide sequence of SEQ ID NO: 2.

Clause 30. The method of clause 28, wherein the *Oplophorus*-derived luciferase is irreversibly inhibited.

Clause 31. A method for modulating luminescence of an *Oplophorus*-derived luciferase in a sample, the method comprising,
(a) contacting the sample with a coelenterazine substrate and the compound of any of clauses 1-36; and
(b) detecting luminescence in the sample,
wherein the compound of any of clauses 1-27 causes a decrease in the luminescence from the *Oplophorus*-derived luciferase.

Clause 32. A method to detect an interaction between a first protein and a second protein in a sample, the method comprising:
(a) contacting a sample with a coelenterazine substrate and the compound of any one of clauses 1-27, wherein the sample comprises:
 (i) a first polynucleotide encoding a first fusion protein, wherein the first fusion protein comprises a first fragment of an *Oplophorus*-derived luciferase and a first protein; and
 (ii) a second polynucleotide encoding a second fusion protein, wherein the second fusion protein comprises a second fragment of the *Oplophorus*-derived luciferase and a second protein; and
(b) detecting luminescence in the sample,
wherein the detection of luminescence indicates an interaction between the first protein and the second protein.

Clause 33. The method of any of clauses 31-32, comprising contacting the sample with the coelenterazine substrate prior to contacting the sample with the compound of any one of clauses 1-27.

Clause 34. The method of clause 32, wherein when the first protein and second protein interact, the first fragment of the *Oplophorus*-derived luciferase and the second fragment of the *Oplophorus*-derived luciferase reconstitute a full-length enzyme capable of stably binding the coelenterazine substrate.

Clause 35. A method to detect an interaction between a first protein and a second protein in a sample, the method comprising:
(a) contacting a sample with a coelenterazine substrate and the compound of any one of clauses 1-27, wherein the sample comprises:
 (i) a first polynucleotide encoding a first fusion protein, wherein the first fusion protein comprises an *Oplophorus*-derived luciferase and a first protein, wherein the *Oplophorus*-derived luciferase is a bioluminescent donor; and
 (ii) a second polynucleotide encoding a second fusion protein, wherein the second fusion protein comprises a fluorescent acceptor molecule and a second protein;
(b) detecting bioluminescence resonance energy transfer (BRET) in the sample, indicating an interaction or close proximity of the bioluminescent donor and the fluorescence acceptor.

Clause 36. A method to detect protease activity in a sample, the method comprising:
(a) contacting a sample with a coelenterazine substrate and a compound of any one of clauses 1-27, wherein the sample comprises a protease sensitive *Oplophorus*-derived luciferase fusion protein;
(b) measuring luminescence;
(c) activating protease; and
(d) repeating the luminescence measurement;
wherein an increased luminescence in step (d) indicates an increase in protease activity.

Clause 37. A method to detect protease activity in a sample, the method comprising
(a) contacting a sample with a coelenterazine substrate and a compound of any one of clauses 1-27, wherein the sample comprises a protease sensitive *Oplophorus*-derived luciferase fusion protein and an energy acceptor;
(b) measuring the BRET ratio;
(c) activating protease; and
(d) repeating the BRET ratio measurement;
wherein a decreased BRET ratio in step (d) indicates an increase in protease activity.

Clause 38. A method for isolating an *Oplophorus*-derived luciferase fusion protein from a sample, the method comprising:
(a) contacting a sample with a compound of any one of clauses 1-27, the sample comprising an *Oplophorus*-derived luciferase fusion protein;
(b) capturing the *Oplophorus*-derived luciferase fusion protein;
(c) isolating the *Oplophorus*-derived luciferase fusion protein captured in step (b).

Clause 39. The method of any one of clauses 31-38, wherein the sample comprises a cell.

Clause 40. The method of clause 39, wherein the cell comprises the *Oplophorus*-derived luciferase.

Clause 41. The method of clause 39, wherein the cell expresses the *Oplophorus*-derived luciferase.

Clause 42. The method of any one of clauses 31-41, wherein the coelenterazine substrate is a coelenterazine, coelenterazine derivatives, coelenterazine analogs, pro-coelenterazine, or quinone-masked coelenterazine.

Clause 43. A bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a fluorescent acceptor molecule; a coelenterazine substrate, and the compound of any one of clauses 1-27.

Clause 44. A kit comprising:
(a) a compound of any one of clauses 1-27; and
(b) an *Oplophorus*-derived luciferase.

Clause 45. The kit of clause 44, wherein the *Oplophorus*-derived luciferase comprises a polypeptide sequence of SEQ ID NO: 2.

Clause 46. The kit of any of clauses 44-45, further comprising a coelenterazine substrate.

Clause 47. The kit of any of clauses 44-46, further comprising instructions for carrying out a luminescent assay.

Clause 48. A method of inducing protein degradation, the method comprising
contacting a cell with a compound of any one of clauses 1-27, wherein the cell comprising a luciferase fusion protein and at least one protease,
whereby the fusion protein is degraded by the protease.

Clauses 49. A method of labeling a target protein, the method comprising
contacting a target protein with a compound of clause 1, wherein Z is —OR$^4$, R$^4$ is optionally substituted aryl, optionally substituted heteroaryl, or optionally substituted heterocycle,
whereby the target protein forms a covalent bond with R$^4$.

Clause 50. A method to detect an interaction between a molecule of interest and a target protein in a sample, the method comprising:
(a) detecting a first bioluminescence resonance energy transfer (BRET) signal in a sample, the sample comprising:
  (i) a polynucleotide encoding a fusion protein, the fusion protein comprising an *Oplophorus*-derived luciferase and a target protein, wherein the *Oplophorus*-derived luciferase is a bioluminescent donor;
  (ii) a coelenterazine substrate;
  (iii) the compound of any one of clauses 1-27; and
  (iv) a fluorescent tracer comprising a fluorescent acceptor molecule and a ligand that binds to the target protein;
(b) contacting the sample with a molecule of interest; and
(c) detecting a second BRET signal in the sample, wherein a decrease in the second BRET signal compared to the first BRET signal indicates an interaction between the molecule of interest and the target protein.

Clause 51. The method of clause 50, wherein the target protein comprises a kinase, a histone deacetylase, or a bromodomain-containing protein.

Clause 52. A bioluminescence resonance energy transfer (BRET) system comprising: a fusion protein including a target protein and a bioluminescence donor molecule, wherein the bioluminescence donor molecule is an *Oplophorus*-derived luciferase; a fluorescent tracer comprising a fluorescent acceptor molecule and a ligand that binds to the target protein; a coelenterazine substrate, and the compound of any one of clauses 1-27.

Clause 53. A method to detect an interaction between a first target protein and a second target protein in a sample, the method comprising:
(a) contacting a sample with a coelenterazine substrate, the compound of any one of clauses 1-27, and a HALOTAG® ligand, wherein the HALOTAG® ligand comprises a fluorescent acceptor molecule, wherein the sample comprises:
  (i) a first polynucleotide encoding a first fusion protein, wherein the first fusion protein comprises an *Oplophorus*-derived luciferase and a first target protein, wherein the *Oplophorus*-derived luciferase is a bioluminescent donor; and
  (ii) a second polynucleotide encoding a second fusion protein, wherein the second fusion protein comprises a HALOTAG® protein and a second target protein;
(b) detecting bioluminescence resonance energy transfer (BRET) in the sample thereby detecting an interaction or indicating a close proximity of the first target protein and the second target protein.

Clause 54. A bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a HALOTAG® protein; a HALOTAG® ligand comprising a fluorescent acceptor molecule; a coelenterazine substrate, and the compound of any one of clauses 1-27.

APPENDIX

SEQ ID NO: 1 - Native Mature *Oplophorus* luciferase amino acid sequence
FTLADFVGDWQQTAGYNQDQVLEQGGLSSLFQALGVSVTPIQKVVLSGEN
GLKADIHVIIPYEGLSGFQMGLIEMIFKVVYPVDDHHFKIILHYGTLVID
GVTPNMIDYFGRPYPGIAVFDGKQITVTGTLWNGNKIYDERLINPDGSLL
FR- VTIN GVTGWRLCENILA SEQ ID NO: 2 - Nluc amino acid sequence
MVFTLEDFVGDWRQTAGYNLDQVLEQGGVSSLFQNLGVSVTPIQRIVLSG
ENGLKIDIHVIIPYEGLSGDQMGQIEKIFKVVYPVDDHHFKVILHYGTLV
IDGVTPNMIDYFGRPYEGIAVFDGKKITVTGTLWNGNKIIDERLINPDGS
LLFRVTINGVTGWRLCERILA

The invention claimed is:

1. A compound of formula (I), or a salt thereof:

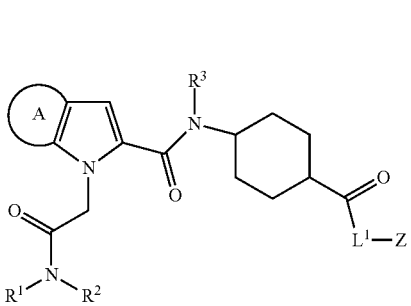

(I)

wherein:

A is absent, an optionally substituted phenyl ring, or an optionally substituted thienyl ring, $L^1$ is —$(CR^{a1}R^{a2})_{m1}$—, wherein m is 1 to 100, optionally wherein one or more $CR^{a1}R^{a2}$ groups are replaced by a heteroatom or heteroatom group selected from the group consisting of O, $N(R^{a3})$, $S(=O)$, and $S(=O)_2$, optionally wherein one or more $CR^{a1}R^{a2}$ groups are replaced by $C(=O)$, optionally wherein two adjacent $CR^{a1}R^{a2}$ groups form $CR^{a1}=CR^{a1}$, and optionally wherein one or more $CR^{a1}R^{a2}$ groups are replaced by a -Cy- group, wherein each Cy is independently selected from the group consisting of aryl, heteroaryl, cycloalkyl, cycloalkenyl, and heterocycle; wherein $R^{a1}$, $R^{a2}$, and $R^{a3}$ are independently selected from the group consisting of hydrogen and $C_1$-$C_4$-alkyl;

Z is $C_1$-$C_{10}$ haloalkyl, a leaving group Y, a bioactive agent, or a dye, wherein the leaving group Y is selected from the group consisting of $OR^4$, halogen, heteroaryl, and heterocyclyl;

$R^1$ is hydrogen or $C_1$-$C_8$ alkyl;

$R^2$ is selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;

$R^3$ is hydrogen or $C_1$-$C_8$ alkyl; and $R^4$ is selected from the group consisting of optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl.

2. The compound of claim 1, or a salt thereof, wherein A is an optionally substituted phenyl ring.

3. The compound of claim 1, or a salt thereof, wherein A is an optionally substituted thienyl ring.

4. The compound of claim 1, or a salt thereof, wherein $R^1$ is selected from the group consisting of hydrogen, $C_1$-$C_8$ alkyl, halo-$C_1$-$C_8$-alkyl, alkoxyalkoxyalkyl and arylalkyl.

5. The compound of claim 1, or a salt thereof, wherein $R^2$ is optionally substituted aryl.

6. The compound of claim 1, or a salt thereof, wherein $R^2$ is phenyl substituted with at least one substituent selected from the group consisting of $C_1$-$C_4$ alkyl, cyano, amido, $C_1$-$C_4$ alkoxy, $C_1$-$C_4$ haloalkyl, and hydroxyalkyl.

7. The compound of claim 1, or a salt thereof, wherein $R^3$ is hydrogen.

8. The compound of claim 1, or a salt thereof, wherein the compound has formula (Ia):

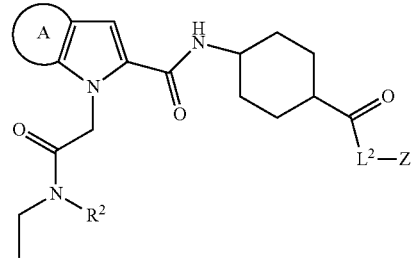

(Ia)

wherein:

A is absent, a phenyl ring, or a thienyl ring;

$R^2$ is phenyl substituted with at least one $C_1$-$C_4$ alkyl or $C_1$-$C_4$ haloalkyl; and $L^2$ is —$(CR^{a1}R^{a2})_{m2}$—, wherein m2 is 1 to 90, and wherein each $CR^{a1}R^{a2}$ is as defined in claim 1.

9. The compound of claim 1, or a salt thereof, wherein the compound has formula (Ib):

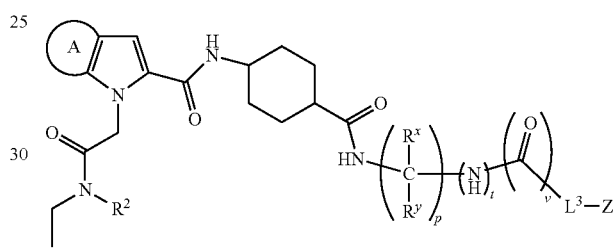

(Ib)

wherein:

A is absent, a phenyl ring, or a thienyl ring;

$R^2$ is phenyl substituted with at least one $C_1$-$C_4$ alkyl or $C_1$-$C_4$ haloalkyl;

$R^x$ and $R^y$ at each occurrence is independently hydrogen or $C_1$-$C_4$ alkyl;

p is 4, 5, 6, 7, 8, 9, or 10;

t is 0 or 1;

v is 0 or 1; and $L^3$ is absent or —$(CR^{a1}R^{a2})_{m3}$—, wherein m3 is 1 to 80, and wherein each $CR^{a1}R^{a2}$ is as defined in claim 1.

10. The compound of claim 9, or a salt thereof, wherein $L^3$ is —$(CR^{a1}R^{a2})_{m3}$—, wherein m3 is 1-20, and $R^{a1}$ and $R^{a2}$, at each occurrence are independently hydrogen or $C_1$-$C_4$ alkyl.

11. The compound of claim 9, or a salt thereof, wherein $L^3$ is -$Q^1$-$(CH_2$—$CH_2$—$O)_{k1}$-$Q^2$-$(CH_2$—$CH_2$—$O)_{k2}$-$Q^3$-$(CH_2$—$CH_2$—$O)_{k3}$—, wherein:

$Q^1$ is absent, O, or NH;

$Q^2$ is absent,

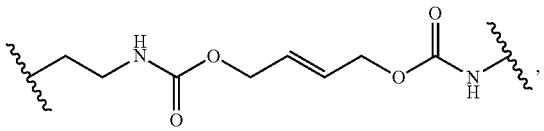 [SMILES: *CCNC(=O)OC/C=C/COC(=O)N*]

—CO—NH—, —$CH_2$—$CH_2$—CO—, —$CH_2$—$CH_2$—NH—CO, or —$CH_2$—$CH_2$—CO—NH—

$Q^3$ is absent, —CO—NH—, or —$CH_2$—$CH_2$—;

k1 is 1-10;

k2 is 0-10; and k3 is 0-10.

12. The compound of claim 9, or a salt thereof, wherein $L^3$ is selected from the group consisting of:
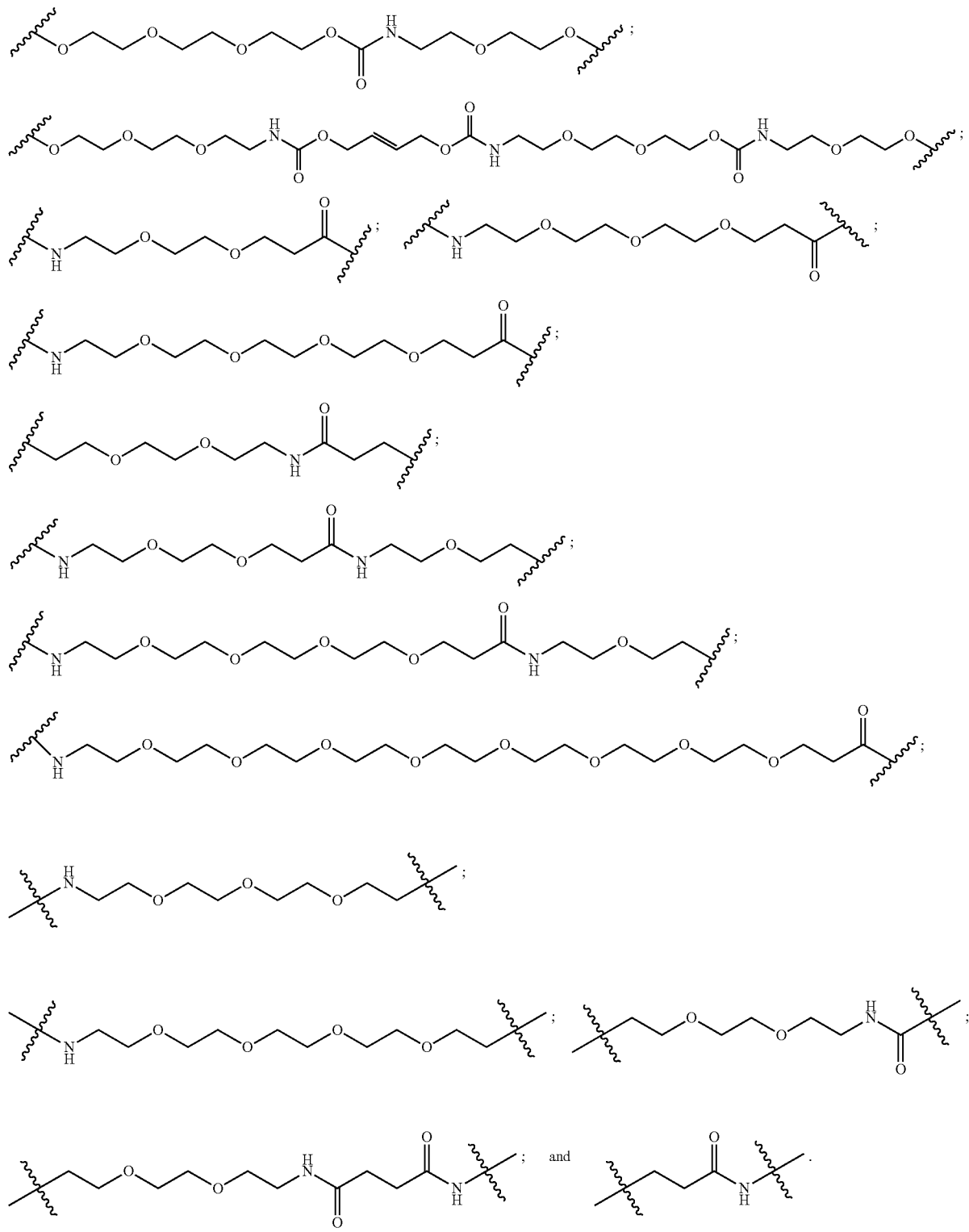

13. The compound of claim 1, or a salt thereof, wherein Z is $C_1$-$C_{10}$ haloalkyl.

14. The compound of claim 13, or a salt thereof, wherein the compound has formula (Ic):

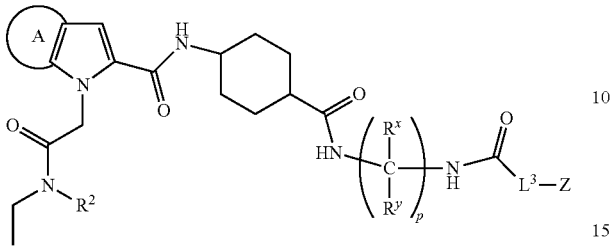

(Ic)

wherein:
A is a phenyl ring or thienyl ring;
$R^2$ is phenyl substituted with one methyl or ethyl group;
$R^x$ and $R^y$ at each occurrence is independently hydrogen or $C_1$-$C_4$ alkyl;
p is 4, 5, 6, 7, 8, 9, or 10; and
$L^3$ is

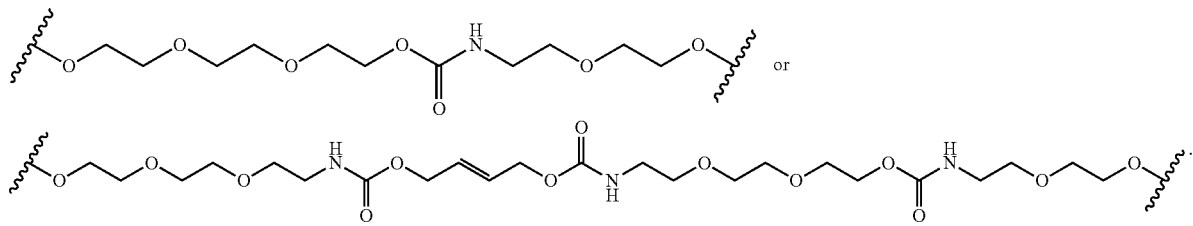

15. The compound of claim 13, or a salt thereof, wherein Z is —$(CH_2)_6$—Cl.

16. The compound of claim 1, or a salt thereof, wherein Z is a leaving group Y selected from the group consisting of $OR^4$, halogen, heteroaryl, and heterocyclyl.

17. The compound of claim 16, or a salt thereof, wherein the compound has formula (Id):

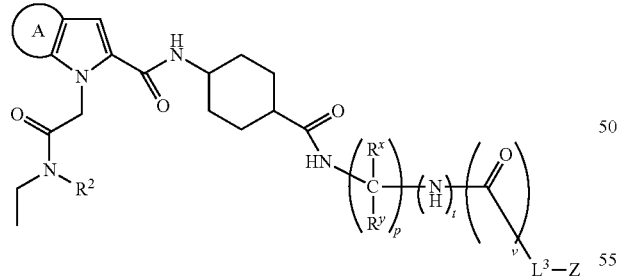

(Id)

wherein:
A is a phenyl ring or a thienyl ring,
$R^2$ is phenyl substituted with one substituent selected from the group consisting of methyl, ethyl, —$CH_2Br$, and —$CH_2CH_2CH_2Br$;
$R^x$ and $R^y$ at each occurrence is independently hydrogen or $C_1$-$C_4$ alkyl;
p is 4, 5, 6, 7, 8, 9, or 10;
t is 0 or 1;
v is 0 or 1; and
$L^3$ is absent, $C_1$-$C_4$ alkylene, 221
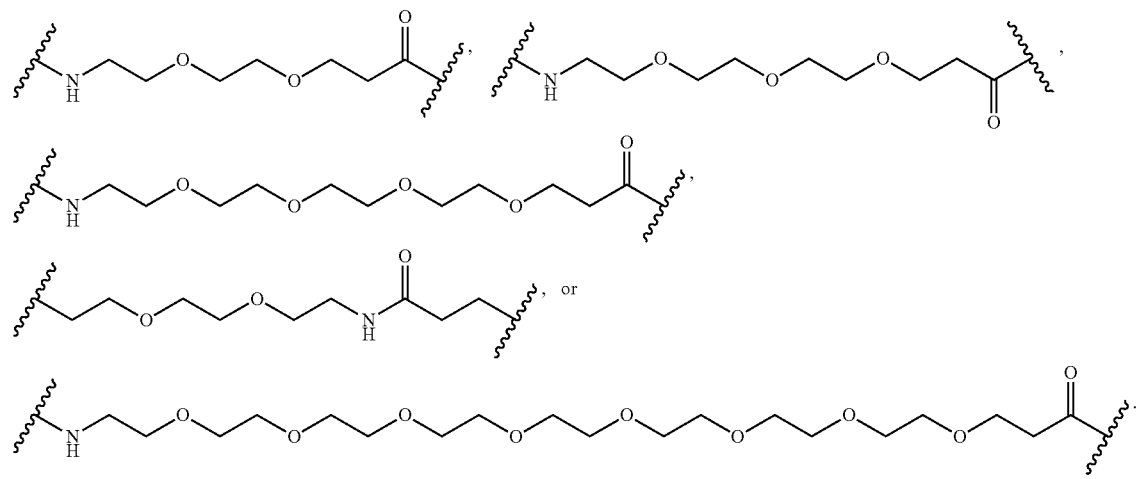
18. The compound of claim 17, or a salt thereof, wherein Z is chloro, bromo, iodo, $C_1$-$C_4$ alkoxy, phenoxy,
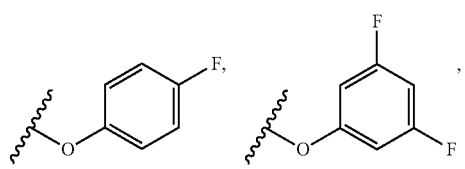
222
-continued
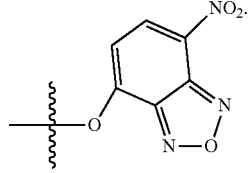
19. The compound of claim 17, or a salt thereof, wherein $L^3$ is absent,
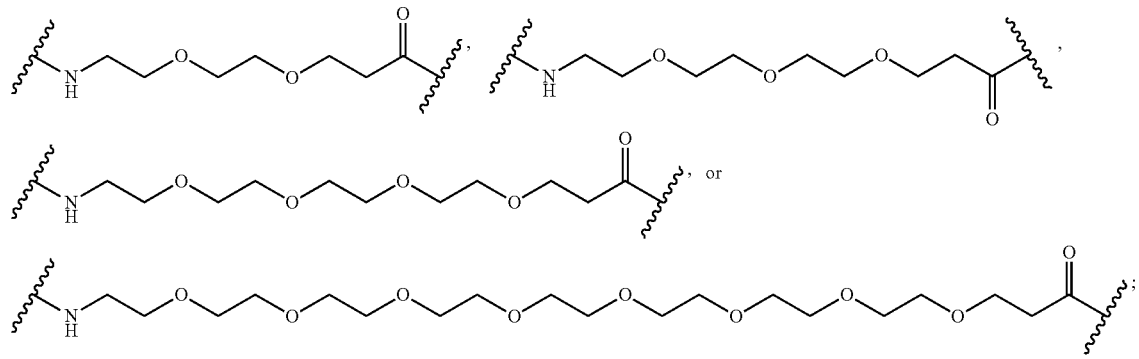
-continued
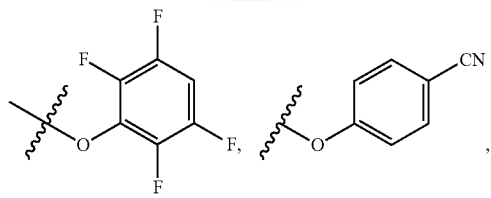
and
Z is $C_1$-$C_4$ alkoxy, phenoxy,
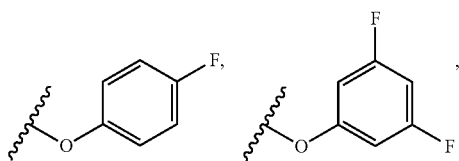
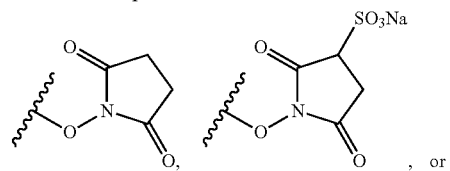

-continued

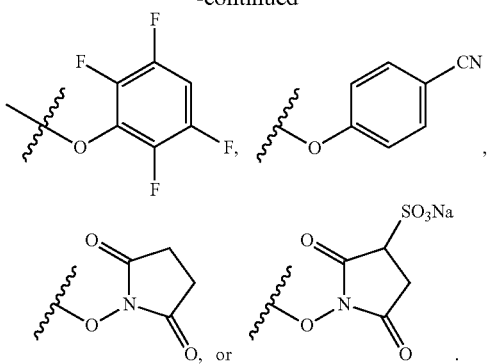

20. The compound of claim 17, or a salt thereof, wherein L³ is —CH₂—CH₂—, or

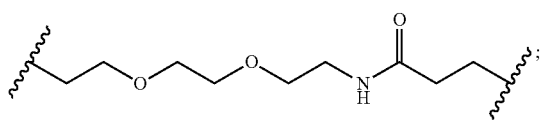 [SMILES: *CCOCCOCCNC(=O)CC*]

and Z is

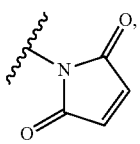 [SMILES: *N1C(=O)C=CC1=O]

or

L³ is C₁-C₄ alkylene; and Z is chloro, bromo, or iodo.

21. The compound of claim 17, or a salt thereof wherein,
t is 0;
v is 0;
L³ is absent; and
Z is bromo, iodo, or

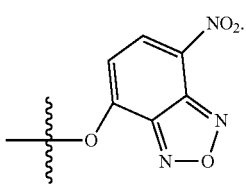 [SMILES: *Oc1ccc([N+](=O)[O-])c2nonc12]

22. The compound of claim 1, or a salt thereof, wherein Z is a bioactive agent selected from the group consisting of an enzyme inhibitor, a receptor inhibitor, and a moiety which induces protein degradation.

23. The compound of claim 22, or a salt thereof, wherein Z is a kinase inhibitor.

24. The compound of claim 22, or a salt thereof, wherein the compound has formula (Ie):

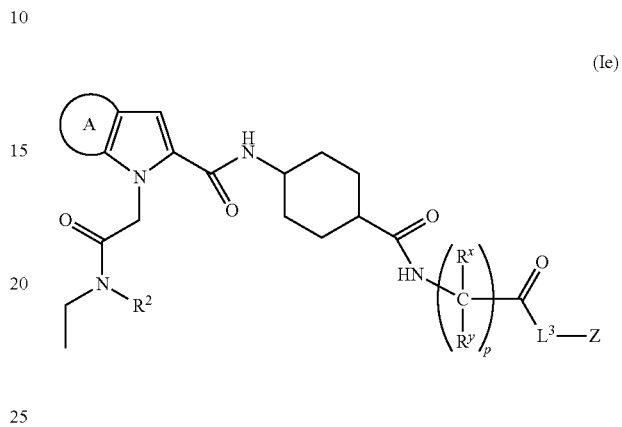

(Ie)

wherein:
A is absent, a phenyl ring or a thienyl ring,
R² is phenyl substituted with one methyl or ethyl group;
Rˣ and Rʸ at each occurrence is independently hydrogen or C₁-C₄ alkyl;
p is 4, 5, 6, 7, 8, 9, or 10;
L³ is

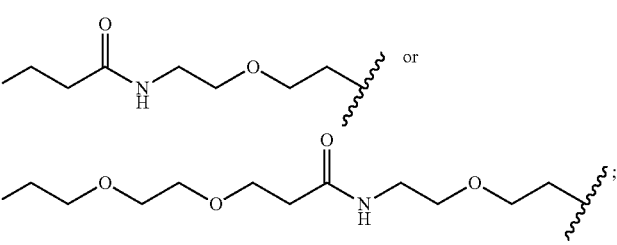

and
Z is

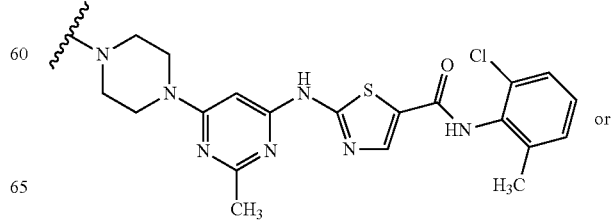

225

-continued

L³ is

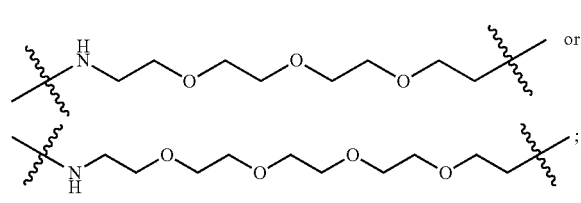

and

Z is

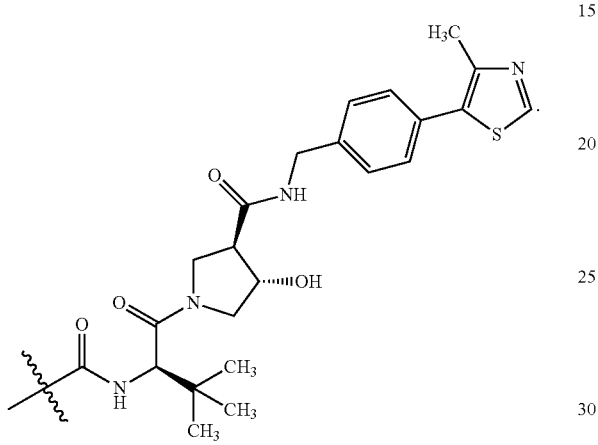

25. The compound of claim 1, or a salt thereof, wherein Z is a dye.

26. The compound of claim 25, or a salt thereof, wherein the compound has formula (If'):

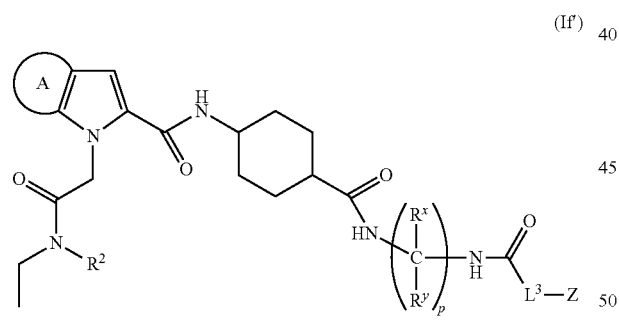

(If')

wherein:
A is a phenyl ring or thienyl ring;
R² is phenyl substituted with one methyl or ethyl group;
$R^x$ and $R^y$ at each occurrence is independently hydrogen or $C_1$-$C_4$ alkyl;
p is 4, 5, 6, 7, 8, 9, or 10;
L³ is absent,

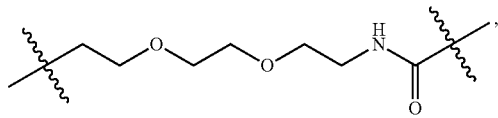

226

-continued

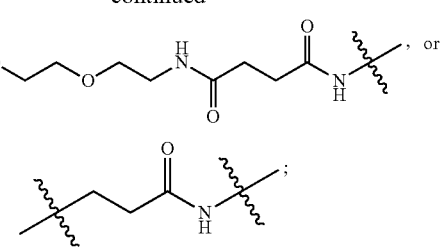

and

Z is

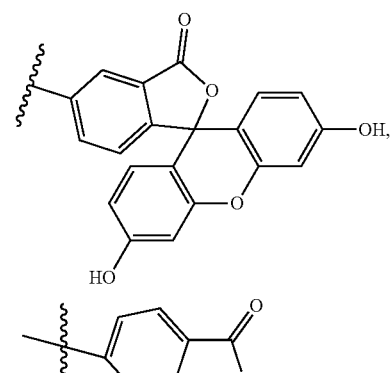

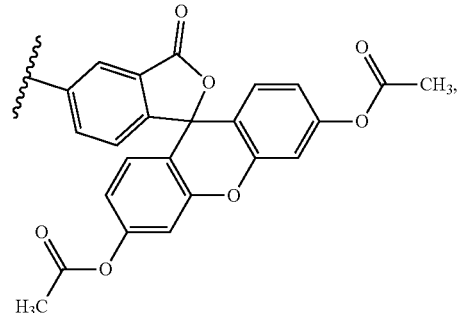

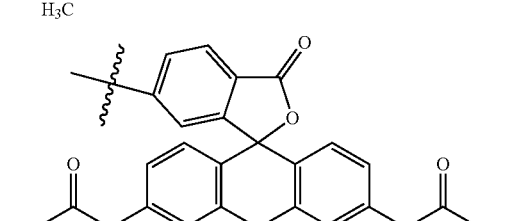

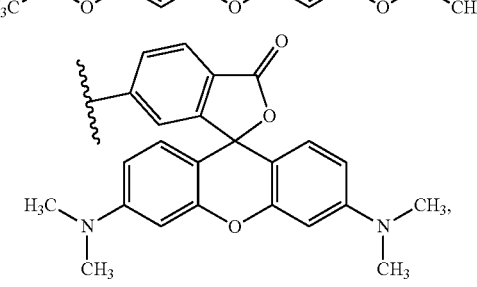

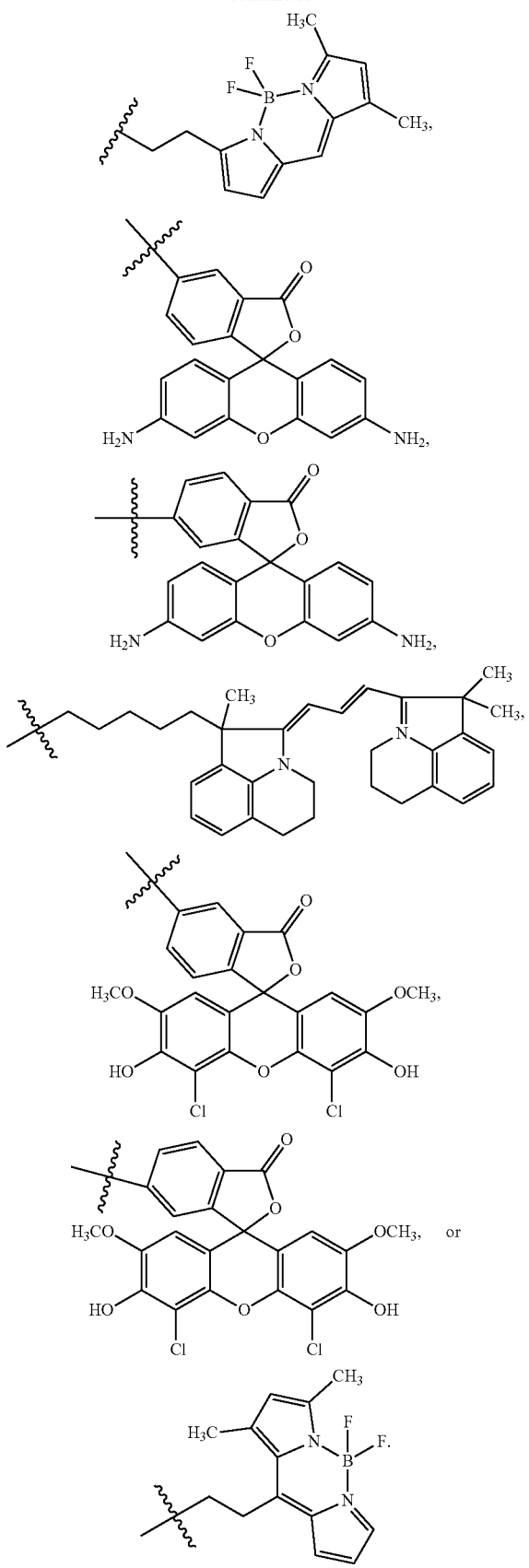

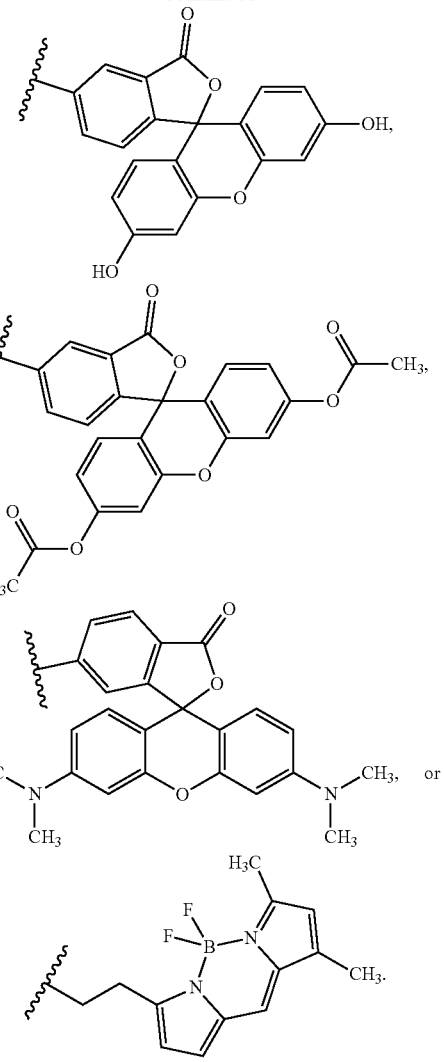

27. The compound of claim 1, wherein the compound is selected from the group consisting of:

1-(trans-4-(4-(2-(ethyl(m-tolyl)amino)-2-oxoethyl)-4H-thieno[3,2-b]pyrrole-5-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

[(E)-30-chloro-6,17-dioxo-5,10,13,16,21,24-hexaoxa-7,18-diazatriacont-2-en-1-yl (1-(trans-4-(4-(2-(ethyl(3-ethylphenyl)amino)-2-oxoethyl)-4H-thieno[3,2-b]pyrrole-5-carboxamido)cyclohexyl)-1,10-dioxo-11,14,17-trioxa-2,9-diazanonadecan-19-yl)carbamate;

[(E)-30-chloro-6,17-dioxo-5,10,13,16,21,24-hexaoxa-7,18-diazatriacont-2-en-1-yl (1-(trans-4-(1-(2-(ethyl(3-ethylphenyl)amino)-2-oxoethyl)-1H-indole-2-carboxamido)cyclohexyl)-1,10-dioxo-11,14,17-trioxa-2,9-diazanonadecan-19-yl)carbamate;

1-(trans-4-(4-(2-(ethyl(3-ethylphenyl)amino)-2-oxoethyl)-4H-thieno[3,2-b]pyrrole-5-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

1-(trans-4-(1-(2-(ethyl(3-ethylphenyl)amino)-2-oxoethyl)-1H-indole-2-carboxamido)cyclohexyl)-1,10-dioxo-11,14,17-trioxa-2,9-diazanonadecan-19-yl (2-(2-((6-chlorohexyl)oxy)ethoxy)ethyl)carbamate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15-dioxa-2,9-diazaoctadecan-18-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18-trioxa-2,9-diazahenicosan-21-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21-tetraoxa-2,9-diazatetracosan-24-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17-dioxa-2,11-diazaicosan-20-oate;

2,5-dioxopyrrolidin-1-yl 1-((1r,4r)-4-(4-(2-(ethyl(m-tolyl)amino)-2-oxoethyl)-4H-thieno[3,2-b]pyrrole-5-carboxamido)cyclohexyl)-1,10-dioxo-14,17,20-trioxa-2,11-diazatricosan-23-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,10-dioxo-14,17,20,23-tetraoxa-2,11-diazahexacosan-26-oate;

2,5-dioxopyrrolidin-1-yl 1-(trans-4-(4-(2-(ethyl(m-tolyl)amino)-2-oxoethyl)-4H-thieno[3,2-b]pyrrole-5-carboxamido)cyclohexyl)-1,8-dioxo-12,15,18,21,24,27,30,33-octaoxa-2,9-diazahexatriacontan-36-oate;

N-(trans-4-((6-(3-(2,5-dioxo-2,5-dihydro-1H-pyrrol-1-yl)propanamido)hexyl)carbamoyl)cyclohexyl)-4-(2-(ethyl(m-tolyl)amino)-2-oxoethyl)-4H-thieno[3,2-b]pyrrole-5-carboxamide;

N-(trans-4-((1-(2,5-dioxo-2,5-dihydro-1H-pyrrol-1-yl)-3,13-dioxo-7,10-dioxa-4,14-diazaicosan-20-yl)carbamoyl)cyclohexyl)-4-(2-(ethyl(m-tolyl)amino)-2-oxoethyl)-4H-thieno[3,2-b]pyrrole-5-carboxamide;

2,5-dioxopyrrolidin-1-yl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

methyl 8-(trans-4-(1-(2-(ethyl(3-ethylphenyl)amino)-2-oxoethyl)-1H-indole-2-carboxamido)cyclohexane-1-carboxamido)octanoate;

methyl 6-(trans-4-(1-(2-(ethyl(3-ethylphenyl)amino)-2-oxoethyl)-14H-indole-2-carboxamido)cyclohexane-1-carboxamido)hexanoate;

2,5-dioxopyrrolidin-1-yl 8-(trans-4-(1-(2-(ethyl(3-ethylphenyl)amino)-2-oxoethyl)-1H-indole-2-carboxamido)cyclohexane-1-carboxamido)octanoate;

2,5-dioxopyrrolidin-1-yl 6-(trans-4-(1-(2-(ethyl(3-ethylphenyl)amino)-2-oxoethyl)-1H-indole-2-carboxamido)cyclohexane-1-carboxamido)hexanoate;

phenyl 8-(trans-4-(1-(2-(ethyl(3-ethylphenyl)amino)-2-oxoethyl)-1H-indole-2-carboxamido)cyclohexane-1-carboxamido)octanoate;

phenyl 6-(trans-4-(1-(2-(ethyl(3-ethylphenyl)amino)-2-oxoethyl)-1H-indole-2-carboxamido)cyclohexane-1-carboxamido)hexanoate;

1-(2-(ethyl(3-ethylphenyl)amino)-2-oxoethyl)-N-(trans-4-((6-iodohexyl)carbamoyl)cyclohexyl)-1H-indole-2-carboxamide;

N-(trans-4-((6-bromohexyl)carbamoyl)cyclohexyl)-1-(2-(ethyl(3-ethylphenyl)amino)-2-oxoethyl)-1H-indole-2-carboxamide;

1-(2-(ethyl(3-ethylphenyl)amino)-2-oxoethyl)-N-(trans-4-((8-iodooctyl)carbamoyl)cyclohexyl)-1H-indole-2-carboxamide;

4-fluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

3,5-difluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

4-cyanophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

sodium 1-((8-(trans-4-(4-(2-(ethyl(m-tolyl)amino)-2-oxoethyl)-4H-thieno[3,2-b]pyrrole-5-carboxamido)cyclohexane-1-carboxamido)octanoyl)oxy)-2,5-dioxopyrrolidine-3-sulfonate;

N-(trans-4-((5-(2-chloroacetamido)pentyl)carbamoyl)cyclohexyl)-4-(2-(ethyl(m-tolyl)amino)-2-oxoethyl)-4H-thieno[3,2-b]pyrrole-5-carboxamide;

N-(trans-4-((6-(2-chloroacetamido)hexyl)carbamoyl)cyclohexyl)-4-(2-(ethyl(m-tolyl)amino)-2-oxoethyl)-4H-thieno[3,2-b]pyrrole-5-carboxamide;

2,3,5,6-tetrafluorophenyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate;

N-(trans-4-((5-(2-bromoacetamido)pentyl)carbamoyl)cyclohexyl)-4-(2-(ethyl(m-tolyl)amino)-2-oxoethyl)-4H-thieno[3,2-b]pyrrole-5-carboxamide;

N-(trans-4-((1-(4-(6-((5-((2-chloro-6-methylphenyl)carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl(m-tolyl)amino)-2-oxoethyl)-4H-thieno[3,2-b]pyrrole-5-carboxamide;

N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,18-trioxo-12,15,22-trioxa-2,9,19-triazatetracosan-24-yl)piperazin-1-yl)-2-methylpyrimidin-4-yl)amino)thiazole-5-carboxamide;

N-(trans-4-((1-(4-(6-((5-((2-chloro-6-methylphenyl)carbamoyl)thiazol-2-yl)amino)-2-methylpyrimidin-4-yl)piperazin-1-yl)-7,17-dioxo-3,10,13-trioxa-6,16-diazadocosan-22-yl)carbamoyl)cyclohexyl)-4-(2-(ethyl(3-ethylphenyl)amino)-2-oxoethyl)-4H-thieno[3,2-b]pyrrole-5-carboxamide;

N-(2-chloro-6-methylphenyl)-2-((6-(4-(1-(trans-4-(1-(2-(ethyl(m-tolyl)amino)-2-oxoethyl)-1H-pyrrole-2-carboxamido)cyclohexyl)-1,8,24-trioxo-12,15,18,21,28-pentaoxa-2,9,25-triazatriacontan-30-yl)piperazin-1-yl)-2-methylpyrimidin-4-yl)amino)thiazole-5-carboxamide;

N-(trans-4-((1-(4-(6-((5-((2-chloro-6-methylphenyl)carbamoyl)thiazol-2-yl)amino)-2-methylpyrimidin-4-yl)piperazin-1-yl)-7,23-dioxo-3,10,13,16,19-pentaoxa-6,22-diazaoctacosan-28-yl)carbamoyl)cyclohexyl)-4-(2-(ethyl(3-ethylphenyl)amino)-2-oxoethyl)-4H-thieno[3,2-b]pyrrole-5-carboxamide;

N-(trans-4-((6-(3',6'-dihydroxy-3-oxo-3H-spiro[isobenzofuran-1,9'-xanthene]-5-carboxamido)hexyl)carbamoyl)cyclohexyl)-4-(2-(ethyl(m-tolyl)amino)-2-oxoethyl)-4H-thieno[3,2-b]pyrrole-5-carboxamide;

5-((6-(trans-4-(1-(2-(ethyl(3-ethylphenyl)amino)-2-oxoethyl)-1H-indole-2-carboxamido)cyclohexane-1-carboxamido)hexyl)carbamoyl)-3-oxo-3H-spiro[isobenzofuran-1,9'-xanthene]-3',6'-diyl diacetate;

N-(trans-4-((6-(3',6'-dihydroxy-3-oxo-3H-spiro[isobenzofuran-1,9'-xanthene]-5-carboxamido)hexyl)carbamoyl)cyclohexyl)-1-(2-(ethyl(3-ethylphenyl)amino)-2-oxoethyl)-1H-indole-2-carboxamide;

N-(trans-4-((6-(3',6'-bis(dimethylamino)-3-oxo-3H-spiro[isobenzofuran-1,9'-xanthene]-6-carboxamido)hexyl)carbamoyl)cyclohexyl)-1-(2-(ethyl(3-ethylphenyl)amino)-2-oxoethyl)-1H-indole-2-carboxamide;

N-(trans-4-((6-(3',6'-bis(dimethylamino)-3-oxo-3H-spiro[isobenzofuran-1,9'-xanthene]-6-carboxamido)hexyl)carbamoyl)cyclohexyl)-4-(2-(ethyl(m-tolyl)amino)-2-oxoethyl)-4H-thieno[3,2-b]pyrrole-5-carboxamide;

N-(trans-4-((6-(3-(5,5-difluoro-7,9-dimethyl-5H-5I4,6I4-dipyrrolo[1,2-c:2',1'-f][1,3,2]diazaborinin-3-yl)propanamido)hexyl)carbamoyl)cyclohexyl)-1-(2-(ethyl(3-ethylphenyl)amino)-2-oxoethyl)-1H-indole-2-carboxamide;

N-(trans-4-((6-(3-(5,5-difluoro-7,9-dimethyl-5H-5I4,6I4-dipyrrolo[1,2-c:2',1'-f][1,3,2]diazaborinin-3-yl)propanamido)hexyl)carbamoyl)cyclohexyl)-4-(2-(ethyl(m-tolyl)amino)-2-oxoethyl)-4H-thieno[3,2-b]pyrrole-5-carboxamide;

N-(trans-4-((6-(3',6'-diamino-3-oxo-3H-spiro[isobenzofuran-1,9'-xanthene]-5,6-carboxamido)hexyl)carbamoyl)cyclohexyl)-1-(2-(ethyl(3-ethylphenyl)amino)-2-oxoethyl)-1H-indole-2-carboxamide;

N-(trans-4-((6-(3',6'-diamino-3-oxo-3H-spiro[isobenzofuran-1,9'-xanthene]-6-carboxamido)hexyl)carbamoyl)cyclohexyl)-4-(2-(ethyl(m-tolyl)amino)-2-oxoethyl)-4H-thieno[3,2-b]pyrrole-5,6-carboxamide;

N-(trans-4-((8-(3',6'-dihydroxy-3-oxo-3H-spiro[isobenzofuran-1,9'-xanthene]-5-carboxamido)octyl)carbamoyl)cyclohexyl)-1-(2-(ethyl(3-ethylphenyl)amino)-2-oxoethyl)-1H-indole-2-carboxamide;

N-(trans-4-((8-(3',6'-dihydroxy-3-oxo-3H-spiro[isobenzofuran-1,9'-xanthene]-5-carboxamido)octyl)carbamoyl)cyclohexyl)-4-(2-(ethyl(m-tolyl)amino)-2-oxoethyl)-4H-thieno[3,2-b]pyrrole-5-carboxamide;

N-(trans-4-((8-(3',6'-diamino-3-oxo-3H-spiro[isobenzofuran-1,9'-xanthene]-5,6-carboxamido)octyl)carbamoyl)cyclohexyl)-1-(2-(ethyl(3-ethylphenyl)amino)-2-oxoethyl)-1H-indole-2-carboxamide;

N-(trans-4-((8-(3',6'-diamino-3-oxo-3H-spiro[isobenzofuran-1,9'-xanthene]-5-carboxamido)octyl)carbamoyl)cyclohexyl)-4-(2-(ethyl(m-tolyl)amino)-2-oxoethyl)-4H-thieno[3,2-b]pyrrole-5,6-carboxamide;

N-(trans-4-((8-(3-(5,5-difluoro-7,9-dimethyl-5H-5λ,6λ4-dipyrrolo[1,2-c:2',1'-f][1,3,2]diazaborinin-3-yl)propanamido)octyl)carbamoyl)cyclohexyl)-1-(2-(ethyl(3-ethylphenyl)amino)-2-oxoethyl)-1H-indole-2-carboxamide;

N-(trans-4-((8-(3-(5,5-difluoro-7,9-dimethyl-5H-5λ4,6λ4-dipyrrolo[1,2-c:2',1'-f][1,3,2]diazaborinin-3-yl)propanamido)octyl)carbamoyl)cyclohexyl)-4-(2-(ethyl(m-tolyl)amino)-2-oxoethyl)-4H-thieno[3,2-b]pyrrole-5-carboxamide;

N-(trans-4-((1-(3',6'-bis(dimethylamino)-3-oxo-3H-spiro[isobenzofuran-1,9'-xanthen]-6-yl)-1,11-dioxo-5,8-dioxa-2,12-diazaoctadecan-18-yl)carbamoyl)cyclohexyl)-1-(2-(ethyl(3-ethylphenyl)amino)-2-oxoethyl)-1H-indole-2-carboxamide;

N-(trans-4-((1-(3',6'-dihydroxy-3-oxo-3H-spiro[isobenzofuran-1,9'-xanthen]-5,6-yl)-1,11-dioxo-5,8-dioxa-2,12-diazaicosan-20-yl)carbamoyl)cyclohexyl)-1-(2-(ethyl(3-ethylphenyl)amino)-2-oxoethyl)-1H-indole-2-carboxamide;

N-(trans-4-((1-(3',6'-bis(dimethylamino)-3-oxo-3H-spiro[isobenzofuran-1,9'-xanthen]-6-yl)-1,11-dioxo-5,8-dioxa-2,12-diazaicosan-20-yl)carbamoyl)cyclohexyl)-1-(2-(ethyl(3-ethylphenyl)amino)-2-oxoethyl)-1H-indole-2-carboxamide;

N-(trans-4-((8-(6-((Z)-2-((E)-3-(1,1-dimethyl-1,4,5,6-tetrahydro-3λ4-pyrrolo[3,2,1-ij]quinolin-2-yl)allylidene)-1-methyl-1,2,5,6-tetrahydro-4H-pyrrolo[3,2,1-ij]quinolin-1-yl)hexanamido)octyl)carbamoyl)cyclohexyl)-1-(2-(ethyl(3-ethylphenyl)amino)-2-oxoethyl)-1H-indole-2-carboxamide;

N-(trans-4-((8-(4',5'-dichloro-3',6'-dihydroxy-2',7'-dimethoxy-3-oxo-3H-spiro[isobenzofuran-1,9'-xanthene]-5,6-carboxamido)octyl)carbamoyl)cyclohexyl)-1-(2-(ethyl(3-ethylphenyl)amino)-2-oxoethyl)-1H-indole-2-carboxamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(1-(trans-4-(1-(2-(ethyl(3-ethylphenyl)amino)-2-oxoethyl)-1H-indole-2-carboxamido)cyclohexyl)-1,10-dioxo-13,16-dioxa-2,9-diazaoctadecan-18-yl)succinamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(8-(trans-4-(1-(2-(ethyl(3-ethylphenyl)amino)-2-oxoethyl)-1H-indole-2-carboxamido)cyclohexane-1-carboxamido)octyl)succinamide;

N1-(2-(5,5-difluoro-1,3-dimethyl-5H-5λ4,6λ4-dipyrrolo[1,2-c:2',1'-f][1,3,2]diazaborinin-10-yl)ethyl)-N4-(1-(trans-4-(1-(2-(ethyl(3-ethylphenyl)amino)-2-oxoethyl)-1H-indole-2-carboxamido)cyclohexyl)-1,12-dioxo-15,18-dioxa-2,11-diazaicosan-20-yl)succinamide;

4-(2-(ethyl(m-tolyl)amino)-2-oxoethyl)-N-(trans-4-((8-((7-nitrobenzo[c][1,2,5]oxadiazol-4-yl)oxy)octyl)carbamoyl)cyclohexyl)-4H-thieno[3,2-b]pyrrole-5-carboxamide;

4-(2-(ethyl(m-tolyl)amino)-2-oxoethyl)-N-(trans-4-((6-((7-nitrobenzo[c][1,2,5]oxadiazol-4-yl)oxy)hexyl)carbamoyl)cyclohexyl)-4H-thieno[3,2-b]pyrrole-5-carboxamide;

1-(2-(ethyl(3-ethylphenyl)amino)-2-oxoethyl)-N-(trans-4-((8-((7-nitrobenzo[c][1,2,5]oxadiazol-4-yl)oxy)octyl)carbamoyl)cyclohexyl)-1H-indole-2-carboxamide;

1-(2-(ethyl(3-ethylphenyl)amino)-2-oxoethyl)-N-(trans-4-((6-((7-nitrobenzo[c][1,2,5]oxadiazol-4-yl)oxy)hexyl)carbamoyl)cyclohexyl)-1H-indole-2-carboxamide;

4-(2-(ethyl(m-tolyl)amino)-2-oxoethyl)-N-(trans-4-(((R)-3-((3S,4R)-3-hydroxy-4-((4-(4-methylthiazol-5-yl)benzyl)carbamoyl)pyrrolidine-1-carbonyl)-2,2-dimethyl-5,18-dioxo-8,11,14-trioxa-4,17-diazatricosan-23-yl)carbamoyl)cyclohexyl)-4H-thieno[3,2-b]pyrrole-5-carboxamide;

4-(2-(ethyl(m-tolyl)amino)-2-oxoethyl)-N-(trans-4-(((R)-3-((3S,4R)-3-hydroxy-4-((4-(4-methylthiazol-5-yl)benzyl)carbamoyl)pyrrolidine-1-carbonyl)-2,2-dimethyl-5,21-dioxo-8,11,14,17-tetraoxa-4,20-diazahexacosan-26-yl)carbamoyl)cyclohexyl)-4H-thieno[3,2-b]pyrrole-5-carboxamide;

4-(2-(ethyl(m-tolyl)amino)-2-oxoethyl)-N-(trans-4-(((R)-3-((3S,4R)-3-hydroxy-4-((4-(4-methylthiazol-5-yl)benzyl)carbamoyl)pyrrolidine-1-carbonyl)-2,2-dimethyl-5,18-dioxo-8,11,14-trioxa-4,17-diazapentacosan-25-yl)carbamoyl)cyclohexyl)-4H-thieno[3,2-b]pyrrole-5-carboxamide; and 4-(2-(ethyl(m-tolyl)amino)-2-oxoethyl)-N-(trans-4-(((R)-3-((3S,4R)-3-hydroxy-4-((4-(4-methylthiazol-5-yl)benzyl)carbamoyl)pyrrolidine-1-carbonyl)-2,2-dimethyl-5,21-dioxo-8,11,14,17-tetraoxa-4,20-diazaoctacosan-28-yl)carbamoyl)cyclohexyl)-4H-thieno[3,2-b]pyrrole-5-carboxamide, or a salt thereof.

28. A method of inhibiting an *Oplophorus*-derived luciferase the method comprising contacting the *Oplophorus*-derived luciferase with a compound of claim 1 or a salt thereof.

29. The method of claim 28, wherein the *Oplophorus*-derived luciferase comprises a polypeptide of the amino acid sequence of SEQ ID NO: 2.

30. A method for modulating luminescence of an *Oplophorus*-derived luciferase in a sample, the method comprising,
(a) contacting the sample with a coelenterazine substrate and the compound of claim 1 or a salt thereof; and
(b) detecting luminescence in the sample,
wherein the compound of claim 1 causes a decrease in the luminescence from the *Oplophorus*-derived luciferase.

31. A method to detect an interaction between a first protein and a second protein in a sample, the method comprising:
(a) contacting a sample with a coelenterazine substrate and the compound of claim 1 or a salt thereof, wherein the sample comprises:
(i) a first polynucleotide encoding a first fusion protein, wherein the first fusion protein comprises a first fragment of an *Oplophorus*-derived luciferase and a first protein; and
(ii) a second polynucleotide encoding a second fusion protein, wherein the second fusion protein comprises a second fragment of the *Oplophorus*-derived luciferase and a second protein; and
(b) detecting luminescence in the sample,
wherein the detection of luminescence indicates an interaction between the first protein and the second protein.

32. The method of claim 31, wherein when the first protein and second protein interact, the first fragment of the *Oplophorus*-derived luciferase and the second fragment of the *Oplophorus*-derived luciferase reconstitute a full-length enzyme capable of stably binding the coelenterazine substrate.

33. A method to detect an interaction between a first protein and a second protein in a sample, the method comprising:
(a) contacting a sample with a coelenterazine substrate and the compound of claim 1 or a salt thereof, wherein the sample comprises:
(i) a first polynucleotide encoding a first fusion protein, wherein the first fusion protein comprises an *Oplophorus*-derived luciferase and a first protein, wherein the *Oplophorus*-derived luciferase is a bioluminescent donor; and
(ii) a second polynucleotide encoding a second fusion protein, wherein the second fusion protein comprises a fluorescent acceptor molecule and a second protein;
(b) detecting bioluminescence resonance energy transfer (BRET) in the sample, indicating an interaction or close proximity of the bioluminescent donor and the fluorescence acceptor.

34. The method of claim 30, wherein the coelenterazine substrate is a coelenterazine, coelenterazine derivatives, coelenterazine analogs, pro-coelenterazine, or quinone-masked coelenterazine.

35. A bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a fluorescent acceptor molecule; a coelenterazine substrate, and the compound of claim 1 or a salt thereof.

36. A kit comprising:
(a) a compound of claim 1 or a salt thereof; and
(b) an *Oplophorus*-derived luciferase.

37. The kit of claim 36, wherein the *Oplophorus*-derived luciferase comprises a polypeptide sequence of SEQ ID NO: 2.

38. The kit of claim 36, further comprising a coelenterazine substrate.

39. A method to detect an interaction between a molecule of interest and a target protein in a sample, the method comprising:
(a) detecting a first bioluminescence resonance energy transfer (BRET) signal in a sample, the sample comprising:
(i) a polynucleotide encoding a fusion protein, the fusion protein comprising an *Oplophorus*-derived luciferase and a target protein, wherein the *Oplophorus*-derived luciferase is a bioluminescent donor;
(ii) a coelenterazine substrate;
(iii) the compound of claim 1 or a salt thereof; and
(iv) a fluorescent tracer comprising a fluorescent acceptor molecule and a ligand that binds to the target protein;
(b) contacting the sample with a molecule of interest; and
(c) detecting a second BRET signal in the sample, wherein a decrease in the second BRET signal compared to the first BRET signal indicates an interaction between the molecule of interest and the target protein.

40. A bioluminescence resonance energy transfer (BRET) system comprising: a fusion protein including a target protein and a bioluminescence donor molecule, wherein the bioluminescence donor molecule is an *Oplophorus*-derived luciferase; a fluorescent tracer comprising a fluorescent acceptor molecule and a ligand that binds to the target protein; a coelenterazine substrate, and the compound of claim 1 or a salt thereof.

* * * * *